(12) United States Patent
Jackson et al.

(10) Patent No.: US 11,229,711 B2
(45) Date of Patent: Jan. 25, 2022

(54) LINKERS FOR ANTIBODY-DRUG CONJUGATES AND RELATED COMPOUNDS, COMPOSITIONS, AND METHODS OF USE

(71) Applicant: Magenta Therapeutics, Inc., Cambridge, MA (US)

(72) Inventors: David Y. Jackson, Belmont, CA (US); Edward Ha, Solano Beach, CA (US)

(73) Assignee: Magenta Therapeutics, Inc., Cambridge, MA (US)

( * ) Notice: Subject to any disclaimer, the term of this patent is extended or adjusted under 35 U.S.C. 154(b) by 152 days.

(21) Appl. No.: 14/895,893

(22) PCT Filed: Jun. 6, 2014

(86) PCT No.: PCT/US2014/041399
§ 371 (c)(1),
(2) Date: Dec. 3, 2015

(87) PCT Pub. No.: WO2014/197854
PCT Pub. Date: Dec. 11, 2014

(65) Prior Publication Data
US 2016/0367699 A1 Dec. 22, 2016

Related U.S. Application Data

(63) Continuation of application No. PCT/US2013/064147, filed on Oct. 9, 2013.

(60) Provisional application No. 61/981,154, filed on Apr. 17, 2014, provisional application No. 61/891,390, filed on Oct. 15, 2013, provisional application No. 61/832,130, filed on Jun. 6, 2013.

(51) Int. Cl.
A61K 47/48 (2006.01)
A61K 47/68 (2017.01)

(52) U.S. Cl.
CPC ...... *A61K 47/6889* (2017.08); *A61K 47/6817* (2017.08); *A61K 47/6819* (2017.08); *A61K 47/6851* (2017.08)

(58) Field of Classification Search
None
See application file for complete search history.

(56) References Cited

U.S. PATENT DOCUMENTS

| 1,381,195 | A | 4/1983 | Hyzak |
| 1,500,467 | A | 2/1985 | Kubinyi et al. |
| 7,994,135 | B2 * | 8/2011 | Doronina ............... C07K 16/32 514/19.3 |
| 2005/0201964 | A1 | 9/2005 | Malle et al. |

FOREIGN PATENT DOCUMENTS

WO 2011/036075 A1 3/2011

OTHER PUBLICATIONS

Ryan et al. ("Ryan", Chem. Comm. 2011, 47, 5452-5454).*

(Continued)

*Primary Examiner* — Karl J Puttlitz
(74) *Attorney, Agent, or Firm* — McCarter & English, LLP; Jonathan M. Sparks

(57) ABSTRACT

Provided herein are antibody-cytotoxin antibody-drug conjugates and related compounds, such as linker-cytotoxin conjugates and the linkers used to make them, and intermediates in their synthesis; compositions; and methods, including methods of treating cancers.

5 Claims, 5 Drawing Sheets

Human IgG Sub-types

(56) References Cited

OTHER PUBLICATIONS

Ryan et al. ("Ryan", Chem. Commun. 2011, 47, 5452-5454) (Year: 2011).*
Balan et al. ("Balan" Bioconjugate Chem, 2007, 18, 61-76) (Year: 2007).*
McKenzie et al., Journal of Protein Chemistry (1988), 7(5), 581-92 (Year: 1988).*
Brocchini et al., PEGylation of native disulfide bonds in proteins. Nat Protoc. 2006;1(5):2241-52.
Castañeda et al., Acid-cleavable thiomaleamic add linker for homogeneous antibody-drug conjugation. Chem Commun (Camb). Sep. 25, 2013;49(74):8187-9.
Del Rosario et al., Sulfhydryl site-specific cross-linking and labeling of monoclonal antibodies by a fluorescent equilibrium transfer alkylation cross-link reagent. Bioconjug Chem. Jan.-Feb. 1990;1(1): 51-9.
Ducry et al., Antibody-drug conjugates: linking cytotoxic payloads to monoclonal antibodies. Bioconjug Chem. Jan. 2010;21(1):5-13.
Filigheddu et al., Small Ring Constrained Peptidomimetics. Synthesis of Aziridine Parallel beta-Sheet Mimetics. Tetrahedron Letters. 1998;39:3857-3860.
Fischer, Synthese von Potypeptiden II. Berichte der Deutschen Chemischen Gesellschaft. Wiley-VCH Verlag GmbH & Co. pp. 2486-2511, Jan. 1, 1904.
Fliege et al., Electrophilic Properties of Patulin. Adduct Structures and Reaction Pathways with 4-Bromothiophenol and Other Model Nucleophiles. Chem Res Toxicol. 2000;13:363-372.
Hirao et al., Stereoselective Synthesis of (±)-11-Hydroxy-trans-8-dodecenoic Acid from 10-Undecenoic Acid. J Org Chem. 1985;50:279-281.
Schumacher et al.. Homogeneous antibody fragment conjugation by disulfide bridging introduces 'spinostics'. Sci Rep. 2013;3:1525. 8 pages.
International Search Report for Application No. PCT/US2014/041399, dated Oct. 10, 2014. 5 pages.
International Preliminary Report on Patentability for Application No. PCT/US2014/041399, dated Dec. 17, 2015. 11 pages.

* cited by examiner

Fig. 3

| Type | Name Contains | Examples |
|---|---|---|
| | | Chimeric monoclonal antibodies ("-xi-") |
| Tumor | "-tuxi-" | bavituximab, brentuximab, cetuximab, siltuximab, rituximab |
| Cardiovascular | "-cixi-" | abciximab, votociximab |
| Imune system | "-lixi-" | basiliximab, clenoliximab, galiximab, gomiliximab, infliximab, keliximab, lumiliximab, keliximab, lumiliximab, priliximab, teneliximab, vapaliximab |
| Melanoma | "-mexi-" | ecromeximab |
| Bacterial | "-baxi-" | pagibaximab |
| | | Humanized monoclonal antibodies ("-zu-") |
| Tumor | "-tuzu-" | afutuzumab, alemtuzumab, bevacizumab, bivatuzumab, cantuzumab, citatuzumab, dacetuzumab, elotuzumab, etaracizumab, farletuzumab, gemtuzumab, inotuzumab, labetuzumab, lintuzumab, matuzumab, milatuzumab, nimotuzumab, oportuzumab, pertuzumab, sibrotuzumab, tacatuzumab, tigatuzumab, trastuzumab, tucotuzumab, veltuzumab |
| Immune system | "-lizu-" | *Immunosuppressive*: aselizumab, apolizumab, benralizumab, cedelizumab, certolizumab, daclizumab, eculizumab, efalizumab, epratuzumab, erlizumab, fontolizumab, mepolizumab, natalizumab, ocrelizumab, omalizumab, pascolizumab, pexelizumab, PRO 140, reslizumab, rontalizumab, rovelizumab, ruplizumab, sipilizumab, talizumab, teplizumab, tocilizumab, toralizumab, vedolizumab, visilizumab, TGN1412 *Non-immunosuppressive*: Ibalizumab |
| Bacterial | "-bazu-" | tefibazumab |
| Cardiovascular | "-cizu-" | alacizumab, bevacizumab/ranibizumab, etaracizumab, tadocizumab |
| Nervous system | "-nezu-"/"-neuzu-" | bapineuzumab, solanezumab, tanezumab |
| Toxin target | "-toxazu-" | urtoxazumab |
| Viral | "-vizu-" | felvizumab, motavizumab, palivizumab |
| Inerleukin | "-kizu-" | lebrikizumab |
| Angiogensis | "-anibizu-" | ranibizumab |
| | | Fully Human monoclonal antibodies ("-u-") |
| Tumor | "-tumu-"/"-tu-" | adecatumumab, belimumab, cixutumumab, conatumumab, figitumumab, iratumumab, lexatumumab, lucatumumab, mapatumumab, necitumumab, ofatumumab, olaratumab, panitumumab, pritumumab, robatumumab, votumumab, zalutumumab |
| Immune system | "-limu-" | Immunosuppression: adalimumab, atorolimumab, fresolimumab, golimumab, lerdelimumab, metelimumab, morolimumab Activation: Ipilimumab, Tremelimumab — Other: bertilimumab, zanolimumab |
| Bacterial | "-bacu-" | nebacumab, panobacumab, raxibacumab |
| Bone | "-osu-" | denosumab |
| Nervous system | "-neru-" | gantenerumab |
| Musculo-skeletal | "-mulu-" | stamulumab |
| Viral | "-viru-" | exbivirumab, foravirumab, libivirumab, rafivirumab, regavirumab, sevirumab, tuvirumab |
| Inerleukin | "-kinu-" | briakinumab, canakinumab, ustekinumab |
| Fungal | "-fungu-" | efungumab |
| Cardiovascular | "-ciru-" | ramucirumab |

- LC-MS analysis of a homogeneous ADC containing a novel bifunctional linker identified via SDS-PAGE screening
- The major peak has a MW consistent with an IgG conjugated to 4 payloads

LINKERS FOR ANTIBODY-DRUG CONJUGATES AND RELATED COMPOUNDS, COMPOSITIONS, AND METHODS OF USE

CROSS-REFERENCE

This application claims the benefit of priority of U.S. Provisional Patent Application No. 61/832,130, filed Jun. 6, 2013, U.S. Provisional Patent Application No. 61/891,390, filed Oct. 15, 2013, and U.S. Provisional Patent Application No. 61/981,154, filed Apr. 17, 2014, the content of each of which is incorporated herein by reference in its entirety. This application also claims benefit of priority of International Patent Application No. PCT/US2013/064147, filed Oct. 9, 2013, the content of which is incorporated herein by reference in its entirety.

FIELD

This invention relates to novel linkers for antibody-drug conjugates (ADCs) and related compounds, such as linkers used to make them, and intermediates in their synthesis; compositions; and methods, including methods of treating cancers.

BACKGROUND

Cancer is the second most prevalent cause of death in the U.S, yet there are few effective treatment options beyond surgical resection. Of the medical treatments for cancers, the use of monoclonal antibodies targeting antigens present on the cancer cells has become common. Anticancer antibodies approved for therapeutic use in the USA include alemtuzumab (CAMPATH®), a humanized anti-CD52 antibody used in the treatment of chronic lymphocytic leukemia; bevacizumab (AVASTIN®), a humanized anti-VEGF antibody used in colorectal cancer; cetuximab (ERBITUX®), a chimeric anti-epidermal growth factor antibody used in colorectal cancer, head and neck cancer, and squamous cell carcinoma; ipilimumab (YERVOY®), a human anti-CTLA-4 antibody used in melanoma; ofatumumab (ARZERRA®), a human anti-CD20 antibody used in chronic lymphocytic leukemia; panitumumab (VECTIBIX®), a human anti-epidermal growth factor receptor antibody used in colorectal cancer; rituximab (RITUXAN®), a chimeric anti-CD20 antibody used in non-Hodgkin lymphoma; tositumomab (BEXXAR®), a murine anti-CD20 antibody used in non-Hodgkin lymphoma; and trastuzumab (HERCEPTIN®), a humanized anti-HER2 antibody used in breast cancer. While these antibodies have proven useful in the treatments of the cancers for which they are indicated, they are rarely curative as single agents, and are generally used in combination with standard chemotherapy for the cancer.

As an example, trastuzumab is a recombinant DNA-derived humanized monoclonal antibody that selectively binds with high affinity to the extracellular domain of the human epidermal growth factor receptor2 protein, HER2 (ErbB2) (Coussens et al., *Science* 1985, 230, 1132-9; Salmon et al., *Science* 1989, 244, 707-12), thereby inhibiting the growth of HER2-positive cancerous cells.

Although HERCEPTIN is useful in treating patients with HER2-overexpressing breast cancers that have received extensive prior anti-cancer therapy, some patients in this population fail to respond or respond only poorly to HERCEPTIN treatment. Therefore, there is a significant clinical need for developing further HER2-directed cancer therapies for those patients with HER2-overexpressing tumors or other diseases associated with HER2 expression that do not respond, or respond poorly, to HERCEPTIN treatment.

Antibody drug conjugates (ADCs), a rapidly growing class of targeted therapeutics, represent a promising new approach toward improving both the selectivity and the cytotoxic activity of cancer drugs. See, for example, Trail et al., "Monoclonal antibody drug immunoconjugates for targeted treatment of cancer", *Cancer Immunol. Immunother.* 2003, 52, 328-337; and Chari, "Targeted Cancer Therapy: Conferring Specificity to Cytotoxic Drugs", *Acc. Chem. Res.*, 2008, 41(1), 98-107. These ADCs have three components: (1) a monoclonal antibody conjugated through a (2) linker to a (3) cytotoxin. The cytotoxins are attached to either lysine or cysteine sidechains on the antibody through linkers that react selectively with primary amines on lysine or with sulfhydryl groups on cysteine. The maximum number of linkers/drugs that can be conjugated depends on the number of reactive amino or sulfhydryl groups that are present on the antibody. A typical antibody contains up to 90 lysines as potential conjugation sites; however, the optimal number of cytotoxins per antibody for most ADCs is typically between 2 and 4 due to aggregation of ADCs with higher numbers of cytotoxins. As a result, conventional lysine linked ADCs currently in clinical development are heterogeneous mixtures that contain from 0 to 10 cytotoxins per antibody conjugated to different amino groups on the antibody. Key factors in the success of an ADC include that the monoclonal antibody is cancer antigen specific, non-immunogenic, low toxicity, and internalized by cancer cells; the cytotoxin is highly potent and is suitable for linker attachment; while the linker may be specific for cysteine (S) or lysine (N) binding, is stable in circulation, may be protease cleavable and/or pH sensitive, and is suitable for attachment to the cytotoxin.

Anticancer ADCs approved for therapeutic use in the USA include brentuximab vedotin (ADCETRIS®), a chimeric anti-CD30 antibody conjugated to monomethylauristatin E used in anaplastic large cell lymphoma and Hodgkin lymphoma; and gemtuzumab ozogamicin (MYLOTARG®), a humanized anti-CD33 antibody conjugated to calicheamicin γ used in acute myelogeneous leukemia—though this was withdrawn in 2010 for lack of efficacy.

Although several ADCs have demonstrated recent clinical success, the utility of most ADCs currently in development may be limited by cumbersome synthetic processes resulting in high cost of goods, insufficient anti-tumor activity associated with limited potency of the cytotoxic drug, and questionable safety due to linker instability and ADC heterogeneity. See, for example, Ducry et al., "Antibody-Drug Conjugates: Linking Cytotoxic Payloads to Monoclonal Antibodies", *Bioconjugate Chem.* 2010, 21, 5-13; Chari, "Targeted Cancer Therapy: Conferring Specificity to Cytotoxic Drugs", *Acc. Chem. Res.* 2008, 41, 98-107; and Senter, "Recent advancements in the use of antibody drug conjugates for cancer therapy", *Biotechnol.: Pharma. Aspects*, 2010, 11, 309-322.

As an example, trastuzumab has been conjugated to the maytansinoid drug mertansine to form the ADC trastuzumab emtansine, also called trastuzumab-DM1 or trastuzumab-MC-DM1, abbreviated T-DM1 (LoRusso et al., "Trastuzumab Emtansine: A Unique Antibody-Drug Conjugate in Development for Human Epidermal Growth Factor Receptor 2-Positive Cancer", *Clin. Cancer Res.* 2011, 17, 6437-6447; Burris et al., "Trastuzumab emtansine: a novel antibody-drug conjugate for HER2-positive breast cancer",

*Expert Opin. Biol. Ther.* 2011, 11, 807-819). It is now in Phase III studies in the US for that indication. The mertansine is conjugated to the trastuzumab through a maleimidocaproyl (MC) linker which bonds at the maleimide to the 4-thiovaleric acid terminus of the mertansine side chain and forms an amide bond between the carboxyl group of the linker and a lysine basic amine of the trastuzumab. Trastuzumab has 88 lysines (and 32 cysteines). As a result, trastuzumab emtansine is highly heterogeneous, containing dozens of different molecules containing from 0 to 8 mertansine units per trastuzumab, with an average mertansine/trastuzumab ratio of 3.4.

Antibody cysteines can also be used for conjugation to cytotoxins through linkers that contain maleimides or other thiol specific functional groups. A typical antibody contains 4, or sometimes 5, interchain disulfide bonds (2 between the heavy chains and 2 between heavy and light chains) that covalently bond the heavy and light chains together and contribute to the stability of the antibodies in vivo. These interchain disulfides can be selectively reduced with dithiothreitol, tris(2-carboxyethyl)phosphine, or other mild reducing agents to afford 8 reactive sulfhydryl groups for conjugation. Cysteine linked ADCs are less heterogeneous than lysine linked ADCs because there are fewer potential conjugation sites; however, they also tend to be less stable due to partial loss of the interchain disulfide bonds during conjugation, since current cysteine linkers bond to only one sulfur atom. The optimal number of cytotoxins per antibody for cysteine linked ADCs is also 2 to 4. For example, ADCETRIS is a heterogeneous mixture that contains 0 to 8 monomethylauristatin E residues per antibody conjugated through cysteines.

Schumacher et al., "In Situ Maleimide Bridging of Disulfides and a New Approach to Protein PEGylation", *Bioconjugate Chem.* 2011, 22, 132-136, disclose the synthesis of 3,4-disubstituted maleimides such as 3,4-bis(2-hydroxyethylsulfanyl)pyrrole-2,5-dione [referred to by Schumacher et al. as "dimercaptoethanolmaleimide"] and 3,4-bis(phenylsulfanyl)pyrrole-2,5-dione ["dithiophenolmaleimide"], and their N-PEGylated derivatives as PEGylating agents for somatostatin, where the substituted maleimide bonds to the two sulfur atoms of an opened cysteine-cysteine disulfide bond.

It would be desirable to develop linkers with improved in vivo stability as well as potent, homogeneous ADCs, compositions containing them and methods for their use in treating cancers, and methods and intermediates in their preparation.

SUMMARY

In one aspect, provided herein is a linker of the following formula (I):

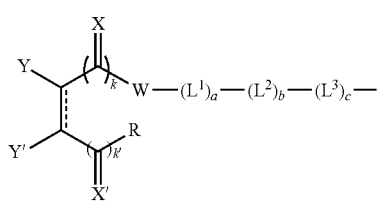

(I)

or an enantiomer, diasteriomer, or mixtures thereof;
wherein:
each X and X' is independently O, S, NH or NR¹ wherein R¹ is $C_{1-3}$ alkyl;
each Y and Y' is independently hydrogen or an electrophilic leaving group that reacts selectively with thiols, provided if one of Y and Y' is hydrogen, the other is the electrophilic leaving group;
W is —NH—, —N(R¹)—, —CH₂—, —CH₂—NH—, —CH₂—N(R¹)—, —CH₂CH₂—, —CH(R²)—, or —CH₂CH(R²)—; wherein R¹ and R² are independently $C_{1-3}$ alkyl;
Z is —CO₂H, —NH₂, —OH, —NH—R³ᵃ, or —CO₂R³ᵇ; wherein R³ᵃ is an amino protecting group, and R³ᵇ is a carboxyl protecting group;
R is any chemical group; or R is absent;
each L¹, L² and L³ is independently a linker selected from the group consisting of —O—, —C(O)—, —S—, —S(O)—, —S(O)₂—, —NH—, —NCH₃—, —(CH₂)_q—, —NH(CH₂)₂NH—, —OC(O)—, —CO₂—, —NHCH₂CH₂C(O)—, —C(O)NHCH₂CH₂NH—, —NHCH₂C(O)—, —NHC(O)—, —C(O)NH—, —NCH₂C(O)—, —C(O)NCH₃—, —(CH₂CH₂O)_p—, —(CH₂CH₂O)_pCH₂CH₂—, —CH₂CH₂—(CH₂CH₂O)_p—, —OCH(CH₂O—)₂, -(AA)_r-, cyclopentanyl, cyclohexanyl, unsubstituted phenylenyl, and phenylenyl substituted by 1 or 2 substituents selected from the group consisting of halo, CF₃—, CF₃O—, CH₃O—, —C(O)OH, —C(O)OC_{1-3} alkyl, —C(O)CH₃, —CN, —NH—, —NH₂, —O—, —OH, —NHCH₃, —N(CH₃)₂, and $C_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer or 1 to 12;
each AA is independently an amino acid;
each r is 1 to 12; and
the ===== bond represents a single or a double bond.

In certain embodiments of the linker of formula (I), the ===== bond represents a single bond.

In certain embodiments of the linker of formula (I), each Y and Y' is independently selected from the group consisting of a halo, a substituted thiol, and a substituted sulfonate. In certain embodiments, each Y and Y' is independently selected from the group consisting of chloro, bromo, fluoro, and iodo. In certain embodiments, each Y and Y' is independently selected from an optionally substituted thiophenyl, an optionally substituted thionaphthyl, an optionally substituted thiopyridyl, an optionally substituted isoquinolinyl, and an optionally substituted phenylsulfonate.

In certain embodiments of the linker of formula (I), each Y and Y' is independently selected from the group consisting of:

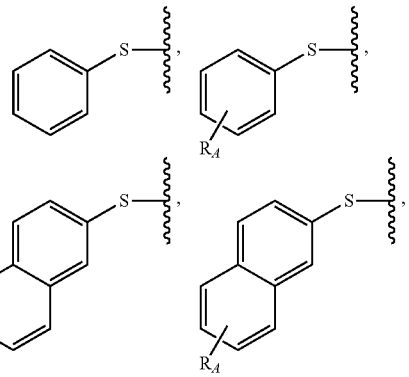

-continued

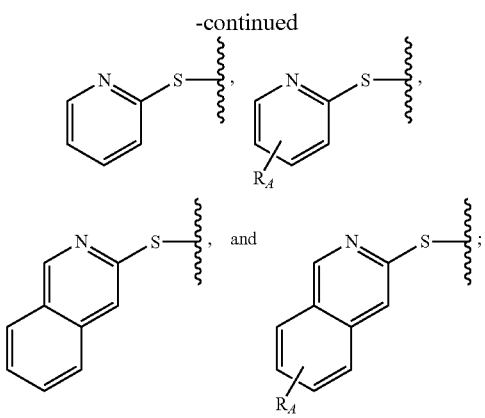

wherein
$R_A$ is selected from the group consisting of hydroxyl, amino, nitro, cyano, chloro, bromo, fluoro, iodo, oxo, carboxyl, $C_{1-6}$ alkoxycarbonyl, $C_{1-6}$ alkyl, $C_{2-6}$ alkenyl, and $C_{1-6}$ alkoxy.

In certain embodiments of the linker of formula (I), each Y and Y' is independently selected from the group consisting of:

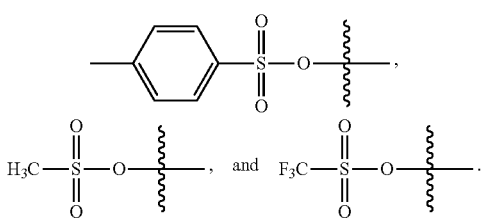

In certain embodiments of the linker of formula (I), each $L^1$, $L^2$ and $L^3$ is independently selected from the group consisting of —$(CH_2)_q$—, —$NH(CH_2)_2NH$—, —$OC(O)$—, —$CO_2$—, —$NHCH_2CH_2C(O)$—, —$C(O)NHCH_2CH_2NH$—, —$NHCH_2C(O)$—, —$NHC(O)$—, —$C(O)NH$—, —$NCH_3C(O)$—, —$C(O)NCH_3$—, —$(CH_2CH_2O)_p$—, —$(CH_2CH_2O)_pCH_2CH_2$—, —$CH_2CH_2(CH_2CH_2O)_p$—, and -$(AA)_r$-, where a, b and c are each independently 0, 1 or 2; and each p, q and r is independently 1, 2, 3 or 4.

In certain embodiments of the linker of formula (I), each AA is an amino acid selected from the group consisting of Ala, Arg, Asn, Asp, Cys, Glu, Gln, Gly, His, Ile, Leu, Lys, Met, Phe, Pro, Ser, Thr, Trp, Tyr and Val. In certain embodiments, each AA is an amino acid selected from the group consisting of Gly, Arg, Val, Ala, Cys, Gln, Leu, Ile, Leu, Lys and Ser or their N-methylated analogues.

In certain embodiments of the linker of formula (I), $R^{3a}$ is selected from the group consisting of 9-fluorenylmethyloxycarbamate (FMOC), tert-butyloxycarbonyl (BOC), benzyl carbamate (Cbz), acetamide, trifluroacetamide, phthalimide, benzylamine, triphenylmethylamine, benzylideneamine, and p-toluenesulfonamide (p-TOS).

In certain embodiments of the linker of formula (I), $R^{3b}$ is selected from the group consisting of a methyl ester, a tert-butyl ester, a benzyl ester, an S-tert-butyl ester, and 2-alkyl-1,3-oxazoline.

In certain embodiments of the linker of formula (I), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined above. In certain embodiments, R is a detectable probe.

In certain embodiments of the linker of formula (I), k and k' are both 1.

In another aspect, provided herein is a linker-cytotoxin conjugate of the following formula (II):

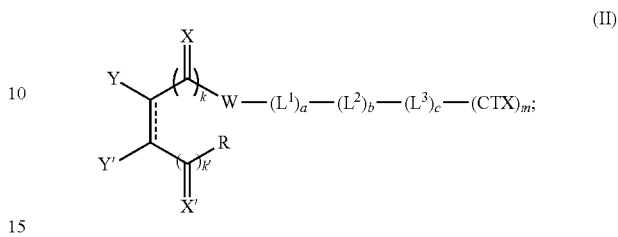

or an enantiomer, diasteriomer, or mixtures thereof;
wherein:
each X and X' is independently O, S, NH or $NR^1$ wherein $R^1$ is $C_{1-3}$ alkyl;
each Y and Y' is independently hydrogen or an electrophilic leaving group that reacts selectively with thiols, provided if one of Y and Y' is hydrogen, the other is the electrophilic leaving group;
W is —NH—, —$N(R^1)$—, —$CH_2$—, —$CH_2$—NH—, —$CH_2$—$N(R^1)$—, —$CH_2CH_2$—, —$CH(R^2)$—, or —$CH_2CH(R^2)$—; wherein $R^1$ and $R^2$ are independently $C_{1-3}$ alkyl;
CTX is a cytotoxin;
R is any chemical group; or R is absent;
each $L^1$, $L^2$ and $L^3$ is independently a linker selected from the group consisting of —O—, —C(O)—, —S—, —S(O)—, —$S(O)_2$—, —NH—, —$NCH_3$—, —$(CH_2)_q$—, —$NH(CH_2)_2NH$—, —OC(O)—, —$CO_2$—, —$NHCH_2CH_2C(O)$—, —$C(O)NHCH_2CH_2NH$—, —$NHCH_2C(O)$—, —$NHC(O)$—, —$C(O)NH$—, —$NCH_3C(O)$—, —$C(O)NCH_3$—, —$(CH_2CH_2O)_p$—, —$(CH_2CH_2O)_pCH_2CH_2$—, —$CH_2CH_2$—$(CH_2CH_2O)_p$—, —$OCH(CH_2O$—$)_2$, -$(AA)_r$-, cyclopentanyl, cyclohexanyl, unsubstituted phenylenyl, and phenylenyl substituted by 1 or 2 substituents selected from the group consisting of halo, $CF_3$—, $CF_3O$—, $CH_3O$—, —C(O)OH, —C(O)O$C_{1-3}$ alkyl, —C(O)$CH_3$, —CN, —NH—, —$NH_2$, —O—, —OH, —$NHCH_3$, —$N(CH_3)_2$, and $C_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer or 1 to 12;
m is an integer of 1 to 4;
each AA is independently an amino acid;
each r is 1 to 12; and
the ===== bond represents a single or a double bond.

In certain embodiments of the linker-cytotoxin conjugate of formula (II), the ===== bond represents a single bond.

In certain embodiments of the linker-cytotoxin conjugate of formula (II), CTX is bonded to $(L^1)_a$-$(L^2)_b$-$(L^3)_c$ via an amide, an N—($C_{1-6}$alkyl)amide, a carbamate, an N—($C_{1-6}$ alkyl)carbamate, an amine, an N—($C_{1-6}$alkyl)amine, an ether, a thioether, an urea, an N—($C_{1-6}$alkyl)urea, or an N,N-di($C_{1-6}$alkyl)urea bond.

In certain embodiments of the linker-cytotoxin conjugate of formula (II), CTX is bonded to $(L^1)_a$-$(L^2)_b$-$(L^3)_c$ via a bond selected from the group consisting of:

[chemical structures]

wherein each $R_B$ is independently branched or unbranched $C_{1-6}$ alkyl.

In certain embodiments of the linker-cytotoxin conjugate of formula (II), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. In certain embodiments, the CTX is selected from the group consisting of Actinomycin-D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine.

In certain embodiments of the linker-cytotoxin conjugate of formula (II), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined above. In certain embodiments, R is a detectable probe. In certain embodiments, R is an antibody fragment.

In another aspect, provided herein antibody-drug conjugate of the following formula (III):

[chemical structure (III)]

a pharmaceutically acceptable salt thereof;
wherein:
A is an antibody or antibody fragment;
the two depicted cysteine residues are from an opened cysteine-cysteine disulfide bond in A;
each X and X' is independently O, S, NH or $NR^1$ wherein $R^1$ is $C_{1-3}$ alkyl;
W is —NH—, —N($R^1$)—, —$CH_2$—, —$CH_2$—NH—, —$CH_2$—N($R^1$)—, —$CH_2CH_2$—, —CH($R^2$)—, or —$CH_2CH(R^2)$—; wherein $R^1$ and $R^2$ are independently $C_{1-3}$ alkyl;
CTX is a cytotoxin;
R is any chemical group; or R is absent;
each $L^1$, $L^2$ and $L^3$ is independently a linker selected from the group consisting of —O—, —C(O)—, —S—, —S(O)—, —S(O)$_2$—, —NH—, —$NCH_3$—, —$(CH_2)_q$—, —NH$(CH_2)_2$NH—, —OC(O)—, —$CO_2$—, —$NHCH_2CH_2C(O)$—, —C(O)$NHCH_2CH_2NH$—, —$NHCH_2C(O)$—, —NHC(O)—, —C(O)NH—, —$NCH_3C(O)$—, —C(O)$NCH_3$—, —$(CH_2CH_2O)_p$—, —$(CH_2CH_2O)_pCH_2CH_2$—, —$CH_2CH_2$—$(CH_2CH_2O)_p$—, —$OCH(CH_2O$—$)_2$, -$(AA)_r$-, cyclopentanyl, cyclohexanyl, unsubstituted phenylenyl, and phenylenyl substituted by 1 or 2 substituents selected from the group consisting of halo, $CF_3$—, $CF_3O$—, $CH_3O$—, —C(O)OH, —C(O)O$C_{1-3}$ alkyl, —C(O)$CH_3$, —CN, —NH—, —$NH_2$, —O—, —OH, —$NHCH_3$, —$N(CH_3)_2$, and $C_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer or 1 to 12;
each AA is independently an amino acid;
each r is 1 to 12;
m is an integer of 1 to 4;
n is an integer of 1 to 4; and
the ===== bond represents a single or a double bond.

In certain embodiments of the antibody-drug conjugate of formula (III), the ===== bond represents a single bond.

In certain embodiments of the antibody-drug conjugate of formula (III), A is an antibody that is specific to a cancer antigen. In certain embodiments, A is selected from the group consisting of alemtuzumab, anitumumab, bevacizumab, brentuximab, cetuximab, gemtuzumab, glembatumumab, inotuzumab, ipilimumab, lovortumumab, milatuzumab, ofatumumab, rituximab, tositumomab, and trastuzumab.

In certain embodiments of the antibody-drug conjugate of formula (III), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin. In certain embodiments, the CTX is monomethylauristatin E, monomethylauristatin F, calicheamicin γ, mertansine, tubulysin T3, or tubulysin T4.

In certain embodiments of the antibody-drug conjugate of formula (III), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined above. In certain embodiments, R is a detectable probe.

In certain embodiments of the antibody-drug conjugate of formula (III), k and k' are both 1.

In another aspect, provided herein is a pharmaceutical composition comprising the antibody-drug conjugate of formula (III) or a pharmaceutically acceptable salt thereof, and a pharmaceutically acceptable diluents, carrier or excipient.

In another aspect, provided herein is a method of treating a cancer by administering to a human suffering therefrom an effective amount of the antibody-drug conjugate of formula (III) or a pharmaceutical composition comprising such antibody-drug conjugate.

DETAILED DESCRIPTION

Brief Description of the Drawings

FIG. 3: List of Antibodies in Clinical Trials

DEFINITIONS

Figure 1:
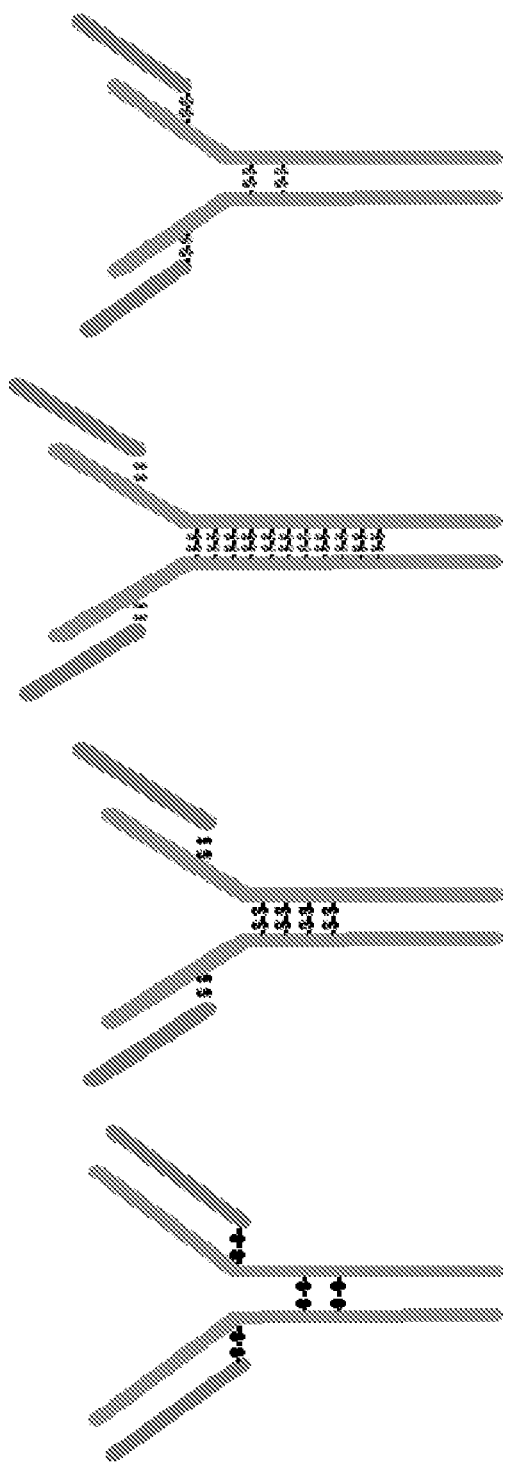
FIG. 1: Human IgG Sub-types
Figure 2:
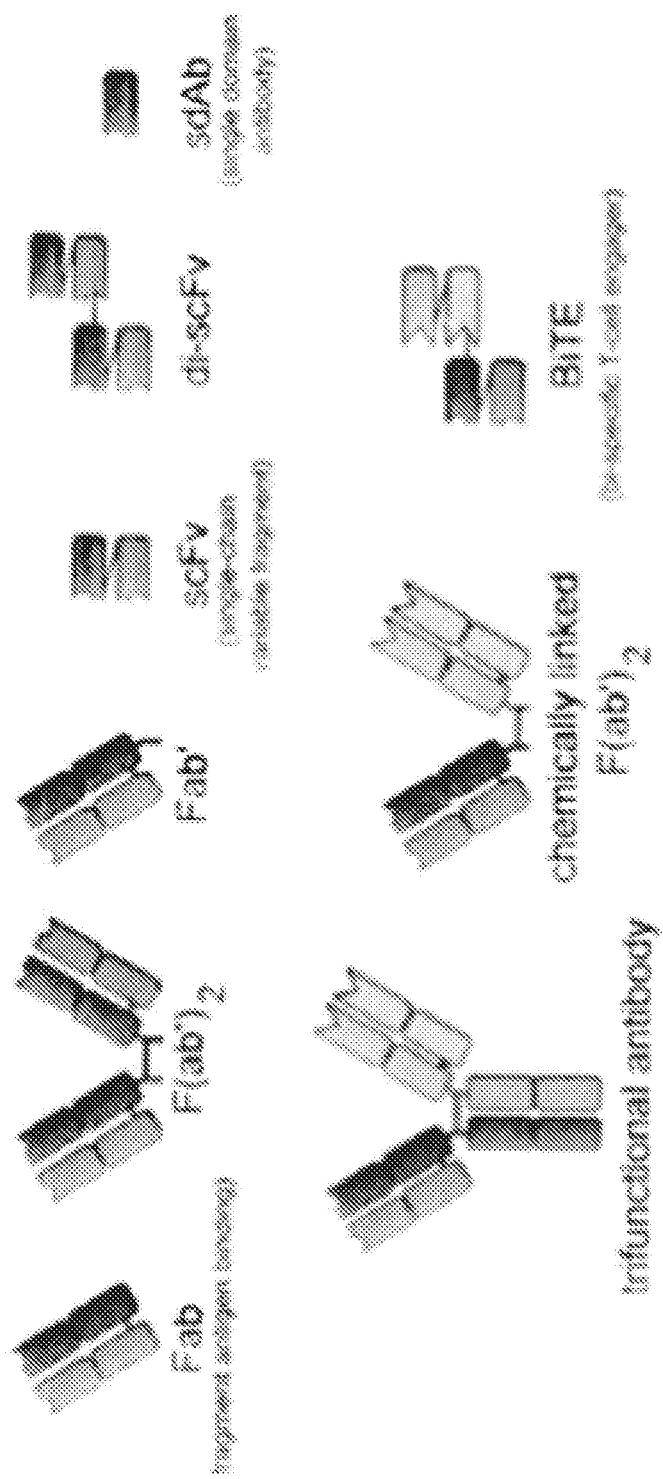
FIG. 2: Forms of Antibodies and Antibody Fragments

An "antibody," also known as an immunoglobulin, is a large Y-shaped protein that binds to an antigen. Antibodies are used by the immune system to identify and neutralize foreign objects such as bacteria and viruses. The antibody recognizes a unique part of the antigen, because each tip of the "Y" of the antibody contains a site that is specific to a site on an antigen, allowing these two structures to bind with precision. An antibody may consist of four polypeptide chains, two heavy chains and two light chains connected by interchain cysteine disulfide bonds (see, e.g., FIG. 1). A "monoclonal antibody" is a monospecific antibody where all the antibody molecules are identical because they are made by identical immune cells that are all clones of a unique parent cell. Initially, monoclonal antibodies are typically prepared by fusing myeloma cells with the spleen cells from a mouse (or B-cells from a rabbit) that has been immunized with the desired antigen, then purifying the resulting hybridomas by such techniques as affinity purification. Recombinant monoclonal antibodies are prepared in viruses or yeast cells rather than in mice, through technologies referred to as repertoire cloning or phage display/yeast display, the cloning of immunoglobulin gene segments to create libraries of antibodies with slightly different amino acid sequences from which antibodies with desired specificities may be obtained. The resulting antibodies may be prepared on a large scale by fermentation. "Chimeric" or "humanized" antibodies are antibodies containing a combination of the original (usually mouse) and human DNA sequences used in the recombinant process, such as those in which mouse DNA encoding the binding portion of a monoclonal antibody is merged with human antibody-producing DNA to yield a partially-mouse, partially-human monoclonal antibody. Full-humanized antibodies are produced using transgenic mice (engineered to produce human antibodies) or phage display libraries. Antibodies (Abs) and "immunoglobulins" (Igs) are glycoproteins having similar structural characteristics. While antibodies exhibit binding specificity to a specific antigen, immunoglobulins include both antibodies and other antibody-like molecules which generally lack antigen specificity. Polypeptides of antibody-like molecules are produced at low levels by the lymph system and at increased levels by myelomas. The terms "antibody" and "immunoglobulin" are used interchangeably in the broadest sense and include monoclonal antibodies (e.g., full length or intact monoclonal antibodies), polyclonal antibodies, monovalent antibodies, multivalent antibodies, multispecific antibodies (e.g., bispecific antibodies so long as they exhibit the desired biological activity). Forms of antibodies and antibody fragments are shown schematically in FIG. 2. These antibodies may also include certain antibody fragments. An antibody can be chimeric, human, humanized and/or affinity matured. Exemplary antibodies are shown in FIG. 3. Antibodies of particular interest are those that are specific to cancer antigens, are non-immunogenic, have low toxicity, and are readily internalized by cancer cells; and suitable antibodies include alemtuzumab, bevacizumab, brentuximab, cetuximab, gemtuzumab, ipilimumab, ofatumumab, panitumumab, rituximab, tositumomab, inotuzumab, glembatumumab, lovortuzumab and trastuzumab. Additional antibodies include adecatumumab, afutuzumab, bavituximab, belimumab, bivatuzumab, cantuzumab, citatuzumab, cixutumumab, conatumumab, dacetuzumab, elotuzumab, etaracizumab, farletuzumab, figitumumab, iratumumab, labetuzumab, lexatumumab, lintuzumab, lucatumumab, mapatumumab, matuzumab, milatuzumab, necitumumab, nimotuzumab, olaratumab, oportuzumab, pertuzumab, pritumumab, ranibizumab, robatumumab, sibrotuzumab, siltuximab, tacatuzumab, tigatuzumab, tucotuzumab, veltuzumab votumumab, and zalutumumab.

The terms "full length antibody," "intact antibody" and "whole antibody" are used herein interchangeably to refer to an antibody in its substantially intact form, and are not antibody fragments as defined below. The terms particularly refer to an antibody with heavy chains that contain the Fc region.

"Antibody fragments" comprise only a portion of an intact antibody, wherein the portion retains at least one, two, three and as many as most or all of the functions normally associated with that portion when present in an intact antibody. In one aspect, an antibody fragment comprises an antigen binding site of the intact antibody and thus retains the ability to bind antigen. In another aspect, an antibody fragment, such as an antibody fragment that comprises the Fc region, retains at least one of the biological functions normally associated with the Fc region when present in an intact antibody. Such functions may include FcRn binding, antibody half life modulation, ADCC function and complement binding. In another aspect, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody," as used herein, refers to an antibody obtained from a population of substantially homogeneous antibodies, e.g., the individual antibodies comprising the population are identical except for possible mutations, e.g., naturally occurring mutations, that may be present in minor amounts. The modifier term "monoclonal" indicates the character of the antibody as not being a mixture of discrete antibodies. In certain aspects, such a monoclonal antibody may include an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. In addition to their specificity, monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. (See, Kohler et al., Nature, 256: 495 (1975); Harlow et al., Antibodies: A Laboratory Manual, (Cold Spring Harbor Laboratory Press, 2.sup.nd ed. 1988); Hammerling et al., in: Monoclonal Antibodies and T-Cell Hybridomas 563-681 (Elsevier, N.Y., 1981)), recombinant DNA methods (see, e.g., U.S. Pat. No. 4,816,567), and technologies for producing human or human-like antibodies in animals that have parts or all of the human immunoglobulin loci or genes encoding human immunoglobulin sequences (see, WO98/24893; WO96/34096; WO96/33735 and WO91/10741). The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). "Humanized" forms of non-human (e.g., murine) antibodies are chimeric antibodies that contain minimal sequence derived from non-human immunoglobulin. In one aspect, a humanized antibody is a human immunoglobulin (recipient antibody) in which residues from a hypervariable region of the recipient are replaced by residues from a hypervariable region of a non-human species (donor antibody) such as mouse, rat, rabbit, or nonhuman primate having the desired specificity, affinity, and/or capacity. In another aspect, framework region (FR) residues of the human immunoglobulin are replaced by corresponding non-human residues. In general, a humanized antibody will comprise substantially all of at least one, and typically two, variable domains, in which all or substantially all of the hypervariable loops correspond to those of a non-human immunoglobulin, and all or substantially all the FRs are those of a human immunoglobulin sequence. The humanized antibody may comprise at least a portion of an immunoglobulin constant region (Fc), typically that of a human immunoglobulin. See Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Framework" or "FR" residues are those variable domain residues other than the hypervariable region residues. "Fc receptor" or "FcR" is a receptor that binds to the Fc region of an antibody. In certain embodiments, an FcR is a native human FcR. In one aspect, an FcR is one which binds an IgG antibody (a gamma receptor) and includes receptors of the FcγRI, FcγRII and FcγRIII subclasses. (See Daeron, Annu. Rev. Immunol. 15:203-234 (1997)).

The term "alkyl," as used herein, means a straight, branched chain, or cyclic (in this case, it would also be known as "cycloalkyl") hydrocarbon containing from 1-10 carbon atoms. Examples of alkyl include, but are not limited to, methyl, ethyl, n-propyl, iso-propyl, n-butyl, sec-butyl, tert-butyl, n-pentyl, isopentyl, neopentyl, n-hexyl, 3-methylhexyl, 2,2-dimethylpentyl, 2,3-dimethylhexyl, n-heptyl, n-octyl, n-nonyl, and n-decyl. In certain embodiments, such alkyl groups can optionally be substituted with 1 to 5 substituents selected from the group consisting of halo, cyano, nitro, $CF_3-$, $CF_3O-$, $CH_3O-$, $-CO_2H$, $-C(O)CH_3$, $-NH_2$, $-OH$, $-SH$, $-NHCH_3$, $-N(CH_3)_2$, $-SMe$, and the like.

The term "$C_{1-6}$alkyl," as used herein, means a straight, branched chain, or cyclic (in this case, it would also be known as "cycloalkyl") hydrocarbon containing from 1-6 carbon atoms.

The term "$C_{1-3}$alkyl," as used herein, means a straight or branched chain hydrocarbon containing from 1-3 carbon atoms.

The term "alkenyl," as used herein, means a straight, branched chain, or cyclic (in which case, it would also be known as a "cycloalkenyl") hydrocarbon containing from 2-10 carbons and containing at least one carbon-carbon double bond formed by the removal of two hydrogens. In some embodiments, depending on the structure, an alkenyl group is a monoradical or a diradical (i.e., an alkenylene group). In some embodiments, alkenyl groups are optionally substituted. Examples of alkenyl include, but are not limited to, ethenyl, 2-propenyl, 2-methyl-2-propenyl, 3-butenyl, 4-pentenyl, 5-hexenyl, 2-heptenyl, and 2-methyl-1-heptenyl. In certain embodiments, such alkenyl groups can optionally be substituted with 1 to 5 substituents selected from the group consisting of halo, cyano, nitro, $CF_3-$, $CF_3O-$, $CH_3O-$, $-CO_2H$, $-C(O)CH_3$, $-NH_2$, $-OH$, $-SH$, $-NHCH_3$, $-N(CH_3)_2$, $-SMe$, and the like.

The term "alkoxy," as used herein, means an alkyl group, as defined herein, appended to the parent molecular moiety through an oxygen atom. Examples of alkoxy include, but are not limited to, methoxy, ethoxy, propoxy, 2-propoxy, butoxy, tert-butoxy, pentyloxy, and hexyloxy.

The term "$C_{2-6}$ alkenyl," as used herein, means a straight, branched chain, or cyclic (in this case, it would also be known as "cycloalkyl") hydrocarbon containing from 2-6 carbon atoms and at least one carbon-carbon double bond formed by the removal of two hydrogens.

The term "cycloalkyl," as used herein, means a monocyclic or polycyclic radical that contains only carbon and hydrogen, and includes those that are saturated, partially unsaturated, or fully unsaturated. Cycloalkyl groups include groups having from 3 to 10 ring atoms.

The term "amino," as used herein, refers to the radical $-NH_2$.

The term "hydroxyl" or "hydroxy," as used herein, refers to the radical $-OH$.

The term "carboxyl" as used herein, refers to the radical $-CO_2H$.

The term "phenyl," as used herein, refers to a $C_6H_5$ group as known in the art. "Phenylene," as used herein, refers to a divalent phenyl group, wherein the phenyl group is substituted at two positions on the phenyl ring that may be ortho (o-$C_6H_4$) or para (p-$C_6H_4$).

The term "thiol," as used herein, refers to the radical $-SH$. The term "substituted thiol," as used herein, refers to a radical such as $-SR$ wherein R is any optionally substituted chemical group described herein. In certain embodiments, "substituted thiol" refers to a radical —SR where R is an alkyl, cycloalkyl, aryl or heteroaryl group as defined herein that may be optionally substituted as defined herein. Representative examples of substituted thiol include, but are not limited to, thiophenyl, thionaphthyl, thiopyridyl, thioisoquinolinyl, as depicted below:

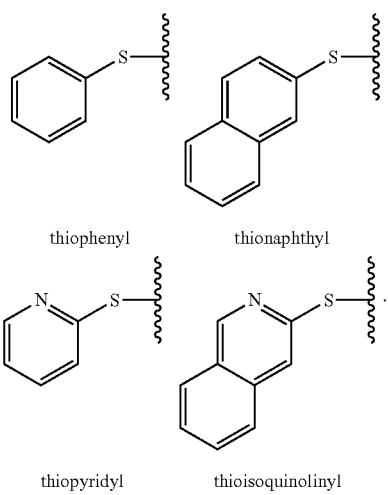

The term "sulfonate," as used herein, refers to the radical —OS(O$_2$)H. "Substituted sulfonate" refers to a radical such as —OS(O$_2$)R wherein R is an alkyl, cycloalkyl, aryl or heteroaryl group as defined herein that may be optionally substituted as defined herein. In certain embodiments, R is selected from lower alkyl, alkyl, aryl and heteroaryl. Representative examples of substituted sulfonate include, but are not limited to, tosylate, mesylate and triflate, as depicted below:

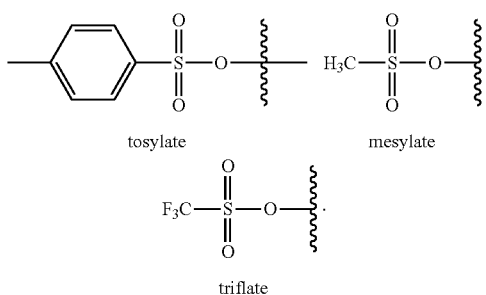

The term "aryl," as used herein, refers to an unsaturated aromatic carbocyclic group of from 6 to 14 carbon atoms having a single ring (e.g., phenyl) or multiple condensed rings (e.g., naphthyl or anthryl). Preferred aryls include phenyl, biphenyl, naphthyl and the like. Unless otherwise constrained by the definition for the individual substituent, such aryl groups can optionally be substituted with 1 or more substituents, for example, 1 to 5 substituents, such as, hydroxyl, amino, nitro, cyano, chloro, bromo, fluoro, iodo, oxo, carboxyl, C$_{1-6}$ alkoxycarbonyl, C$_{1-6}$ alkyl, C$_{2-6}$ alkenyl, and C$_{1-6}$alkoxy, and the like. In certain embodiments, such aryl groups can optionally be substituted with 1 to 5 substituents selected from the group consisting of halo, cyano, nitro, CF$_3$—, CF$_3$O—, CH$_3$O—, —CO$_2$H, —C(O)CH$_3$, —NH$_2$, —OH, —SH, —NHCH$_3$, —N(CH$_3$)$_2$, —SMe and C$_{1-3}$ alkyl.

The term "heteroaryl," as used herein, refers to an aryl ring system having one to four heteroatoms as ring atoms in a heteroaromatic ring system, wherein the remainder of the atoms are carbon atoms. Suitable heteroatoms include oxygen, sulfur and nitrogen. Preferably, the heterocyclic ring system is monocyclic or bicyclic. Unless otherwise constrained by the definition for the individual substituent, such heteroaryl groups can optionally be substituted with 1 or more substituents, for example, 1 to 5 substituents, such as, hydroxyl, amino, nitro, cyano, chloro, bromo, fluoro, iodo, oxo, carboxyl, C$_{1-6}$ alkoxycarbonyl, C$_{1-6}$ alkyl, C$_{2-6}$ alkenyl, and C$_{1-6}$alkoxy, and the like. In certain embodiments, such heteroaryl groups can optionally be substituted with 1 to 5 substituents selected from the group consisting of halo, cyano, nitro, CF$_3$—, CF$_3$O—, CH$_3$O—, —CO$_2$H, —C(O)CH$_3$, —NH$_2$, —OH, —SH, —NHCH$_3$, —N(CH$_3$)$_2$, —SMe and C$_{1-3}$ alkyl. Examples of heteroaryl include, but are not limited to:

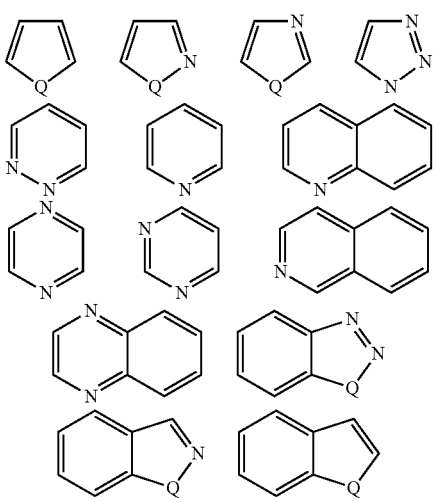

where Q is O, NR$^2$ or S.

The term "chemical group," as used herein, refers to two or more atoms bound together as a single unit and forming part of a molecule.

The term "protecting group," as used herein, refers to a chemical group that is introduced into a molecule by chemical modification of a functional group in order to obtain chemoselectivity. Examples of protecting groups are disclosed, for example, in Greene, T. W. and Wuts, P. G. M., 1991, Protective Groups In Organic Synthesis, 3rd ed.; John Wiley & Sons: New York, and similar documents.

The term "amino protecting group," as used herein, as used herein, refers to a protecting group that serves to protect an amino functional group. The term includes, without limitation, 9-fluorenylmethyloxycarbamate (FMOC), tert-butyloxycarbonyl (BOO), benzyl carbamate (Cbz), acetamide, trifluroacetamide, phthalimide, benzylamine, triphenylmethylamine, benzylideneamine, and p-toluenesulfonamide (p-TOS), and the like.

The term "carboxyl protecting group," as used herein, refers to a protecting group that serves to protect a carboxylic acid functional group. The term includes, without limitation, a methyl ester, a tert-butyl ester, a benzyl ester, an S-tert-butyl ester, 2-alkyl-1,3-oxazoline, and the like.

An "amino acid" (or AA) or amino acid residue includes all 20 naturally occurring amino acids, commonly designated by three letter symbols (e.g., alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), lysine (Lys), methionine (Met), phenylalanine (Phe), proline (Pro), serine (Ser), threonine (Thr), tryptophan (Trp), tyrosine (Tyr), and valine (Val)). The amino acid residue of the present application also includes citrulline (Cit), 4-hydroxyproline, hydroxylysine, demosine, isodemosine, 3-methylhistidine, norvalin, beta-alanine, gamma-aminobutyric acid, homocysteine, homoserine, ornithine and methionine sulfone. The amino acid residue of the present application also includes the corresponding N-methyl amino acids, such as —N(CH$_3$)CH$_2$C(O)O—, —NHC(O)CH$_2$CH$_2$CH(NHCH$_3$)C(O)O—, etc. The amino acids, dipeptides, tripeptides, oligomers and polypeptides designated as -(AA)$_r$- of the present application may include the corresponding non-N-alkylated amino acids and peptides (such as non-N-methylated amino acids in the peptides), as well as a mixture of the non-N-alkylated amino acids and the N-alkylated amino acids of the peptides.

A "cytotoxin" (CTX) is a molecule that, when released within a cancer cell, is toxic to that cell.

A "linker" (noted as L or L$^1$, L$^2$ and L$^3$) is a molecule with two reactive termini, one for conjugation to an antibody or to another linker and the other for conjugation to a cytotoxin. The antibody conjugation reactive terminus of the linker is typically a site that is capable of conjugation to the antibody through a cysteine thiol or lysine amine group on the antibody, and so is typically a thiol-reactive group such as a double bond (as in maleimide) or a leaving group such as a chloro, bromo or iodo or an R-sulfanyl group or sulfonyl group, or an amine-reactive group such as a carboxyl group or as defined herein; while the antibody conjugation reactive terminus of the linker is typically a site that is capable of conjugation to the cytotoxin through formation of an amide bond with a basic amine or carboxyl group on the cytotoxin, and so is typically a carboxyl or basic amine group. In one embodiment, when the term "linker" is used in describing the linker in conjugated form, one or both of the reactive termini will be absent (such as the leaving group of the thiol-reactive group) or incomplete (such as the being only the carbonyl of the carboxylic acid) because of the formation of the bonds between the linker and/or the cytotoxin.

The term "leaving group," as used herein, refers to any group that leaves in the course of a chemical reaction involving the group as described herein and includes but is not limited to halogen, sulfonates (brosylate, mesylate, tosylate triflate etc. . . . ), p-nitrobenzoate and phosphonate groups, for example.

The term "electrophilic leaving group," as used herein, refers to a leaving group that accepts an electron pair to make a covalent bond. In general, electrophiles are susceptible to attack by complementary nucleophiles, including the reduced thiols from the disulfide bond of an antibody.

The term "electrophilic leaving group that reacts selectively with thiols," as used herein, refers to electrophilic leaving group that reacts selectively with thiols, over other nucleophiles. In certain embodiments, an electrophilic leaving group that reacts selectively with thiols reacts selectively with the reduced thiols from the disulfide bond of an antibody.

The term "detectable probe," as used herein, refers to a composition that provides a detectable signal. The term includes, without limitation, any fluorophore, chromophore, radiolabel, enzyme, antibody or antibody fragment, and the like, that provide a detectable signal via its activity.

An "antibody-drug conjugate" (ADC) is an antibody that is conjugated to one or more cytotoxins, through one or more linkers. The antibody is typically a monoclonal antibody specific to a therapeutic target such as a cancer antigen.

A "cytotoxic agent" or "cytotoxin" is a molecule that has a cytotoxic effect on cells (e.g., when released within a cancer cell, is toxic to that cell).

"Tubulysin" includes both the natural products described as tubulysins, such as by Sasse et al. and other authors mentioned in the Description of the related art, and also the tubulysin analogs described in US Patent Application Publication No. US 2011/0021568 A1. Tubulysins disclosed in the present application are noted herein and may include the tubulysins of the formulae T3 and T4, and other tubulysins where the terminal N-methylpiperidine has been replaced by an unsubstituted piperidine, as illustrated below for T3 and T4:

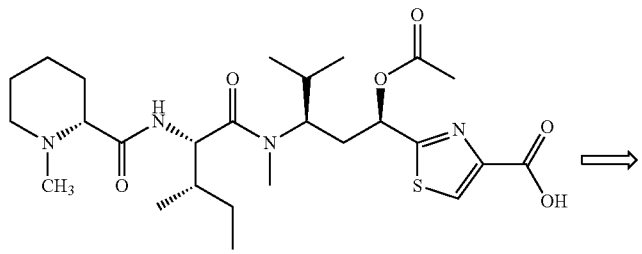

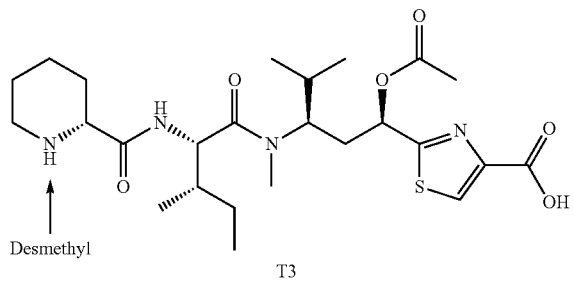

T3

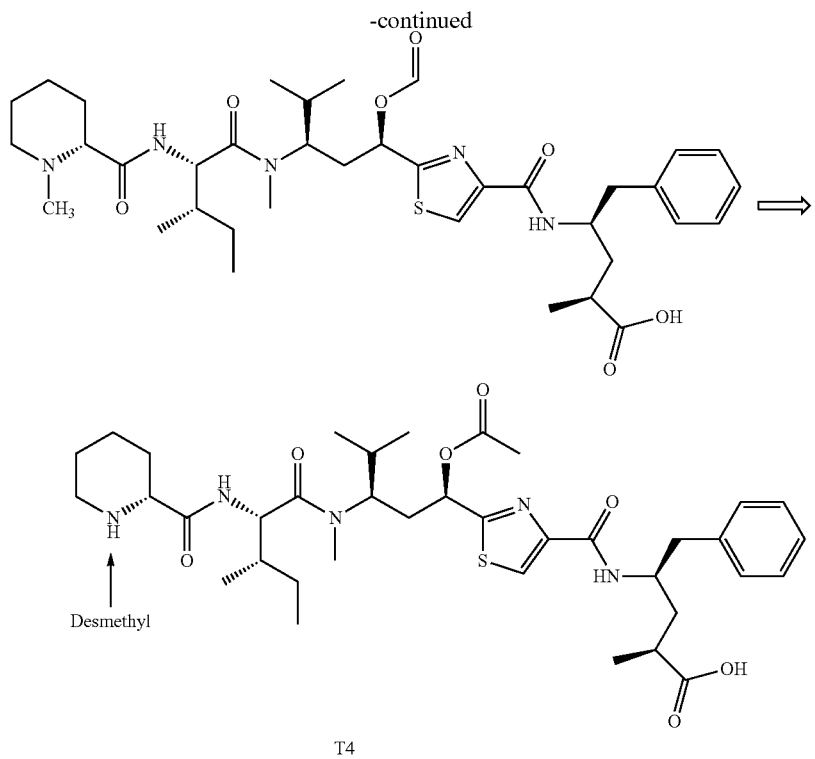

T4

Des-methyl tubulysin compounds correspond to the terminal non-N-methylated piperidine analogs;

allowing amide bond formation between the terminal piperidine and a linker.

The term "MMAF" generally refers to (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid. In some embodiments, MMAF may refer to ((2R,3R)-3-((S)-1-((3R,4S,5R)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalanine.

The terms "cell proliferative disorder" and "proliferative disorder" refer to disorders that are associated with some degree of abnormal cell proliferation. In one aspect, the cell-proliferative disorder is cancer.

"Tumor," refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive. The terms "cancer" and "cancerous" refer to the physiological condition in mammals that is typically characterized by unregulated cell growth. Examples of cancer include, but are not limited to, carcinoma, lymphoma, blastoma, sarcoma and leukemia or lymphoid malignancies.

A "basic amine", such as the amine forming a part of the terminal piperidine group of the tubulysins, such as that of the formulae T3 and T4, is a primary or secondary amine that is not part of an amide.

A "therapeutically effective amount" means that amount of an ADC or composition disclosed herein which, when administered to a human suffering from a cancer, is sufficient to effect treatment for the cancer. "Treating" or "treatment" of the cancer includes one or more of:

(1) limiting/inhibiting growth of the cancer, e.g. limiting its development;

(2) reducing/preventing spread of the cancer, e.g. reducing/preventing metastases;

(3) relieving the cancer, e.g. causing regression of the cancer, (4) reducing/preventing recurrence of the cancer; and (5) palliating symptoms of the cancer.

As used herein, the term "pharmaceutically acceptable salt" refers to those salts of the ADCs formed by the process of the present application which are suitable for use in contact with the tissues of humans and lower animals without undue toxicity, irritation, allergic response and the like. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the ADC compounds, or separately by reacting the free base function or group of a compound with a suitable organic acid. Examples of pharmaceutically acceptable salts include, but are not limited to, nontoxic acid addition salts, or salts of an amino group formed with inorganic acids such as hydrochloric acid, hydrobromic acid, phosphoric acid, etc., or with organic acids such as acetic acid, maleic acid, tartaric acid, citric acid, succinic acid or malonic acid. Other pharmaceutically acceptable salts include, but are not limited to, adipate, alginate, ascorbate, benzenesulfonate, benzoate, bisulfate, citrate, digluconate, dodecylsulfate, ethanesulfonate, formate, fumarate, gluconate, 2-hydroxy-ethanesulfonate, lactate, laurate, malate, maleate, malonate, methanesulfonate, oleate, oxalate, palmitate, phosphate, propionate, stearate, succinate, sulfate, tartrate, p-toluenesulfonate, valerate salts, and the like. Representative alkali or alkaline earth metal salts include sodium, lithium, potassium, calcium, or magnesium salts, and the like. Further pharmaceutically acceptable salts include, nontoxic ammonium, quaternary ammonium, and amine cations formed using counterions such as halide, hydroxide, carboxylate, sulfate, phosphate, nitrate, alkyl groups having from 1 to 6 carbon atoms (e.g., $C_{1-6}$ alkyl), sulfonate and aryl sulfonate.

Cancers of interest for treatment include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, oral cancer, liver cancer, bladder cancer, cancer of the urinary tract, hepatoma, breast cancer including, for example, HER2-positive breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, acute myeloid leukemia (AML), chronic lymphocytic leukemia (CML), multiple myeloma and B-cell lymphoma, brain cancer, head and neck cancers and associated metastases.

Abbreviations/Acronyms

ADC: antibody-drug conjugate; BOC: tert-butyloxycarbonyl; BRA: bromoacrylamide; Cbz: benzyl carbamate; DAR: Drug-to-antibody ratio; DBB: dibromobenzyl; DBMA: dibromomaleamide; DBP: dibromopropanamide; DBSC: dibromosuccinamide; DEA: diethylamine; DEPC: diethylpyrocarbonate; DCC: 1,3-dicyclohexylcarbodiimide; DIAD: diisopropyl azodicarboxylate; DIPC: 1,3-diisopropylcarbodiimide; DIPEA: diisopropylethylamine; DMA: dimethyacetamide; DMF: N,N-dimethylformamide; DPBS: Dulbecco's phosphate-buffered saline; DTNB: 5,5'-dithiobis-(2-nitrobenzoic acid); DTPA: diethylenetriaminepentaacetic acid; DTT: dithiothreitol; EDC: ethyl 3-(3-dimethylaminopropyl)carbodiimide; EEDQ: ethoxycarbonyl-ethoxy-dihydroquinoline; Fmoc or FMOC: 9-fluorenylmethoxycarbonyl chloride; HATU: O-(7-azabenzotriazol-1-yl)-N,N,N',N'-tetramethyluronium hexafluorophosphate; HIC: hydrophobic interaction chromatography; HOBT: N-hydroxybenzotriazole; HPLC: High Performance Liquid Chromatography; NHS: N-hydroxysuccinimide; NMM: N-methylmorpholine; MC: maleimido caproyl; MMAE: monomethylauristatin E; MMAF: monomethylauristatin F, monomethylauristatin phenylalanine; MC: maleimidocaproyl, 6-(2,5-dioxopyrrolyl)hexanoyl; PAB: para amino benzyl; PBD: pyrrolobenzodiazepine; PBS: phosphate-buffered saline; PEG: poly(ethyleneglycol); p-TOS; p-toluenesulfonamide; TBTU: 2-(1H-benzotriazol-1-yl)-1,1,3,3-tetramethyluronium tetrafluoroborate; TCEP: tris(2-carboxyethyl)phosphine; TFA: trifluoroacetic acid; TGI: tumor growth inhibition; TEA: triethanolamine; THF: tetrahydrofuran; VA: Valine-Alanine; VAP: Valine-Alanine-para amino benzyl; VA(PAB): Valine-Alanine-para amino benzyl.

Abbreviations/Acronyms (Antibodies)

ATZ: alemtuzumab; ATM: anitumumab; BCZ: bevacizumab; BTX: brentuximab; CTX: cetuximab; GTZ: gemtuzumab; GBT: glembatumumab; ITZ: inotuzumab; ILM: ipilimumab; LVT: lovortumumab; MTZ: milatuzumab; OTM: ofatumumab; RTX: rituximab; TTM: tositumomab; and TTZ: trastuzumab.

Linkers

The linkers disclosed herein are "opened ring" structures, such that the linker is capable of being chemically modified at two positions of the structure, the Z position, and the R position (see arrowed positions below):

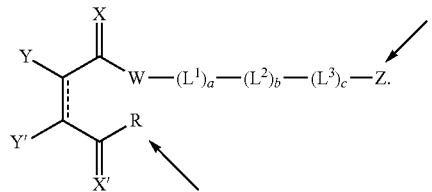

Without intending to be bound by any particular theory or mechanism, it is believed that the linkers disclosed herein, which have "opened ring" structures, display improved in vivo stability with regard to the antibody-linker interface.

The "opened ring" structure of the linkers disclosed herein also allow greater flexibility in making ADCs capable of carrying two drug payloads or one drug payload and a detectable probe, as explained below.

For example, in certain embodiments, where R is selected from the group consisting of Z, $(L^1)_a$-$(L^2)_b$-$(L^3)_c$-Z, and W-$(L^1)_a$-$(L^2)_b$-$(L^3)_c$-Z, two cytotoxin (CTX) molecules may be conjugated to the linker. Such linker may be used to make an ADC that is capable of carrying two drug payloads. Alternatively, in certain embodiments, where R is "capped off" with an unreactive side chain, for example, where R is W, $(L^1)_a$, $(L^2)_b$, $(L^3)_c$, or W-$(L^1)_a$-$(L^2)_b$-$(L^3)_c$, only one CTX may be conjugated to the linker. Such linker may be used to make an ADC that is capable of carrying one drug payload.

In certain embodiments, where R is a detectable probe (e.g., a fluorophore, chromophore, radiolabel, enzyme, antibody or antibody fragment that provides a detectable signal via its activity), such a linker may be used to make an ADC capable of carrying one drug payload and a detectable probe. In certain embodiments, where R is a radiolabel, such a linker may be used to make an ADC that is capable of carrying one drug payload (CTX) and one radiolabel. The resultant radiolabeled ADC can be useful for imaging and/or therapy.

Antibody-Drug Conjugate (ADC)s

As mentioned in the Description of the related art, ADCs of the prior art that coordinate to cysteine thiols of the antibody have employed monofunctional linkers, of which the MC linker is an example. Reduction and opening of the cysteine-cysteine disulfide bonds to give free thiols for conjugation decreases the stability of the antibody, and the formation of the ADC by reaction of the reduced thiols does not re-form the interchain disulfide bond, as illustrated for an exemplary antibody depicted with four interchain disulfide bonds in the following Scheme A:

In contrast, the linkers disclosed herein contain two reactive functional groups (Y and Y' in the scheme below) that selectively target the two sulfur atoms of an opened

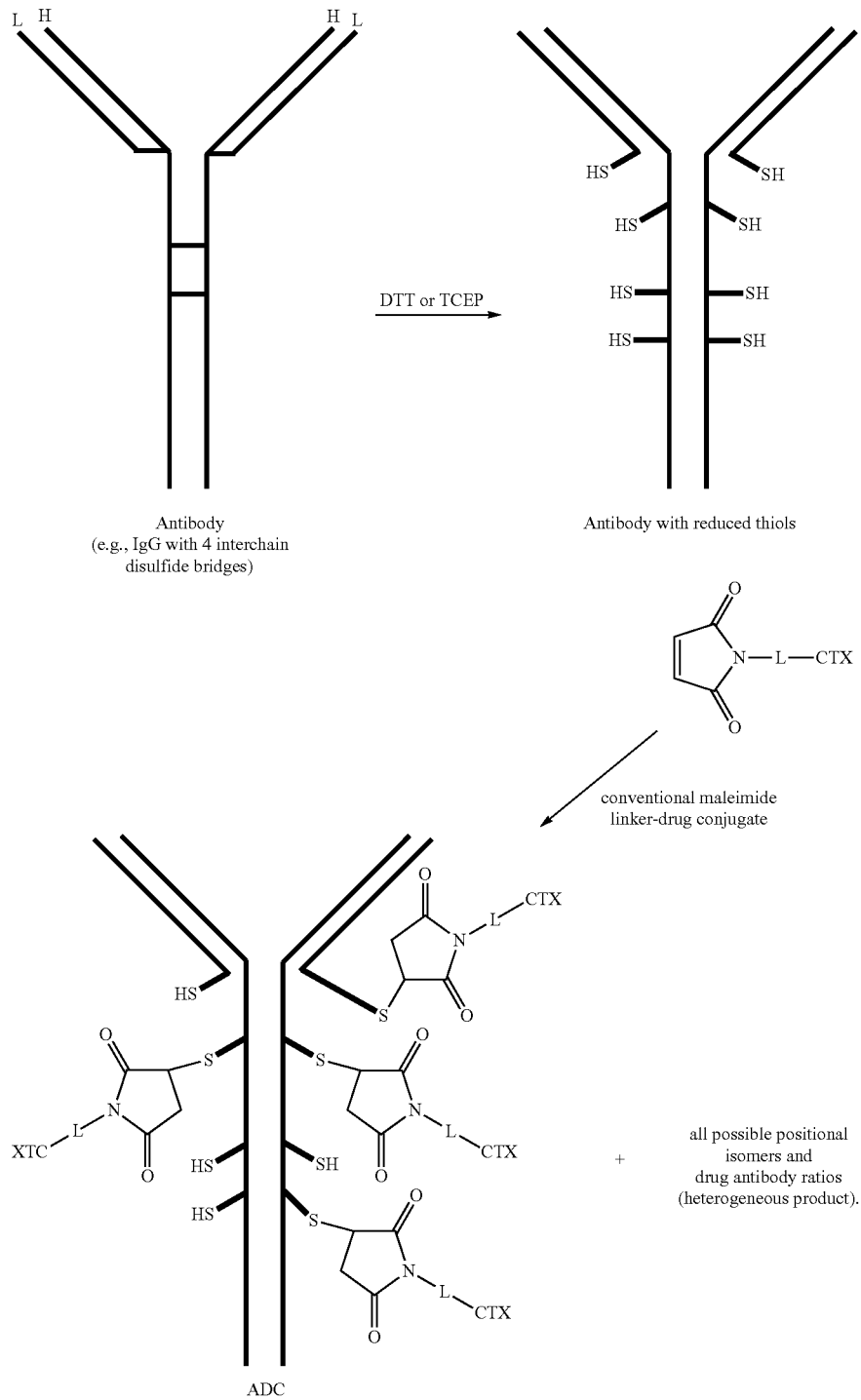

Scheme A: ADCs with conventional maleimide linker-drug conjugates

As a result, a heterogenous mixture of ADCs is produced, which may comprise all possible positional isomers of drug conjugate to cysteine thiol, and may comprise all possible drug antibody ratios (1, 2, 3, 4, . . . , and 8).

cysteine-cysteine disulfide bond (e.g., one or more opened interchain cysteine-cysteine disulfide bonds). Reaction of the bifunctional linker with the two cysteines of an opened cysteine-cysteine disulfide bond gives a "stapled" or "snapped" antibody conjugate with one linker per disulfide (e.g., one or more interchain disulfides) connected through two thioether bonds, as shown in the following exemplary Scheme B:

For ease of viewing, the linker-cytotoxin conjugate is represented by a cartoon, where the linker between W and CTX is the squiggly line, k and k' are both 0, m is 1, and R is the black dot.

Scheme B: Exemplary ADCs of the present disclosure

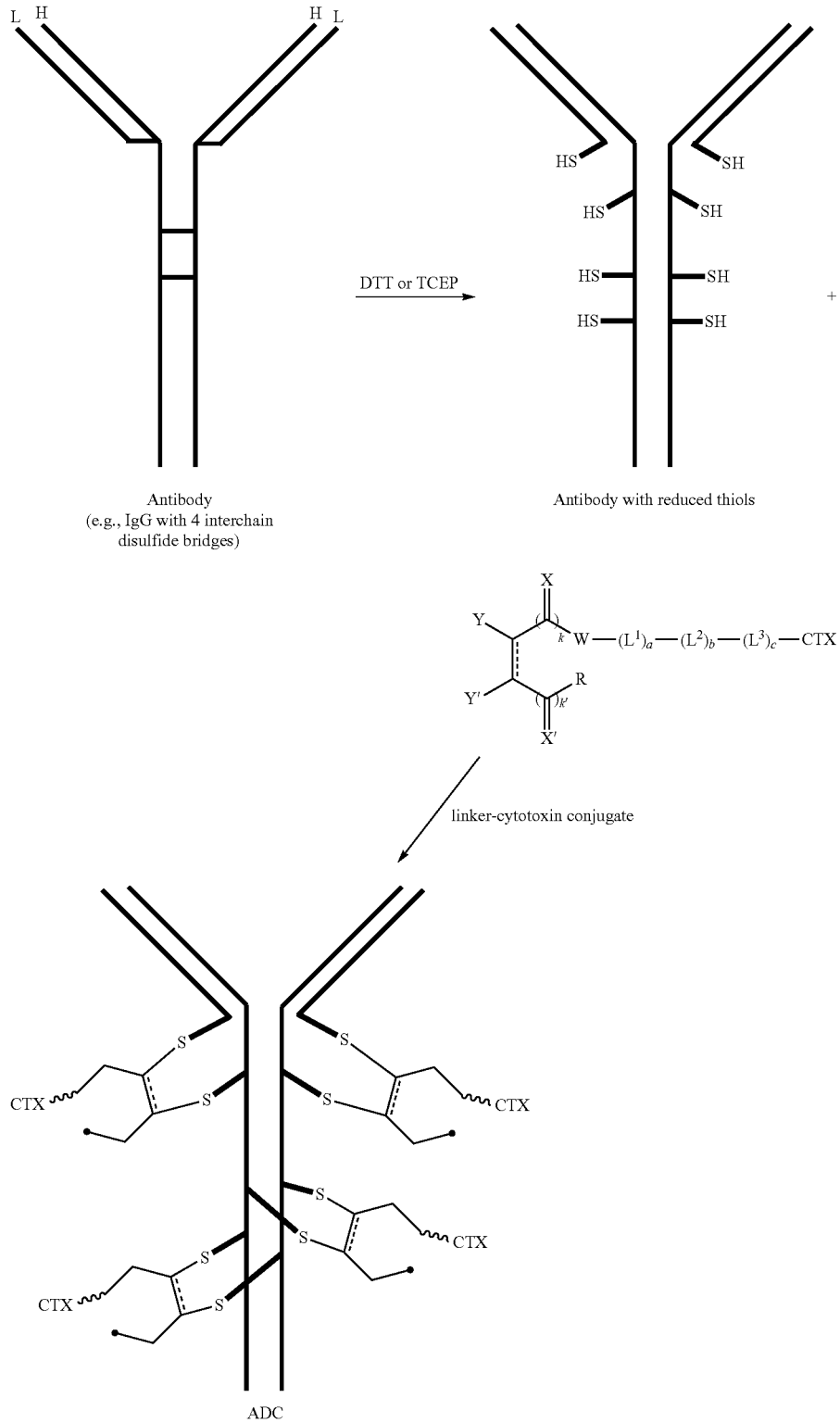

A homogenous ADC, for example, with an drug-to-antibody ratio of four (4) is produced. Scheme B depicts a homogenous ADC, where, for example, the four (4) inter-chain disulfide bonds of the antibody (2 H—H disulfide bonds, and 2 H-L disulfide bonds) are conjugated.

Unlike conventional methods for cysteine conjugation, the reaction re-forms a covalently bonded structure between the 2 cysteine sulfur atoms and therefore does not compromise the overall stability of the antibody. The method also enables conjugation of an optimal 4 drugs for an antibody to afford a homogeneous ADC in which the reactive cysteines are used. The overall result is replacement of a relatively labile disulfide with a stable "staple" or "snap" between the cysteines. The monosubstituted linkers (where one of Y and Y' is hydrogen) are also effectively bifunctional in conjugation with the antibody because the double bond is capable of conjugation to one of the cysteine sulfur atoms and the Y group with the other.

Preparation of the Linkers

Linkers may be prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

The linkers disclosed herein may be cleavable under normal physiological and/or intracellular conditions, or may remain stable (e.g., uncleaved or non-cleavable) under those same conditions.

For example, cleavable linkers may remain stable during systemic circulation but may be cleaved under certain intracellular conditions, such as in an acidic environment. For example, where an ADC is processed in a lysosome of a cell, the linker may be cleaved by the acidic environment and/or the enzymes in the lysosome, releasing the cytotoxin from the antibody. Examples of cleavable linkers are linkers which contain dipeptide moieties, where the peptide bond connecting the two peptides has the potential to be selectively cleaved by lysosomal proteases (e.g., cathepsin-B). Valine-citruline (Val-Cit) is a dipeptide moiety commonly used in cleavable linkers.

Noncleavable linkers may remain stable, both during systemic circulation and under certain intracellular conditions, such as in an acidic environment. Examples of stable linkers are linkers which do not contain dipeptide moieties, for example, alkyl and/or PEG linkers.

The following schemes a, b, c, and d illustrate general synthetic schemes for the stable linkers (e.g., uncleaved or non-cleavable) disclosed herein, which may be synthesized by the methods disclosed herein:

Illustrative General Synthetic Schemes for the Stable Linkers Disclosed Herein:

Scheme a

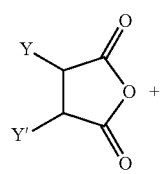

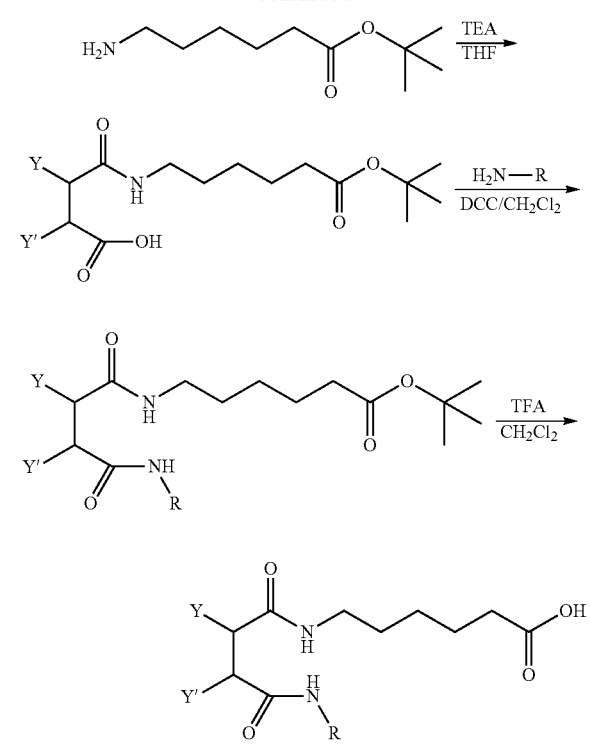

Scheme b

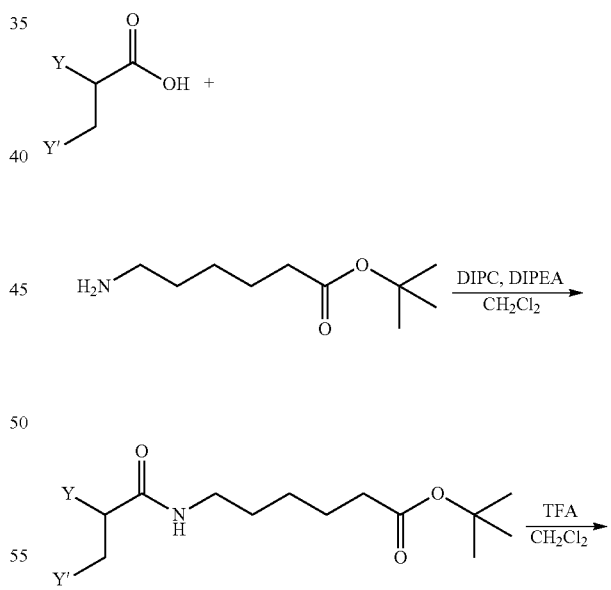

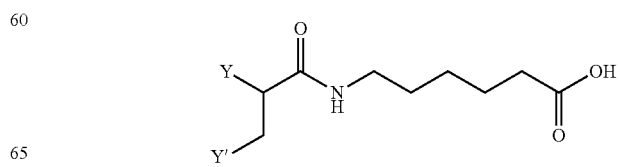

Scheme c
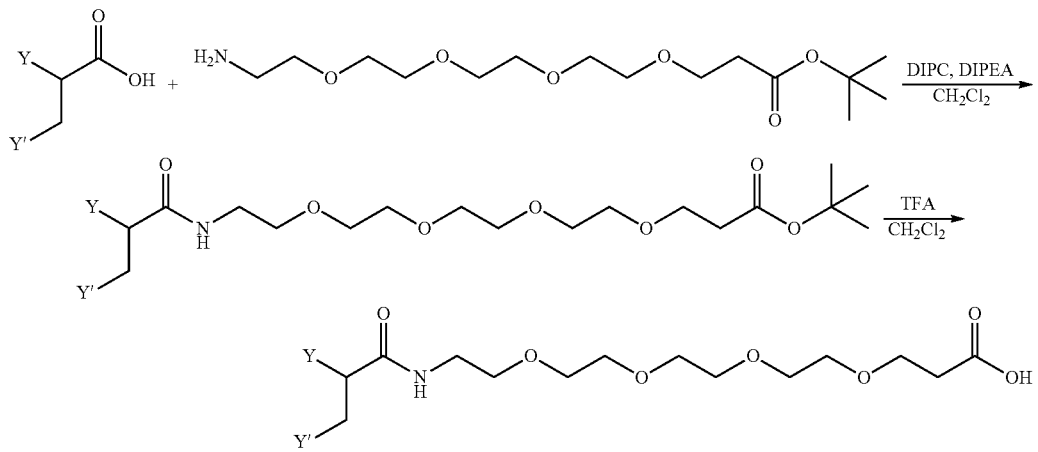
Scheme d
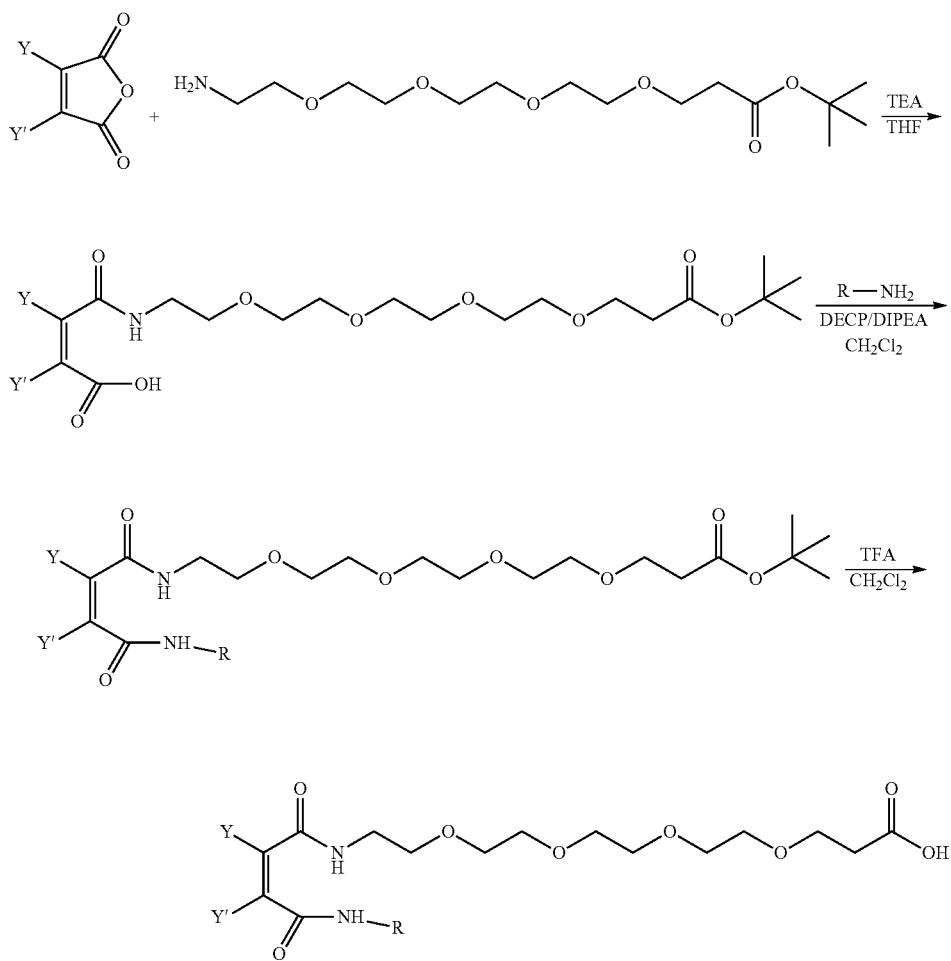
R = alkyl, PEG, peptide, CTX, detectable probe, fluorophore, chromophore, radiolabel, enzyme, antibody or antibody fragment, etc.

The above schemes are merely illustrative, and not meant to be limiting.
The following schemes e and f illustrates a general synthetic schemes for the cleavable linkers disclosed herein, which may be synthesized by the methods disclosed herein:
Illustrative General Synthetic Schemes for Cleavable Linkers Disclosed Herein:
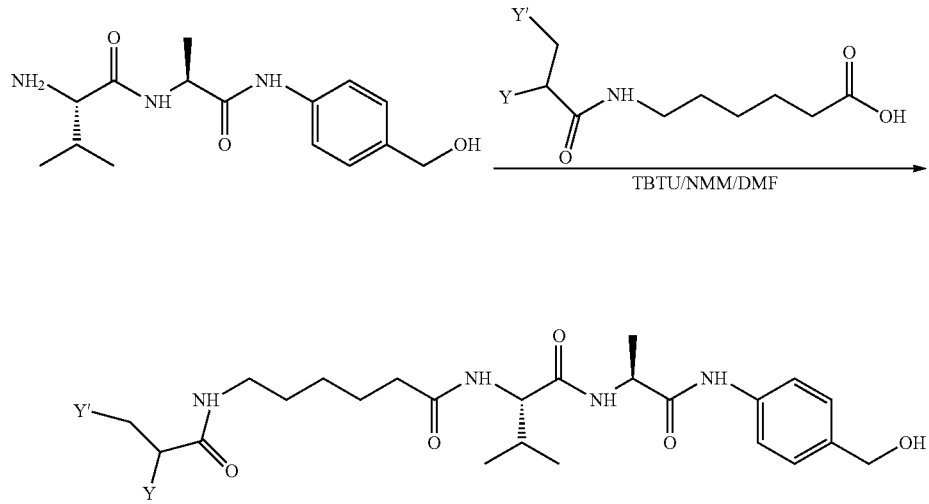
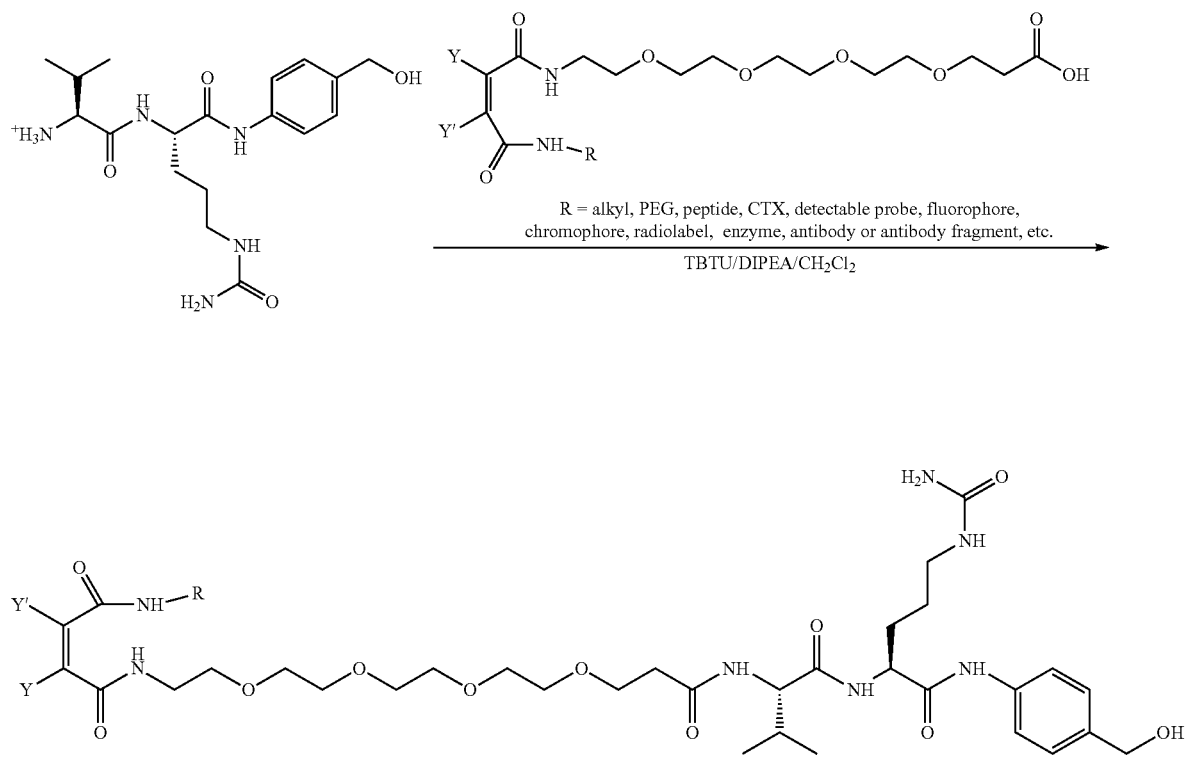

The above schemes are merely illustrative, and not meant to be limiting.

Exemplary stable and cleavable linkers which may be synthesized by the methods disclosed herein, are provided below:

Examples of Linkers

Stable and Cleavable

| Name | Stable | Name | Cleavable |
|------|--------|------|-----------|
| BRA (C6) | | BRA-VAP | |
| DBP (C6) | | DBP-VAP | |
| DBMA (C6) | | DBMA-VAP | |
| BRA (C6) | | BRA-PEGn-VAP | |
| DBP (C6) | | DBP-PEGn-VAP | |
| DBMA (C6) | | DBMA-PEGn-VAP | | n = 4, 8, or 12

In certain embodiments, stable linkers which may be synthesized by the methods disclosed herein are provided below:

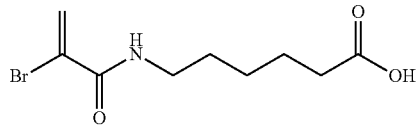

6-(2-bromoacrylamido)hexanoic acid

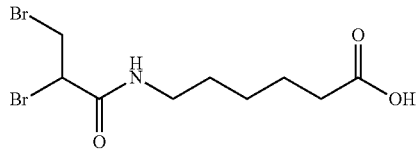

6-(2,3-dibromopropanamido)hexanoic acid

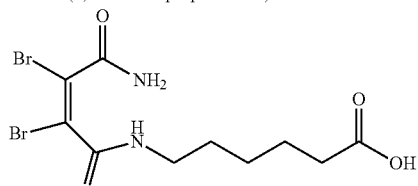

(Z)-6-(4-amino-2,3-dibromo-4-oxobut-2-enamido)
hexanoic acid

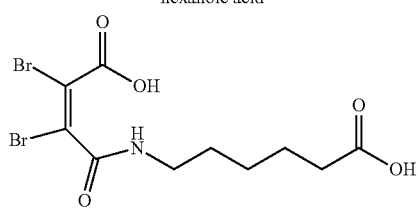

(Z)-6-(2,3-dibromo-3-carboxyacrylamido)
hexanoic acid

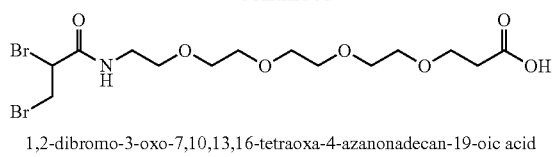

1,2-dibromo-3-oxo-7,10,13,16-tetraoxa-4-azanonadecan-19-oic acid

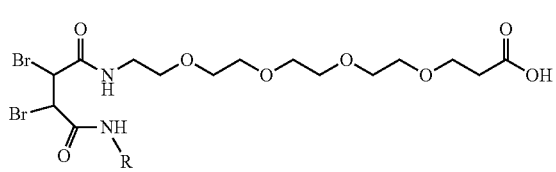

R = methyl
18,19-dibromo-20-(methylamino)-17,20-dioxo-4,7,10,13-tetraoxa-16-azaicosan-1-oic acid Preparation of the Linker-Cytotoxin Conjugates Linker-cytotoxin conjugates may be prepared by methods analogous to those of Doronina et al., *Bioconjugate Chem.* 2006, 17, 114-124, and similar documents. The linker, 1 equivalent, and HATU, 1 equivalent, are dissolved in anhydrous DMF, followed by the addition of DIPEA, 2 equivalents. The resulting solution is added to the cytotoxin, 0.5 equivalents, dissolved in DMF, and the reaction stirred at ambient temperature for 3 hr. The linker-cytotoxin conjugate is purified by reverse phase HPLC on a C-18 column.

The following schemes illustrate various embodiments of the linker-cytotoxin conjugates disclosed herein, which may be synthesized by the methods disclosed herein:

Illustrative General Synthetic Schemes for the Linker-Cytotoxin Conjugates Disclosed Herein (e.g., Stable Linkers):

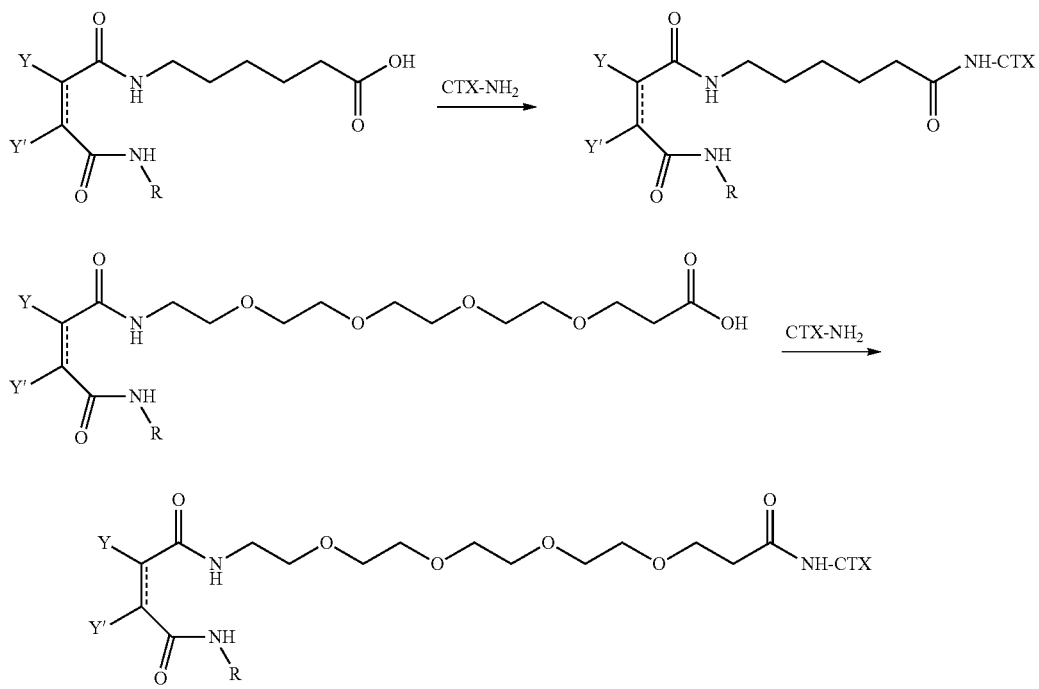

The following scheme illustrate an additional embodiment of the linker-cytotoxin conjugates disclosed herein, which may be synthesized by the methods disclosed herein: Illustrative General Synthetic Schemes for the Linker-Cytotoxin Conjugates Disclosed Herein (e.g., Cleavable Linkers):

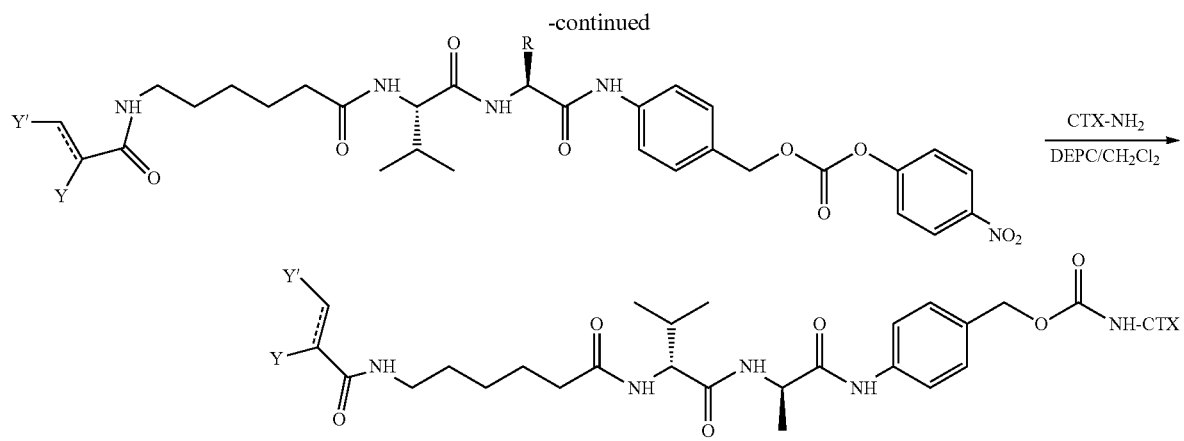

The above schemes are merely illustrative, and are not meant to be limiting. The linker-cytotoxin conjugates may be synthesized using any possible combination of linker and cytotoxin disclosed herein.

Exemplary linker-cytotoxin conjugates (stable or cleavable linkers), where CTX may be any cytotoxin disclosed herein, and which may be synthesized by the methods disclosed herein, are provided below:

Examples of Linker-Cytotoxin Conjugates

| Name | Stable | Name | Cleavable |
|---|---|---|---|
| BRA (C6) | | BRA-VAP | |
| DBP (C6) | | DBP-VAP | |
| DBMA (C6) | | DBMA-VAP | |
| BRA (C6) | | BRA-PEGn-VAP | |
| DBP (C6) | | DBP-PEGn-VAP | |
| DBMA (C6) | | DBMA-PEGn-VAP | | n = 4, 8 or 12

Further exemplary linker-cytotoxin conjugates disclosed herein (stable linkers), where CTX may be any cytotoxin disclosed herein, and which may be synthesized by the methods disclosed herein, are provided below:

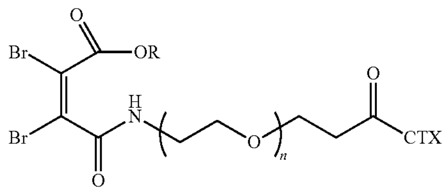

n = 4, 8 or 12 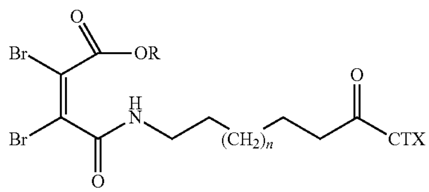 n = 1-6 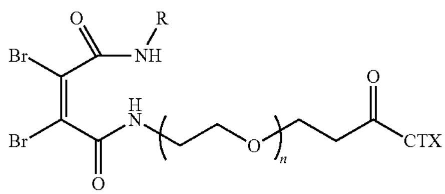 n = 4, 8 or 12 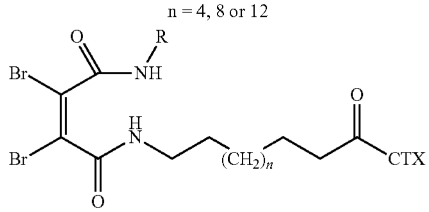 n = 1-6 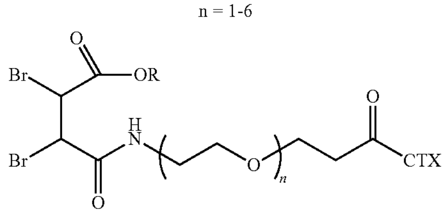 n = 4, 8 or 12 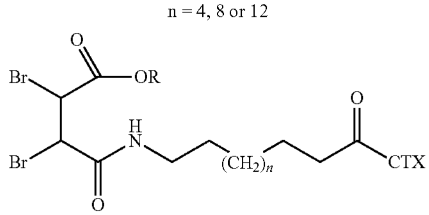 n = 1-6 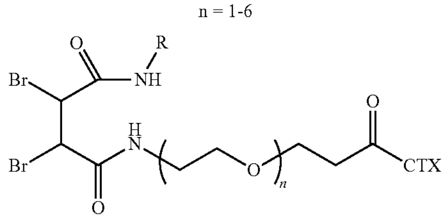 n = 4, 8 or 12

-continued 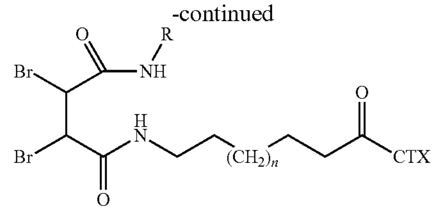 n = 1-6 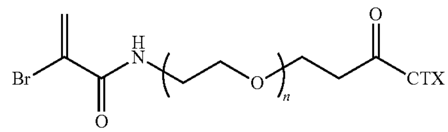 n = 4, 8 or 12 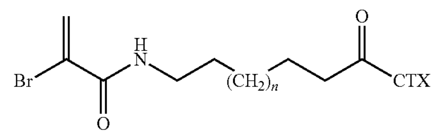 n = 1-6 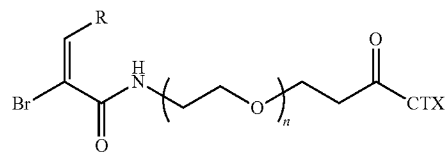 n = 2-12 n = 1-6 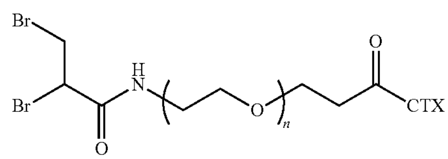 n = 4, 8 or 12 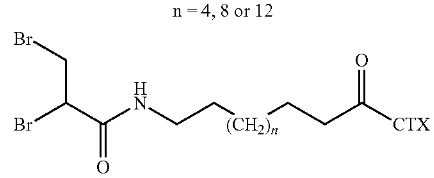 n = 1-6 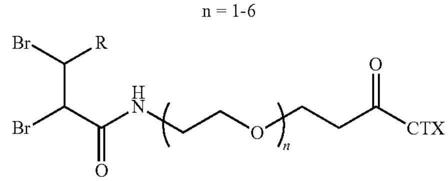 n = 2-12 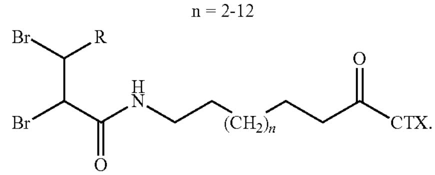 n = 1-6

It will be understood that for certain CTX (e.g., tubulysins or modified tubulysins disclosed herein), the amine or carboxyl group may be part of the CTX molecule itself, as illustrated below for the following molecule fragment:

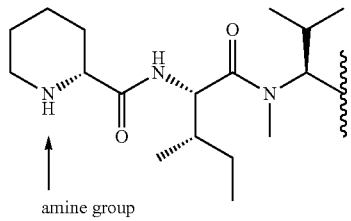 [SMILES: *[C@H](C(C)C)N(C)C(=O)[C@@H](NC(=O)[C@H]1CCCCN1)[C@@H](C)CC]

amine group

Preparation of ADCs

Antibodies, typically monoclonal antibodies are raised against a specific cancer target (antigen), and purified and characterized. Therapeutic ADCs containing that antibody are prepared by standard methods for cysteine conjugation, such as by methods analogous to those of Hamblett et al., "Effects of Drug Loading on the Antitumor Activity of a Monoclonal Antibody Drug Conjugate", *Clin. Cancer Res.* 2004, 10, 7063-7070; Doronina et al., "Development of potent and highly efficacious monoclonal antibody auristatin conjugates for cancer therapy", *Nat. Biotechnol.*, 2003, 21(7), 778-784; and Francisco et al., "cAC10-vcMMAE, an anti-CD30-monomethylauristatin E conjugate with potent and selective antitumor activity", *Blood,* 2003, 102, 1458-1465. Antibody-drug conjugates with four drugs per antibody are prepared by partial reduction of the antibody with an excess of a reducing reagent such as DTT or TCEP at 37° C. for 30 min, then the buffer exchanged by elution through SEPHADEX® G-25 resin with 1 mM DTPA in DPBS. The eluent is diluted with further DPBS, and the thiol concentration of the antibody may be measured using 5,5'-dithiobis (2-nitrobenzoic acid) [Ellman's reagent]. An excess, for example 5-fold, of the linker-cytotoxin conjugate is added at 4° C. for 1 hr, and the conjugation reaction may be quenched by addition of a substantial excess, for example 20-fold, of cysteine. The resulting ADC mixture may be purified on SEPHADEX G-25 equilibrated in PBS to remove unreacted linker-cytotoxin conjugate, desalted if desired, and purified by size-exclusion chromatography. The resulting ADC may then be then sterile filtered, for example, through a 0.2 μM filter, and lyophilized if desired for storage.

The formation of an ADC disclosed herein includes a homogenous ADC with a drug-to-antibody ratio of 4 (e.g., for an IgG1). Scheme B above depicts a "Y"-shaped structure denoting an antibody, for example, an IgG1, where all four (4) interchain disulfide bonds of the antibody (2 H—H disulfide bonds, and 2 H-L disulfide bonds) are conjugated with a drug-to-antibody ratio of 4.

The Linker:

In one aspect, provided herein is a linker of the following formula (I):

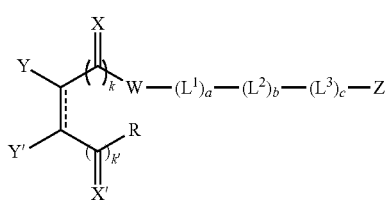

(I)

or an enantiomer, diasteriomer, or mixtures thereof;
wherein:
each X and X' is independently O, S, NH or NR$^1$ wherein R$^1$ is C$_{1-6}$ alkyl;
each Y and Y' is independently hydrogen or an electrophilic leaving group that reacts selectively with thiols, provided if one of Y and Y' is hydrogen, the other is the electrophilic leaving group;
W is —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;
Z is —CO$_2$H, —NH$_2$, —OH, —NH—R$^{3a}$, or —CO$_2$R$^{3b}$; wherein R$^{3a}$ is an amino protecting group, and R$^{3b}$ is a carboxyl protecting group; or Z is any chemical group;
R is any chemical group; or R is absent;
each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer or 1 to 12;
each AA is independently an amino acid;
each r is 1 to 12; and
the ═══ bond represents a single or a double bond.

In certain embodiments of the linker of formula (I), k and k' are both 1.

In another aspect, provided herein is a linker of the following formula (I'):

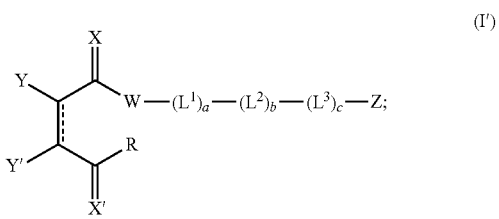

(I')

or an enantiomer, diasteriomer, or mixtures thereof;
wherein:
each X and X' is independently O, S, NH or NR$^1$ wherein R$^1$ is C$_{1-6}$ alkyl;
each Y and Y' is independently hydrogen or an electrophilic leaving group that reacts selectively with thiols, provided if one of Y and Y' is hydrogen, the other is the electrophilic leaving group;
W is —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;

Z is —CO$_2$H, —NH$_2$, —OH, —NH—R$^{3a}$, or —CO$_2$R$^{3b}$; wherein R$^{3a}$ is an amino protecting group, and R$^{3b}$ is a carboxyl protecting group;

R is any chemical group, provided that R is not OH;

each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$, —(CH$_2$CH$_2$O)$_p$CH$_2$CH$_2$—, —CH$_2$CH$_2$(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;

a, b and c are each independently an integer of 0, 1, 2 or 3, provided that at least one of a, b or c is 1;

each p is independently an integer of 1 to 14;

each q is independently an integer or 1 to 12;

each AA is independently an amino acid;

each r is 1 to 12; and the ═══ bond represents a single or a double bond.

In certain embodiments of the linker of formula (I) or (I'), the ═══ bond represents a single bond. In certain embodiments of the linker of formula (I) or (I'), the ═══ bond represents a double bond.

In certain embodiments of the linker of formula (I) or (I'), X and X' are O.

In certain embodiments of the linker of formula (I) or (I'), W is —NH— or —N(R$^1$)—, wherein R$^1$ is C$_{1-6}$ alkyl. In certain embodiments, W is —NH— or —N(R$^1$)—, wherein R$^1$ is C$_{1-3}$ alkyl. In certain embodiments, W is —CH$_2$NH— or —CH$_2$N(R$^1$)—, wherein R$^1$ is C$_{1-6}$ alkyl. In certain embodiments, W is —CH$_2$NH— or —CH$_2$N(R$^1$)—, wherein R$^1$ is C$_{1-3}$ alkyl. In certain embodiments, W is —CH$_2$—, —CH$_2$CH$_2$—, —CH(R$^2$)—, or —CH$_2$CH(R$^2$), wherein R$^2$ is C$_{1-6}$ alkyl. In certain embodiments, W is —CH$_2$—, —CH$_2$CH$_2$—, —CH(R$^2$)—, or —CH$_2$CH(R$^2$), wherein R$^2$ is C$_{1-3}$ alkyl.

In certain embodiments of the linker of formula (I) or (I'), X and X' are O, and W is —NH—.

In certain embodiments of the linker of formula (I) or (I'), each Y and Y' is independently hydrogen or an electrophilic leaving group that reacts selectively with thiol.

In certain embodiments of the linker of formula (I) or (I'), each Y and Y' is independently selected from the group consisting of a halo, a substituted thiol, and a substituted sulfonate. In certain embodiments, each Y and Y' is independently selected from the group consisting of chloro, bromo, fluoro, and iodo. In certain embodiments, each Y and Y' is independently selected from an optionally substituted thiophenyl, an optionally substituted thionaphthyl, an optionally substituted thiopyridyl, an optionally substituted isoquinolinyl, and an optionally substituted phenylsulfonate.

In certain embodiments of the linker of formula (I) or (I'), when one or both of Y and Y' is a substituted thiol, the substituent is selected from the group consisting of C$_{6-10}$ aryl and C$_{6-10}$ heteroaryl.

In certain embodiments of the linker of formula (I) or (I'), when one or both of Y and Y' is a substituted thiol, the substituent is selected from the group consisting of C$_{1-6}$ alkyl optionally substituted with halo or hydroxyl; phenyl optionally substituted with halo, hydroxyl, carboxyl, C$_{1-3}$ alkoxycarbonyl, or C$_{1-3}$ alkyl; naphthyl optionally substituted with halo, hydroxyl, carboxyl, C$_{1-3}$ alkoxycarbonyl, or C$_{1-3}$ alkyl; and 2-pyridyl optionally substituted with halo, hydroxyl, carboxyl, C$_{1-3}$ alkoxycarbonyl or C$_{1-3}$ alkyl.

In certain embodiments of the linker of formula (I) or (I'), when one or both of Y and Y' is a substituted sulfonate, the substituent is selected from the group consisting of C$_{1-6}$ alkyl, C$_{2-10}$ cycloalkyl, C$_{6-10}$ aryl, and C$_{6-10}$ heteroaryl.

In certain embodiments of the linker of formula (I) or (I'), each Y and Y' is independently selected from the group consisting of:

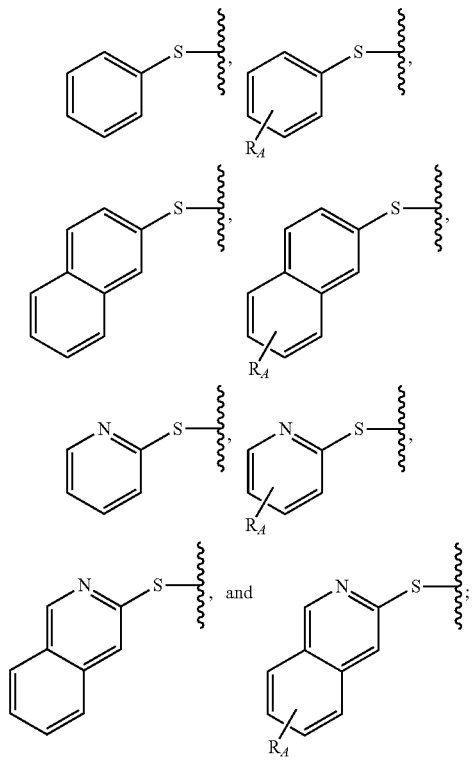

wherein

R$_A$ is selected from the group consisting of hydroxyl, amino, nitro, cyano, chloro, bromo, fluoro, iodo, oxo, carboxyl, C$_{1-6}$ alkoxycarbonyl, C$_{1-6}$ alkyl, C$_{2-6}$ alkenyl, and C$_{1-6}$ alkoxy. In certain embodiments, R$_A$ is selected from the group consisting of halo, CF$_3$—, CF$_3$O—, CH$_3$O—, —C(O)OH, —C(O)OC$_{1-3}$ alkyl, —C(O)CH$_3$, —CN, —NH$_2$, —OH, —NHCH$_3$, —N(CH$_3$)$_2$ and C$_{1-3}$ alkyl.

In certain embodiments of the linker of formula (I) or (I'), each Y and Y' is independently selected from the group consisting of:

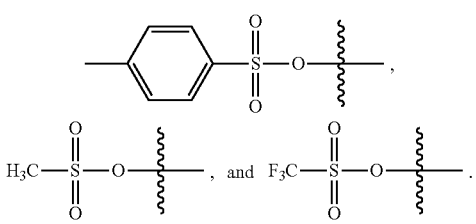

In certain embodiments of the linker of formula (I) or (I'), Z is —CO$_2$H, —NH$_2$, —OH, —NH—R$^{3a}$, or —CO$_2$R$^{3b}$;

wherein $R^{3a}$ is an amino protecting group, and $R^{3b}$ is a carboxyl protecting group, as disclosed, for example, in Greene, T. W.; Wuts, P. G. M., 1991, Protective Groups In Organic Synthesis, 3rd ed.; John Wiley & Sons: New York, and similar documents. Those of ordinary skill in the art will be able to select appropriate amino or carboxyl protecting groups.

In certain embodiments of the linker of formula (I) or (I'), Z is —$CO_2H$ or —$CO_2R^{3b}$, and $R^{3b}$ is a carboxyl protecting group.

In certain embodiments of the linker of formula (I) or (I'), $R^{3a}$ is selected from the group consisting of 9-fluorenylmethyloxycarbamate (FMOC), tert-butyloxycarbonyl (BOC), benzyl carbamate (Cbz), acetamide, trifluroacetamide, phthalimide, benzylamine, nitrobenzene, triphenylmethylamine, benzylideneamine, and p-toluenesulfonamide (p-TOS).

In certain embodiments of the linker of formula (I) or (I'), $R^{3b}$ is selected from the group consisting of a methyl ester, a tert-butyl ester, a benzyl ester, an S-tert-butyl ester, and 2-alkyl-1,3-oxazoline.

In certain embodiments of the linker of formula (I) or (I'), Z is a detectable probe, a ligand, or an antibody. In certain embodiments, Z is a fluorophore, chromophore, radiolabel, enzyme, ligand, antibody or antibody fragment.

In certain embodiments of the linker of formula (I) or (I'), R is selected from the group consisting of W, $(^{L1})_a$, $(^{L2})_b$, $(^{L3})_c$, Z, W-$(^{L1})_a$-$(^{L2})_b$-$(^{L3})_c$, $(^{L1})_a$-$(^{L2})_b$-$(^{L3})_c$-Z, and W-$(^{L1})_a$-$(^{L2})_b$-$(^{L3})_c$-Z, as defined herein. In certain embodiments, R is selected from the group consisting of W, $(^{L1})_a$, $(^{L2})_b$, $(^{L3})_c$, and W-$(^{L1})_a$-$(^{L2})_b$-$(^{L3})_c$. In certain embodiments, R is selected from the group consisting of Z, $(^{L1})_a$-$(^{L2})_b$-$(^{L3})_c$-Z, and W-$(^{L1})_a$-$(^{L2})_b$-$(^{L3})_c$-Z.

In certain embodiments of the linker of formula (I) or (I'), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the linker of formula (I) or (I'), R is bonded to the rest of the linker molecule via an amide, an N—($C_{1-6}$alkyl)amide, a carbamate, an N—($C_{1-6}$alkyl) carbamate, an amine, an N—($C_{1-6}$alkyl)amine, an ether, a thioether, an urea, an N—($C_{1-6}$alkyl)urea, or an N,N-di($C_{1-6}$alkyl)urea bond.

In certain embodiments of the linker of formula (I) or (I'), each $L^1$, $L^2$ and $L^3$ is independently selected from the group consisting of —$(CH_2)_q$—, —$NH(CH_2)_2NH$—, —$OC(O)$—, —$CO_2$—, —$NHCH_2CH_2C(O)$—, —$C(O)NHCH_2CH_2NH$—, —$C(O)NHCH_2CH_2$—, —$NHCH_2C(O)$—, —$NHC(O)$—, —$C(O)NH$—, —$NCH_3C(O)$—, —$C(O)NCH_3$—, —$C(O)CH_2CH_2$—, —$(CH_2CH_2O)_p$—, —$(OCH_2CH_2)_p$—, —$(CH_2CH_2O)_pCH_2CH_2$—, —$CH_2CH_2$—$(CH_2CH_2O)_p$—, —$OCH_2(p-C_6H_4)$—$NH$—, —$OCH_2(o-C_6H_4)$—$NH$—, —$NH-(p-C_6H_4)$—$CH_2O$—, —$NH-(o-C_6H_4)$—$CH_2O$—, —$OCH(CH_2O$—$)_2$ and -$(AA)_r$-; a, b and c are each independently 0, 1 or 2; each p, q and r is independently 1, 2, 3 or 4.

In certain embodiments of the linker of formula (I) or (I'), each L', $L^2$ and $L^3$ is independently selected from the group consisting of —$(CH_2)_q$—, —$NH(CH_2)_2NH$—, —$OC(O)$—, —$CO_2$—, $NHCH_2CH_2C(O)$—, —$C(O)NHCH_2CH_2NH$—, —$NHCH_2C(O)$—, —$NHC(O)$—, —$C(O)NH$—, —$NCH_3C(O)$—, —$C(O)NCH_3$—, —$(CH_2CH_2O)_p$, —$(CH_2CH_2O)_pCH_2CH_2$—, —$CH_2CH_2$—$(CH_2CH_2O)_p$—, —$OCH(CH_2O$—$)_2$ and -$(AA)_r$-; a, b and c are each independently 0, 1 or 2; and each p, q and r is independently 1, 2, 3 or 4.

In certain embodiments of the linker of formula (I) or (I'), each $L^1$, $L^2$ and $L^3$ is independently selected from the group consisting of —$(CH_2)_q$—, —$NH(CH_2)_2NH$—, —$OC(O)$—, —$CO_2$—, $NHCH_2CH_2C(O)$—, —$C(O)NHCH_2CH_2NH$—, —$NHCH_2C(O)$—, —$NHC(O)$—, —$C(O)NH$—, —$NCH_3C(O)$—, —$OCH(CH_2O$—$)_2$ and —$C(O)NCH_3$—; a, b and c are each independently 0, 1 or 2; and each p and q is independently 1 or 2.

In certain embodiments of the linker of formula (I) or (I'), each $L^1$, $L^2$ and $L^3$ is independently selected from the group consisting of —$NH(CH_2)_2NH$—, —$NHCH_2CH_2C(O)$—, —$C(O)NHCH_2CH_2NH$—, —$NHCH_2C(O)$—, —$NHC(O)$—, —$C(O)NH$—, —$NCH_3C(O)$—, —$OCH(CH_2O$—$)_2$ and —$C(O)NCH_3$—; and a, b and c are each independently 0 or 1.

In certain embodiments of the linker of formula (I) or (I'), each $L^1$, $L^2$ and $L^3$ is independently selected from the group consisting of —$NHC(O)$—, —$C(O)NH$—, —$(CH_2CH_2O)_p$, —$(CH_2CH_2O)_pCH_2CH_2$—, —$CH_2CH_2$—$(CH_2CH_2O)_p$—, —$OCH(CH_2O$—$)_2$ and -$(AA)_r$-; a, b and c are each independently 0 or 1; and each p and r is independently 1, 2 or 3.

In certain embodiments of the linker of formula (I) or (I'), each $L^1$, $L^2$ and $L^3$ is independently selected from the group consisting of —$NHC(O)$—, —$C(O)NH$—, —$(CH_2CH_2O)_p$, —$(CH_2CH_2O)_pCH_2CH_2$—, —$CH_2CH_2$—$(CH_2CH_2O)_p$—, —$OCH(CH_2O$—$)_2$, -$(AA)_r$-, unsubstituted phenylenyl, and phenylenyl substituted by 1 or 2 substituents selected from the group consisting of halo, $CF_3$—, $CF_3O$—, $CH_3O$—, —$C(O)OH$, —$C(O)OC_{1-3}$ alkyl, —$C(O)CH_3$, —$CN$, —$NH$—, —$NH_2$, —$O$—, —$OH$, —$NHCH_3$, —$N(CH_3)_2$, and $C_{1-3}$ alkyl; where a, b and c are each independently 0 or 1; and each p and r is independently 1, 2 or 3. In certain embodiments, one or more of the $L^1$, $L^2$ and $L^3$ is -$(AA)_r$-, wherein -$(AA)_r$- is ValCit (e.g., the first amino acid is Valine, the second amino acid is Citrulline, and r is 1). In certain embodiments, one or more of the $L^1$, $L^2$ and $L^3$ is -$(AA)_r$-, wherein -$(AA)_r$- is ValAla (e.g., the first amino acid is Valine, the second amino acid is Alanine, and r is 1). In certain embodiments, one or more of the $L^1$, $L^2$ and $L^3$ is phenylenyl substituted by —$C(O)OH$ and —$NH_2$. In certain embodiments, one or more of the $L^1$, $L^2$ and $L^3$ is phenylenyl substituted by —$C(O)O$— and —$NH$—. In certain embodiments, one or more of the $L^1$, $L^2$ and $L^3$ is phenylenyl substituted by —$OC(O)$— and —$NH$—. In certain embodiments, one or more of the $L^1$, $L^2$ and $L^3$ is phenylenyl substituted by —$O$— and —$NH$—. In certain embodiments, one or more of the $L^1$, $L^2$ and $L^3$ is a moiety of the following structure:

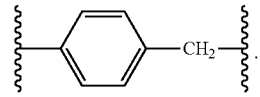

In certain embodiments, one or more of the $L^1$, $L^2$ and $L^3$ is a moiety of the following structure:

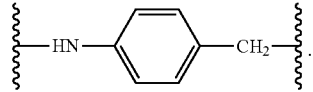

In certain embodiments, one or more of the $L^1$, $L^2$ and $L^3$ is a moiety of the following structure:

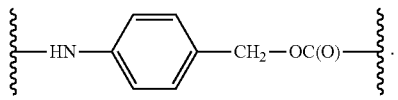

In certain embodiments, one or more of the $L^1$, $L^2$ and $L^3$ is a moiety of the following structure:

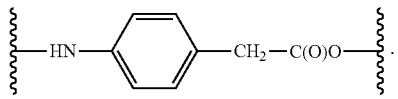

In certain embodiments, one or more of the $L^1$, $L^2$ and $L^3$ is a moiety of the following structure:

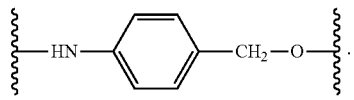 [SMILES: *Nc1ccc(CO*)cc1]

In certain embodiments, one or more of the $L^1$, $L^2$ and $L^3$ is a moiety of the following structure:

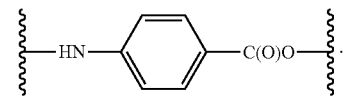

In certain embodiments, one or more of the $L^1$, $L^2$ and $L^3$ is

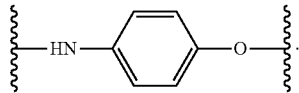 [SMILES: *Nc1ccc(O*)cc1 ; "."]

In certain embodiments, one or more of the $L^1$, $L^2$ and $L^3$ is para aminobenzyl (PAB), which is optionally substituted with —C(O)O—, —OC(O)— or —O—.

In certain embodiments of the linker of formula (I) or (I'), each AA is an amino acid selected from the group consisting of Ala, Arg, Asn, Asp, Cit, Cys, Glu, Gln, Gly, His, Ile, Leu, Lys, Met, Phe, Pro, Ser, Thr, Trp, Tyr and Val. In one variation of the above, $(AA)_r$ is a single amino acid selected from the group consisting of Cit, Gly, Arg, Val, Ala, Cys, Gln, Leu, Ile, Leu, Lys and Ser or their N-methylated analogues. In another variation of the above, $(AA)_r$ is selected from the group consisting of Ala-Val, Val-Ala, Gly-Gly, Gly-Arg, Gly-Val, Gly-Ala, Gly-Cys, Gly-Gln, Gly-Ile, Leu, Lys-Leu, Gly-Lys, Val-Arg, Ala-Cit, Val-Cit, and Gly-Ser or their N-methylated analogues. In another variation of the above, $(AA)_r$ is selected from the group consisting of Gly-Gly-Gly, Gly-Arg-Gly, Gly-Val-Gly, Gly-Ala-Gly, Gly-Cys-Gly, Gly-Gln-Gly, Gly-Ile-Gly, Lys-Leu-Gly, Gly-Lys-Gly and Gly-Ser-Gly or their N-methylated analogues. In another variation of the above, $(AA)_r$ is selected from the group consisting of Ala-Ala, Ala-Gly, Ala-Arg, Ala-Val, Ala-Ala, Ala-Cys, Ala-Gln, Ala-Ile, Ala-Leu, Ala-Lys, Ala-Cit, and Ala-Ser or their N-methylated analogues. In another variation of the above, $(AA)_r$ is selected from the group consisting of Ala-Ala-Ala, Ala-Gly-ALa, Ala-Arg-Ala, Ala-Val-Ala, Ala-Ala-Ala, Ala-Cys-Ala, Ala-Gln-Ala, Ala-Ile-Ala, Ala-Leu-Ala, Ala-Lys-Ala and Ala-Ser-Ala or their N-methylated analogues.

In certain embodiments of the linker of formula (I) or (I'), $L^1$ is —$(CH_2)_q$—, $L^2$ is absent, $L^3$ is absent, and Z is —$CO_2H$.

In certain embodiments of the linker of formula (I) or (I'), $L^1$ is —$(CH_2)_q$—, $L^2$ is —$(OCH_2CH_2)_p$—, $L^3$ is absent, and Z is —$CO_2H$.

In certain embodiments of the linker of formula (I) or (I'), $L^1$ is —$(CH_2CH_2O)_p$—, $L^2$ is —$(CH_2)_q$—, $L^3$ is absent, and Z is —$CO_2H$.

In certain embodiments of the linker of formula (I) or (I'), each $L^1$ is independently selected from the group consisting of —$(CH_2CH_2O)_pCH_2CH_2$— and —$CH_2CH_2$—$(CH_2CH_2O)_p$—, $L^2$ is absent, $L^3$ is absent, and Z is —$CO_2H$.

In certain embodiments of the linker of formula (I) or (I'), each $L^1$ is independently selected from the group consisting of —$(CH_2)_q$—, —$(CH_2CH_2O)_p$—, —$(CH_2CH_2O)_pCH_2CH_2$—, —$CH_2CH_2$—$(CH_2CH_2O)_p$—, and —C(O)—, $L^2$ is Val-Cit, $L^3$ is PAB, and Z is —$CO_2H$.

In certain embodiments of the linker of formula (I) or (I'), each $L^1$ is independently selected from the group consisting of —$(CH_2)_q$—, —$(CH_2CH_2O)_p$—, —$(CH_2CH_2O)_pCH_2CH_2$—, —$CH_2CH_2$—$(CH_2CH_2O)_p$—, and —C(O)—, $L^2$ is Val-Cit, $L^3$ is PAB, and Z is —$CO_2H$.

In certain embodiments of the linker of formula (I) or (I'), each $L^1$ is independently selected from the group consisting of —$(CH_2)_q$—, —$(CH_2CH_2O)_p$—, —$(CH_2CH_2O)_pCH_2CH_2$—, —$CH_2CH_2$—$(CH_2CH_2O)_p$—, and —C(O)—, $L^2$ is Val-Ala, $L^3$ is PAB, and Z is —$CO_2H$.

In certain embodiments, -$(L^1)_a$-$(L^2)_b$-$(L^3)_c$- is selected from the group consisting of —$(CH_2)_{1-5}C(O)$-Val-Ala-NH-(p-$C_6H_4$)—$CH_2OC(O)$-(p-$C_6H_4$)—$NO_2$, —$(CH_2CH_2O)_{1-12}$—$(CH_2CH_2)C(O)$-Val-Ala-NH-(p-$C_6H_4$)—$CH_2OC(O)$-(p-$C_6H_4$)—$NO_2$, —$(CH_2)_{1-5}C(O)$-Val-Cit-NH-(p-$C_6H_4$)—$CH_2OC(O)$-(p-$C_6H_4$)—$NO_2$, —$(CH_2CH_2O)_{1-12}$—$(CH_2CH_2)C(O)$-Val-Cit-NH-(p-$C_6H_4$)—$CH_2OC(O)$-(p-$C_6H_4$)—$NO_2$.

The Cytotoxin (CTX):

In certain embodiments, disclosed herein are cytotoxins for use in conjugation to the linkers or ADCs disclosed herein. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments, the cytotoxin (CTX) may be any FDA-approved chemotherapeutic agent. In certain embodiments, the CTX may be any FDA-approved chemotherapeutic agent available for cancer treatment.

In certain embodiments, the CTX is selected from the group consisting of an alkylating agent, an anthracycline, a cytoskeletal disrupter (taxane), an epothilone, an histone deacetylase Inhibitor (HDAC), an inhibitor of Topoisomerase I, an Inhibitor of Topoisomerase II, a kinase inhibitor, a monoclonal antibody, a nucleotide analog, a peptide antibiotic, a platinum-based agent, a retinoid, a Vinca alkaloid or a derivative thereof, and a radioisotope.

In certain embodiments, the CTX is selected from the group consisting of: thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, *Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN®, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

In certain embodiments, the CTX is selected from the group consisting of: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY 117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RI VISor® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as ME inhibitors (WO 2007/044515); (v) lipid kinase inhibitors; (vi) anti-sense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAX1D®; PROLEUKIN® rIL-2; topoisomerase 1 inhibitors such as LURTOTECAN®; ABARELIX® rmRH; and (ix) anti-angiogenic agents such as bevacizumab (AVASTIN®, Genentech); and pharmaceutically acceptable salts, acids and derivatives of any of the above of.

In certain embodiments, the CTX is selected from the group consisting of: alkylating agents such as chlorambucil, bendamustine hydrochloride or cyclophosphamide (CYTOXAN®); purine analogs such as fludarabine (FLUDARA®), pentostatin (NIPENT®), cladribine or nelarabine; pyrimidine analogs such as cytarabine; corticosteroids such as prednisone, prednisolone or methylprednisolone, immunomodulatory agents such as lenalidomide or thalidomide, synthetic flavons such as flavopiridol, Bcl2 antagonists such as oblimersen or ABT-263, antibiotics such as doxorubicin (ADRIAMYCIN®), daunorubicin, idarubicin, or mitoxentrone; anti-metabolites such as methotrexate and clofarabine; tyrosine kinase inhibitors such as imatinib mesylate (GLEEVEC®), bosutinib, dasatinib, and nilotinib; a hypomethylating agents such as azacytidine or decitabine, an FLT3 inhibitor such as midostaurin, sorafenib, or AC220; arsenic trioxide; all-trans retinoic acid; vincristine sulfate; and monoclonal antibodies such as rituximab (RITUXAN®), ofatumumab, obinutuzumab, veltuzumab, ocrelizumab, lumiliximab or alemtuzumab (CAMPATH®); pharmaceutically acceptable salts, acids or derivatives of any of the above; as well as combinations of two or more of the above; as well as combinations of two or more of the above such as fludarabine plus cyclophosphamide (FC), cladribine plus cyclophosphamide (CC), fludarabine plus rituximab, fludarabine plus cyclophosphamide plus rituximab (FCR), and FCR plus alemtuzumab (CFAR). Chemotherapeutic agents may also include agents used in the treatment of multiple myeloma, including thalidomide, lenalidomide, bortezomib, dexamethesone, prednisone, and melphalan, as well as combinations of two or more of the above, such as thalidomide or lenalidomide plus dexamethasone, or bortezomib or lenalidomide plus melphalan and prednisone.

In certain embodiments, the CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments, the CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin.

In certain embodiments, the CTX is monomethylauristatin E (MMAE), monomethylauristatin F (MMAF), a pyrrolobenzodiazepine (PDB), calicheamicin γ, mertansine, or tubulysin T2. In certain embodiments, the CTX is MMAE or MMAF. In certain embodiments, the CTX is a PDB. In certain embodiments, the CTX is tubulysin T2. In certain embodiments, the CTX is tubulysin T3 or tubulysin T4, the structures for which are provided below:

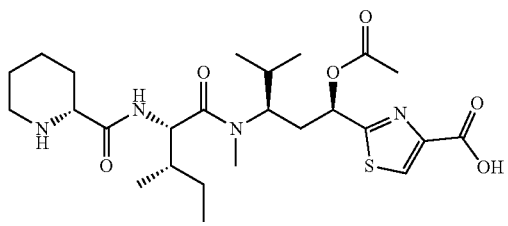
T3

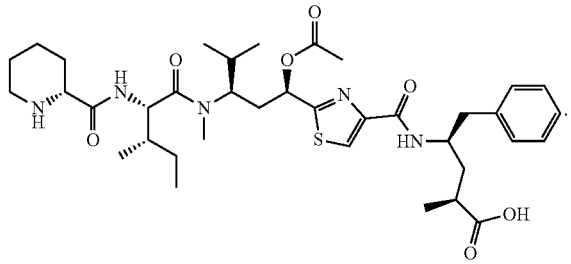
T4

The Cytotoxin (CTX): Modified Tubulysins

In certain embodiments, the CTX is of the formula:

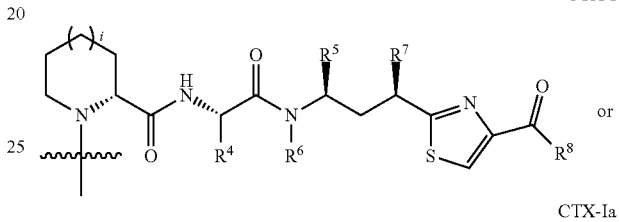
CTX-I or

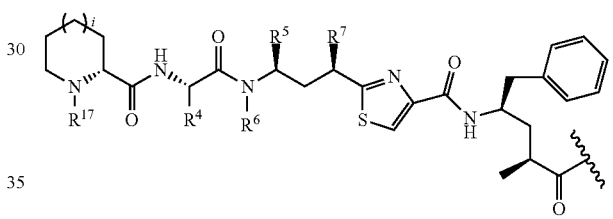
CTX-Ia wherein:
i is 0 or 1;
$R^4$ is a $C_{1-6}$ alkyl; $R^5$ is a $C_{1-6}$ alkyl; $R^6$ is $C_{1-6}$ alkyl;
$R^7$ is selected from the group consisting of $C_{1-6}$alkyl, —$OC_{1-6}$alkyl, —$OC(O)C_{1-6}$alkyl, —$OC(O)NHC_{1-6}$alkyl and —$OC(O)NHC_{6-10}$aryl; and
$R^8$ is selected from the group consisting of —OH, —$OC_{1-6}$alkyl, —$CO_2C_{1-6}$alkyl, —$CO_2C_{6-10}$aryl, —$CH(C_{1-6}alkyl)CO_2R^c$, —$CH(C_{6-10}aryl)CO_2R^c$, —NH—$CH(C_5H_6)_2$, —$NHC_{1-6}$alkyl, —$NH(CH_2)_3$—$CO_2R^c$, —NH$(CH_2CH_2)_2C_{6-10}$aryl, —$NHCH(CH_2C_{6-10}aryl)CH_2CH(CH_3)CO_2R^c$ and —$NHCH(CH_2CO_2R^c)CH_2$-p-$C_6H_4$—$NHC_{1-6}$alkyl;
where each $R^c$ is independently H or $C_{1-6}$alkyl; and
$R^{17}$ is selected from the group consisting of H, —$CH_3$ and —$C(O)CH_3$.

In certain embodiments, the CTX is of the formula:

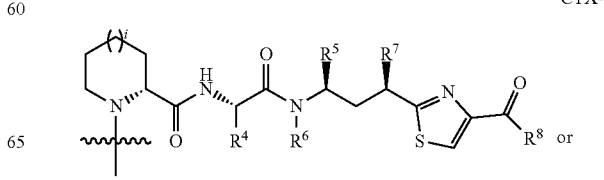
CTX-II or

-continued

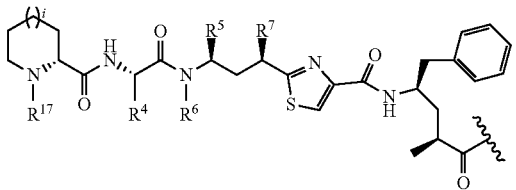

CTX-IIa wherein:
i is 0 or 1;
$R^4$ is a $C_{1-6}$alkyl; $R^5$ is a $C_{1-6}$alkyl;
$R^6$ is selected from the group consisting of $C_{1-6}$alkyl, $C_{6-10}$aryl;
$R^7$ is selected from the group consisting of $C_{1-6}$alkyl, —$OC_{1-6}$alkyl, —NHC(O)$C_{1-6}$alkyl, —OC(O)$C_{1-6}$alkyl, —OC(O)$C_{6-10}$aryl, —OC(O)NH$C_{1-6}$alkyl and —OC(O)NH$C_{6-10}$aryl; and
$R^8$ is selected from the group consisting of —OH, —$OC_{1-6}$alkyl, —$CO_2C_{1-6}$alkyl, —$CO_2C_{6-10}$aryl, —CH($C_{1-6}$alkyl)$CO_2R^c$, —CH($C_{6-10}$aryl)$CO_2R^c$, —NH—CH($C_5H_6$)$_2$, —NH$C_{1-6}$alkyl, —NH(CH$_2$)$_3$—$CO_2R^c$, —NH(CH$_2$CH$_2$)$_2C_{6-10}$aryl, —NHCH(CH$_2C_{6-10}$aryl)CH$_2$CH(CH$_3$)$CO_2R^c$, —NHCH($CO_2R^c$)CH$_2$-p-$C_6H_4$—NH$_2$, —NHCH($CO_2R^c$)CH$_2$-p-$C_6H_4$—NH$C_{1-6}$alkyl and —NHCH(CH$_2CO_2R^c$)CH$_2$-p-$C_6H_4$—NH$C_{1-6}$alkyl;
where each $R^c$ is independently selected from the group consisting of H, $C_{1-6}$alkyl and $C_{6-10}$aryl; and
$R^{17}$ is selected from the group consisting of H, —CH$_3$ and —C(O)CH$_3$.

In certain embodiments, the CTX is of the formula:

CTX-III

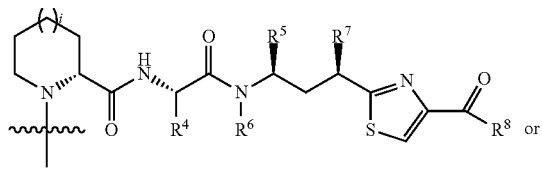

or

CTX-IIIa

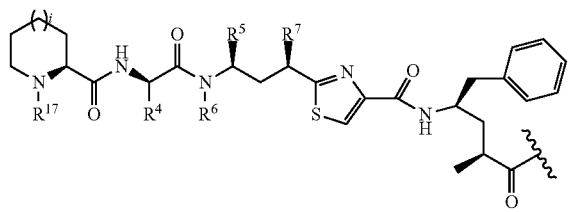

wherein:
i is 0 or 1;
$R^4$ is a $C_{1-6}$alkyl or $C_{6-10}$aryl;
$R^5$ is a $C_{1-6}$alkyl or $C_{6-10}$aryl;
$R^6$ is selected from the group consisting of $C_{1-6}$alkyl, $C_{6-10}$aryl, —CH$_2$OCO$C_{1-6}$alkyl, —CH$_2$CO$_2C_{1-6}$alkyl, —CH$_2$CONH$C_{1-6}$alkyl, —$CO_2C_{1-6}$alkyl, —CH($C_{1-6}$alkyl)$CO_2H$ and —CH($C_{1-6}$alkyl)$CO_2C_{1-6}$alkyl;
$R^7$ is selected from the group consisting of $C_{1-6}$alkyl, —$OC_{1-6}$alkyl, —NHC(O)$C_{1-6}$alkyl, —OC(O)$C_{1-6}$alkyl, —OC(O)$C_{6-10}$aryl, —OC(O)NH$C_{1-6}$alkyl and —OC(O)NH$C_{6-10}$aryl; and $R^8$ is selected from the group consisting of —OH, —$OC_{1-6}$alkyl, —$CO_2C_{1-6}$alkyl, —$CO_2C_{6-10}$aryl, —CH($C_{1-6}$alkyl)$CO_2R^c$, —CH($C_{6-10}$aryl)$CO_2R^c$, —NH—CH($C_5H_6$)$_2$, —NH$C_{1-6}$alkyl, —NH(CH$_2$)$_3$—$CO_2R^c$, —NH(CH$_2$CH$_2$)$_2C_{6-10}$aryl, —NHCH(CH$_2C_{6-10}$aryl)CH$_2$CH(CH$_3$)$CO_2R^c$, —NHCH(CH$_2$CH(CH$_3$)COOR$^c$)CH$_2$-p-$C_6H_4$—NHC(O)CH(NHC(O)(CH$_2$)$_5$NHR$^c$)(CH$_2$)$_4$NHR$^c$, —NHCH($CO_2R^c$)CH$_2$-p-$C_6H_4$—NH$_2$, —NHCH($CO_2R^c$)CH$_2$-p-$C_6H_4$—NH$C_{1-6}$alkyl, —NHCH(CH$_2CO_2R^c$)CH$_2$-p-$C_6H_4$—NH$C_{1-6}$alkyl, —NHCH(CH$_2CO_2R^c$)CH$_2$-p-$C_6H_4$—NH$C_{1-6}$alkyl and —NHCH(CH$_2$CH(CH$_3$)$CO_2R^c$)CH$_2$-p-$C_6H_4$—NH$C_{1-6}$alkyl;
where each $R^c$ is independently selected from the group consisting of H, $C_{1-6}$alkyl and $C_{6-10}$aryl; and
$R^{17}$ is selected from the group consisting of H, —CH$_3$ and —C(O)CH$_3$.

In certain embodiments, the CTX is of the formula:

CTX-IIIb

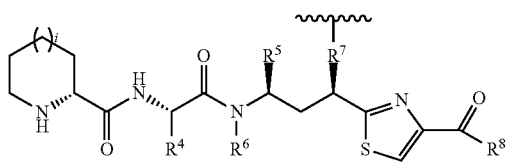

wherein:
i is 0 or 1;
$R^4$ is a $C_{1-6}$alkyl or $C_{6-10}$aryl;
$R^5$ is a $C_{1-6}$alkyl or $C_{6-10}$aryl;
$R^6$ is selected from the group consisting of $C_{1-6}$alkyl, $C_{6-10}$aryl, —CH$_2$OCO$C_{1-6}$alkyl, —CH$_2$CO$_2C_{1-6}$alkyl, —CH$_2$CONH$C_{1-6}$alkyl, —$CO_2C_{1-6}$alkyl, —CH($C_{1-6}$alkyl)$CO_2H$ and —CH($C_{1-6}$alkyl)$CO_2C_{1-6}$alkyl;
$R^7$ is a bond to the linker $L^1$, $L^2$ and/or $L^3$; and
for CTX-III, $R^8$ is selected from the group consisting of —OH, —$OC_{1-6}$alkyl, —$CO_2C_{1-6}$alkyl, —$CO_2C_{6-10}$aryl, —CH($C_{1-6}$alkyl)$CO_2R^c$, —CH($C_{6-10}$aryl)$CO_2R^c$, —NH—CH($C_5H_6$)$_2$, —NH$C_{1-6}$alkyl, —NH(CH$_2$)$_3$—$CO_2R^c$, —NH(CH$_2$CH$_2$)$_2C_{6-10}$aryl, —NHCH(CH$_2C_{6-10}$aryl)CH$_2$CH(CH$_3$)$CO_2R^c$, —NHCH(CH$_2$CH(CH$_3$)COOR$^c$)CH$_2$-p-$C_6H_4$—NHC(O)CH(NHC(O)(CH$_2$)$_5$NHR$^c$)(CH$_2$)$_4$NHR$^c$, —NHCH($CO_2R^c$)CH$_2$-p-$C_6H_4$—NH$_2$, —NHCH($CO_2R^c$)CH$_2$-p-$C_6H_4$—NH$C_{1-6}$alkyl, —NHCH(CH$_2CO_2R^c$)CH$_2$-p-$C_6H_4$—NH$C_{1-6}$alkyl, —NHCH(CH$_2CO_2R^c$)CH$_2$-p-$C_6H_4$—NH$C_{1-6}$alkyl and —NHCH(CH$_2$CH(CH$_3$)$CO_2R^c$)CH$_2$-p-$C_6H_4$—NH$C_{1-6}$alkyl;
where each $R^c$ is independently selected from the group consisting of H, $C_{1-6}$alkyl and $C_{6-10}$aryl.

In certain embodiments, as provided herein, where $R^7$ is a bond to the linker L (or $L^1$-$L^2$-$L^3$), then the CTX is bonded to the linker from both at the squiggly line (~) and at the bond that is $R^7$; or the CTX is bonded to the linker only from the bond that is $R^7$ and not on the squiggly line bond at the amine nitrogen of the CTX of Formula CTX-III.

In certain embodiments, the CTX is of the formula CTX-IIIa:
where i is 1;
$R^4$ is a $C_{1-6}$alkyl; $R^5$ is a $C_{1-3}$alkyl;
$R^6$ is selected from the group consisting of $C_{1-3}$alkyl, —CH$_2$OCO$C_{1-3}$alkyl, —CH$_2$CO$_2C_{1-3}$alkyl, —CH$_2$CONH$C_{1-3}$alkyl, —CH($C_{1-3}$alkyl)$CO_2H$ and —CH($C_{1-3}$alkyl)$CO_2C_{1-3}$alkyl;

R⁷ is selected from the group consisting of —OC$_{1-3}$alkyl, —NHC(O)C$_{1-3}$alkyl, —OC(O)C$_{1-3}$alkyl, —OC(O)-phenyl, —OC(O)NHC$_{1-6}$alkyl and —OC(O)NHC$_{6-10}$aryl; and R⁸ is selected from the group consisting of —NH(CH$_2$CH$_2$)$_2$-phenyl, —NHCH(CH$_2$-phenyl)CH$_2$CH(CH$_3$)CO$_2$R$^c$, —NHCH(CO$_2$R$^c$)CH$_2$-p-C$_6$H$_4$—NHC$_{1-3}$alkyl, —NHCH(CH$_2$CO$_2$R$^c$)CH$_2$-p-C$_6$H$_4$—NHC$_{1-3}$alkyl, —NHCH(CH$_2$CH$_2$CO$_2$R$^c$)CH$_2$-p-C$_6$H$_4$—NHC$_{1-3}$alkyl and —NHCH(CH$_2$CH(CH$_3$)CO$_2$R$^c$)CH$_2$-p-C$_6$H$_4$—NHC$_{1-3}$alkyl; and wherein R$^c$ is H or C$_{1-3}$alkyl.

In certain embodiments, the CTX is of the formula CTX-IIIa:
where i is 1;
R⁴ is a C$_{1-6}$alkyl; R⁵ is a C$_{1-3}$alkyl;
R⁶ is selected from the group consisting of C$_{1-3}$alkyl, —CH$_2$CO$_2$C$_{1-3}$alkyl and —CH(C$_{1-3}$alkyl)CO$_2$C$_{1-3}$alkyl;
R⁷ is selected from the group consisting of —OC$_{1-3}$alkyl, —NHC(O)C$_{1-3}$alkyl, —OC(O)C$_{1-3}$alkyl, —OC(O)-phenyl, —OC(O)NHC$_{1-6}$alkyl and —OC(O)NHC$_{6-10}$aryl; and
R⁸ is selected from the group consisting of —NH(CH$_2$CH$_2$)$_2$-phenyl, —NHCH(CO$_2$R$^c$)CH$_2$-p-C$_6$H$_4$—NHC$_{1-3}$alkyl and —NHCH(CH$_2$CH$_2$CO$_2$R$^c$)CH$_2$-p-C$_6$H$_4$—NHC$_{1-3}$alkyl; and wherein R$^c$ is H or C$_{1-3}$alkyl.

In certain embodiments of the formulas of CTX-I, CTX-II, CTX-IIIa, or CTX-IIIb, the CTX is not T3 or T4.

In certain embodiments, the CTX is of the formula:

CTX-IV

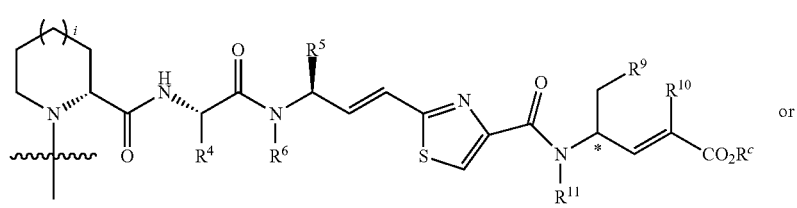

CTX-IVa where:
R⁴ is a C$_{1-6}$alkyl or C$_{6-10}$aryl; R⁵ is a C$_{1-6}$alkyl or C$_{6-10}$aryl;
R⁶ is selected from the group consisting of C$_{1-6}$alkyl, C$_{6-10}$aryl, —CH$_2$OCOC$_{1-6}$alkyl, —CH$_2$CO$_2$C$_{1-6}$alkyl, —CH$_2$CONHC$_{1-6}$alkyl, —CO$_2$C$_{1-6}$alkyl, —CH(C$_{1-6}$alkyl)CO$_2$H and —CH(C$_{1-6}$alkyl)CO$_2$C$_{1-6}$alkyl;
R⁷ is selected from the group consisting of halo, C$_{1-6}$alkyl, —OC$_{1-6}$alkyl, —NHC(O)C$_{1-6}$alkyl, —OC(O)C$_{1-6}$alkyl, —OC(O)C$_{6-10}$aryl, —OC(O)NHC$_{1-6}$alkyl and —OC(O)NHC$_{6-10}$aryl; or R⁷ is a bond to the linker L¹, L² and/or L³; and R⁸ is selected from the group consisting of —OH, —OC$_{1-6}$alkyl, —CH(C$_{1-6}$alkyl)CO$_2$R$^c$, —CH(C$_{6-10}$aryl)CO$_2$R$^c$, —NH—CH(C$_5$H$_6$)$_2$, —NHC$_{1-6}$alkyl, —NH(CH$_2$)$_3$—CO$_2$R$^c$, —NH(CH$_2$CH$_2$)$_2$C$_{6-10}$aryl, —NHCH(CH$_2$C$_{6-10}$aryl)CH$_2$CH(CH$_3$)CO$_2$R$^c$, —NHCH(CH$_2$CH(CH$_3$)CO$_2$R$^c$)CH$_2$-p-C$_6$H$_4$—NHC(O)CH(NHC(O)(CH$_2$)$_5$NHR$^c$)(CH$_2$)$_4$NHR$^c$, —NHCH(CO$_2$R$^c$)CH$_2$-p-C$_6$H$_4$, —NHCH(CO$_2$R$^c$)CH$_2$-p-C$_6$H$_4$—NH$_2$, —NHCH(CH$_2$CO$_2$R$^c$)CH$_2$-phenyl, —NHCH(CH$_2$CO$_2$R$^c$)CH$_2$-p-C$_6$H$_4$—NH$_2$, —NHCH(CH$_2$CH$_2$CO$_2$R$^c$)CH$_2$-phenyl, —NHCH(CH$_2$CH$_2$CO$_2$R$^c$)CH$_2$-p-C$_6$H$_4$—NH$_2$, —NHCH(CH$_2$CH(CH$_3$)CO$_2$R$^c$)CH$_2$-phenyl, —NHCH(CH$_2$CH(CH$_3$)CO$_2$R$^c$)CH$_2$-p-C$_6$H$_4$—NH$_2$, —NHCH(CO$_2$R$^c$)CH$_2$-p-C$_6$H$_4$—NH$_2$, —NHCH(CO$_2$R$^c$)CH$_2$-p-C$_6$H$_4$—NHC$_{1-6}$alkyl, —NHCH(CH$_2$CO$_2$R$^c$)CH$_2$-p-C$_6$H$_4$—NHC$_{1-6}$alkyl, —NHCH(CH$_2$CH$_2$CO$_2$R$^c$)CH$_2$-p-C$_6$H$_4$—NHC$_{1-6}$alkyl and —NHCH(CH$_2$CH(CH$_3$)CO$_2$R$^c$)CH$_2$-p-C$_6$H$_4$—NHC$_{1-6}$alkyl;
wherein each R$^c$ is independently selected from the group consisting of H, C$_{1-6}$alkyl and C$_{6-10}$aryl; and
R$^{18}$ is selected from the group consisting of H, —CH$_3$ and —C(O)CH$_3$.

In certain embodiments, the CTX is of the formula CTX-IV or CTX-IVa:
wherein: R⁴ is a C$_{1-6}$alkyl; R⁵ is a C$_{1-6}$alkyl;
R⁶ is selected from the group consisting of C$_{1-3}$alkyl, —CH$_2$OCOC$_{1-3}$alkyl, —CH$_2$CO$_2$C$_{1-3}$alkyl, —CH$_2$CONHC$_{1-3}$alkyl and —CH(C$_{1-6}$alkyl)CO$_2$C$_{1-3}$alkyl;
R⁷ is selected from the group consisting of C$_{1-6}$alkyl, —OC$_{1-6}$alkyl, —NHC(O)C$_{1-3}$alkyl, —OC(O)C$_{1-3}$alkyl, —OC(O)phenyl, —OC(O)NHC$_{1-6}$alkyl and —OC(O)NHC$_{6-10}$aryl; and
R⁸ is selected from the group consisting of —NH—CH(C$_5$H$_6$)$_2$, —NHC$_{1-6}$alkyl, —NH(CH$_2$)$_3$—CO$_2$R$^c$, —NH(CH$_2$CH$_2$)$_2$-phenyl, —NHCH(CH$_2$-phenyl)CH$_2$CH(CH$_3$)CO$_2$R$^c$, —NHCH(CO$_2$R$^c$)CH$_2$-phenyl, —NHCH(CH$_2$CO$_2$R$^c$)CH$_2$-phenyl and —NHCH(CO$_2$R$^c$)CH$_2$-p-C$_6$H$_4$—NHC$_{1-3}$alkyl; wherein each R$^c$ is independently selected from the group consisting of H and C$_{1-3}$alkyl.

In certain embodiments, the CTX is of the formula CTX-IV or CTX-IVa:
wherein: R⁴ is a C$_{1-6}$alkyl; R⁵ is a C$_{1-6}$alkyl; R⁶ is C$_{1-3}$alkyl;
R⁷ is selected from the group consisting of C$_{1-6}$alkyl, —OC$_{1-6}$alkyl and —OC(O)C$_{1-3}$alkyl; and
R⁸ is selected from the group consisting of —NH—CH(C$_5$H$_6$)$_2$, —NH(CH$_2$CH$_2$)$_2$-phenyl, —NHCH(CO$_2$R$^c$)CH$_2$-phenyl and —NHCH(CO$_2$R$^c$)CH$_2$-p-C$_6$H$_4$—NHC$_{1-3}$alkyl;
wherein each R$^c$ is independently selected from the group consisting of H and C$_{1-3}$alkyl.

In certain embodiments, the CTX is of the formula:

CTX-V

-continued

CTX-Va

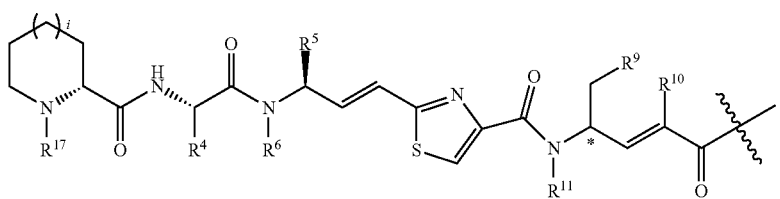

wherein:
$R^4$ is a $C_{1-6}$alkyl or $C_{6-10}$aryl; $R^5$ is a $C_{1-6}$alkyl or $C_{6-10}$aryl;
$R^6$ is H or is selected from the group consisting of $C_{1-6}$alkyl, $C_{6-10}$aryl, —$CH_2OCOC_{1-6}$alkyl, —$CH_2CO_2C_{1-6}$alkyl, —$CH_2CONHC_{1-6}$alkyl, —$CO_2C_{1-6}$alkyl, —CH($C_{1-6}$alkyl)$CO_2$H and —CH($C_{1-6}$alkyl)$CO_2C_{1-6}$alkyl;
$R^9$ is selected from the group consisting $C_{1-6}$alkyl, -phenyl, 1-naphthyl and 2-napthyl, wherein each -phenyl, 1-naphthyl and 2-naphthyl group is unsubstituted or substituted by 1 or 2 substituents selected from the group consisting of halo, cyano, nitro, $CF_3$—, $CF_3O$—, $CH_3O$—, —$C(O)CH_3$, —$NH_2$, —OH, —SH, —$NHCH_3$, —$N(CH_3)_2$, —SMe and $C_{1-3}$alkyl; and
$R^{10}$ is selected from the group consisting of $C_{1-3}$alkyl, $C_{2-6}$alkenyl, —O—$C_{1-3}$alkyl and —$OC_{6-10}$aryl;

$R^{10}$ is selected from the group consisting of $C_{1-3}$alkyl, $C_{2-6}$alkenyl, —O—$C_{1-3}$alkyl and —O-phenyl; and
$R^{17}$ is selected from the group consisting of H, —$CH_3$ and —$C(O)CH_3$.

In certain embodiments, the CTX is of the formula CTX-V:
wherein: $R^4$ is a $C_{1-3}$alkyl; $R^5$ is a $C_{1-3}$alkyl; $R^6$ is $C_{1-3}$alkyl;
$R^9$ is selected from the group consisting $C_{1-6}$alkyl, -phenyl, 1-naphthyl and 2-napthyl; and
$R^{10}$ is selected from the group consisting of $C_{1-3}$alkyl and $C_{2-6}$alkenyl.

In certain embodiments, the CTX is of the formula:

CTX-VI

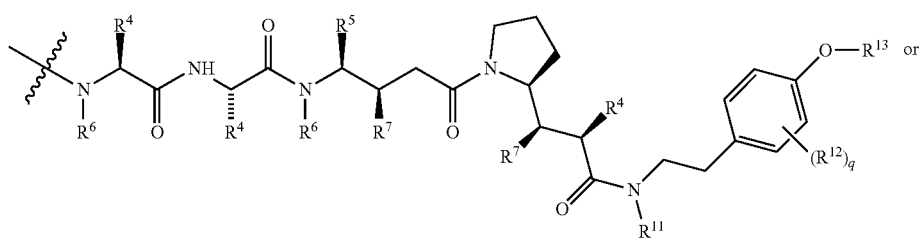

CTX-VIa

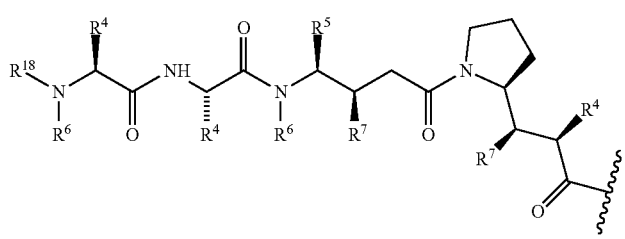

$R^{11}$ is H or $C_{1-3}$alkyl;
wherein $R^e$ is selected from the group consisting of H, $C_{1-6}$alkyl and $C_{6-10}$aryl; and
wherein * designates an R chiral center, an S chiral center or a mixture of R and S isomers.

In certain embodiments, the CTX is of the formula CTX-V or CTX-Va:
wherein: $R^4$ is a $C_{1-3}$alkyl; $R^5$ is a $C_{1-3}$alkyl;
$R^6$ is selected from the group consisting of $C_{1-3}$alkyl, —$CH_2OCOC_{1-3}$alkyl, —$CH_2CO_2C_{1-3}$alkyl, —$CO_2C_{1-3}$alkyl and —CH($C_{1-3}$alkyl)$CO_2C_{1-3}$alkyl;
$R^9$ is selected from the group consisting $C_{1-6}$alkyl, -phenyl, 1-naphthyl and 2-napthyl, wherein each -phenyl, 1-naphthyl and 2-naphthyl is unsubstituted or substituted by 1 or 2 substituents selected from the group consisting of $CF_3$—, $CH_3O$—, —$C(O)CH_3$, —$NHCH_3$, —$N(CH_3)_2$ and $C_{1-3}$alkyl; and wherein:
each $R^4$ is independently a $C_{1-6}$alkyl or $C_{6-10}$aryl;
$R^5$ is a $C_{1-6}$alkyl or $C_{6-10}$aryl;
each $R^6$ is independently selected from the group consisting of H, $C_{1-6}$alkyl, $C_{6-10}$aryl, —$CH_2OCOC_{1-6}$alkyl, —$CH_2CO_2C_{1-6}$alkyl, —$CH_2CONHC_{1-6}$alkyl, —$CO_2C_{1-6}$alkyl, —CH($C_{1-6}$alkyl)$CO_2$H and —CH($C_{1-6}$alkyl)$CO_2C_{1-6}$alkyl;
each $R^7$ is independently selected from the group consisting of —CN, —$OC_{1-6}$alkyl, $C_{1-6}$alkyl, —$NHC(O)C_{1-6}$alkyl, —$OC(O)C_{1-6}$alkyl, —$OC(O)C_{6-10}$aryl, —$OC(O)NHC_{1-6}$alkyl and —$OC(O)NHC_{6-10}$aryl;
$R^{11}$ is H or $C_{1-3}$alkyl;
each $R^{12}$ is independently selected from the group consisting of halo, cyano, nitro, $CF_3$—, $CF_3O$—, $CH_3O$—, —$CO_2$H, —$NH_2$, —OH, —SH, —$NHCH_3$, —$N(CH_3)_2$, —SMe, $C_{1-3}$ alkyl and $C_{6-10}$aryl;

R$^{13}$ is H or is selected from the group consisting of C$_{1-3}$alkyl, —CF$_3$, —C$_{1-3}$alkyl-phenyl and C$_{6-10}$aryl;

R$^{18}$ is selected from the group consisting of H, —CH$_3$ and —C(O)CH$_3$; and q is 0, 1 or 2.

In certain embodiments, the CTX is of the formula CTX-VI or CTX-VIa:

wherein: each R$^4$ is independently a C$_{1-3}$alkyl; R$^5$ is a C$_{1-3}$alkyl;

each R$^6$ is independently selected from the group consisting of H, C$_{1-6}$alkyl, —CH$_2$OCOC$_{1-6}$alkyl, —CH$_2$CO$_2$C$_{1-3}$alkyl, —CH(C$_{1-3}$alkyl)CO$_2$H and —CH(C$_{1-3}$alkyl)CO$_2$C$_{1-3}$alkyl;

each R$^7$ is independently selected from the group consisting of —OC$_{1-3}$alkyl, C$_{1-3}$alkyl, —NHC(O)C$_{1-3}$alkyl, —OC(O)C$_{1-3}$alkyl and —OC(O)C$_{6-10}$aryl;

R$^{11}$ is H or C$_{1-3}$alkyl;

each R$^{12}$ is independently selected from the group consisting of halo, CF$_3$—, CF$_3$O—, CH$_3$O—, —NHCH$_3$, —N(CH$_3$)$_2$, and C$_{1-3}$alkyl;

R$^{13}$ is H or is selected from the group consisting of C$_{1-3}$alkyl, —CF$_3$, —C$_{1-3}$alkyl-phenyl.

In certain embodiments, the CTX is of the formula CTX-VI:

wherein: each R$^4$ is independently a C$_{1-3}$alkyl; R$^5$ is a C$_{1-3}$alkyl;

each R$^6$ is independently H or C$_{1-6}$alkyl;

each R$^7$ is independently selected from the group consisting of —OC$_{1-3}$alkyl, —OC(O)C$_{1-3}$alkyl, —OC(O)C$_{6-10}$aryl, —OC(O)NHC$_{1-6}$alkyl and —OC(O)NHC$_{6-10}$aryl;

R$^{11}$ is H or C$_{1-3}$alkyl;

each R$^{12}$ is independently selected from the group consisting of CF$_3$O—, CH$_3$O— and C$_{1-3}$alkyl; and R$^{13}$ is H or is selected from the group consisting of C$_{1-3}$alkyl, —CF$_3$, —C$_{1-3}$alkyl-phenyl.

In certain embodiments, the CTX is of the formula:

wherein:

R$^{11}$ is H or C$_{1-3}$alkyl;

each R$^{12}$ is independently selected from the group consisting of halo, cyano, nitro, CF$_3$—, CF$_3$O—, CH$_3$O—, —CO$_2$H, —NH$_2$, —OH, —SH, —NHCH$_3$, —N(CH$_3$)$_2$, —SMe, C$_{1-3}$alkyl and C$_{6-10}$aryl;

R$^{13}$ is H or is selected from the group consisting of C$_{1-3}$alkyl, —CF$_3$, —C$_{1-2}$alkyl-phenyl and C$_{6-10}$aryl; and q is 0, 1 or 2.

In certain embodiments, the CTX is of the formula CTX-VII:

wherein: R$^{11}$ is H;

R$^{12}$ is selected from the group consisting of CF$_3$—, CF$_3$O—, CH$_3$O—, —CO$_2$H, —NHCH$_3$, —N(CH$_3$)$_2$, —C$_{1-3}$alkyl and phenyl;

R$^{13}$ is H or is selected from the group consisting of C$_{1-3}$alkyl, —C$_{1-2}$alkyl-phenyl and phenyl;

R$^{18}$ is selected from the group consisting of H, —CH$_3$ and —C(O)CH$_3$; and q is 1.

In certain embodiments, the CTX is of the formula CTX-VII:

wherein: R$^{11}$ is H and

R$^{13}$ is H, C$_{1-3}$alkyl or —C$_{1-2}$alkyl-phenyl; and q is 0.

CTX-VII

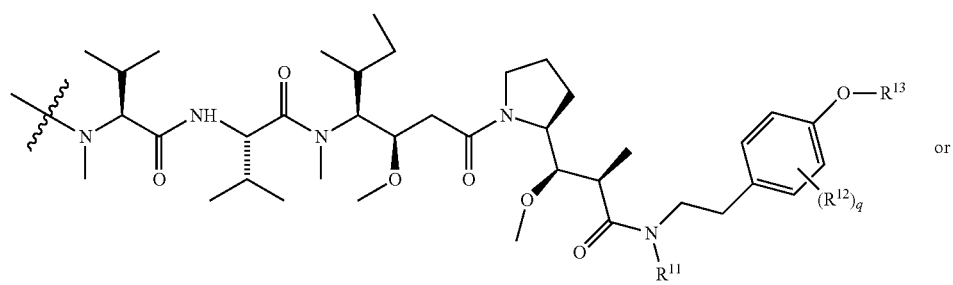

or

CTX-VIIa

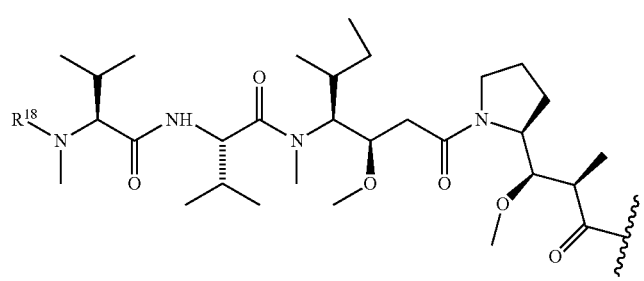

In certain embodiments, the CTX is of the formula:

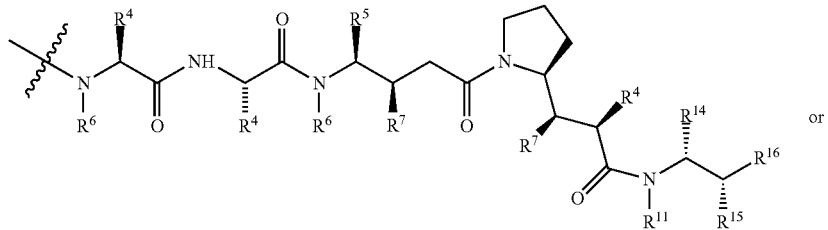
CTX-VIII

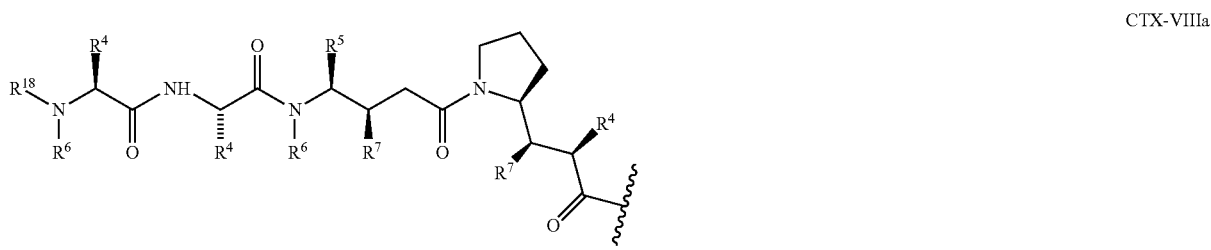
CTX-VIIIa wherein:
each $R^4$ is independently a $C_{1-6}$alkyl or $C_{6-10}$aryl;
$R^5$ is a $C_{1-6}$alkyl or $C_{6-10}$aryl;
each $R^6$ is independently selected from the group consisting of H, $C_{1-6}$alkyl, $C_{6-10}$aryl, —$CH_2OCOC_{1-6}$alkyl, —$CH_2CO_2C_{1-6}$alkyl, —$CH_2CONHC_{1-6}$alkyl, —$CO_2C_{1-6}$alkyl, —$CH(C_{1-6}$alkyl)$CO_2H$ and —$CH(C_{1-6}$alkyl)$CO_2C_{1-6}$alkyl;
each $R^7$ is independently selected from the group consisting of —CN, —$OC_{1-6}$alkyl, $C_{1-6}$alkyl, —NHC(O)$C_{1-6}$alkyl, —OC(O)$C_{1-6}$alkyl, —OC(O)$C_{6-10}$aryl, —OC(O)NH$C_{1-6}$alkyl and —OC(O)NH$C_{6-10}$aryl;
$R^{11}$ is H or $C_{1-3}$alkyl;
$R^{14}$ is selected from the group consisting of $C_{1-3}$alkyl and $C_{6-10}$aryl;
$R^{15}$ is H or is selected from the group consisting of —OH, $NH_2$, —$NHCH_3$, $C_{1-3}$alkyl, —$OC_{1-3}$alkyl and —$OC_{6-10}$aryl; and
$R^{16}$ is selected from the group consisting of $C_{1-6}$alkyl, $C_{6-10}$aryl and heteroaryl; and $R^{18}$ is selected from the group consisting of H, —$CH_3$ and —C(O)$CH_3$.

In certain embodiments, the CTX is of the formula CTX-VIII or CTX-VIIIa:
wherein: each $R^4$ is independently a $C_{1-3}$alkyl; $R^5$ is a $C_{1-3}$alkyl;
each $R^6$ is independently selected from the group consisting of H, $C_{1-6}$alkyl, —$CH_2OCOC_{1-6}$alkyl, —$CH_2CO_2C_{1-3}$alkyl, —$CH(C_{1-3}$alkyl)$CO_2H$ and —$CH(C_{1-3}$alkyl)$CO_2C_{1-3}$alkyl;
each $R^7$ is independently selected from the group consisting of —$OC_{1-3}$alkyl, $C_{1-3}$alkyl, —NHC(O)$C_{1-3}$alkyl, —OC(O)$C_{1-3}$alkyl, —OC(O)$C_{6-10}$aryl, —OC(O)NH$C_{1-6}$alkyl and —OC(O)NH$C_{6-10}$aryl;
$R^{11}$ is H or $C_{1-3}$alkyl;
$R^{14}$ is $C_{1-3}$alkyl;
$R^{15}$ is H or is selected from the group consisting of —OH, $NH_2$, —$NHCH_3$ and —$OC_{1-3}$alkyl; and
$R^{16}$ is $C_{6-10}$aryl.

In certain embodiments, the CTX is of the formula CTX-VIII or CTX-VIIIa:
wherein: each $R^4$ is independently a $C_{1-3}$alkyl; $R^5$ is a $C_{1-3}$alkyl;
each $R^6$ is independently H or $C_{1-6}$alkyl;
each $R^7$ is independently selected from the group consisting of —$OC_{1-3}$alkyl, —OC(O)$C_{1-3}$alkyl, —OC(O)$C_{6-10}$aryl, —OC(O)NH$C_{1-6}$alkyl and —OC(O)NH$C_{6-10}$aryl;
$R^{11}$ is H or $C_{1-3}$alkyl;
$R^{14}$ is $C_{1-3}$alkyl;
$R^{15}$ is selected from the group consisting of —OH, $NH_2$ and —$NHCH_3$; and
$R^{16}$ is $C_{6-10}$aryl.

In certain embodiments of the above variables, any designated aryl group, such as a $C_{6-10}$aryl, may be a phenyl group, a 1-naphthyl or 2-naphthyl group, and the aryl group is unsubstituted or substituted with 1 or 2 substituents selected from the group consisting of halo, cyano, nitro, $CF_3$—$CF_3O$—, $CH_3O$—, —$CO_2H$, —C(O)$CH_3$, —$NH_2$, —OH, —SH, —$NHCH_3$, —$N(CH_3)_2$, —SMe and $C_{1-3}$alkyl.

The Linker-Cytotoxin Conjugate:

In another aspect, provided herein is a linker-cytotoxin conjugate of the following formula (II):

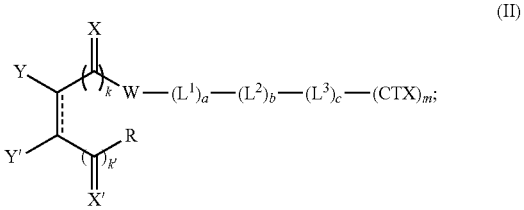
(II)

or an enantiomer, diasteriomer, or mixtures thereof;
wherein:
each X and X' is independently O, S, NH or $NR^1$ wherein $R^1$ is $C_{1-6}$ alkyl;

each Y and Y' is independently hydrogen or an electrophilic leaving group that reacts selectively with thiols, provided if one of Y and Y' is hydrogen, the other is the electrophilic leaving group;

W is —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;

CTX is a cytotoxin;

R is any chemical group; or R is absent;

each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;

a, b and c are each independently an integer of 0, 1, 2 or 3, provided that at least one of a, b or c is 1;

each k and k' is independently an integer of 0 or 1;

each p is independently an integer of 1 to 14;

each q is independently an integer or 1 to 12;

m is an integer of 1 to 4;

each AA is independently an amino acid;

each r is 1 to 12; and the ===== bond represents a single or a double bond.

In certain embodiments of the linker-cytotoxin conjugate of formula (II), k and k' are both 1.

In another aspect, provided herein is a linker-cytotoxin conjugate of the following formula (II'):

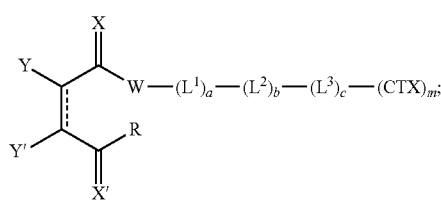

(II')

or an enantiomer, diasteriomer, or mixtures thereof;
wherein:
each X and X' is independently O, S, NH or NR$^1$ wherein R$^1$ is C$_{1-6}$ alkyl;
each Y and Y' is independently hydrogen or an electrophilic leaving group that reacts selectively with thiols, provided if one of Y and Y' is hydrogen, the other is the electrophilic leaving group;

W is —NH—, —N(R$^1$)—, —CH$_2$—, —CH$_2$—NH—, —CH$_2$—N(R$^1$)—, —CH$_2$CH$_2$—, —CH(R$^2$)—, or —CH$_2$CH(R$^2$)—; wherein R$^1$ and R$^2$ are independently C$_{1-6}$ alkyl;

CTX is a cytotoxin;

R is any chemical group, provided that R is not OH;

each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;

a, b and c are each independently an integer of 0, 1, 2 or 3, provided that at least one of a, b or c is 1;

each p is independently an integer of 1 to 14;

each q is independently an integer or 1 to 12;

m is an integer of 1 to 4;

each AA is independently an amino acid;

each r is 1 to 12; and the ===== bond represents a single or a double bond.

In certain embodiments of the linker-cytotoxin conjugate of formula (II) or (II'), the ===== bond represents a single bond. In certain embodiments of the linker of formula (I) or (I'), the ===== bond represents a double bond.

In certain embodiments of the linker-cytotoxin conjugate of formula (II) or (II'), m is 1.

In certain embodiments of the linker-cytotoxin conjugate of formula (II) or (II'), X and X' are O.

In certain embodiments of the linker-cytotoxin conjugate of formula (II) or (II'), W is —NH— or —N(R$^1$)—, wherein R$^1$ is C$_{1-6}$ alkyl. In certain embodiments, W is —NH— or —N(R$^1$)—, wherein R$^1$ is C$_{1-3}$ alkyl. In certain embodiments, W is —CH$_2$NH— or —CH$_2$N(R$^1$)—, wherein R$^1$ is C$_{1-6}$ alkyl. In certain embodiments, W is —CH$_2$NH— or —CH$_2$N(R$^1$)—, wherein R$^1$ is C$_{1-3}$ alkyl. In certain embodiments, W is —CH$_2$—, —CH$_2$CH$_2$—, —CH(R$^2$)—, or —CH$_2$CH(R$^2$)—, wherein R$^2$ is C$_{1-6}$ alkyl. In certain embodiments, W is —CH$_2$—, —CH$_2$CH$_2$—, —CH(R$^2$)—, or —CH$_2$CH(R$^2$)—, wherein R$^2$ is C$_{1-3}$ alkyl.

In certain embodiments of the linker-cytotoxin conjugate of formula (II) or (II'), X and X' are O, and W is —NH—.

In certain embodiments of the linker-cytotoxin conjugate of formula (II) or (II'), each Y and Y' is independently hydrogen or an electrophilic leaving group that reacts selectively with thiol.

In certain embodiments of the linker-cytotoxin conjugate of formula (II) or (II'), each Y and Y' is independently selected from the group consisting of a halo, a substituted thiol, and a substituted sulfonate. In certain embodiments, each Y and Y' is independently selected from the group consisting of chloro, bromo, fluoro, and iodo. In certain embodiments, each Y and Y' is independently selected from an optionally substituted thiophenyl, an optionally substituted thionaphthyl, an optionally substituted thiopyridyl, an optionally substituted isoquinolinyl, and an optionally substituted phenylsulfonate.

In certain embodiments of the linker-cytotoxin conjugate of formula (II) or (II'), when one or both of Y and Y' is a substituted thiol, the substituent is selected from the group consisting of C$_{6-10}$ aryl and C$_{6-10}$ heteroaryl.

In certain embodiments of the linker-cytotoxin conjugate of formula (II) or (II'), when one or both of Y and Y' is a substituted thiol, the substituent is selected from the group consisting of C$_{1-6}$alkyl optionally substituted with halo or hydroxyl; phenyl optionally substituted with halo, hydroxyl, carboxyl, $C_{1-3}$alkoxycarbonyl, or $C_{1-3}$alkyl; naphthyl optionally substituted with halo, hydroxyl, carboxyl, $C_{1-3}$alkoxycarbonyl, or $C_{1-3}$alkyl; and 2-pyridyl optionally substituted with halo, hydroxyl, carboxyl, $C_{1-3}$alkoxycarbonyl or $C_{1-3}$alkyl.

In certain embodiments of linker-cytotoxin conjugate of formula (II) or (II'), when one or both of Y and Y' is a substituted sulfonate, the substituent is selected from the group consisting of $C_{1-6}$alkyl, $C_{2-10}$cycloalkyl, $C_{6-10}$aryl, and $C_{6-10}$heteroaryl.

In certain embodiments of the linker-cytotoxin conjugate of formula (II) or (II'), each Y and Y' is independently selected from the group consisting of:

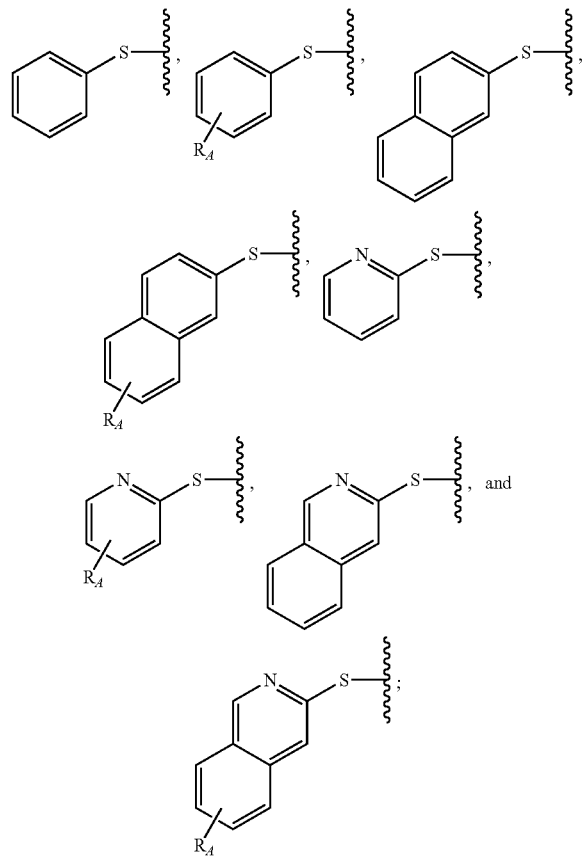

wherein
$R_A$ is selected from the group consisting of hydroxyl, amino, nitro, cyano, chloro, bromo, fluoro, iodo, oxo, carboxyl, $C_{1-6}$ alkoxycarbonyl, $C_{1-6}$ alkyl, $C_{2-6}$ alkenyl, and $C_{1-6}$alkoxy. In certain embodiments, $R_A$ is selected from the group consisting of halo, $CF_3$—, $CF_3O$—, $CH_3O$—, —C(O)OH, —C(O)OC$_{1-3}$alkyl, —C(O)CH$_3$, —CN, —NH$_2$, —OH, —NHCH$_3$, —N(CH$_3$)$_2$ and $C_{1-3}$alkyl.

In certain embodiments of the linker-cytotoxin conjugate of formula (II) or (II'), each Y and Y' is independently selected from the group consisting of:

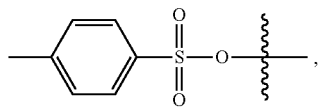

-continued

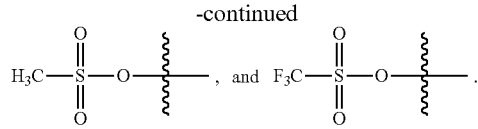

In certain embodiments of the linker-cytotoxin conjugate of formula (II) or (II'), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined herein. In certain embodiments, R is selected from the group consisting of W, $(L^1)_a$, $(L^2)_b$, $(L^3)_c$, and W-$(L^1)_a$-$(L^2)_b$-$(L^3)_c$. In certain embodiments, R is selected from the group consisting of Z, $(L^1)_a$-$(L^2)_b$-$(L^3)_c$-Z, and W-$(L^1)_a$-$(L^2)_b$-$(L^3)_c$-Z.

In certain embodiments of the linker-cytotoxin conjugate of formula (II) or (II'), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the linker-cytotoxin conjugate of formula (II) or (II'), R is bonded to the rest of the linker molecule via an amide, an N—($C_{1-6}$ alkyl)amide, a carbamate, an N—($C_{1-6}$ alkyl)carbamate, an amine, an N—($C_{1-6}$ alkyl)amine, an ether, a thioether, an urea, an N—($C_{1-6}$alkyl) urea, or an N,N-di($C_{1-6}$ alkyl)urea bond.

In certain embodiments of the linker-cytotoxin conjugate of formula (II) or (II'), each $L^1$, $L^2$ and $L^3$ is independently selected from the group consisting of —(CH$_2$)$_q$—, —NH(CH$_2$)$_2$NH—, —OC(O)—, —CO$_2$—, NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$ and -(AA)$_r$-; a, b and c are each independently 0, 1 or 2; and each p, q and r is independently 1, 2, 3 or 4.

In certain embodiments of the linker-cytotoxin conjugate of formula (II) or (II'), each $L^1$, $L^2$ and $L^3$ is independently selected from the group consisting of —(CH$_2$)$_q$—, —NH(CH$_2$)$_2$NH—, —OC(O)—, —CO$_2$—, NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —OCH(CH$_2$O—)$_2$ and —C(O)NCH$_3$—; a, b and c are each independently 0, 1 or 2; and each p and q is independently 1 or 2.

In certain embodiments of the linker-cytotoxin conjugate of formula (II) or (II'), each $L^1$, $L^2$ and $L^3$ is independently selected from the group consisting of —NH(CH$_2$)$_2$NH—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —OCH(CH$_2$O—)$_2$ and —C(O)NCH$_3$—; and a, b and c are each independently 0 or 1.

In certain embodiments of the linker-cytotoxin conjugate of formula (II) or (II'), each $L^1$, $L^2$ and $L^3$ is independently selected from the group consisting of —NHC(O)—, —C(O)NH—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, —OCH(CH$_2$O—)$_2$ and -(AA)$_r$-; a, b and c are each independently 0 or 1; and each p and r is independently 1, 2 or 3.

In certain embodiments of the linker-cytotoxin conjugate of formula (II) or (II'), each AA is an amino acid selected from the group consisting of Ala, Arg, Asn, Asp, Cys, Glu, Gln, Gly, His, Ile, Leu, Lys, Met, Phe, Pro, Ser, Thr, Trp, Tyr and Val. In one variation of the above, (AA)$_r$ is a single amino acid selected from the group consisting of Gly, Arg, Val, Ala, Cys, Gln, Leu, Ile, Leu, Lys and Ser or their N-methylated analogues. In another variation of the above, $(AA)_r$ is selected from the group consisting of Gly-Gly, Gly-Arg, Gly-Val, Gly-Ala, Gly-Cys, Gly-Gln, Gly-Ile, Leu, Lys-Leu, Gly-Lys and Gly-Ser or their N-methylated analogues. In another variation of the above, $(AA)_r$ is selected from the group consisting of Gly-Gly-Gly, Gly-Arg-Gly, Gly-Val-Gly, Gly-Ala-Gly, Gly-Cys-Gly, Gly-Gln-Gly, Gly-Ile-Gly, Lys-Leu-Gly, Gly-Lys-Gly and Gly-Ser-Gly or their N-methylated analogues. In another variation of the above, $(AA)_r$ is selected from the group consisting of Ala-Ala, Ala-Gly, Ala-Arg, Ala-Val, Ala-Ala, Ala-Cys, Ala-Gln, Ala-Ile, Ala-Leu, Ala-Lys and Ala-Ser or their N-methylated analogues. In another variation of the above, $(AA)_r$ is selected from the group consisting of Ala-Ala-Ala, Ala-Gly-ALa, Ala-Arg-Ala, Ala-Val-Ala, Ala-Ala-Ala, Ala-Cys-Ala, Ala-Gln-Ala, Ala-Ile-Ala, Ala-Leu-Ala, Ala-Lys-Ala and Ala-Ser-Ala or their N-methylated analogues.

In certain embodiments of the linker-cytotoxin conjugate of formula (II) or (II'), $L^1$ is $-(CH_2)_q-$, $L^2$ is absent, $L^3$ is absent, and the CTX is bonded to $(L^1)_a$-$(L^2)_b$-$(L^3)_c$ via an amide bond.

In certain embodiments of the linker-cytotoxin conjugate of formula (II) or (II'), $L^1$ is $-(CH_2)_q-$, $L^2$ is $-(OCH_2CH_2)_p-$, $L^3$ is absent, and the CTX is bonded to $(L^1)_a$-$(L^2)_b$-$(L^3)_c$ via an amide bond.

In certain embodiments of the linker-cytotoxin conjugate of formula (II) or (II'), $L^1$ is $-(CH_2CH_2O)_p-$, $L^2$ is $-(CH_2)_q-$, $L^3$ is absent, and the CTX is bonded to $(L^1)_a$-$(L^2)_b$-$(L^3)_c$ via an amide bond.

In certain embodiments of the linker-cytotoxin conjugate of formula (II) or (II'), each $L^1$ is independently selected from the group consisting of $-(CH_2CH_2O)_pCH_2CH_2-$ and $-CH_2CH_2-(CH_2CH_2O)_p-$, $L^2$ is absent, $L^3$ is absent, and the CTX is bonded to $(L^1)_a$-$(L^2)_b$-$(L^3)_c$ via an amide bond.

In certain embodiments of the linker-cytotoxin conjugate of formula (II) or (II'), each $L^1$ is independently selected from the group consisting of $-(CH_2)_q-$, $-(CH_2CH_2O)_p-$, $-(CH_2CH_2O)_pCH_2CH_2-$, $-CH_2CH_2-(CH_2CH_2O)_p-$, and $-C(O)-$, $L^2$ is Val-Cit, $L^3$ is PAB, and the CTX is bonded to $(L^1)_a$-$(L^2)_b$-$(L^3)_c$ via an amide bond.

In certain embodiments of the linker-cytotoxin conjugate of formula (II) or (II'), each $L^1$ is independently selected from the group consisting of $-(CH_2)_q-$, $-(CH_2CH_2O)_p-$, $-(CH_2CH_2O)_pCH_2CH_2-$, $-CH_2CH_2-(CH_2CH_2O)_p-$, and $-C(O)-$, $L^2$ is Val-Cit, $L^3$ is PAB, and the CTX is bonded to $(L^1)_a$-$(L^2)_b$-$(L^3)_c$ via an amide bond.

In certain embodiments of the linker-cytotoxin conjugate of formula (II) or (II'), each $L^1$ is independently selected from the group consisting of $-(CH_2)_q-$, $-(CH_2CH_2O)_p-$, $-(CH_2CH_2O)_pCH_2CH_2-$, $-CH_2CH_2-(CH_2CH_2O)_p-$, and $-C(O)-$, $L^2$ is Val-Ala, $L^3$ is PAB, and the CTX is bonded to $(L^1)_a$-$(L^2)_b$-$(L^3)_c$ via an amide bond.

In certain embodiments of the linker-cytotoxin conjugate of formula (II) or (II'), CTX is bonded to $(L^1)_a$-$(L^2)_b$-$(L^3)_c$ via an amide, an N—$(C_{1-6}$alkyl)amide, a carbamate, an N—$(C_{1-6}$alkyl)carbamate, an amine, an N—$(C_{1-6}$alkyl) amine, an ether, a thioether, an urea, an N—$(C_{1-6}$alkyl)urea, or an N,N-di($C_{1-6}$alkyl)urea bond.

In certain embodiments of the linker-cytotoxin conjugate of formula (II) or (II'), CTX is bonded to $(L^1)_a$-$(L^2)_b$-$(L^3)_c$ via a group selected from —NHC(O)—, —NHC(O)O—, —N($C_{1-3}$alkyl)C(O)O—, —NH—, —N($C_{1-3}$alkyl)-, —N($C_{1-3}$alkyl)C(O)NH— and —N($C_{1-3}$alkyl)C(O)N ($C_{1-3}$alkyl)-.

In certain embodiments of the linker-cytotoxin conjugate of formula (II) or (II'), when $(L^1)_a$-$(L^2)_b$-$(L^3)_c$ together is $-(CH_2)_{1-12}-$ or $-(CH_2CH_2O)_{1-12}CH_2CH_2-$ then $L^1$, $L^2$ and $L^3$ are not bonded to CTX by an amide bond.

In certain embodiments of the linker-cytotoxin conjugate of formula (II) or (II'), CTX is bonded to $(L^1)_a$-$(L^2)_b$-$(L^3)_c$ via a bond selected from the group consisting of:

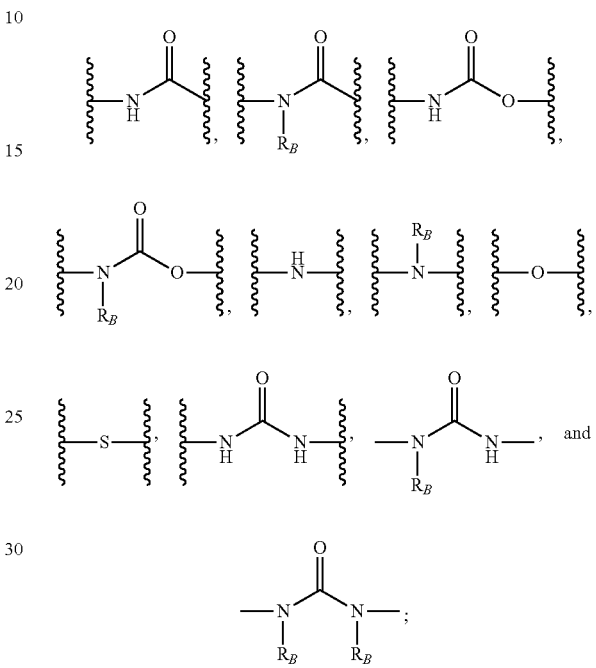

wherein each $R_B$ is independently branched or unbranched $C_{1-6}$ alkyl.

In certain embodiments of the linker-cytotoxin conjugate of formula (II) or (II'), the CTX is monomethylauristatin E (MMAE), monomethylauristatin F (MMAF), a pyrrolobenzodiazepine (PDB), calicheamicin γ, mertansine, or tubulysin T2. In certain embodiments of the linker-cytotoxin conjugate of formula (II) or (II'), the CTX is MMAE or MMAF.

In certain embodiments, the CTX is a PDB. In certain embodiments, the CTX is tubulysin T2. In certain embodiments, the CTX is tubulysin T3 or tubulysin T4.

The Antibody (A):

In certain embodiments, disclosed herein are antibodies or antibody fragments (A) for use in the ADCs disclosed herein.

In certain embodiments, A is an antibody or an antibody fragment. In certain embodiments, A is a monoclonal antibody or monoclonal antibody fragment.

In certain embodiments, the antibody (A) is a monoclonal antibody or a humanized antibody. In certain embodiments, the antibody is specific to a cancer antigen. In another embodiment, the antibody employed in the ADC of the present application is selected from the group consisting of alemtuzumab, bevacizumab, cetuximab, ipilimumab, ofatumumab, anitumumab, rituximab, tositumomab, inotuzumab, glembatumumab, lovortuzumab, milatuzumab and trastuzumab.

The Antibody-Drug Conjugate (ADC):

In another aspect, provided herein is antibody-drug conjugate of the following formula (III):

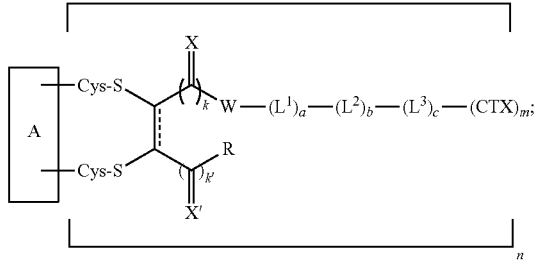

(III)

or pharmaceutically acceptable salt thereof,
wherein:
A is an antibody or antibody fragment;
the two depicted cysteine residues are from an opened cysteine-cysteine disulfide bond in A;
each X and X' is independently O, S, NH or $NR^1$ wherein $R^1$ is $C_{1-6}$ alkyl;
W is —NH—, —N($R^1$)—, —$CH_2$—, —$CH_2$—NH—, —$CH_2$—N($R^1$)—, —$CH_2CH_2$—, —CH($R^2$)—, or —$CH_2$CH($R^2$)—; wherein $R^1$ and $R^2$ are independently $C_{1-6}$ alkyl;
CTX is a cytotoxin;
R is any chemical group; or R is absent;
each $L^1$, $L^2$ and $L^3$ is independently a linker selected from the group consisting of —O—, —C(O)—, —S—, —S(O)—, —S(O)$_2$—, —NH—, —$NCH_3$—, —$(CH_2)_q$—, —NH($CH_2$)$_2$NH—, —OC(O)—, —$CO_2$—, —$NHCH_2CH_2C(O)$—, —C(O)$NHCH_2CH_2NH$—, —$NHCH_2C(O)$—, —NHC(O)—, —C(O)NH—, —$NCH_3C(O)$—, —C(O)$NCH_3$—, —($CH_2CH_2O$)$_p$, —($CH_2CH_2O$)$_p CH_2CH_2$—, —$CH_2CH_2$—($CH_2CH_2O$)$_p$—, —OCH($CH_2O$—)$_2$, -(AA)$_r$-, cyclopentanyl, cyclohexanyl, unsubstituted phenylenyl, and phenylenyl substituted by 1 or 2 substituents selected from the group consisting of halo, $CF_3$—, $CF_3O$—, $CH_3O$—, —C(O)OH, —C(O)O$C_{1-3}$ alkyl, —C(O)$CH_3$, —CN, —NH—, —$NH_2$, —O—, —OH, —$NHCH_3$, —N($CH_3$)$_2$, and $C_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer or 1 to 12;
each AA is independently an amino acid;
each r is 1 to 12;
m is an integer of 1 to 4;
n is an integer of 1 to 4; and
the ===== bond represents a single or a double bond.

In certain embodiments of the antibody-drug conjugate of formula (III), k and k' are both 1.

In another aspect, provided herein is antibody-drug conjugate of the following formula (III'):

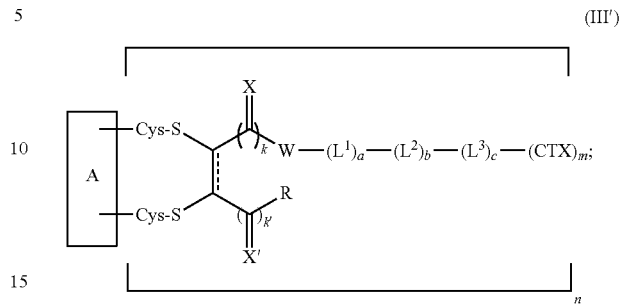

(III')

wherein:
A is an antibody or antibody fragment;
the two depicted cysteine residues are from an opened cysteine-cysteine disulfide bond in A;
each X and X' is independently O, S, NH or $NR^1$ wherein $R^1$ is $C_{1-6}$ alkyl;
W is —NH—, —N($R^1$)—, —$CH_2$—, —$CH_2$—NH—, —$CH_2$—N($R^1$)—, —$CH_2CH_2$—, —CH($R^2$)—, or —$CH_2$CH($R^2$)—; wherein $R^1$ and $R^2$ are independently $C_{1-6}$ alkyl;
CTX is a cytotoxin;
R is any chemical group, provided that R is not OH;
each $L^1$, $L^2$ and $L^3$ is independently a linker selected from the group consisting of —O—, —C(O)—, —S—, —S(O)—, —S(O)$_2$—, —NH—, —$NCH_3$—, —$(CH_2)_q$—, —NH($CH_2$)$_2$NH—, —OC(O)—, —$CO_2$—, —$NHCH_2CH_2C(O)$—, —C(O)$NHCH_2CH_2NH$—, —$NHCH_2C(O)$—, —NHC(O)—, —C(O)NH—, —$NCH_3C(O)$—, —C(O)$NCH_3$—, —($CH_2CH_2O$)$_p$, —($CH_2CH_2O$)$_p CH_2CH_2$—, —$CH_2CH_2$—($CH_2CH_2O$)$_p$—, —OCH($CH_2O$—)$_2$, -(AA)$_r$-, cyclopentanyl, cyclohexanyl, unsubstituted phenylenyl, and phenylenyl substituted by 1 or 2 substituents selected from the group consisting of halo, $CF_3$—, $CF_3O$—, $CH_3O$—, —C(O)OH, —C(O)O$C_{1-3}$ alkyl, —C(O)$CH_3$, —CN, —NH—, —$NH_2$, —O—, —OH, —$NHCH_3$, —N($CH_3$)$_2$, and $C_{1-3}$ alkyl;
a, b and c are each independently 0, 1, 2 or 3, provided that at least one of a, b or c is 1;
each p is independently an integer of 1 to 14;
each q is independently an integer or 1 to 12;
each AA is independently an amino acid;
each r is 1 to 12;
m is an integer of 1 to 4;
n is an integer of 1 to 4; and
the ===== bond represents a single or a double bond.

In certain embodiments of the antibody-drug conjugate of formula (III) or (III'), the ===== bond represents a single bond. In certain embodiments of the antibody-drug conjugate of formula (III) or (III'), the ===== bond represents a double bond.

In certain embodiments of the antibody-drug conjugate of formula (III) or (III'), m is 1.

In certain embodiments of the antibody-drug conjugate of formula (III) or (III'), X and X' are O.

In certain embodiments of the antibody-drug conjugate of formula (III) or (III'), W is —NH— or —N($R^1$)—, wherein $R^1$ is $C_{1-6}$ alkyl. In certain embodiments, W is —NH— or —N($R^1$)—, wherein $R^1$ is $C_{1-3}$ alkyl. In certain embodiments, W is —$CH_2$NH— or —$CH_2$N($R^1$)—, wherein $R^1$ is $C_{1-6}$ alkyl. In certain embodiments, W is —$CH_2NH$— or —$CH_2N(R^1)$—, wherein $R^1$ is $C_{1-3}$ alkyl. In certain embodiments, W is —$CH_2$—, —$CH_2CH_2$—, —$CH(R^2)$—, or —$CH_2CH(R^2)$, wherein $R^2$ is $C_{1-6}$ alkyl. In certain embodiments, W is —$CH_2$—, —$CH_2CH_2$—, —$CH(R^2)$—, or —$CH_2CH(R^2)$, wherein $R^2$ is $C_{1-3}$ alkyl.

In certain embodiments of the antibody-drug conjugate of formula (III) or (III'), X and X' are O, and W is —NH—.

In certain embodiments of the antibody-drug conjugate of formula (III) or (III'), R is selected from the group consisting of W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, and W-$(L^1)_a$-$(L^2)_b$-$(L^3)_c$-Z, as defined herein. In certain embodiments, R is selected from the group consisting of W, $(L^1)_a$, $(L^2)_b$, $(L^3)_c$, and W-$(L^1)_a$-$(L^2)_b$-$(L^3)_c$. In certain embodiments, R is selected from the group consisting of Z, $(L^1)_a$-$(L^2)_b$-$(L^3)_c$-Z, and W-$(L^1)_a$-$(L^2)_b$-$(L^3)_c$-Z.

In certain embodiments of the antibody-drug conjugate of formula (III) or (III'), R is selected from the group consisting of W-$(L^1)_a$-$(L^2)_b$-$(L^3)_c$-$(CTX)_m$.

In certain embodiments of the antibody-drug conjugate of formula (III) or (III'), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the antibody-drug conjugate of formula (III) or (III'), R is bonded to the rest of the linker molecule via an amide, an N—($C_{1-6}$alkyl)amide, a carbamate, an N—($C_{1-6}$alkyl)carbamate, an amine, an N—($C_{1-6}$alkyl)amine, an ether, a thioether, an urea, an N—($C_{1-6}$alkyl)urea, or an N,N-di($C_{1-6}$alkyl)urea bond.

In certain embodiments of the antibody-drug conjugate of formula (III) or (III'), each $L^1$, $L^2$ and $L^3$ is independently selected from the group consisting of —$(CH_2)_q$—, —NH$(CH_2)_2NH$—, —OC(O)—, —$CO_2$—, $NHCH_2CH_2C(O)$—, —$C(O)NHCH_2CH_2NH$—, —$NHCH_2C(O)$—, —NHC(O)—, —C(O)NH—, —$NCH_3C(O)$—, —$C(O)NCH_3$—, —$(CH_2CH_2O)_p$, —$(CH_2CH_2O)_pCH_2CH_2$—, —$CH_2CH_2$-$(CH_2CH_2O)_p$—, —$OCH(CH_2O)_2$ and -$(AA)_r$-; a, b and c are each independently 0, 1 or 2; each p, q and r is independently 1, 2, 3 or 4; and n is an integer of 1 to 4.

In certain embodiments of the antibody-drug conjugate of formula (III) or (III'), each $L^1$, $L^2$ and $L^3$ is independently selected from the group consisting of —$(CH_2)_q$—, —NH$(CH_2)_2NH$—, —OC(O)—, —$CO_2$—, $NHCH_2CH_2C(O)$—, —$C(O)NHCH_2CH_2NH$—, —$NHCH_2C(O)$—, —NHC(O)—, —C(O)NH—, —$NCH_3C(O)$—, —$OCH(CH_2O)_2$ and —$C(O)NCH_3$—; a, b and c are each independently 0, 1 or 2; each p and q is independently 1 or 2; and n is an integer of 1 to 4.

In certain embodiments of the antibody-drug conjugate of formula (III) or (III'), each $L^1$, $L^2$ and $L^3$ is independently selected from the group consisting of —$NH(CH_2)_2NH$—, —$NHCH_2CH_2C(O)$—, —$C(O)NHCH_2CH_2NH$—, —$NHCH_2C(O)$—, —NHC(O)—, —C(O)NH—, —$NCH_3C(O)$—, —$OCH(CH_2O)_2$ and —$C(O)NCH_3$—; a, b and c are each independently 0 or 1; and n is an integer of 1 to 4.

In certain embodiments of the antibody-drug conjugate of formula (III) or (III'), each $L^1$, $L^2$ and $L^3$ is independently selected from the group consisting of —NHC(O)—, —C(O)NH—, —$(CH_2CH_2O)_p$, —$(CH_2CH_2O)_pCH_2CH_2$—, —$CH_2CH_2$-$(CH_2CH_2O)_p$—, —$OCH(CH_2O)_2$ and -$(AA)_r$-; a, b and c are each independently 0 or 1; each p and r is independently 1, 2 or 3; and n is an integer of 1 to 4.

In certain embodiments of the antibody-drug conjugate of formula (III) or (III'), each AA is an amino acid selected from the group consisting of Ala, Arg, Asn, Asp, Cys, Glu, Gln, Gly, His, Ile, Leu, Lys, Met, Phe, Pro, Ser, Thr, Trp, Tyr and Val. In one variation of the above, $(AA)_r$ is a single amino acid selected from the group consisting of Gly, Arg, Val, Ala, Cys, Gln, Leu, Ile, Leu, Lys and Ser or their N-methylated analogues. In another variation of the above, $(AA)_r$ is selected from the group consisting of Gly-Gly, Gly-Arg, Gly-Val, Gly-Ala, Gly-Cys, Gly-Gln, Gly-Ile, Leu, Lys-Leu, Gly-Lys and Gly-Ser or their N-methylated analogues. In another variation of the above, $(AA)_r$ is selected from the group consisting of Gly-Gly-Gly, Gly-Arg-Gly, Gly-Val-Gly, Gly-Ala-Gly, Gly-Cys-Gly, Gly-Gln-Gly, Gly-Ile-Gly, Lys-Leu-Gly, Gly-Lys-Gly and Gly-Ser-Gly or their N-methylated analogues. In another variation of the above, $(AA)_r$ is selected from the group consisting of Ala-Ala, Ala-Gly, Ala-Arg, Ala-Val, Ala-Ala, Ala-Cys, Ala-Gln, Ala-Ile, Ala-Leu, Ala-Lys and Ala-Ser or their N-methylated analogues. In another variation of the above, $(AA)_r$ is selected from the group consisting of Ala-Ala-Ala, Ala-Gly-ALa, Ala-Arg-Ala, Ala-Val-Ala, Ala-Ala-Ala, Ala-Cys-Ala, Ala-Gln-Ala, Ala-Ile-Ala, Ala-Leu-Ala, Ala-Lys-Ala and Ala-Ser-Ala or their N-methylated analogues.

In certain embodiments of the antibody-drug conjugate of formula (III) or (III'), CTX is bonded to $(L^1)_a$-$(L^2)_b$-$(L^3)_c$ via a group selected from —NHC(O)—, —NHC(O)O—, —$N(C_{1-3}alkyl)C(O)O$—, —NH—, —$N(C_{1-3}alkyl)$-, —$N(C_{1-3}alkyl)C(O)NH$— and —$N(C_{1-3}alkyl)C(O)N(C_{1-3}alkyl)$-.

In certain embodiments of the antibody-drug conjugate of formula (III) or (III'), when $(L^1)_a$-$(L^2)_b$-$(L^3)_c$ together is —$(CH_2)_{1-12}$- or —$(CH_2CH_2O)_{1-12}CH_2CH_2$— then $L^1$, $L^2$ and $L^3$ are not bonded to CTX by an amide bond.

In certain embodiments of the antibody-drug conjugate of formula (III) or (III'), CTX is bonded to $(L^1)_a$-$(L^2)_b$-$(L^3)_c$ via a bond selected from the group consisting of:

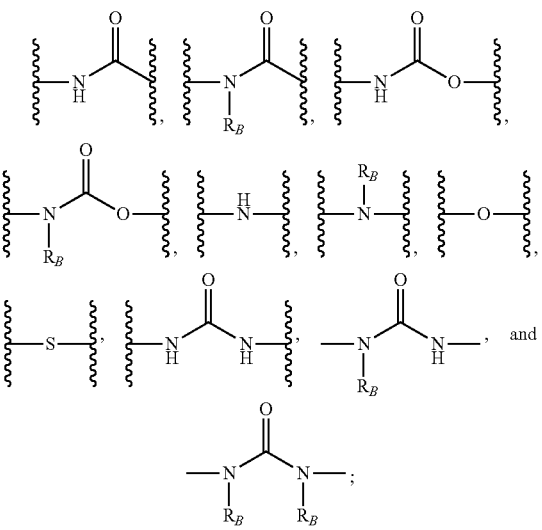

wherein each $R_B$ is independently branched or unbranched $C_{1-6}$ alkyl.

In certain embodiments of the antibody-drug conjugate of formula (III) or (III'), A is an antibody that is specific to a cancer antigen. In certain embodiments, A is selected from the group consisting of alemtuzumab, anitumumab, bevacizumab, brentuximab, cetuximab, gemtuzumab, glembatumumab, inotuzumab, ipilimumab, lovortumumab, milatuzumab, ofatumumab, rituximab, tositumomab, and trastuzumab.

In certain embodiments of the antibody-drug conjugate of formula (III) or (III'), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite. In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin. In certain embodiments, the CTX is monomethylauristatin E (MMAE), monomethylauristatin F (MMAF), a pyrrolobenzodiazepine (PDB), calicheamicin γ, mertansine, or tubulysin T2.

In certain embodiments of the antibody-drug conjugate of formula (III) or (III'), the CTX is MMAE or MMAF. In certain embodiments, the CTX is a PDB. In certain embodiments, the CTX is tubulysin T2. In certain embodiments, the CTX is tubulysin T3 or tubulysin T4.

The following tables illustrate embodiments of the linkers (Tables 1 and 4), linker-conjugates (Tables 2 and 5) and the ADCs (Tables 3 and 6) disclosed herein.

TABLE 1

Linkers

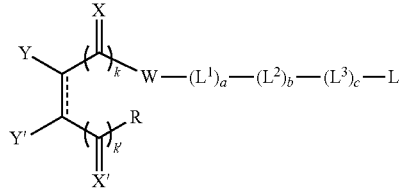

(I)

| Entry | ------ | Y, Y' | X, X' | W | L$^1$ | L$^2$ | L$^3$ | Z |
|---|---|---|---|---|---|---|---|---|
| 1 | single | halo | O or S | —NH— or —N(R$^1$)— | — | —(CH$_2$)$_2$— | —OC(O)— | —CO$_2$H, —NH$_2$, —OH, —NH—R$^{3a}$, or —CO$_2$R$^{3b}$ |
| 2 | single | halo | O or S | —NH— or —N(R$^1$)— | — | —(CH$_2$CH$_2$O)$_{12}$— | —CH$_2$CH$_2$C(O)— | —CO$_2$H, —NH$_2$, —OH, —NH—R$^{3a}$, or —CO$_2$R$^{3b}$ |
| 3 | single | halo | O or S | —NH— or —N(R$^1$)— | — | —(CH$_2$CH$_2$O)$_6$— | —CH$_2$CH$_2$C(O)— | —CO$_2$H, —NH$_2$, —OH, —NH—R$^{3a}$, or —CO$_2$R$^{3b}$ |
| 4 | single | halo | O or S | —NH— or —N(R$^1$)— | —(CH$_2$)$_2$CO— | —NHCH$_2$CH$_2$— | —OC(O)— | —CO$_2$H, —NH$_2$, —OH, —NH—R$^{3a}$, or —CO$_2$R$^{3b}$ |
| 5 | single | halo | O or S | —NH— or —N(R$^1$)— | —(CH$_2$)$_4$CO— | —NHCH$_2$CH$_2$— | —OC(O)— | —CO$_2$H, —NH$_2$, —OH, —NH—R$^{3a}$, or —CO$_2$R$^{3b}$ |
| 6 | single | halo | O or S | —NH— or —N(R$^1$)— | —(CH$_2$)$_5$CO— | —NHCH$_2$CH$_2$— | —OC(O)— | —CO$_2$H, —NH$_2$, —OH, —NH—R$^{3a}$, or —CO$_2$R$^{3b}$ |
| 7 | single | halo | O or S | —NH— or —N(R$^1$)— | — | —(CH$_2$)$_2$— | —NHC(O)— | —CO$_2$H, —NH$_2$, —OH, —NH—R$^{3a}$, or —CO$_2$R$^{3b}$ |
| 8 | single | halo | O or S | —NH— or —N(R$^1$)— | — | —(CH$_2$CH$_2$O)$_{12}$— | —NHC(O)— | —CO$_2$H, —NH$_2$, —OH, —NH—R$^{3a}$, or —CO$_2$R$^{3b}$ |
| 9 | single | halo | O or S | —NH— or —N(R$^1$)— | — | —(CH$_2$CH$_2$O)$_6$— | —NHC(O)— | —CO$_2$H, —NH$_2$, —OH, —NH—R$^{3a}$, or —CO$_2$R$^{3b}$ |
| 10 | single | halo | O or S | —NH— or —N(R$^1$)— | —(CH$_2$)$_2$CO— | —NHCH$_2$CH$_2$— | —NHC(O)— | —CO$_2$H, —NH$_2$, —OH, —NH—R$^{3a}$, or —CO$_2$R$^{3b}$ |
| 11 | single | halo | O or S | —NH— or —N(R$^1$)— | —(CH$_2$)$_4$CO— | —NHCH$_2$CH$_2$— | —NHC(O)— | —CO$_2$H, —NH$_2$, —OH, —NH—R$^{3a}$, or —CO$_2$R$^{3b}$ |
| 12 | single | halo | O or S | —NH— or —N(R$^1$)— | —(CH$_2$)$_5$CO— | —NHCH$_2$CH$_2$— | —NHC(O)— | —CO$_2$H, —NH$_2$, —OH, —NH—R$^{3a}$, or —CO$_2$R$^{3b}$ |
| 13 | single | halo | O or S | —NH— or —N(R$^1$)— | — | —(CH$_2$)$_2$— | —NCH$_3$C(O)— | —CO$_2$H, —NH$_2$, —OH, —NH—R$^{3a}$, or —CO$_2$R$^{3b}$ |
| 14 | single | halo | O or S | —NH— or —N(R$^1$)— | — | —(CH$_2$CH$_2$O)$_{12}$— | —NCH$_3$C(O)— | —CO$_2$H, —NH$_2$, —OH, —NH—R$^{3a}$, or —CO$_2$R$^{3b}$ |
| 15 | single | halo | O or S | —NH— or —N(R$^1$)— | — | —(CH$_2$CH$_2$O)$_6$— | —NCH$_3$C(O)— | —CO$_2$H, —NH$_2$, —OH, —NH—R$^{3a}$, or —CO$_2$R$^{3b}$ |
| 16 | single | halo | O or S | —NH— or —N(R$^1$)— | —(CH$_2$)$_2$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 17 | single | halo | O or S | —NH— or —N(R$^1$)— | —(CH$_2$)$_4$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 18 | single | halo | O or S | —NH— or —N(R$^1$)— | —(CH$_2$)$_5$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 19 | single | halo | O or S | —CH$_2$—, —CH$_2$CH$_2$—, —CH(R$^2$)—, or —CH$_2$CH(R$^2$)— | — | —(CH$_2$)$_2$— | —OC(O)— | —CO$_2$H, —NH$_2$, —OH, —NH—R$^{3a}$, or —CO$_2$R$^{3b}$ |
| 20 | single | halo | O or S | —CH$_2$—, —CH$_2$CH$_2$—, —CH(R$^2$)—, or —CH$_2$CH(R$^2$)— | — | —(CH$_2$CH$_2$O)$_{12}$— | —CH$_2$CH$_2$C(O)— | —CO$_2$H, —NH$_2$, —OH, —NH—R$^{3a}$, or —CO$_2$R$^{3b}$ |

TABLE 1-continued

Linkers

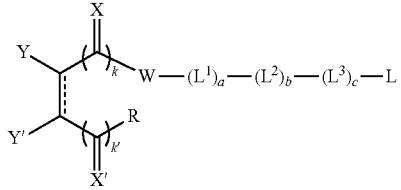

(I)

| Entry | ====== | Y, Y' | X, X' | W | $L^1$ | $L^2$ | $L^3$ | Z |
|---|---|---|---|---|---|---|---|---|
| 21 | single | halo | O or S | $-CH_2-$, $-CH_2CH_2-$, $-CH(R^2)-$, or $-CH_2CH(R^2)-$ | — | $-(CH_2CH_2O)_6-$ | $-CH_2CH_2C(O)-$ | $-CO_2H$, $-NH_2$, $-OH$, $-NH-R^{3a}$, or $-CO_2R^{3b}$ |
| 22 | single | halo | O or S | $-CH_2-$, $-CH_2CH_2-$, $-CH(R^2)-$, or $-CH_2CH(R^2)-$ | $-(CH_2)_2CO-$ | $-NHCH_2CH_2-$ | $-OC(O)-$ | $-CO_2H$, $-NH_2$, $-OH$, $-NH-R^{3a}$, or $-CO_2R^{3b}$ |
| 23 | single | halo | O or S | $-CH_2-$, $-CH_2CH_2-$, $-CH(R^2)-$, or $-CH_2CH(R^2)-$ | $-(CH_2)_4CO-$ | $-NHCH_2CH_2-$ | $-OC(O)-$ | $-CO_2H$, $-NH_2$, $-OH$, $-NH-R^{3a}$, or $-CO_2R^{3b}$ |
| 24 | single | halo | O or S | $-CH_2-$, $-CH_2CH_2-$, $-CH(R^2)-$, or $-CH_2CH(R^2)-$ | $-(CH_2)_5CO-$ | $-NHCH_2CH_2-$ | $-OC(O)-$ | $-CO_2H$, $-NH_2$, $-OH$, $-NH-R^{3a}$, or $-CO_2R^{3b}$ |
| 25 | single | halo | O or S | $-CH_2-$, $-CH_2CH_2-$, $-CH(R^2)-$, or $-CH_2CH(R^2)-$ | — | $-(CH_2)_2-$ | $-NHC(O)-$ | $-CO_2H$, $-NH_2$, $-OH$, $-NH-R^{3a}$, or $-CO_2R^{3b}$ |
| 26 | single | halo | O or S | $-CH_2-$, $-CH_2CH_2-$, $-CH(R^2)-$, or $-CH_2CH(R^2)-$ | — | $-(CH_2CH_2O)_{12}-$ | $-NHC(O)-$ | $-CO_2H$, $-NH_2$, $-OH$, $-NH-R^{3a}$, or $-CO_2R^{3b}$ |
| 27 | single | halo | O or S | $-CH_2-$, $-CH_2CH_2-$, $-CH(R^2)-$, or $-CH_2CH(R^2)-$ | — | $-(CH_2CH_2O)_6-$ | $-NHC(O)-$ | $-CO_2H$, $-NH_2$, $-OH$, $-NH-R^{3a}$, or $-CO_2R^{3b}$ |
| 28 | single | halo | O or S | $-CH_2-$, $-CH_2CH_2-$, $-CH(R^2)-$, or $-CH_2CH(R^2)-$ | $-(CH_2)_2CO-$ | $-NHCH_2CH_2-$ | $-NHC(O)-$ | $-CO_2H$, $-NH_2$, $-OH$, $-NH-R^{3a}$, or $-CO_2R^{3b}$ |
| 29 | single | halo | O or S | $-CH_2-$, $-CH_2CH_2-$, $-CH(R^2)-$, or $-CH_2CH(R^2)-$ | $-(CH_2)_4CO-$ | $-NHCH_2CH_2-$ | $-NHC(O)-$ | $-CO_2H$, $-NH_2$, $-OH$, $-NH-R^{3a}$, or $-CO_2R^{3b}$ |
| 30 | single | halo | O or S | $-CH_2-$, $-CH_2CH_2-$, $-CH(R^2)-$, or $-CH_2CH(R^2)-$ | $-(CH_2)_5CO-$ | $-NHCH_2CH_2-$ | $-NHC(O)-$ | $-CO_2H$, $-NH_2$, $-OH$, $-NH-R^{3a}$, or $-CO_2R^{3b}$ |
| 31 | single | halo | O or S | $-CH_2-$, $-CH_2CH_2-$, $-CH(R^2)-$, or $-CH_2CH(R^2)-$ | — | $-(CH_2)_2-$ | $-NCH_3C(O)-$ | $-CO_2H$, $-NH_2$, $-OH$, $-NH-R^{3a}$, or $-CO_2R^{3b}$ |
| 32 | single | halo | O or S | $-CH_2-$, $-CH_2CH_2-$, $-CH(R^2)-$, or $-CH_2CH(R^2)-$ | — | $-(CH_2CH_2O)_{12}-$ | $-NCH_3C(O)-$ | $-CO_2H$, $-NH_2$, $-OH$, $-NH-R^{3a}$, or $-CO_2R^{3b}$ |
| 33 | single | halo | O or S | $-CH_2-$, $-CH_2CH_2-$, $-CH(R^2)-$, or $-CH_2CH(R^2)-$ | — | $-(CH_2CH_2O)_6-$ | $-NCH_3C(O)-$ | $-CO_2H$, $-NH_2$, $-OH$, $-NH-R^{3a}$, or $-CO_2R^{3b}$ |
| 34 | single | halo | O or S | $-CH_2-$, $-CH_2CH_2-$, $-CH(R^2)-$, or $-CH_2CH(R^2)-$ | $-(CH_2)_2CO-$ | $-NHCH_2CH_2-$ | $-NCH_3C(O)-$ | $-CO_2H$, $-NH_2$, $-OH$, $-NH-R^{3a}$, or $-CO_2R^{3b}$ |
| 35 | single | halo | O or S | $-CH_2-$, $-CH_2CH_2-$, $-CH(R^2)-$, or $-CH_2CH(R^2)-$ | $-(CH_2)_4CO-$ | $-NHCH_2CH_2-$ | $-NCH_3C(O)-$ | $-CO_2H$, $-NH_2$, $-OH$, $-NH-R^{3a}$, or $-CO_2R^{3b}$ |
| 36 | single | halo | O or S | $-CH_2-$, $-CH_2CH_2-$, $-CH(R^2)-$, or $-CH_2CH(R^2)-$ | $-(CH_2)_5CO-$ | $-NHCH_2CH_2-$ | $-NCH_3C(O)-$ | $-CO_2H$, $-NH_2$, $-OH$, $-NH-R^{3a}$, or $-CO_2R^{3b}$ |
| 37 | single | substituted thiol | O or S | $-NH-$ or $-N(R^1)-$ | — | $-(CH_2)_2-$ | $-OC(O)-$ | $-CO_2H$, $-NH_2$, $-OH$, $-NH-R^{3a}$, or $-CO_2R^{3b}$ |
| 38 | single | substituted thiol | O or S | $-NH-$ or $-N(R^1)-$ | — | $-(CH_2CH_2O)_{12}-$ | $-CH_2CH_2C(O)-$ | $-CO_2H$, $-NH_2$, $-OH$, $-NH-R^{3a}$, or $-CO_2R^{3b}$ |
| 39 | single | substituted thiol | O or S | $-NH-$ or $-N(R^1)-$ | — | $-(CH_2CH_2O)_6-$ | $-CH_2CH_2C(O)-$ | $-CO_2H$, $-NH_2$, $-OH$, $-NH-R^{3a}$, or $-CO_2R^{3b}$ |
| 40 | single | substituted thiol | O or S | $-NH-$ or $-N(R^1)-$ | $-(CH_2)_2CO-$ | $-NHCH_2CH_2-$ | $-OC(O)-$ | $-CO_2H$, $-NH_2$, $-OH$, $-NH-R^{3a}$, or $-CO_2R^{3b}$ |
| 41 | single | substituted thiol | O or S | $-NH-$ or $-N(R^1)-$ | $-(CH_2)_4CO-$ | $-NHCH_2CH_2-$ | $-OC(O)-$ | $-CO_2H$, $-NH_2$, $-OH$, $-NH-R^{3a}$, or $-CO_2R^{3b}$ |

TABLE 1-continued

Linkers

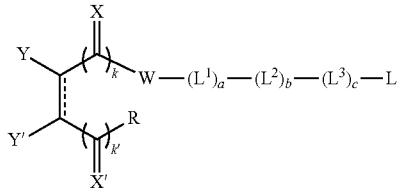

(I)

| Entry | ===== | Y, Y' | X, X' | W | L¹ | L² | L³ | Z |
|---|---|---|---|---|---|---|---|---|
| 42 | single | substituted thiol | O or S | —NH— or —N(R¹)— | —(CH₂)₅CO— | —NHCH₂CH₂— | —OC(O)— | —CO₂H, —NH₂, —OH, —NH—R³ᵃ, or —CO₂R³ᵇ |
| 43 | single | substituted thiol | O or S | —NH— or —N(R¹)— | — | —(CH₂)₂— | —NHC(O)— | —CO₂H, —NH₂, —OH, —NH—R³ᵃ, or —CO₂R³ᵇ |
| 44 | single | substituted thiol | O or S | —NH— or —N(R¹)— | — | —(CH₂CH₂O)₁₂— | —NHC(O)— | —CO₂H, —NH₂, —OH, —NH—R³ᵃ, or —CO₂R³ᵇ |
| 45 | single | substituted thiol | O or S | —NH— or —N(R¹)— | — | —(CH₂CH₂O)₆— | —NHC(O)— | —CO₂H, —NH₂, —OH, —NH—R³ᵃ, or —CO₂R³ᵇ |
| 46 | single | substituted thiol | O or S | —NH— or —N(R¹)— | —(CH₂)₂CO— | —NHCH₂CH₂— | —NHC(O)— | —CO₂H, —NH₂, —OH, —NH—R³ᵃ, or —CO₂R³ᵇ |
| 47 | single | substituted thiol | O or S | —NH— or —N(R¹)— | —(CH₂)₄CO— | —NHCH₂CH₂— | —NHC(O)— | —CO₂H, —NH₂, —OH, —NH—R³ᵃ, or —CO₂R³ᵇ |
| 48 | single | substituted thiol | O or S | —NH— or —N(R¹)— | —(CH₂)₅CO— | —NHCH₂CH₂— | —NHC(O)— | —CO₂H, —NH₂, —OH, —NH—R³ᵃ, or —CO₂R³ᵇ |
| 49 | single | substituted thiol | O or S | —NH— or —N(R¹)— | — | —(CH₂)₂— | —NCH₃C(O)— | —CO₂H, —NH₂, —OH, —NH—R³ᵃ, or —CO₂R³ᵇ |
| 50 | single | substituted thiol | O or S | —NH— or —N(R¹)— | — | —(CH₂CH₂O)₁₂— | —NCH₃C(O)— | —CO₂H, —NH₂, —OH, —NH—R³ᵃ, or —CO₂R³ᵇ |
| 51 | single | substituted thiol | O or S | —NH— or —N(R¹)— | — | —(CH₂CH₂O)₆— | —NCH₃C(O)— | —CO₂H, —NH₂, —OH, —NH—R³ᵃ, or —CO₂R³ᵇ |
| 52 | single | substituted thiol | O or S | —NH— or —N(R¹)— | —(CH₂)₂CO— | —NHCH₂CH₂— | —NCH₃C(O)— | —CO₂H, —NH₂, —OH, —NH—R³ᵃ, or —CO₂R³ᵇ |
| 53 | single | substituted thiol | O or S | —NH— or —N(R¹)— | —(CH₂)₄CO— | —NHCH₂CH₂— | —NCH₃C(O)— | —CO₂H, —NH₂, —OH, |
| 54 | single | substituted thiol | O or S | —NH— or —N(R¹)— | —(CH₂)₅CO— | —NHCH₂CH₂— | —NCH₃C(O)— | —CO₂H, —NH₂, —OH, —NH—R³ᵃ, or —CO₂R³ᵇ |
| 55 | single | substituted thiol | O or S | —CH₂—, —CH₂CH₂—, —CH(R²)—, or —CH₂CH(R²)— | — | —(CH₂)₂— | —OC(O)— | —CO₂H, —NH₂, —OH, —NH—R³ᵃ, or —CO₂R³ᵇ |
| 56 | single | substituted thiol | O or S | —CH₂—, —CH₂CH₂—, —CH(R²)—, or —CH₂CH(R²)— | — | —(CH₂CH₂O)₁₂— | —CH₂CH₂C(O)— | —CO₂H, —NH₂, —OH, —NH—R³ᵃ, or —CO₂R³ᵇ |
| 57 | single | substituted thiol | O or S | —CH₂—, —CH₂CH₂—, —CH(R²)—, or —CH₂CH(R²)— | — | —(CH₂CH₂O)₆— | —CH₂CH₂C(O)— | —CO₂H, —NH₂, —OH, —NH—R³ᵃ, or —CO₂R³ᵇ |
| 58 | single | substituted thiol | O or S | —CH₂—, —CH₂CH₂—, —CH(R²)—, or —CH₂CH(R²)— | —(CH₂)₂CO— | —NHCH₂CH₂— | —OC(O)— | —CO₂H, —NH₂, —OH, —NH—R³ᵃ, or —CO₂R³ᵇ |
| 59 | single | substituted thiol | O or S | —CH₂—, —CH₂CH₂—, —CH(R²)—, or —CH₂CH(R²)— | —(CH₂)₄CO— | —NHCH₂CH₂— | —OC(O)— | —CO₂H, —NH₂, —OH, —NH—R³ᵃ, or —CO₂R³ᵇ |
| 60 | single | substituted thiol | O or S | —CH₂—, —CH₂CH₂—, —CH(R²)—, or —CH₂CH(R²)— | —(CH₂)₅CO— | —NHCH₂CH₂— | —OC(O)— | —CO₂H, —NH₂, —OH, —NH—R³ᵃ, or —CO₂R³ᵇ |
| 61 | single | substituted thiol | O or S | —CH₂—, —CH₂CH₂—, —CH(R²)—, or —CH₂CH(R²)— | — | —(CH₂)₂— | —NHC(O)— | —CO₂H, —NH₂, —OH, —NH—R³ᵃ, or —CO₂R³ᵇ |
| 62 | single | substituted thiol | O or S | —CH₂—, —CH₂CH₂—, —CH(R²)—, or —CH₂CH(R²)— | — | —(CH₂CH₂O)₁₂— | —NHC(O)— | —CO₂H, —NH₂, —OH, —NH—R³ᵃ, or —CO₂R³ᵇ |

TABLE 1-continued

Linkers

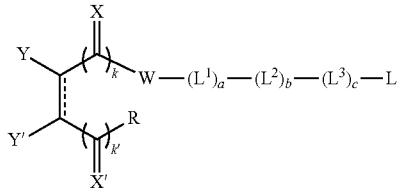

(I)

| Entry | ===== | Y, Y' | X, X' | W | L¹ | L² | L³ | Z |
|---|---|---|---|---|---|---|---|---|
| 63 | single | substituted thiol | O or S | —$CH_2$—, —$CH_2CH_2$—, —$CH(R^2)$—, or —$CH_2CH(R^2)$— | — | —$(CH_2CH_2O)_6$— | —NHC(O)— | —$CO_2H$, —$NH_2$, —OH, —NH—$R^{3a}$, or —$CO_2R^{3b}$ |
| 64 | single | substituted thiol | O or S | —$CH_2$—, —$CH_2CH_2$—, —$CH(R^2)$—, or —$CH_2CH(R^2)$— | —$(CH_2)_2CO$— | —$NHCH_2CH_2$— | —NHC(O)— | —$CO_2H$, —$NH_2$, —OH, —NH—$R^{3a}$, or —$CO_2R^{3b}$ |
| 65 | single | substituted thiol | O or S | —$CH_2$—, —$CH_2CH_2$—, —$CH(R^2)$—, or —$CH_2CH(R^2)$— | —$(CH_2)_4CO$— | —$NHCH_2CH_2$— | —NHC(O)— | —$CO_2H$, —$NH_2$, —OH, —NH—$R^{3a}$, or —$CO_2R^{3b}$ |
| 66 | single | substituted thiol | O or S | —$CH_2$—, —$CH_2CH_2$—, —$CH(R^2)$—, or —$CH_2CH(R^2)$— | —$(CH_2)_5CO$— | —$NHCH_2CH_2$— | —NHC(O)— | —$CO_2H$, —$NH_2$, —OH, —NH—$R^{3a}$, or —$CO_2R^{3b}$ |
| 67 | single | substituted thiol | O or S | —$CH_2$—, —$CH_2CH_2$—, —$CH(R^2)$—, or —$CH_2CH(R^2)$— | — | —$(CH_2)_2$— | —$NCH_3C(O)$— | —$CO_2H$, —$NH_2$, —OH, —NH—$R^{3a}$, or —$CO_2R^{3b}$ |
| 68 | single | substituted thiol | O or S | —$CH_2$—, —$CH_2CH_2$—, —$CH(R^2)$—, or —$CH_2CH(R^2)$— | — | —$(CH_2CH_2O)_{12}$— | —$NCH_3C(O)$— | —$CO_2H$, —$NH_2$, —OH, —NH—$R^{3a}$, or —$CO_2R^{3b}$ |
| 69 | single | substituted thiol | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | —$CO_2H$, —$NH_2$, —OH, —NH—$R^{3a}$, or —$CO_2R^{3b}$ |
| 70 | single | substituted thiol | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | —$CO_2H$, —$NH_2$, —OH, —NH—$R^{3a}$, or —$CO_2R^{3b}$ |
| 71 | single | substituted thiol | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | —$CO_2H$, —$NH_2$, —OH, —NH—$R^{3a}$, or —$CO_2R^{3b}$ |
| 72 | single | substituted thiol | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | —$CO_2H$, —$NH_2$, —OH, —NH—$R^{3a}$, or —$CO_2R^{3b}$ |
| 73 | single | substituted sulfonate | O or S | —NH— or —$N(R^1)$— | — | —$(CH_2)_2$— | —OC(O)— | —$CO_2H$, —$NH_2$, —OH, —NH—$R^{3a}$, or —$CO_2R^{3b}$ |
| 74 | single | substituted sulfonate | O or S | —NH— or —$N(R^1)$— | — | —$(CH_2CH_2O)_{12}$— | —$CH_2CH_2C(O)$— | —$CO_2H$, —$NH_2$, —OH, —NH—$R^{3a}$, or —$CO_2R^{3b}$ |
| 75 | single | substituted sulfonate | O or S | —NH— or —$N(R^1)$— | — | —$(CH_2CH_2O)_6$— | —$CH_2CH_2C(O)$— | —$CO_2H$, —$NH_2$, —OH, —NH—$R^{3a}$, or —$CO_2R^{3b}$ |
| 76 | single | substituted sulfonate | O or S | —NH— or —$N(R^1)$— | —$(CH_2)_2CO$— | —$NHCH_2CH_2$— | —OC(O)— | —$CO_2H$, —$NH_2$, —OH, —NH—$R^{3a}$, or —$CO_2R^{3b}$ |
| 77 | single | substituted sulfonate | O or S | —NH— or —$N(R^1)$— | —$(CH_2)_4CO$— | —$NHCH_2CH_2$— | —OC(O)— | —$CO_2H$, —$NH_2$, —OH, —NH—$R^{3a}$, or —$CO_2R^{3b}$ |
| 78 | single | substituted sulfonate | O or S | —NH— or —$N(R^1)$— | —$(CH_2)_5CO$— | —$NHCH_2CH_2$— | —OC(O)— | —$CO_2H$, —$NH_2$, —OH, —NH—$R^{3a}$, or —$CO_2R^{3b}$ |
| 79 | single | substituted sulfonate | O or S | —NH— or —$N(R^1)$— | — | —$(CH_2)_2$— | —NHC(O)— | —$CO_2H$, —$NH_2$, —OH, —NH—$R^{3a}$, or —$CO_2R^{3b}$ |
| 80 | single | substituted sulfonate | O or S | —NH— or —$N(R^1)$— | — | —$(CH_2CH_2O)_{12}$— | —NHC(O)— | —$CO_2H$, —$NH_2$, —OH, —NH—$R^{3a}$, or —$CO_2R^{3b}$ |
| 81 | single | substituted sulfonate | O or S | —NH— or —$N(R^1)$— | — | —$(CH_2CH_2O)_6$— | —NHC(O)— | —$CO_2H$, —$NH_2$, —OH, —NH—$R^{3a}$, or —$CO_2R^{3b}$ |
| 82 | single | substituted sulfonate | O or S | —NH— or —$N(R^1)$— | —$(CH_2)_2CO$— | —$NHCH_2CH_2$— | —NHC(O)— | —$CO_2H$, —$NH_2$, —OH, —NH—$R^{3a}$, or —$CO_2R^{3b}$ |
| 83 | single | substituted sulfonate | O or S | —NH— or —$N(R^1)$— | —$(CH_2)_4CO$— | —$NHCH_2CH_2$— | —NHC(O)— | —$CO_2H$, —$NH_2$, —OH, —NH—$R^{3a}$, or —$CO_2R^{3b}$ |

TABLE 1-continued

Linkers

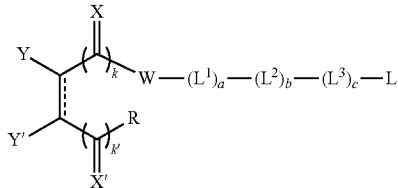

(I)

| Entry | ===== | Y, Y' | X, X' | W | L¹ | L² | L³ | Z |
|---|---|---|---|---|---|---|---|---|
| 84 | single | substituted sulfonate | O or S | —NH— or —N(R¹)— | —(CH$_2$)$_5$CO— | —NHCH$_2$CH$_2$— | —NHC(O)— | —CO$_2$H, —NH$_2$, —OH, —NH—R$^{3a}$, or —CO$_2$R$^{3b}$ |
| 85 | single | substituted sulfonate | O or S | —NH— or —N(R¹)— | — | —(CH$_2$)$_2$— | —NCH$_3$C(O)— | —CO$_2$H, —NH$_2$, —OH, —NH—R$^{3a}$, or —CO$_2$R$^{3b}$ |
| 86 | single | substituted sulfonate | O or S | —NH— or —N(R¹)— | — | —(CH$_2$CH$_2$O)$_{12}$— | —NCH$_3$C(O)— | —CO$_2$H, —NH$_2$, —OH, —NH—R$^{3a}$, or —CO$_2$R$^{3b}$ |
| 87 | single | substituted sulfonate | O or S | —NH— or —N(R¹)— | — | —(CH$_2$CH$_2$O)$_6$— | —NCH$_3$C(O)— | —CO$_2$H, —NH$_2$, —OH, —NH—R$^{3a}$, or —CO$_2$R$^{3b}$ |
| 88 | single | substituted sulfonate | O or S | —NH— or —N(R¹)— | —(CH$_2$)$_2$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 89 | single | substituted sulfonate | O or S | —NH— or —N(R¹)— | —(CH$_2$)$_4$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 90 | single | substituted sulfonate | O or S | —NH— or —N(R¹)— | —(CH$_2$)$_5$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 91 | single | substituted sulfonate | O or S | —CH$_2$—, —CH$_2$CH$_2$—, —CH(R²)—, or —CH$_2$CH(R²)— | — | —(CH$_2$)$_2$— | —OC(O)— | —CO$_2$H, —NH$_2$, —OH, —NH—R$^{3a}$, or —CO$_2$R$^{3b}$ |
| 92 | single | substituted sulfonate | O or S | —CH$_2$—, —CH$_2$CH$_2$—, —CH(R²)—, or —CH$_2$CH(R²)— | — | —(CH$_2$CH$_2$O)$_{12}$— | —CH$_2$CH$_2$C(O)— | —CO$_2$H, —NH$_2$, —OH, —NH—R$^{3a}$, or —CO$_2$R$^{3b}$ |
| 93 | single | substituted sulfonate | O or S | —CH$_2$—, —CH$_2$CH$_2$—, —CH(R²)—, or —CH$_2$CH(R²)— | — | —(CH$_2$CH$_2$O)$_6$— | —CH$_2$CH$_2$C(O)— | —CO$_2$H, —NH$_2$, —OH, —NH—R$^{3a}$, or —CO$_2$R$^{3b}$ |
| 94 | single | substituted sulfonate | O or S | —CH$_2$—, —CH$_2$CH$_2$—, —CH(R²)—, or —CH$_2$CH(R²)— | —(CH$_2$)$_2$CO— | —NHCH$_2$CH$_2$— | —OC(O)— | —CO$_2$H, —NH$_2$, —OH, —NH—R$^{3a}$, or —CO$_2$R$^{3b}$ |
| 95 | single | substituted sulfonate | O or S | —CH$_2$—, —CH$_2$CH$_2$—, —CH(R²)—, or —CH$_2$CH(R²)— | —(CH$_2$)$_4$CO— | —NHCH$_2$CH$_2$— | —OC(O)— | —CO$_2$H, —NH$_2$, —OH, —NH—R$^{3a}$, or —CO$_2$R$^{3b}$ |
| 96 | single | substituted sulfonate | O or S | —CH$_2$—, —CH$_2$CH$_2$—, —CH(R²)—, or —CH$_2$CH(R²)— | —(CH$_2$)$_5$CO— | —NHCH$_2$CH$_2$— | —OC(O)— | —CO$_2$H, —NH$_2$, —OH, —NH—R$^{3a}$, or —CO$_2$R$^{3b}$ |
| 97 | single | substituted sulfonate | O or S | —CH$_2$—, —CH$_2$CH$_2$—, —CH(R²)—, or —CH$_2$CH(R²)— | — | —(CH$_2$)$_2$— | —NHC(O)— | —CO$_2$H, —NH$_2$, —OH, —NH—R$^{3a}$, or —CO$_2$R$^{3b}$ |
| 98 | single | substituted sulfonate | O or S | —CH$_2$—, —CH$_2$CH$_2$—, —CH(R²)—, or —CH$_2$CH(R²)— | — | —(CH$_2$CH$_2$O)$_{12}$— | —NHC(O)— | —CO$_2$H, —NH$_2$, —OH, —NH—R$^{3a}$, or —CO$_2$R$^{3b}$ |
| 99 | single | substituted sulfonate | O or S | —CH$_2$—, —CH$_2$CH$_2$—, —CH(R²)—, or —CH$_2$CH(R²)— | — | —(CH$_2$CH$_2$O)$_6$— | —NHC(O)— | —CO$_2$H, —NH$_2$, —OH, —NH—R$^{3a}$, or —CO$_2$R$^{3b}$ |
| 100 | single | substituted sulfonate | O or S | —CH$_2$—, —CH$_2$CH$_2$—, —CH(R²)—, or —CH$_2$CH(R²)— | —(CH$_2$)$_2$CO— | —NHCH$_2$CH$_2$— | —NHC(O)— | —CO$_2$H, —NH$_2$, —OH, —NH—R$^{3a}$, or —CO$_2$R$^{3b}$ |
| 101 | single | substituted sulfonate | O or S | —CH$_2$—, —CH$_2$CH$_2$—, —CH(R²)—, or —CH$_2$CH(R²)— | —(CH$_2$)$_4$CO— | —NHCH$_2$CH$_2$— | —NHC(O)— | —CO$_2$H, —NH$_2$, —OH, —NH—R$^{3a}$, or —CO$_2$R$^{3b}$ |
| 102 | single | substituted sulfonate | O or S | —CH$_2$—, —CH$_2$CH$_2$—, —CH(R²)—, or —CH$_2$CH(R²)— | —(CH$_2$)$_5$CO— | —NHCH$_2$CH$_2$— | —NHC(O)— | —CO$_2$H, —NH$_2$, —OH, —NH—R$^{3a}$, or —CO$_2$R$^{3b}$ |
| 103 | single | substituted sulfonate | O or S | —CH$_2$—, —CH$_2$CH$_2$—, —CH(R²)—, or —CH$_2$CH(R²)— | — | —(CH$_2$)$_2$— | —NCH$_3$C(O)— | —CO$_2$H, —NH$_2$, —OH, —NH—R$^{3a}$, or —CO$_2$R$^{3b}$ |
| 104 | single | substituted sulfonate | O or S | —CH$_2$—, —CH$_2$CH$_2$—, —CH(R²)—, or —CH$_2$CH(R²)— | — | —(CH$_2$CH$_2$O)$_{12}$— | —NCH$_3$C(O)— | —CO$_2$H, —NH$_2$, —OH, —NH—R$^{3a}$, or —CO$_2$R$^{3b}$ |

TABLE 1-continued

Linkers

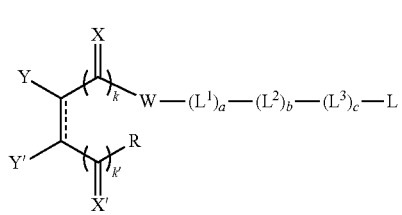

(I)

| Entry | ===== | Y, Y' | X, X' | W | L¹ | L² | L³ | Z |
|---|---|---|---|---|---|---|---|---|
| 105 | single | substituted sulfonate | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | —$CO_2H$, —$NH_2$, —OH, —NH—$R^{3a}$, or —$CO_2R^{3b}$ |
| 106 | single | substituted sulfonate | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | —$CO_2H$, —$NH_2$, —OH, —NH—$R^{3a}$, or —$CO_2R^{3b}$ |
| 107 | single | substituted sulfonate | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | —$CO_2H$, —$NH_2$, —OH, —NH—$R^{3a}$, or —$CO_2R^{3b}$ |
| 108 | single | substituted sulfonate | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | —$CO_2H$, —$NH_2$, —OH, —NH—$R^{3a}$, or —$CO_2R^{3b}$ |
| 109 | double | halo | O or S | —NH— or —N($R^1$)— | — | —$(CH_2)_2$— | —OC(O)— | —$CO_2H$, —$NH_2$, —OH, —NH—$R^{3a}$, or —$CO_2R^{3b}$ |
| 110 | double | halo | O or S | —NH— or —N($R^1$)— | — | —$(CH_2CH_2O)_{12}$— | —$CH_2CH_2C(O)$— | —$CO_2H$, —$NH_2$, —OH, —NH—$R^{3a}$, or —$CO_2R^{3b}$ |
| 111 | double | halo | O or S | —NH— or —N($R^1$)— | — | —$(CH_2CH_2O)_6$— | —$CH_2CH_2C(O)$— | —$CO_2H$, —$NH_2$, —OH, —NH—$R^{3a}$, or —$CO_2R^{3b}$ |
| 112 | double | halo | O or S | —NH— or —N($R^1$)— | —$(CH_2)_2CO$— | —$NHCH_2CH_2$— | —OC(O)— | —$CO_2H$, —$NH_2$, —OH, —NH—$R^{3a}$, or —$CO_2R^{3b}$ |
| 113 | double | halo | O or S | —NH— or —N($R^1$)— | —$(CH_2)_4CO$— | —$NHCH_2CH_2$— | —OC(O)— | —$CO_2H$, —$NH_2$, —OH, —NH—$R^{3a}$, or —$CO_2R^{3b}$ |
| 114 | double | halo | O or S | —NH— or —N($R^1$)— | —$(CH_2)_5CO$— | —$NHCH_2CH_2$— | —OC(O)— | —$CO_2H$, —$NH_2$, —OH, —NH—$R^{3a}$, or —$CO_2R^{3b}$ |
| 115 | double | halo | O or S | —NH— or —N($R^1$)— | — | —$(CH_2)_2$— | —NHC(O)— | —$CO_2H$, —$NH_2$, —OH, —NH—$R^{3a}$, or —$CO_2R^{3b}$ |
| 116 | double | halo | O or S | —NH— or —N($R^1$)— | — | —$(CH_2CH_2O)_{12}$— | —NHC(O)— | —$CO_2H$, —$NH_2$, —OH, —NH—$R^{3a}$, or —$CO_2R^{3b}$ |
| 117 | double | halo | O or S | —NH— or —N($R^1$)— | — | —$(CH_2CH_2O)_6$— | —NHC(O)— | —$CO_2H$, —$NH_2$, —OH, —NH—$R^{3a}$, or —$CO_2R^{3b}$ |
| 118 | double | halo | O or S | —NH— or —N($R^1$)— | —$(CH_2)_2CO$— | —$NHCH_2CH_2$— | —NHC(O)— | —$CO_2H$, —$NH_2$, —OH, —NH—$R^{3a}$, or —$CO_2R^{3b}$ |
| 119 | double | halo | O or S | —NH— or —N($R^1$)— | —$(CH_2)_4CO$— | —$NHCH_2CH_2$— | —NHC(O)— | —$CO_2H$, —$NH_2$, —OH, —NH—$R^{3a}$, or —$CO_2R^{3b}$ |
| 120 | double | halo | O or S | —NH— or —N($R^1$)— | —$(CH_2)_5CO$— | —$NHCH_2CH_2$— | —NHC(O)— | —$CO_2H$, —$NH_2$, —OH, —NH—$R^{3a}$, or —$CO_2R^{3b}$ |
| 121 | double | halo | O or S | —NH— or —N($R^1$)— | — | —$(CH_2)_2$— | —$NCH_3C(O)$— | —$CO_2H$, —$NH_2$, —OH, —NH—$R^{3a}$, or —$CO_2R^{3b}$ |
| 122 | double | halo | O or S | —NH— or —N($R^1$)— | — | —$(CH_2CH_2O)_{12}$— | —$NCH_3C(O)$— | —$CO_2H$, —$NH_2$, —OH, —NH—$R^{3a}$, or —$CO_2R^{3b}$ |
| 123 | double | halo | O or S | —NH— or —N($R^1$)— | — | —$(CH_2CH_2O)_6$— | —$NCH_3C(O)$— | —$CO_2H$, —$NH_2$, —OH, —NH—$R^{3a}$, or —$CO_2R^{3b}$ |
| 124 | double | halo | O or S | —NH— or —N($R^1$)— | —$(CH_2)_2CO$— | —$NHCH_2CH_2$— | —$NCH_3C(O)$— | —$CO_2H$, —$NH_2$, —OH, —NH—$R^{3a}$, or —$CO_2R^{3b}$ |
| 125 | double | halo | O or S | —NH— or —N($R^1$)— | —$(CH_2)_4CO$— | —$NHCH_2CH_2$— | —$NCH_3C(O)$— | —$CO_2H$, —$NH_2$, —OH, —NH—$R^{3a}$, or —$CO_2R^{3b}$ |
| 126 | double | halo | O or S | —NH— or —N($R^1$)— | —$(CH_2)_5CO$— | —$NHCH_2CH_2$— | —$NCH_3C(O)$— | —$CO_2H$, —$NH_2$, —OH, —NH—$R^{3a}$, or —$CO_2R^{3b}$ |
| 127 | double | halo | O or S | —$CH_2$—, —$CH_2CH_2$—, —$CH(R^2)$—, or —$CH_2CH(R^2)$— | — | —$(CH_2)_2$— | —OC(O)— | —$CO_2H$, —$NH_2$, —OH, —NH—$R^{3a}$, or —$CO_2R^{3b}$ |
| 128 | double | halo | O or S | —$CH_2$—, —$CH_2CH_2$—, —$CH(R^2)$—, or —$CH_2CH(R^2)$— | — | —$(CH_2CH_2O)_{12}$— | —$CH_2CH_2C(O)$— | —$CO_2H$, —$NH_2$, —OH, —NH—$R^{3a}$, or —$CO_2R^{3b}$ |
| 129 | double | halo | O or S | —$CH_2$—, —$CH_2CH_2$—, —$CH(R^2)$—, or —$CH_2CH(R^2)$— | — | —$(CH_2CH_2O)_6$— | —$CH_2CH_2C(O)$— | —$CO_2H$, —$NH_2$, —OH, —NH—$R^{3a}$, or —$CO_2R^{3b}$ |
| 130 | double | halo | O or S | —$CH_2$—, —$CH_2CH_2$—, —$CH(R^2)$—, or —$CH_2CH(R^2)$— | —$(CH_2)_2CO$— | —$NHCH_2CH_2$— | —OC(O)— | —$CO_2H$, —$NH_2$, —OH, —NH—$R^{3a}$, or —$CO_2R^{3b}$ |
| 131 | double | halo | O or S | —$CH_2$—, —$CH_2CH_2$—, —$CH(R^2)$—, or —$CH_2CH(R^2)$— | —$(CH_2)_4CO$— | —$NHCH_2CH_2$— | —OC(O)— | —$CO_2H$, —$NH_2$, —OH, —NH—$R^{3a}$, or —$CO_2R^{3b}$ |

TABLE 1-continued

Linkers

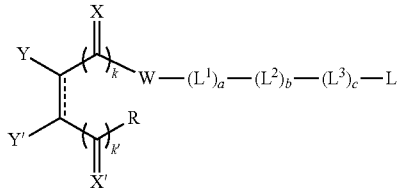

(I)

| Entry | ===== | Y, Y' | X, X' | W | L¹ | L² | L³ | Z |
|---|---|---|---|---|---|---|---|---|
| 132 | double | halo | O or S | —CH₂—, —CH₂CH₂—, —CH(R²)—, or —CH₂CH(R²)— | —(CH₂)₅CO— | —NHCH₂CH₂— | —OC(O)— | —CO₂H, —NH₂, —OH, —NH—R³ᵃ, or —CO₂R³ᵇ |
| 133 | double | halo | O or S | —CH₂—, —CH₂CH₂—, —CH(R²)—, or —CH₂CH(R²)— | — | —(CH₂)₂— | —NHC(O)— | —CO₂H, —NH₂, —OH, —NH—R³ᵃ, or —CO₂R³ᵇ |
| 134 | double | halo | O or S | —CH₂—, —CH₂CH₂—, —CH(R²)—, or —CH₂CH(R²)— | — | —(CH₂CH₂O)₁₂— | —NHC(O)— | —CO₂H, —NH₂, —OH, —NH—R³ᵃ, or —CO₂R³ᵇ |
| 135 | double | halo | O or S | —CH₂—, —CH₂CH₂—, —CH(R²)—, or —CH₂CH(R²)— | — | —(CH₂CH₂O)₆— | —NHC(O)— | —CO₂H, —NH₂, —OH, —NH—R³ᵃ, or —CO₂R³ᵇ |
| 136 | double | halo | O or S | —CH₂—, —CH₂CH₂—, —CH(R²)—, or —CH₂CH(R²)— | —(CH₂)₂CO— | —NHCH₂CH₂— | —NHC(O)— | —CO₂H, —NH₂, —OH, —NH—R³ᵃ, or —CO₂R³ᵇ |
| 137 | double | halo | O or S | —CH₂—, —CH₂CH₂—, —CH(R²)—, or —CH₂CH(R²)— | —(CH₂)₄CO— | —NHCH₂CH₂— | —NHC(O)— | —CO₂H, —NH₂, —OH, —NH—R³ᵃ, or —CO₂R³ᵇ |
| 138 | double | halo | O or S | —CH₂—, —CH₂CH₂—, —CH(R²)—, or —CH₂CH(R²)— | —(CH₂)₅CO— | —NHCH₂CH₂— | —NHC(O)— | —CO₂H, —NH₂, —OH, —NH—R³ᵃ, or —CO₂R³ᵇ |
| 139 | double | halo | O or S | —CH₂—, —CH₂CH₂—, —CH(R²)—, or —CH₂CH(R²)— | — | —(CH₂)₂— | —NCH₃C(O)— | —CO₂H, —NH₂, —OH, —NH—R³ᵃ, or —CO₂R³ᵇ |
| 140 | double | halo | O or S | —CH₂—, —CH₂CH₂—, —CH(R²)—, or —CH₂CH(R²)— | — | —(CH₂CH₂O)₁₂— | —NCH₃C(O)— | —CO₂H, —NH₂, —OH, —NH—R³ᵃ, or —CO₂R³ᵇ |
| 141 | double | halo | O or S | —CH₂—, —CH₂CH₂—, —CH(R²)—, or —CH₂CH(R²)— | — | —(CH₂CH₂O)₆— | —NCH₃C(O)— | —CO₂H, —NH₂, —OH, —NH—R³ᵃ, or —CO₂R³ᵇ |
| 142 | double | halo | O or S | —CH₂—, —CH₂CH₂—, —CH(R²)—, or —CH₂CH(R²)— | —(CH₂)₂CO— | —NHCH₂CH₂— | —NCH₃C(O)— | —CO₂H, —NH₂, —OH, —NH—R³ᵃ, or —CO₂R³ᵇ |
| 143 | double | halo | O or S | —CH₂—, —CH₂CH₂—, —CH(R²)—, or —CH₂CH(R²)— | —(CH₂)₄CO— | —NHCH₂CH₂— | —NCH₃C(O)— | —CO₂H, —NH₂, —OH, —NH—R³ᵃ, or —CO₂R³ᵇ |
| 144 | double | halo | O or S | —CH₂—, —CH₂CH₂—, —CH(R²)—, or —CH₂CH(R²)— | —(CH₂)₅CO— | —NHCH₂CH₂— | —NCH₃C(O)— | —CO₂H, —NH₂, —OH, —NH—R³ᵃ, or —CO₂R³ᵇ |
| 145 | double | substituted thiol | O or S | —NH— or —N(R¹)— | — | —(CH₂)₂— | —OC(O)— | —CO₂H, —NH₂, —OH, —NH—R³ᵃ, or —CO₂R³ᵇ |
| 146 | double | substituted thiol | O or S | —NH— or —N(R¹)— | — | —(CH₂CH₂O)₁₂— | —CH₂CH₂C(O)— | —CO₂H, —NH₂, —OH, —NH—R³ᵃ, or —CO₂R³ᵇ |
| 147 | double | substituted thiol | O or S | —NH— or —N(R¹)— | — | —(CH₂CH₂O)₆— | —CH₂CH₂C(O)— | —CO₂H, —NH₂, —OH, —NH—R³ᵃ, or —CO₂R³ᵇ |
| 148 | double | substituted thiol | O or S | —NH— or —N(R¹)— | —(CH₂)₂CO— | —NHCH₂CH₂— | —OC(O)— | —CO₂H, —NH₂, —OH, —NH—R³ᵃ, or —CO₂R³ᵇ |
| 149 | double | substituted thiol | O or S | —NH— or —N(R¹)— | —(CH₂)₄CO— | —NHCH₂CH₂— | —OC(O)— | —CO₂H, —NH₂, —OH, —NH—R³ᵃ, or —CO₂R³ᵇ |
| 150 | double | substituted thiol | O or S | —NH— or —N(R¹)— | —(CH₂)₅CO— | —NHCH₂CH₂— | —OC(O)— | —CO₂H, —NH₂, —OH, —NH—R³ᵃ, or —CO₂R³ᵇ |
| 151 | double | substituted thiol | O or S | —NH— or —N(R¹)— | — | —(CH₂)₂— | —NHC(O)— | —CO₂H, —NH₂, —OH, —NH—R³ᵃ, or —CO₂R³ᵇ |
| 152 | double | substituted thiol | O or S | —NH— or —N(R¹)— | — | —(CH₂CH₂O)₁₂— | —NHC(O)— | —CO₂H, —NH₂, —OH, —NH—R³ᵃ, or —CO₂R³ᵇ |

TABLE 1-continued

Linkers

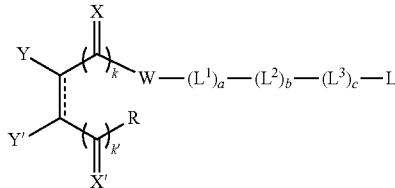

(I)

| Entry | ===== | Y, Y' | X, X' | W | L¹ | L² | L³ | Z |
|---|---|---|---|---|---|---|---|---|
| 153 | double | substituted thiol | O or S | —NH— or —N(R¹)— | — | —(CH₂CH₂O)₆— | —NHC(O)— | —CO₂H, —NH₂, —OH, —NH—R³ᵃ, or —CO₂R³ᵇ |
| 154 | double | substituted thiol | O or S | —NH— or —N(R¹)— | —(CH₂)₂CO— | —NHCH₂CH₂— | —NHC(O)— | —CO₂H, —NH₂, —OH, —NH—R³ᵃ, or —CO₂R³ᵇ |
| 155 | double | substituted thiol | O or S | —NH— or —N(R¹)— | —(CH₂)₄CO— | —NHCH₂CH₂— | —NHC(O)— | —CO₂H, —NH₂, —OH, —NH—R³ᵃ, or —CO₂R³ᵇ |
| 156 | double | substituted thiol | O or S | —NH— or —N(R¹)— | —(CH₂)₅CO— | —NHCH₂CH₂— | —NHC(O)— | —CO₂H, —NH₂, —OH, —NH—R³ᵃ, or —CO₂R³ᵇ |
| 157 | double | substituted thiol | O or S | —NH— or —N(R¹)— | — | —(CH₂)₂— | —NCH₃C(O)— | —CO₂H, —NH₂, —OH, —NH—R³ᵃ, or —CO₂R³ᵇ |
| 158 | double | substituted thiol | O or S | —NH— or —N(R¹)— | — | —(CH₂CH₂O)₁₂— | —NCH₃C(O)— | —CO₂H, —NH₂, —OH, —NH—R³ᵃ, or —CO₂R³ᵇ |
| 159 | double | substituted thiol | O or S | —NH— or —N(R¹)— | — | —(CH₂CH₂O)₆— | —NCH₃C(O)— | —CO₂H, —NH₂, —OH, —NH—R³ᵃ, or —CO₂R³ᵇ |
| 160 | double | substituted thiol | O or S | —NH— or —N(R¹)— | —(CH₂)₂CO— | —NHCH₂CH₂— | —NCH₃C(O)— | —CO₂H, —NH₂, —OH, —NH—R³ᵃ, or —CO₂R³ᵇ |
| 161 | double | substituted thiol | O or S | —NH— or —N(R¹)— | —(CH₂)₄CO— | —NHCH₂CH₂— | —NCH₃C(O)— | —CO₂H, —NH₂, —OH, —NH—R³ᵃ, or —CO₂R³ᵇ |
| 162 | double | substituted thiol | O or S | —NH— or —N(R¹)— | —(CH₂)₅CO— | —NHCH₂CH₂— | —NCH₃C(O)— | —CO₂H, —NH₂, —OH, —NH—R³ᵃ, or —CO₂R³ᵇ |
| 163 | double | substituted thiol | O or S | —CH₂—, —CH₂CH₂—, —CH(R²)—, or —CH₂CH(R²)— | — | —(CH₂)₂— | —OC(O)— | —CO₂H, —NH₂, —OH, —NH—R³ᵃ, or —CO₂R³ᵇ |
| 164 | double | substituted thiol | O or S | —CH₂—, —CH₂CH₂—, —CH(R²)—, or —CH₂CH(R²)— | — | —(CH₂CH₂O)₁₂— | —CH₂CH₂C(O)— | —CO₂H, —NH₂, —OH, —NH—R³ᵃ, or —CO₂R³ᵇ |
| 165 | double | substituted thiol | O or S | —CH₂—, —CH₂CH₂—, —CH(R²)—, or —CH₂CH(R²)— | — | —(CH₂CH₂O)₆— | —CH₂CH₂C(O)— | —CO₂H, —NH₂, —OH, —NH—R³ᵃ, or —CO₂R³ᵇ |
| 166 | double | substituted thiol | O or S | —CH₂—, —CH₂CH₂—, —CH(R²)—, or —CH₂CH(R²)— | —(CH₂)₂CO— | —NHCH₂CH₂— | —OC(O)— | —CO₂H, —NH₂, —OH, —NH—R³ᵃ, or —CO₂R³ᵇ |
| 167 | double | substituted thiol | O or S | —CH₂—, —CH₂CH₂—, —CH(R²)—, or —CH₂CH(R²)— | —(CH₂)₄CO— | —NHCH₂CH₂— | —OC(O)— | —CO₂H, —NH₂, —OH, —NH—R³ᵃ, or —CO₂R³ᵇ |
| 168 | double | substituted thiol | O or S | —CH₂—, —CH₂CH₂—, —CH(R²)—, or —CH₂CH(R²)— | —(CH₂)₅CO— | —NHCH₂CH₂— | —OC(O)— | —CO₂H, —NH₂, —OH, —NH—R³ᵃ, or —CO₂R³ᵇ |
| 169 | double | substituted thiol | O or S | —CH₂—, —CH₂CH₂—, —CH(R²)—, or —CH₂CH(R²)— | — | —(CH₂)₂— | —NHC(O)— | —CO₂H, —NH₂, —OH, —NH—R³ᵃ, or —CO₂R³ᵇ |
| 170 | double | substituted thiol | O or S | —CH₂—, —CH₂CH₂—, —CH(R²)—, or —CH₂CH(R²)— | — | —(CH₂CH₂O)₁₂— | —NHC(O)— | —CO₂H, —NH₂, —OH, —NH—R³ᵃ, or —CO₂R³ᵇ |
| 171 | double | substituted thiol | O or S | —CH₂—, —CH₂CH₂—, —CH(R²)—, or —CH₂CH(R²)— | — | —(CH₂CH₂O)₆— | —NHC(O)— | —CO₂H, —NH₂, —OH, —NH—R³ᵃ, or —CO₂R³ᵇ |
| 172 | double | substituted thiol | O or S | —CH₂—, —CH₂CH₂—, —CH(R²)—, or —CH₂CH(R²)— | —(CH₂)₂CO— | —NHCH₂CH₂— | —NHC(O)— | —CO₂H, —NH₂, —OH, —NH—R³ᵃ, or —CO₂R³ᵇ |
| 173 | double | substituted thiol | O or S | —CH₂—, —CH₂CH₂—, —CH(R²)—, or —CH₂CH(R²)— | —(CH₂)₄CO— | —NHCH₂CH₂— | —NHC(O)— | —CO₂H, —NH₂, —OH, —NH—R³ᵃ, or —CO₂R³ᵇ |

TABLE 1-continued

Linkers

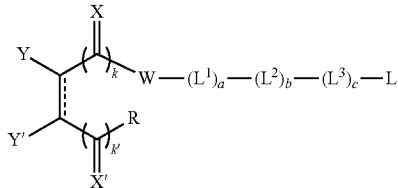

(I)

| Entry | ===== | Y, Y' | X, X' | W | L¹ | L² | L³ | Z |
|---|---|---|---|---|---|---|---|---|
| 174 | double | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NHC(O)— | —CO$_2$H, —NH$_2$, —OH, —NH—R$^{3a}$, or —CO$_2$R$^{3b}$ |
| 175 | double | substituted thiol | O or S | —CH$_2$—, —CH$_2$CH$_2$—, —CH(R$^2$)—, or —CH$_2$CH(R$^2$)— | — | —(CH$_2$)$_2$— | —NCH$_3$C(O)— | —CO$_2$H, —NH$_2$, —OH, —NH—R$^{3a}$, or —CO$_2$R$^{3b}$ |
| 176 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_{12}$— | —NCH$_3$C(O)— | —CO$_2$H, —NH$_2$, —OH, —NH—R$^{3a}$, or —CO$_2$R$^{3b}$ |
| 177 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_6$— | —NCH$_3$C(O)— | —CO$_2$H, —NH$_2$, —OH, —NH—R$^{3a}$, or —CO$_2$R$^{3b}$ |
| 178 | double | substituted thiol | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 179 | double | substituted thiol | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 180 | double | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NCH$_3$C(O)— | —CO$_2$H, —NH$_2$, —OH, —NH—R$^{3a}$, or —CO$_2$R$^{3b}$ |
| 181 | double | substituted sulfonate | O or S | —NH— or —N(R$^1$)— | — | —(CH$_2$)$_2$— | —OC(O)— | —CO$_2$H, —NH$_2$, —OH, —NH—R$^{3a}$, or —CO$_2$R$^{3b}$ |
| 182 | double | substituted sulfonate | O or S | —NH— or —N(R$^1$)— | — | —(CH$_2$CH$_2$O)$_{12}$— | —CH$_2$CH$_2$C(O)— | —CO$_2$H, —NH$_2$, —OH, —NH—R$^{3a}$, or —CO$_2$R$^{3b}$ |
| 183 | double | substituted sulfonate | O or S | —NH— or —N(R$^1$)— | — | —(CH$_2$CH$_2$O)$_6$— | —CH$_2$CH$_2$C(O)— | —CO$_2$H, —NH$_2$, —OH, —NH—R$^{3a}$, or —CO$_2$R$^{3b}$ |
| 184 | double | substituted sulfonate | O or S | —NH— or —N(R$^1$)— | —(CH$_2$)$_2$CO— | —NHCH$_2$CH$_2$— | —OC(O)— | —CO$_2$H, —NH$_2$, —OH, —NH—R$^{3a}$, or —CO$_2$R$^{3b}$ |
| 185 | double | substituted sulfonate | O or S | —NH— or —N(R$^1$)— | —(CH$_2$)$_4$CO— | —NHCH$_2$CH$_2$— | —OC(O)— | —CO$_2$H, —NH$_2$, —OH, —NH—R$^{3a}$, or —CO$_2$R$^{3b}$ |
| 186 | double | substituted sulfonate | O or S | —NH— or —N(R$^1$)— | —(CH$_2$)$_5$CO— | —NHCH$_2$CH$_2$— | —OC(O)— | —CO$_2$H, —NH$_2$, —OH, —NH—R$^{3a}$, or —CO$_2$R$^{3b}$ |
| 187 | double | substituted sulfonate | O or S | —NH— or —N(R$^1$)— | — | —(CH$_2$)$_2$— | —NHC(O)— | —CO$_2$H, —NH$_2$, —OH, —NH—R$^{3a}$, or —CO$_2$R$^{3b}$ |
| 188 | double | substituted sulfonate | O or S | —NH— or —N(R$^1$)— | — | —(CH$_2$CH$_2$O)$_{12}$— | —NHC(O)— | —CO$_2$H, —NH$_2$, —OH, —NH—R$^{3a}$, or —CO$_2$R$^{3b}$ |
| 189 | double | substituted sulfonate | O or S | —NH— or —N(R$^1$)— | — | —(CH$_2$CH$_2$O)$_6$— | —NHC(O)— | —CO$_2$H, —NH$_2$, —OH, —NH—R$^{3a}$, or —CO$_2$R$^{3b}$ |
| 190 | double | substituted sulfonate | O or S | —NH— or —N(R$^1$)— | —(CH$_2$)$_2$CO— | —NHCH$_2$CH$_2$— | —NHC(O)— | —CO$_2$H, —NH$_2$, —OH, —NH—R$^{3a}$, or —CO$_2$R$^{3b}$ |
| 191 | double | substituted sulfonate | O or S | —NH— or —N(R$^1$)— | —(CH$_2$)$_4$CO— | —NHCH$_2$CH$_2$— | —NHC(O)— | —CO$_2$H, —NH$_2$, —OH, —NH—R$^{3a}$, or —CO$_2$R$^{3b}$ |
| 192 | double | substituted sulfonate | O or S | —NH— or —N(R$^1$)— | —(CH$_2$)$_5$CO— | —NHCH$_2$CH$_2$— | —NHC(O)— | —CO$_2$H, —NH$_2$, —OH, —NH—R$^{3a}$, or —CO$_2$R$^{3b}$ |
| 193 | double | substituted sulfonate | O or S | —NH— or —N(R$^1$)— | — | —(CH$_2$)$_2$— | —NCH$_3$C(O)— | —CO$_2$H, —NH$_2$, —OH, —NH—R$^{3a}$, or —CO$_2$R$^{3b}$ |
| 194 | double | substituted sulfonate | O or S | —NH— or —N(R$^1$)— | — | —(CH$_2$CH$_2$O)$_{12}$— | —NCH$_3$C(O)— | —CO$_2$H, —NH$_2$, —OH, —NH—R$^{3a}$, or —CO$_2$R$^{3b}$ |

TABLE 1-continued

Linkers

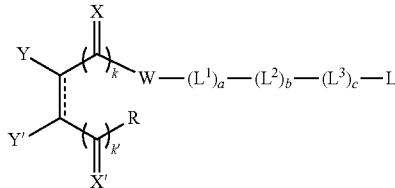

(I)

| Entry | ====== | Y, Y' | X, X' | W | L¹ | L² | L³ | Z |
|---|---|---|---|---|---|---|---|---|
| 195 | double | substituted sulfonate | O or S | —NH— or —N(R¹)— | — | —(CH₂CH₂O)₆— | —NCH₃C(O)— | —CO₂H, —NH₂, —OH, —NH—R³ᵃ, or —CO₂R³ᵇ |
| 196 | double | substituted sulfonate | O or S | —NH— or —N(R¹)— | —(CH₂)₂CO— | —NHCH₂CH₂— | —NCH₃C(O)— | —CO₂H, —NH₂, —OH, —NH—R³ᵃ, or —CO₂R³ᵇ |
| 197 | double | substituted sulfonate | O or S | —NH— or —N(R¹)— | —(CH₂)₄CO— | —NHCH₂CH₂— | —NCH₃C(O)— | —CO₂H, —NH₂, —OH, —NH—R³ᵃ, or —CO₂R³ᵇ |
| 198 | double | substituted sulfonate | O or S | —NH— or —N(R¹)— | —(CH₂)₅CO— | —NHCH₂CH₂— | —NCH₃C(O)— | —CO₂H, —NH₂, —OH, —NH—R³ᵃ, or —CO₂R³ᵇ |
| 199 | double | substituted sulfonate | O or S | —CH₂—, —CH₂CH₂—, —CH(R²)—, or —CH₂CH(R²)— | — | —(CH₂)₂— | —OC(O)— | —CO₂H, —NH₂, —OH, —NH—R³ᵃ, or —CO₂R³ᵇ |
| 200 | double | substituted sulfonate | O or S | —CH₂—, —CH₂CH₂—, —CH(R²)—, or —CH₂CH(R²)— | — | —(CH₂CH₂O)₁₂— | —CH₂CH₂C(O)— | —CO₂H, —NH₂, —OH, —NH—R³ᵃ, or —CO₂R³ᵇ |
| 201 | double | substituted sulfonate | O or S | —CH₂—, —CH₂CH₂—, —CH(R²)—, or —CH₂CH(R²)— | — | —(CH₂CH₂O)₆— | —CH₂CH₂C(O)— | —CO₂H, —NH₂, —OH, —NH—R³ᵃ, or —CO₂R³ᵇ |
| 202 | double | substituted sulfonate | O or S | —CH₂—, —CH₂CH₂—, —CH(R²)—, or —CH₂CH(R²)— | —(CH₂)₂CO— | —NHCH₂CH₂— | —OC(O)— | —CO₂H, —NH₂, —OH, —NH—R³ᵃ, or —CO₂R³ᵇ |
| 203 | double | substituted sulfonate | O or S | —CH₂—, —CH₂CH₂—, —CH(R²)—, or —CH₂CH(R²)— | —(CH₂)₄CO— | —NHCH₂CH₂— | —OC(O)— | —CO₂H, —NH₂, —OH, —NH—R³ᵃ, or —CO₂R³ᵇ |
| 204 | double | substituted sulfonate | O or S | —CH₂—, —CH₂CH₂—, —CH(R²)—, or —CH₂CH(R²)— | —(CH₂)₅CO— | —NHCH₂CH₂— | —OC(O)— | —CO₂H, —NH₂, —OH, —NH—R³ᵃ, or —CO₂R³ᵇ |
| 205 | double | substituted sulfonate | O or S | —CH₂—, —CH₂CH₂—, —CH(R²)—, or —CH₂CH(R²)— | — | —(CH₂)₂— | —NHC(O)— | —CO₂H, —NH₂, —OH, —NH—R³ᵃ, or —CO₂R³ᵇ |
| 206 | double | substituted sulfonate | O or S | —CH₂—, —CH₂CH₂—, —CH(R²)—, or —CH₂CH(R²)— | — | —(CH₂CH₂O)₁₂— | —NHC(O)— | —CO₂H, —NH₂, —OH, —NH—R³ᵃ, or —CO₂R³ᵇ |
| 207 | double | substituted sulfonate | O or S | —CH₂—, —CH₂CH₂—, —CH(R²)—, or —CH₂CH(R²)— | — | —(CH₂CH₂O)₆— | —NHC(O)— | —CO₂H, —NH₂, —OH, —NH—R³ᵃ, or —CO₂R³ᵇ |
| 208 | double | substituted sulfonate | O or S | —CH₂—, —CH₂CH₂—, —CH(R²)—, or —CH₂CH(R²)— | —(CH₂)₂CO— | —NHCH₂CH₂— | —NHC(O)— | —CO₂H, —NH₂, —OH, —NH—R³ᵃ, or —CO₂R³ᵇ |
| 209 | double | substituted sulfonate | O or S | —CH₂—, —CH₂CH₂—, —CH(R²)—, or —CH₂CH(R²)— | —(CH₂)₄CO— | —NHCH₂CH₂— | —NHC(O)— | —CO₂H, —NH₂, —OH, —NH—R³ᵃ, or —CO₂R³ᵇ |
| 210 | double | substituted sulfonate | O or S | —CH₂—, —CH₂CH₂—, —CH(R²)—, or —CH₂CH(R²)— | —(CH₂)₅CO— | —NHCH₂CH₂— | —NHC(O)— | —CO₂H, —NH₂, —OH, —NH—R³ᵃ, or —CO₂R³ᵇ |
| 211 | double | substituted sulfonate | O or S | —CH₂—, —CH₂CH₂—, —CH(R²)—, or —CH₂CH(R²)— | — | —(CH₂)₂— | —NCH₃C(O)— | —CO₂H, —NH₂, —OH, —NH—R³ᵃ, or —CO₂R³ᵇ |
| 212 | double | substituted sulfonate | O or S | —CH₂—, —CH₂CH₂—, —CH(R²)—, or —CH₂CH(R²)— | — | —(CH₂CH₂O)₁₂— | —NCH₃C(O)— | —CO₂H, —NH₂, —OH, —NH—R³ᵃ, or —CO₂R³ᵇ |
| 213 | double | substituted sulfonate | O or S | —CH₂—, —CH₂CH₂—, —CH(R²)—, or —CH₂CH(R²)— | — | —(CH₂CH₂O)₆— | —NCH₃C(O)— | —CO₂H, —NH₂, —OH, —NH—R³ᵃ, or —CO₂R³ᵇ |
| 214 | double | substituted sulfonate | O or S | —CH₂—, —CH₂CH₂—, —CH(R²)—, or —CH₂CH(R²)— | —(CH₂)₂CO— | —NHCH₂CH₂— | —NCH₃C(O)— | —CO₂H, —NH₂, —OH, —NH—R³ᵃ, or —CO₂R³ᵇ |
| 215 | double | substituted sulfonate | O or S | —CH₂—, —CH₂CH₂—, —CH(R²)—, or —CH₂CH(R²)— | —(CH₂)₄CO— | —NHCH₂CH₂— | —NCH₃C(O)— | —CO₂H, —NH₂, —OH, —NH—R³ᵃ, or —CO₂R³ᵇ |

TABLE 1-continued

Linkers $$\text{(I)}$$

$$Y\underset{Y'}{\overset{X}{\underset{\|}{\bigcirc}}}\underset{X'}{\overset{R}{\underset{\|}{\bigcirc}}}W-(L^1)_a-(L^2)_b-(L^3)_c-L$$

| Entry | ------ | Y, Y' | X, X' | W | L¹ | L² | L³ | Z |
|---|---|---|---|---|---|---|---|---|
| 216 | double | substituted sulfonate | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NCH$_3$C(O)— | —CO$_2$H, —NH$_2$, —OH, —NH—R$^{3a}$, or —CO$_2$R$^{3b}$ |

For all Entries 1-216 Provided in Table 1 Above, R, k, k', a, b and c May be Defined as Follows:

R: W, (L$^1$)$_a$, (L$^2$)$_b$, (L$^3$)$_c$, Z, W-(L$^1$)$_a$-(L$^2$)$_b$-(L$^3$)$_c$, (L$^1$)$_a$-(L$^2$)$_b$-(L$^3$)$_c$-Z, W-(L$^1$)$_a$-(L$^2$)$_b$-(L$^3$)$_c$-Z, a detectable probe, a ligand, or an antibody fragment k, k': each independently 0 or 1 a, b and c: each independently 0, 1, 2 or 3, provided that at least one of a, b or c is 1

TABLE 2

Linker-Cytotoxin Conjugates $$\text{(II)}$$

$$Y\underset{Y'}{\overset{X}{\underset{\|}{\bigcirc}}}\underset{X'}{\overset{R}{\underset{\|}{\bigcirc}}}W-(L^1)_a-(L^2)_b-(L^3)_c-(CTX)_m$$

| Entry | ------ | Y, Y' | X, X' | W | L¹ | L² | L³ | Bond to CTX |
|---|---|---|---|---|---|---|---|---|
| 1 | single | halo | O or S | —NH— or —N(R$^1$)— | — | —(CH$_2$)$_2$— | —OC(O)— | amide, N-alkylamide, carbamate, N-alkylcarbamate, amine, N-alkylamine, ether, thioether, urea, N-alkylurea, or N,N-dialkylurea |
| 2 | single | halo | O or S | —NH— or —N(R$^1$)— | — | —(CH$_2$CH$_2$O)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 3 | single | halo | O or S | —NH— or —N(R$^1$)— | — | —(CH$_2$CH$_2$O)$_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 4 | single | halo | O or S | —NH— or —N(R$^1$)— | —(CH$_2$)$_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 5 | single | halo | O or S | —NH— or —N(R$^1$)— | —(CH$_2$)$_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 6 | single | halo | O or S | —NH— or —N(R$^1$)— | —(CH$_2$)$_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 7 | single | halo | O or S | —NH— or —N(R$^1$)— | — | —(CH$_2$)$_2$— | —NHC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

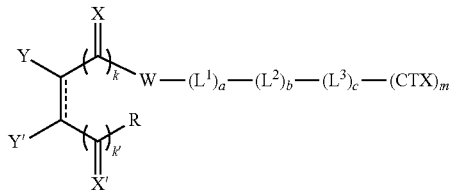
(II)

| Entry | ====== | Y, Y' | X, X' | W | $L^1$ | $L^2$ | $L^3$ | Bond to CTX |
|---|---|---|---|---|---|---|---|---|
| 8 | single | halo | O or S | —NH— or —N($R^1$)— | — | —($CH_2CH_2O)_{12}$— | —NHC(O)— | amide, N-alkylamide, carbamate, N-alkylcarbamate, amine, N-alkylamine, ether, thioether, urea, N-alkylurea, or N,N-dialkylurea |
| 9 | single | halo | O or S | —NH— or —N($R^1$)— | — | —($CH_2CH_2O)_6$— | —NHC(O)— | amide, N-alkylamide, carbamate, N-alkylcarbamate, amine, N-alkylamine, ether, thioether, urea, N-alkylurea, or N,N-dialkylurea |
| 10 | single | halo | O or S | —NH— or —N($R^1$)— | —($CH_2)_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 11 | single | halo | O or S | —NH— or —N($R^1$)— | —($CH_2)_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 12 | single | halo | O or S | —NH— or —N($R^1$)— | —($CH_2)_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 13 | single | halo | O or S | —NH— or —N($R^1$)— | — | —($CH_2)_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 14 | single | halo | O or S | —NH— or —N($R^1$)— | — | —($CH_2CH_2O)_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 15 | single | halo | O or S | —NH— or —N($R^1$)— | — | —($CH_2CH_2O)_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 16 | single | halo | O or S | —NH— or —N($R^1$)— | —($CH_2)_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 17 | single | halo | O or S | —NH— or —N($R^1$)— | —($CH_2)_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 18 | single | halo | O or S | —NH— or —N($R^1$)— | —($CH_2)_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 19 | single | halo | O or S | —CH$_2$—, —CH$_2$CH$_2$—, —CH($R^2$)—, or —CH$_2$CH($R^2$)— | — | —($CH_2)_2$— | —OC(O)— | amide, N-alkylamide, carbamate, N-alkylcarbamate, amine, N-alkylamine, ether, thioether, urea, N-alkylurea, or N,N-dialkylurea |
| 20 | single | halo | O or S | —CH$_2$—, —CH$_2$CH$_2$—, —CH($R^2$)—, or —CH$_2$CH($R^2$)— | — | —($CH_2CH_2O)_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 21 | single | halo | O or S | —CH$_2$—, —CH$_2$CH$_2$—, —CH($R^2$)—, or —CH$_2$CH($R^2$)— | — | —($CH_2CH_2O)_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 22 | single | halo | O or S | —CH$_2$—, —CH$_2$CH$_2$—, —CH($R^2$)—, or —CH$_2$CH($R^2$)— | —($CH_2)_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 23 | single | halo | O or S | —CH$_2$—, —CH$_2$CH$_2$—, —CH($R^2$)—, or —CH$_2$CH($R^2$)— | —($CH_2)_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

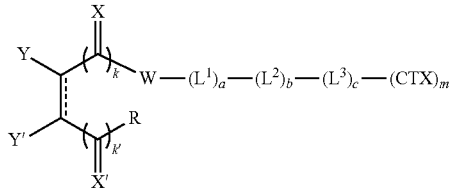

(II)

| Entry | ===== | Y, Y' | X, X' | W | L$^1$ | L$^2$ | L$^3$ | Bond to CTX |
|---|---|---|---|---|---|---|---|---|
| 24 | single | halo | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 25 | single | halo | O or S | —CH$_2$—, —CH$_2$CH$_2$—, —CH(R$^2$)—, or —CH$_2$CH(R$^2$)— | — | —(CH$_2$)$_2$— | —NHC(O)— | amide, N-alkylamide, carbamate, N-alkylcarbamate, amine, N-alkylamine, ether, thioether, urea, N-alkylurea, or N,N-dialkylurea |
| 26 | single | halo | O or S | —CH$_2$—, —CH$_2$CH$_2$—, —CH(R$^2$)—, or —CH$_2$CH(R$^2$)— | — | —(CH$_2$CH$_2$O)$_{12}$— | —NHC(O)— | amide, N-alkylamide, carbamate, N-alkylcarbamate, amine, N-alkylamine, ether, thioether, urea, N-alkylurea, or N,N-dialkylurea |
| 27 | single | halo | O or S | —CH$_2$—, —CH$_2$CH$_2$—, —CH(R$^2$)—, or —CH$_2$CH(R$^2$)— | — | —(CH$_2$CH$_2$O)$_6$— | —NHC(O)— | amide, N-alkylamide, carbamate, N-alkylcarbamate, amine, N-alkylamine, ether, thioether, urea, N-alkylurea, or N,N-dialkylurea |
| 28 | single | halo | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 29 | single | halo | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 30 | single | halo | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 31 | single | halo | O or S | —CH$_2$—, —CH$_2$CH$_2$—, —CH(R$^2$)—, or —CH$_2$CH(R$^2$)— | — | —(CH$_2$)$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 32 | single | halo | O or S | —CH$_2$—, —CH$_2$CH$_2$—, —CH(R$^2$)—, or —CH$_2$CH(R$^2$)— | — | —(CH$_2$CH$_2$O)$_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 33 | single | halo | O or S | —CH$_2$—, —CH$_2$CH$_2$—, —CH(R$^2$)—, or —CH$_2$CH(R$^2$)— | — | —(CH$_2$CH$_2$O)$_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 34 | single | halo | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 35 | single | halo | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 36 | single | halo | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 37 | single | substituted thiol | O or S | —NH— or —N(R$^1$)— | — | —(CH$_2$)$_2$— | —OC(O)— | amide, N-alkylamide, carbamate, N-alkylcarbamate, amine, N-alkylamine, ether, thioether, urea, N-alkylurea, or N,N-dialkylurea |
| 38 | single | substituted thiol | O or S | —NH— or —N(R$^1$)— | — | —(CH$_2$CH$_2$O)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 39 | single | substituted thiol | O or S | —NH— or —N(R$^1$)— | — | —(CH$_2$CH$_2$O)$_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

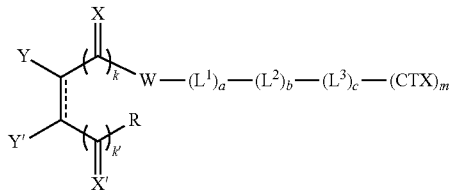

(II)

| Entry | ===== | Y, Y' | X, X' | W | L¹ | L² | L³ | Bond to CTX |
|---|---|---|---|---|---|---|---|---|
| 40 | single | substituted thiol | O or S | —NH— or —N(R¹)— | —(CH₂)₂CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 41 | single | substituted thiol | O or S | —NH— or —N(R¹)— | —(CH₂)₄CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 42 | single | substituted thiol | O or S | —NH— or —N(R¹)— | —(CH₂)₅CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 43 | single | substituted thiol | O or S | —NH— or —N(R¹)— | — | —(CH₂)₂— | —NHC(O)— | amide, N-alkylamide, carbamate, N-alkylcarbamate, amine, N-alkylamine, ether, thioether, urea, N-alkylurea, or N,N-dialkylurea |
| 44 | single | substituted thiol | O or S | —NH— or —N(R¹)— | — | —(CH₂CH₂O)₁₂— | —NHC(O)— | amide, N-alkylamide, carbamate, N-alkylcarbamate, amine, N-alkylamine, ether, thioether, urea, N-alkylurea, or N,N-dialkylurea |
| 45 | single | substituted thiol | O or S | —NH— or —N(R¹)— | — | —(CH₂CH₂O)₆— | —NHC(O)— | amide, N-alkylamide, carbamate, N-alkylcarbamate, amine, N-alkylamine, ether, thioether, urea, N-alkylurea, or N,N-dialkylurea |
| 46 | single | substituted thiol | O or S | —NH— or —N(R¹)— | —(CH₂)₂CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 47 | single | substituted thiol | O or S | —NH— or —N(R¹)— | —(CH₂)₄CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 48 | single | substituted thiol | O or S | —NH— or —N(R¹)— | —(CH₂)₅CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 49 | single | substituted thiol | O or S | —NH— or —N(R¹)— | — | —(CH₂)₂— | —NCH₃C(O)— | amide, N-alkylamide, carbamate, N-alkylcarbamate, amine, N-alkylamine, ether, thioether, urea, N-alkylurea, or N,N-dialkylurea |
| 50 | single | substituted thiol | O or S | —NH— or —N(R¹)— | — | —(CH₂CH₂O)₁₂— | —NCH₃C(O)— | amide, N-alkylamide, carbamate, N-alkylcarbamate, amine, N-alkylamine, ether, thioether, urea, N-alkylurea, or N,N-dialkylurea |
| 51 | single | substituted thiol | O or S | —NH— or —N(R¹)— | — | —(CH₂CH₂O)₆— | —NCH₃C(O)— | amide, N-alkylamide, carbamate, N-alkylcarbamate, amine, N-alkylamine, ether, thioether, urea, N-alkylurea, or N,N-dialkylurea |
| 52 | single | substituted thiol | O or S | —NH— or —N(R¹)— | —(CH₂)₂CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |
| 53 | single | substituted thiol | O or S | —NH— or —N(R¹)— | —(CH₂)₄CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |
| 54 | single | substituted thiol | O or S | —NH— or —N(R¹)— | —(CH₂)₅CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |
| 55 | single | substituted thiol | O or S | —CH₂—, —CH₂CH₂—, —CH(R²)—, or —CH₂CH(R²)— | — | —(CH₂)₂— | —OC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

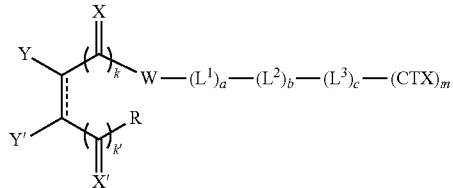
(II)

| En-try | ===== | Y, Y' | X, X' | W | L$^1$ | L$^2$ | L$^3$ | Bond to CTX |
|---|---|---|---|---|---|---|---|---|
| 56 | single | substituted thiol | O or S | —CH$_2$—, —CH$_2$CH$_2$—, —CH(R$^2$)—, or —CH$_2$CH(R$^2$)— | — | —(CH$_2$CH$_2$O)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 57 | single | substituted thiol | O or S | —CH$_2$—, —CH$_2$CH$_2$—, —CH(R$^2$)—, or —CH$_2$CH(R$^2$)— | — | —(CH$_2$CH$_2$O)$_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 58 | single | substituted thiol | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 59 | single | substituted thiol | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 60 | single | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 61 | single | substituted thiol | O or S | —CH$_2$—, —CH$_2$CH$_2$—, —CH(R$^2$)—, or —CH$_2$CH(R$^2$)— | — | —(CH$_2$)$_2$— | —NHC(O)— | amide, N-alkylamide, carbamate, N-alkylcarbamate, amine, N-alkylamine, ether, thioether, urea, N-alkylurea, or N,N-dialkylurea |
| 62 | single | substituted thiol | O or S | —CH$_2$—, —CH$_2$CH$_2$—, —CH(R$^2$)—, or —CH$_2$CH(R$^2$)— | — | —(CH$_2$CH$_2$O)$_{12}$— | —NHC(O)— | amide, N-alkylamide, carbamate, N-alkylcarbamate, amine, N-alkylamine, ether, thioether, urea, N-alkylurea, or N,N-dialkylurea |
| 63 | single | substituted thiol | O or S | —CH$_2$—, —CH$_2$CH$_2$—, —CH(R$^2$)—, or —CH$_2$CH(R$^2$)— | — | —(CH$_2$CH$_2$O)$_6$— | —NHC(O)— | amide, N-alkylamide, carbamate, N-alkylcarbamate, amine, N-alkylamine, ether, thioether, urea, N-alkylurea, or N,N-dialkylurea |
| 64 | single | substituted thiol | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NHC(O)— | am TABLE 2-continued Linker-Cytotoxin Conjugates

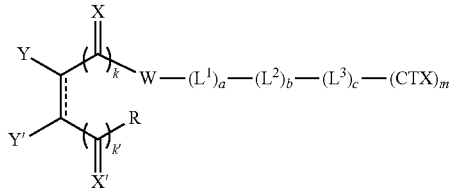

(II)

| Entry | ====== | Y, Y' | X, X' | W | L¹ | L² | L³ | Bond to CTX |
|---|---|---|---|---|---|---|---|---|
| 72 | single | substituted thiol | O or S | —CH₂—, —CH₂CH₂—, —CH(R²)—, or —CH₂CH(R²)— | —(CH₂)₅CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |
| 73 | single | substituted sulfonate | O or S | —NH— or —N(R¹)— | — | —(CH₂)₂— | —OC(O)— | amide, N-alkylamide, carbamate, N-alkylcarbamate, amine, N-alkylamine, ether, thioether, urea, N-alkylurea, or N,N-dialkylurea |
| 74 | single | substituted sulfonate | O or S | —NH— or —N(R¹)— | — | —(CH₂CH₂O)₁₂— | —CH₂CH₂C(O)— | amide, N-alkylamide, carbamate, N-alkylcarbamate, amine, N-alkylamine, ether, thioether, urea, N-alkylurea, or N,N-dialkylurea |
| 75 | single | substituted sulfonate | O or S | —NH— or —N(R¹)— | — | —(CH₂CH₂O)₆— | —CH₂CH₂C(O)— | amide, N-alkylamide, carbamate, N-alkylcarbamate, amine, N-alkylamine, ether, thioether, urea, N-alkylurea, or N,N-dialkylurea |
| 76 | single | substituted sulfonate | O or S | —NH— or —N(R¹)— | —(CH₂)₂CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 77 | single | substituted sulfonate | O or S | —NH— or —N(R¹)— | —(CH₂)₄CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 78 | single | substituted sulfonate | O or S | —NH— or —N(R¹)— | —(CH₂)₅CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 79 | single | substituted sulfonate | O or S | —NH— or —N(R¹)— | — | —(CH₂)₂— | —NHC(O)— | amide, N-alkylamide, carbamate, N-alkylcarbamate, amine, N-alkylamine, ether, thioether, urea, N-alkylurea, or N,N-dialkylurea |
| 80 | single | substituted sulfonate | O or S | —NH— or —N(R¹)— | — | —(CH₂CH₂O)₁₂— | —NHC(O)— | amide, N-alkylamide, carbamate, N-alkylcarbamate, amine, N-alkylamine, ether, thioether, urea, N-alkylurea, or N,N-dialkylurea |
| 81 | single | substituted sulfonate | O or S | —NH— or —N(R¹)— | — | —(CH₂CH₂O)₆— | —NHC(O)— | amide, N-alkylamide, carbamate, N-alkylcarbamate, amine, N-alkylamine, ether, thioether, urea, N-alkylurea, or N,N-dialkylurea |
| 82 | single | substituted sulfonate | O or S | —NH— or —N(R¹)— | —(CH₂)₂CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 83 | single | substituted sulfonate | O or S | —NH— or —N(R¹)— | —(CH₂)₄CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 84 | single | substituted sulfonate | O or S | —NH— or —N(R¹)— | —(CH₂)₅CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 85 | single | substituted sulfonate | O or S | —NH— or —N(R¹)— | — | —(CH₂)₂— | —NCH₃C(O)— | amide, N-alkylamide, carbamate, N-alkylcarbamate, amine, N-alkylamine, ether, thioether, urea, N-alkylurea, or N,N-dialkylurea |
| 86 | single | substituted sulfonate | O or S | —NH— or —N(R¹)— | — | —(CH₂CH₂O)₁₂— | —NCH₃C(O)— | amide, N-alkylamide, carbamate, N-alkylcarbamate, amine, N-alkylamine, ether, thioether, urea, N-alkylurea, or N,N-dialkylurea |
| 87 | single | substituted sulfonate | O or S | —NH— or —N(R¹)— | — | —(CH₂CH₂O)₆— | —NCH₃C(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates (II)

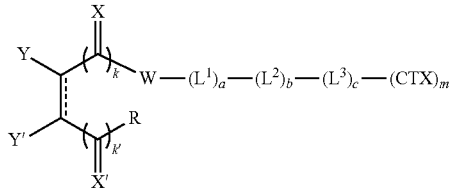

| Entry | ===== | Y, Y' | X, X' | W | $L^1$ | $L^2$ | $L^3$ | Bond to CTX |
|---|---|---|---|---|---|---|---|---|
| 88 | single | substituted sulfonate | O or S | —NH— or —N($R^1$)— | —$(CH_2)_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 89 | single | substituted sulfonate | O or S | —NH— or —N($R^1$)— | —$(CH_2)_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 90 | single | substituted sulfonate | O or S | —NH— or —N($R^1$)— | —$(CH_2)_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 91 | single | substituted sulfonate | O or S | —CH$_2$—, —CH$_2$CH$_2$—, —CH($R^2$)—, or —CH$_2$CH($R^2$)— | — | —$(CH_2)_2$— | —OC(O)— | amide, N-alkylamide, carbamate, N-alkylcarbamate, amine, N-alkylamine, ether, thioether, urea, N-alkylurea, or N,N-dialkylurea |
| 92 | single | substituted sulfonate | O or S | —CH$_2$—, —CH$_2$CH$_2$—, —CH($R^2$)—, or —CH$_2$CH($R^2$)— | — | —$(CH_2CH_2O)_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 93 | single | substituted sulfonate | O or S | —CH$_2$—, —CH$_2$CH$_2$—, —CH($R^2$)—, or —CH$_2$CH($R^2$)— | — | —$(CH_2CH_2O)_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 94 | single | substituted sulfonate | O or S | —CH$_2$—, —CH$_2$CH$_2$—, —CH($R^2$)—, or —CH$_2$CH($R^2$)— | —$(CH_2)_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 95 | single | substituted sulfonate | O or S | —CH$_2$—, —CH$_2$CH$_2$—, —CH($R^2$)—, or —CH$_2$CH($R^2$)— | —$(CH_2)_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 96 | single | substituted sulfonate | O or S | —CH$_2$—, —CH$_2$CH$_2$—, —CH($R^2$)—, or —CH$_2$CH($R^2$)— | —$(CH_2)_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 97 | single | substituted sulfonate | O or S | —CH$_2$—, —CH$_2$CH$_2$—, —CH($R^2$)—, or —CH$_2$CH($R^2$)— | — | —$(CH_2)_2$— | —NHC(O)— | amide, N-alkylamide, carbamate, N-alkylcarbamate, amine, N-alkylamine, ether, thioether, urea, N-alkylurea, or N,N-dialkylurea |
| 98 | single | substituted sulfonate | O or S | —CH$_2$—, —CH$_2$CH$_2$—, —CH($R^2$)—, or —CH$_2$CH($R^2$)— | — | —$(CH_2CH_2O)_{12}$— | —NHC(O)— | amide, N-alkylamide, carbamate, N-alkylcarbamate, amine, N-alkylamine, ether, thioether, urea, N-alkylurea, or N,N-dialkylurea |
| 99 | single | substituted sulfonate | O or S | —CH$_2$—, —CH$_2$CH$_2$—, —CH($R^2$)—, or —CH$_2$CH($R^2$)— | — | —$(CH_2CH_2O)_6$— | —NHC(O)— | amide, N-alkylamide, carbamate, N-alkylcarbamate, amine, N-alkylamine, ether, thioether, urea, N-alkylurea, or N,N-dialkylurea |
| 100 | single | substituted sulfonate | O or S | —CH$_2$—, —CH$_2$CH$_2$—, —CH($R^2$)—, or —CH$_2$CH($R^2$)— | —$(CH_2)_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 101 | single | substituted sulfonate | O or S | —CH$_2$—, —CH$_2$CH$_2$—, —CH($R^2$)—, or —CH$_2$CH($R^2$)— | —$(CH_2)_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 102 | single | substituted sulfonate | O or S | —CH$_2$—, —CH$_2$CH$_2$—, —CH($R^2$)—, or —CH$_2$CH($R^2$)— | —$(CH_2)_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 103 | single | substituted sulfonate | O or S | —CH$_2$—, —CH$_2$CH$_2$—, —CH($R^2$)—, or —CH$_2$CH($R^2$)— | — | —$(CH_2)_2$— | —NCH$_3$C(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

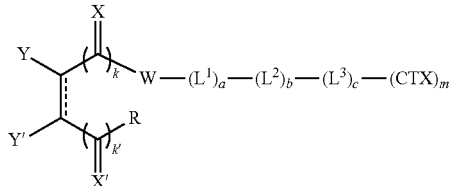

(II)

| Entry | ===== | Y, Y' | X, X' | W | $L^1$ | $L^2$ | $L^3$ | Bond to CTX |
|---|---|---|---|---|---|---|---|---|
| 104 | single | substituted sulfonate | O or S | —$CH_2$—, —$CH_2CH_2$—, —$CH(R^2)$—, or —$CH_2CH(R^2)$— | — | —$(CH_2CH_2O)_{12}$— | —$NCH_3C(O)$— | amide, N-alkylamide, carbamate, N-alkylcarbamate, amine, N-alkylamine, ether, thioether, urea, N-alkylurea, or N,N-dialkylurea |
| 105 | single | substituted sulfonate | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | amide, N-alkylamide, carbamate, N-alkylcarbamate, amine, N-alkylamine, ether, thioether, urea, N-alkylurea, or N,N-dialkylurea |
| 106 | single | substituted sulfonate | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 107 | single | substituted sulfonate | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 108 | single | substituted sulfonate | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 109 | double | halo | O or S | —NH— or —$N(R^1)$— | — | —$(CH_2)_2$— | —$OC(O)$— | amide, N-alkylamide, carbamate, N-alkylcarbamate, amine, N-alkylamine, ether, thioether, urea, N-alkylurea, or N,N-dialkylurea |
| 110 | double | halo | O or S | —NH— or —$N(R^1)$— | — | —$(CH_2CH_2O)_{12}$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 111 | double | halo | O or S | —NH— or —$N(R^1)$— | — | —$(CH_2CH_2O)_6$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 112 | double | halo | O or S | —NH— or —$N(R^1)$— | —$(CH_2)_2CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 113 | double | halo | O or S | —NH— or —$N(R^1)$— | —$(CH_2)_4CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 114 | double | halo | O or S | —NH— or —$N(R^1)$— | —$(CH_2)_5CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 115 | double | halo | O or S | —NH— or —$N(R^1)$— | — | —$(CH_2)_2$— | —$NHC(O)$— | amide, N-alkylamide, carbamate, N-alkylcarbamate, amine, N-alkylamine, ether, thioether, urea, N-alkylurea, or N,N-dialkylurea |
| 116 | double | halo | O or S | —NH— or —$N(R^1)$— | — | —$(CH_2CH_2O)_{12}$— | —$NHC(O)$— | amide, N-alkylamide, carbamate, N-alkylcarbamate, amine, N-alkylamine, ether, thioether, urea, N-alkylurea, or N,N-dialkylurea |
| 117 | double | halo | O or S | —NH— or —$N(R^1)$— | — | —$(CH_2CH_2O)_6$— | —$NHC(O)$— | amide, N-alkylamide, carbamate, N-alkylcarbamate, amine, N-alkylamine, ether, thioether, urea, N-alkylurea, or N,N-dialkylurea |
| 118 | double | halo | O or S | —NH— or —$N(R^1)$— | —$(CH_2)_2CO$— | —$NHCH_2CH_2$— | —$NHC(O)$— | amide, N-alkylamide, carbamate, N-alkylcarbamate, amine, N-alkylamine, ether, thioether, urea, N-alkylurea, or N,N-dialkylurea |
| 119 | double | halo | O or S | —NH— or —$N(R^1)$— | —$(CH_2)_4CO$— | —$NHCH_2CH_2$— | —$NHC(O)$— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

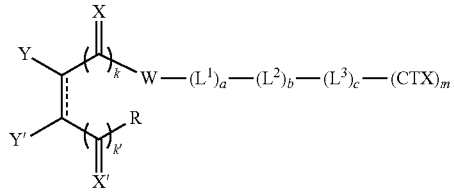
(II)

| Entry | ═══ | Y, Y' | X, X' | W | $L^1$ | $L^2$ | $L^3$ | Bond to CTX |
|---|---|---|---|---|---|---|---|---|
| 120 | double | halo | O or S | —NH— or —N($R^1$)— | —$(CH_2)_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 121 | double | halo | O or S | —NH— or —N($R^1$)— | — | —$(CH_2)_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 122 | double | halo | O or S | —NH— or —N($R^1$)— | — | —(CH$_2$CH$_2$O)$_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 123 | double | halo | O or S | —NH— or —N($R^1$)— | — | —(CH$_2$CH$_2$O)$_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 124 | double | halo | O or S | —NH— or —N($R^1$)— | —(CH$_2$)$_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 125 | double | halo | O or S | —NH— or —N($R^1$)— | —(CH$_2$)$_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 126 | double | halo | O or S | —NH— or —N($R^1$)— | —(CH$_2$)$_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 127 | double | halo | O or S | —CH$_2$—, —CH$_2$CH$_2$—, —CH($R^2$)—, or —CH$_2$CH($R^2$)— | — | —(CH$_2$)$_2$— | —OC(O)— | amide, N-alkylamide, carbamate, N-alkylcarbamate, amine, N-alkylamine, ether, thioether, urea, N-alkylurea, or N,N-dialkylurea |
| 128 | double | halo | O or S | —CH$_2$—, —CH$_2$CH$_2$—, —CH($R^2$)—, or —CH$_2$CH($R^2$)— | — | —(CH$_2$CH$_2$O)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 129 | double | halo | O or S | —CH$_2$—, —CH$_2$CH$_2$—, —CH($R^2$)—, or —CH$_2$CH($R^2$)— | — | —(CH$_2$CH$_2$O)$_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 130 | double | halo | O or S | —CH$_2$—, —CH$_2$CH$_2$—, —CH($R^2$)—, or —CH$_2$CH($R^2$)— | —(CH$_2$)$_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 131 | double | halo | O or S | —CH$_2$—, —CH$_2$CH$_2$—, —CH($R^2$)—, or —CH$_2$CH($R^2$)— | —(CH$_2$)$_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 132 | double | halo | O or S | —CH$_2$—, —CH$_2$CH$_2$—, —CH($R^2$)—, or —CH$_2$CH($R^2$)— | —(CH$_2$)$_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 133 | double | halo | O or S | —CH$_2$—, —CH$_2$CH$_2$—, —CH($R^2$)—, or —CH$_2$CH($R^2$)— | — | —(CH$_2$)$_2$— | —NHC(O)— | amide, N-alkylamide, carbamate, N-alkylcarbamate, amine, N-alkylamine, ether, thioether, urea, N-alkylurea, or N,N-dialkylurea |
| 134 | double | halo | O or S | —CH$_2$—, —CH$_2$CH$_2$—, —CH($R^2$)—, or —CH$_2$CH($R^2$)— | — | —(CH$_2$CH$_2$O)$_{12}$— | —NHC(O)— | amide, N-alkylamide, carbamate, N-alkylcarbamate, amine, N-alkylamine, ether, thioether, urea, N-alkylurea, or N,N-dialkylurea |
| 135 | double | halo | O or S | —CH$_2$—, —CH$_2$CH$_2$—, —CH($R^2$)—, or —CH$_2$CH($R^2$)— | — | —(CH$_2$CH$_2$O)$_6$— | —NHC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

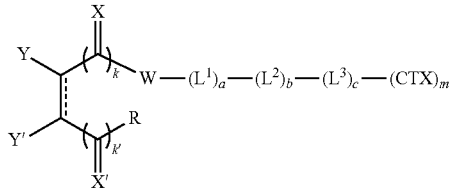

(II)

| Entry | ====== | Y, Y' | X, X' | W | $L^1$ | $L^2$ | $L^3$ | Bond to CTX |
|---|---|---|---|---|---|---|---|---|
| 136 | double | halo | O or S | —$CH_2$—, —$CH_2CH_2$—, —$CH(R^2)$—, or —$CH_2CH(R^2)$— | —$(CH_2)_2CO$— | —$NHCH_2CH_2$— | —$NHC(O)$— | amide, N-alkylamide, carbamate, N-alkylcarbamate, amine, N-alkylamine, ether, thioether, urea, N-alkylurea, or N,N-dialkylurea |
| 137 | double | halo | O or S | —$CH_2$—, —$CH_2CH_2$—, —$CH(R^2)$—, or —$CH_2CH(R^2)$— | —$(CH_2)_4CO$— | —$NHCH_2CH_2$— | —$NHC(O)$— | amide, N-alkylamide, carbamate, N-alkylcarbamate, amine, N-alkylamine, ether, thioether, urea, N-alkylurea, or N,N-dialkylurea |
| 138 | double | halo | O or S | —$CH_2$—, —$CH_2CH_2$—, —$CH(R^2)$—, or —$CH_2CH(R^2)$— | —$(CH_2)_5CO$— | —$NHCH_2CH_2$— | —$NHC(O)$— | amide, N-alkylamide, carbamate, N-alkylcarbamate, amine, N-alkylamine, ether, thioether, urea, N-alkylurea, or N,N-dialkylurea |
| 139 | double | halo | O or S | —$CH_2$—, —$CH_2CH_2$—, —$CH(R^2)$—, or —$CH_2CH(R^2)$— | — | —$(CH_2)_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 140 | double | halo | O or S | —$CH_2$—, —$CH_2CH_2$—, —$CH(R^2)$—, or —$CH_2CH(R^2)$— | — | —$(CH_2CH_2O)_{12}$— | —$NCH_3C(O)$— | amide, N-alkylamide, carbamate, N-alkylcarbamate, amine, N-alkylamine, ether, thioether, urea, N-alkylurea, or N,N-dialkylurea |
| 141 | double | halo | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | amide, N-alkylamide, carbamate, N-alkylcarbamate, amine, N-alkylamine, ether, thioether, urea, N-alkylurea, or N,N-dialkylurea |
| 142 | double | halo | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 143 | double | halo | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 144 | double | halo | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 145 | double | substituted thiol | O or S | —NH— or —$N(R^1)$— | — | —$(CH_2)_2$— | —$OC(O)$— | amide, N-alkylamide, carbamate, N-alkylcarbamate, amine, N-alkylamine, ether, thioether, urea, N-alkylurea, or N,N-dialkylurea |
| 146 | double | substituted thiol | O or S | —NH— or —$N(R^1)$— | — | —$(CH_2CH_2O)_{12}$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 147 | double | substituted thiol | O or S | —NH— or —$N(R^1)$— | — | —$(CH_2CH_2O)_6$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 148 | double | substituted thiol | O or S | —NH— or —$N(R^1)$— | —$(CH_2)_2CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 149 | double | substituted thiol | O or S | —NH— or —$N(R^1)$— | —$(CH_2)_4CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 150 | double | substituted thiol | O or S | —NH— or —$N(R^1)$— | —$(CH_2)_5CO$— | —$NHCH_2CH_2$— | —$OC(O)$— | amide, N-alkylamide, carbamate, N-alkylcarbamate, amine, N-alkylamine, ether, thioether, urea, N-alkylurea, or N,N-dialkylurea |
| 151 | double | substituted thiol | O or S | —NH— or —$N(R^1)$— | — | —$(CH_2)_2$— | —$NHC(O)$— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

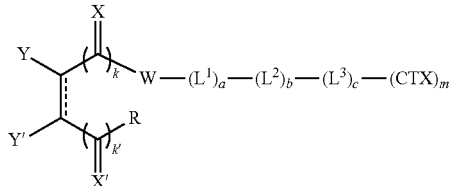
(II)

| Entry | ====== | Y, Y' | X, X' | W | $L^1$ | $L^2$ | $L^3$ | Bond to CTX |
|---|---|---|---|---|---|---|---|---|
| 152 | double | substituted thiol | O or S | —NH— or —N($R^1$)— | — | —($CH_2CH_2O$)$_{12}$— | —NHC(O)— | amide, N-alkylamide, carbamate, N-alkylcarbamate, amine, N-alkylamine, ether, thioether, urea, N-alkylurea, or N,N-dialkylurea |
| 153 | double | substituted thiol | O or S | —NH— or —N($R^1$)— | — | —($CH_2CH_2O$)$_6$— | —NHC(O)— | amide, N-alkylamide, carbamate, N-alkylcarbamate, amine, N-alkylamine, ether, thioether, urea, N-alkylurea, or N,N-dialkylurea |
| 154 | double | substituted thiol | O or S | —NH— or —N($R^1$)— | —($CH_2$)$_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 155 | double | substituted thiol | O or S | —NH— or —N($R^1$)— | —($CH_2$)$_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 156 | double | substituted thiol | O or S | —NH— or —N($R^1$)— | —($CH_2$)$_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 157 | double | substituted thiol | O or S | —NH— or —N($R^1$)— | — | —($CH_2$)$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 158 | double | substituted thiol | O or S | —NH— or —N($R^1$)— | — | —($CH_2CH_2O$)$_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 159 | double | substituted thiol | O or S | —NH— or —N($R^1$)— | — | —($CH_2CH_2O$)$_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 160 | double | substituted thiol | O or S | —NH— or —N($R^1$)— | —($CH_2$)$_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 161 | double | substituted thiol | O or S | —NH— or —N($R^1$)— | —($CH_2$)$_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 162 | double | substituted thiol | O or S | —NH— or —N($R^1$)— | —($CH_2$)$_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 163 | double | substituted thiol | O or S | —CH$_2$—, —CH$_2$CH$_2$—, —CH($R^2$)—, or —CH$_2$CH($R^2$)— | — | —($CH_2$)$_2$— | —OC(O)— | amide, N-alkylamide, carbamate, N-alkylcarbamate, amine, N-alkylamine, ether, thioether, urea, N-alkylurea, or N,N-dialkylurea |
| 164 | double | substituted thiol | O or S | —CH$_2$—, —CH$_2$CH$_2$—, —CH($R^2$)—, or —CH$_2$CH($R^2$)— | — | —($CH_2CH_2O$)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 165 | double | substituted thiol | O or S | —CH$_2$—, —CH$_2$CH$_2$—, —CH($R^2$)—, or —CH$_2$CH($R^2$)— | — | —($CH_2CH_2O$)$_6$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 166 | double | substituted thiol | O or S | —CH$_2$—, —CH$_2$CH$_2$—, —CH($R^2$)—, or —CH$_2$CH($R^2$)— | —($CH_2$)$_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 167 | double | substituted thiol | O or S | —CH$_2$—, —CH$_2$CH$_2$—, —CH($R^2$)—, or —CH$_2$CH($R^2$)— | —($CH_2$)$_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

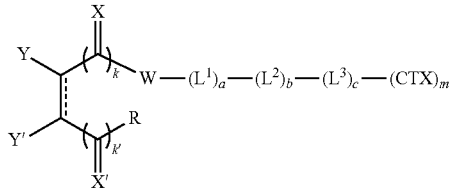
(II)

| Entry | ═══ | Y, Y' | X, X' | W | $L^1$ | $L^2$ | $L^3$ | Bond to CTX |
|---|---|---|---|---|---|---|---|---|
| 168 | double | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 169 | double | substituted thiol | O or S | —CH$_2$—, —CH$_2$CH$_2$—, —CH(R$^2$)—, or —CH$_2$CH(R$^2$)— | — | —(CH$_2$)$_2$— | —NHC(O)— | amide, N-alkylamide, carbamate, N-alkylcarbamate, amine, N-alkylamine, ether, thioether, urea, N-alkylurea, or N,N-dialkylurea |
| 170 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_{12}$— | —NHC(O)— | amide, N-alkylamide, carbamate, N-alkylcarbamate, amine, N-alkylamine, ether, thioether, urea, N-alkylurea, or N,N-dialkylurea |
| 171 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_6$— | —NHC(O)— | amide, N-alkylamide, carbamate, N-alkylcarbamate, amine, N-alkylamine, ether, thioether, urea, N-alkylurea, or N,N-dialkylurea |
| 172 | double | substituted thiol | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 173 | double | substituted thiol | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 174 | double | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 175 | double | substituted thiol | O or S | —CH$_2$—, —CH$_2$CH$_2$—, —CH(R$^2$)—, or —CH$_2$CH(R$^2$)— | — | —(CH$_2$)$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 176 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 177 | double | substituted thiol | O or S | —CH$_2$—, —CH$_2$CH$_2$—, —CH(R$^2$)—, or —CH$_2$CH(R$^2$)— | — | —(CH$_2$CH$_2$O)$_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 178 | double | substituted thiol | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 179 | double | substituted thiol | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 180 | double | substituted thiol | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 181 | double | substituted sulfonate | O or S | —NH— or —N(R$^1$)— | — | —(CH$_2$)$_2$— | —OC(O)— | amide, N-alkylamide, carbamate, N-alkylcarbamate, amine, N-alkylamine, ether, thioether, urea, N-alkylurea, or N,N-dialkylurea |
| 182 | double | substituted sulfonate | O or S | —NH— or —N(R$^1$)— | — | —(CH$_2$CH$_2$O)$_{12}$— | —CH$_2$CH$_2$C(O)— | amide, N-alkylamide, carbamate, N-alkylcarbamate, amine, N-alkylamine, ether, thioether, urea, N-alkylurea, or N,N-dialkylurea |
| 183 | double | substituted sulfonate | O or S | —NH— or —N(R$^1$)— | — | —(CH$_2$CH$_2$O)$_6$— | —CH$_2$CH$_2$C(O)— | amide, N-alkylamide, carbamate, N-alkylcarbamate, amine, N-alkylamine, ether, thioether, ur TABLE 2-continued Linker-Cytotoxin Conjugates

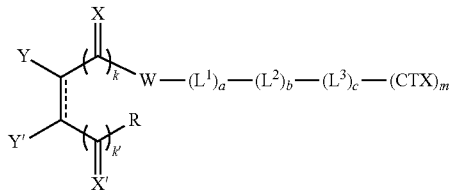
(II)

| Entry | ====== | Y, Y' | X, X' | W | $L^1$ | $L^2$ | $L^3$ | Bond to CTX |
|---|---|---|---|---|---|---|---|---|
| 184 | double | substituted sulfonate | O or S | —NH— or —N($R^1$)— | —$(CH_2)_2$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 185 | double | substituted sulfonate | O or S | —NH— or —N($R^1$)— | —$(CH_2)_4$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 186 | double | substituted sulfonate | O or S | —NH— or —N($R^1$)— | —$(CH_2)_5$CO— | —NHCH$_2$CH$_2$— | —OC(O)— | amide, N-alkylamide, carbamate, N-alkylcarbamate, amine, N-alkylamine, ether, thioether, urea, N-alkylurea, or N,N-dialkylurea |
| 187 | double | substituted sulfonate | O or S | —NH— or —N($R^1$)— | — | —$(CH_2)_2$— | —NHC(O)— | amide, N-alkylamide, carbamate, N-alkylcarbamate, amine, N-alkylamine, ether, thioether, urea, N-alkylurea, or N,N-dialkylurea |
| 188 | double | substituted sulfonate | O or S | —NH— or —N($R^1$)— | — | —$(CH_2CH_2O)_{12}$— | —NHC(O)— | amide, N-alkylamide, carbamate, N-alkylcarbamate, amine, N-alkylamine, ether, thioether, urea, N-alkylurea, or N,N-dialkylurea |
| 189 | double | substituted sulfonate | O or S | —NH— or —N($R^1$)— | — | —$(CH_2CH_2O)_6$— | —NHC(O)— | amide, N-alkylamide, carbamate, N-alkylcarbamate, amine, N-alkylamine, ether, thioether, urea, N-alkylurea, or N,N-dialkylurea |
| 190 | double | substituted sulfonate | O or S | —NH— or —N($R^1$)— | —$(CH_2)_2$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 191 | double | substituted sulfonate | O or S | —NH— or —N($R^1$)— | —$(CH_2)_4$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 192 | double | substituted sulfonate | O or S | —NH— or —N($R^1$)— | —$(CH_2)_5$CO— | —NHCH$_2$CH$_2$— | —NHC(O)— | amide, N-alkylamide, carbamate, N-alkylcarbamate, amine, N-alkylamine, ether, thioether, urea, N-alkylurea, or N,N-dialkylurea |
| 193 | double | substituted sulfonate | O or S | —NH— or —N($R^1$)— | — | —$(CH_2)_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 194 | double | substituted sulfonate | O or S | —NH— or —N($R^1$)— | — | —$(CH_2CH_2O)_{12}$— | —NCH$_3$C(O)— | amide, N-alkylamide, carbamate, N-alkylcarbamate, amine, N-alkylamine, ether, thioether, urea, N-alkylurea, or N,N-dialkylurea |
| 195 | double | substituted sulfonate | O or S | —NH— or —N($R^1$)— | — | —$(CH_2CH_2O)_6$— | —NCH$_3$C(O)— | amide, N-alkylamide, carbamate, N-alkylcarbamate, amine, N-alkylamine, ether, thioether, urea, N-alkylurea, or N,N-dialkylurea |
| 196 | double | substituted sulfonate | O or S | —NH— or —N($R^1$)— | —$(CH_2)_2$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 197 | double | substituted sulfonate | O or S | —NH— or —N($R^1$)— | —$(CH_2)_4$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 198 | double | substituted sulfonate | O or S | —NH— or —N($R^1$)— | —$(CH_2)_5$CO— | —NHCH$_2$CH$_2$— | —NCH$_3$C(O)— | amide, N-alkylamide, carbamate, N-alkylcarbamate, amine, N-alkylamine, ether, thioether, urea, N-alkylurea, or N,N-dialkylurea |
| 199 | double | substituted sulfonate | O or S | —CH$_2$—, —CH$_2$CH$_2$—, —CH($R^2$)—, or —CH$_2$CH($R^2$)— | — | —$(CH_2)_2$— | —OC(O)— | amide, N-alkylamide, carbamate, N-alkylcarbamate, amine, N-alkylamine, ether, thioether, urea, N-alkylurea, or N,N-dialkylurea |

TABLE 2-continued

Linker-Cytotoxin Conjugates

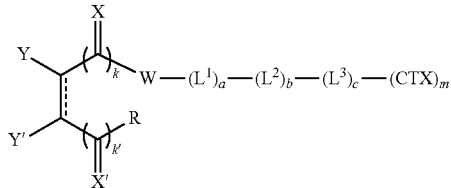
(II)

| Entry | ====== | Y, Y' | X, X' | W | L¹ | L² | L³ | Bond to CTX |
|---|---|---|---|---|---|---|---|---|
| 200 | double | substituted sulfonate | O or S | —CH₂—, —CH₂CH₂—, —CH(R²)—, or —CH₂CH(R²)— | — | —(CH₂CH₂O)₁₂— | —CH₂CH₂C(O)— | amide, N-alkylamide, carbamate, N-alkylcarbamate, amine, N-alkylamine, ether, thioether, urea, N-alkylurea, or N,N-dialkylurea |
| 201 | double | substituted sulfonate | O or S | —CH₂—, —CH₂CH₂—, —CH(R²)—, or —CH₂CH(R²)— | — | —(CH₂CH₂O)₆— | —CH₂CH₂C(O)— | amide, N-alkylamide, carbamate, N-alkylcarbamate, amine, N-alkylamine, ether, thioether, urea, N-alkylurea, or N,N-dialkylurea |
| 202 | double | substituted sulfonate | O or S | —CH₂—, —CH₂CH₂—, —CH(R²)—, or —CH₂CH(R²)— | —(CH₂)₂CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 203 | double | substituted sulfonate | O or S | —CH₂—, —CH₂CH₂—, —CH(R²)—, or —CH₂CH(R²)— | —(CH₂)₄CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 204 | double | substituted sulfonate | O or S | —CH₂—, —CH₂CH₂—, —CH(R²)—, or —CH₂CH(R²)— | —(CH₂)₅CO— | —NHCH₂CH₂— | —OC(O)— | amide, N-alkylamide, carbamate, N-alkylcarbamate, amine, N-alkylamine, ether, thioether, urea, N-alkylurea, or N,N-dialkylurea |
| 205 | double | substituted sulfonate | O or S | —CH₂—, —CH₂CH₂—, —CH(R²)—, or —CH₂CH(R²)— | — | —(CH₂)₂— | —NHC(O)— | amide, N-alkylamide, carbamate, N-alkylcarbamate, amine, N-alkylamine, ether, thioether, urea, N-alkylurea, or N,N-dialkylurea |
| 206 | double | substituted sulfonate | O or S | —CH₂—, —CH₂CH₂—, —CH(R²)—, or —CH₂CH(R²)— | — | —(CH₂CH₂O)₁₂— | —NHC(O)— | amide, N-alkylamide, carbamate, N-alkylcarbamate, amine, N-alkylamine, ether, thioether, urea, N-alkylurea, or N,N-dialkylurea |
| 207 | double | substituted sulfonate | O or S | —CH₂—, —CH₂CH₂—, —CH(R²)—, or —CH₂CH(R²)— | — | —(CH₂CH₂O)₆— | —NHC(O)— | amide, N-alkylamide, carbamate, N-alkylcarbamate, amine, N-alkylamine, ether, thioether, urea, N-alkylurea, or N,N-dialkylurea |
| 208 | double | substituted sulfonate | O or S | —CH₂—, —CH₂CH₂—, —CH(R²)—, or —CH₂CH(R²)— | —(CH₂)₂CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 209 | double | substituted sulfonate | O or S | —CH₂—, —CH₂CH₂—, —CH(R²)—, or —CH₂CH(R²)— | —(CH₂)₄CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 210 | double | substituted sulfonate | O or S | —CH₂—, —CH₂CH₂—, —CH(R²)—, or —CH₂CH(R²)— | —(CH₂)₅CO— | —NHCH₂CH₂— | —NHC(O)— | amide, N-alkylamide, carbamate, N-alkylcarbamate, amine, N-alkylamine, ether, thioether, urea, N-alkylurea, or N,N-dialkylurea |
| 211 | double | substituted sulfonate | O or S | —CH₂—, —CH₂CH₂—, —CH(R²)—, or —CH₂CH(R²)— | — | —(CH₂)₂— | —NCH₃C(O)— | amide, N-alkylamide, carbamate, N-alkylcarbamate, amine, N-alkylamine, ether, thioether, urea, N-alkylurea, or N,N-dialkylurea |
| 212 | double | substituted sulfonate | O or S | —CH₂—, —CH₂CH₂—, —CH(R²)—, or —CH₂CH(R²)— | — | —(CH₂CH₂O)₁₂— | —NCH₃C(O)— | amide, N-alkylamide, carbamate, N-alkylcarbamate, amine, N-alkylamine, ether, thioether, urea, N-alkylurea, or N,N-dialkylurea |
| 213 | double | substituted sulfonate | O or S | —CH₂—, —CH₂CH₂—, —CH(R²)—, or —CH₂CH(R²)— | — | —(CH₂CH₂O)₆— | —NCH₃C(O)— | amide, N-alkylamide, carbamate, N-alkylcarbamate, amine, N-alkylamine, ether, thioether, urea, N-alkylurea, or N,N-dialkylurea |
| 214 | double | substituted sulfonate | O or S | —CH₂—, —CH₂CH₂—, —CH(R²)—, or —CH₂CH(R²)— | —(CH₂)₂CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |
| 215 | double | substituted sulfonate | O or S | —CH₂—, —CH₂CH₂—, —CH(R²)—, or —CH₂CH(R²)— | —(CH₂)₄CO— | —NHCH₂CH₂— | —NCH₃C(O)— | amide, N-alkylamide, carbamate, N-alkylcarbamate, amine, N-alkylamine, ether, thioether, urea, N-alkylurea, or N,N-dialkylurea |

TABLE 2-continued
Linker-Cytotoxin Conjugates
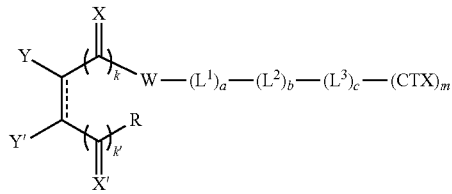
(II)
| Entry | ====== | Y, Y' | X, X' | W | $L^1$ | $L^2$ | $L^3$ | Bond to CTX |
|---|---|---|---|---|---|---|---|---|
| 216 | double | substituted sulfonate | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —NCH$_3$C(O)— | am TABLE 3-continued Antibody-Drug Conjugates

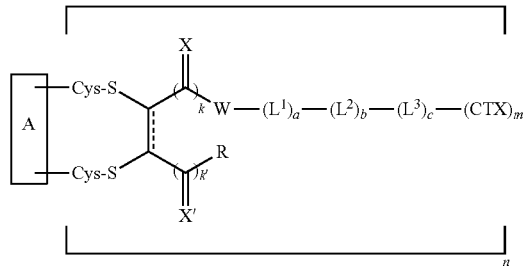

(III)

| Entry | ----- | A | X, X' | W | $L^1$ | $L^2$ | $L^3$ | Bond to CTX |
|---|---|---|---|---|---|---|---|---|
| 4 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_2CO$— | —$NHCH_2CH_2$— | —OC(O)— | amide, N-alkylamide, carbamate, N-alkyl-carbamate, amine, N-alkylamine, ether, thioether, urea, N-alkylurea, or N,N-dialkylurea |
| 5 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_4CO$— | —$NHCH_2CH_2$— | —OC(O)— | amide, N-alkylamide, carbamate, N-alkyl-carbamate, amine, N-alkylamine, ether, thioether, urea, N-alkylurea, or N,N-dialkylurea |
| 6 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_5CO$— | —$NHCH_2CH_2$— | —OC(O)— | amide, N-alkylamide, carbamate, N-alkyl-carbamate, amine, N-alkylamine, ether, thioether, urea, N-alkylurea, or N,N-dialkylurea |
| 7 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2)_2$— | —NHC(O)— | amide, N-alkylamide, carbamate, N-alkyl-carbamate, amine, N-alkylamine, ether, thioether, urea, N-alkylurea, or N,N-dialkylurea |
| 8 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2CH_2O)_{12}$— | —NHC(O)— | amide, N-alkylamide, carbamate, N-alkyl-carbamate, amine, N-alkylamine, ether, thioether, urea, N-alkylurea, or N,N-dialkylurea |
| 9 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2CH_2O)_6$— | —NHC(O)— | amide, N-alkylamide, carbamate, N-alkyl-carbamate, amine, N-alkylamine, ether, thioether, urea, N-alkylurea, or N,N-dialkylurea |
| 10 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_2CO$— | —$NHCH_2CH_2$— | —NHC(O)— | amide, N-alkylamide, carbamate, N-alkyl-carbamate, amine, N-alkylamine, ether, thioether, urea, N-alkylurea, or N,N-dialkylurea |
| 11 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_4CO$— | —$NHCH_2CH_2$— | —NHC(O)— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

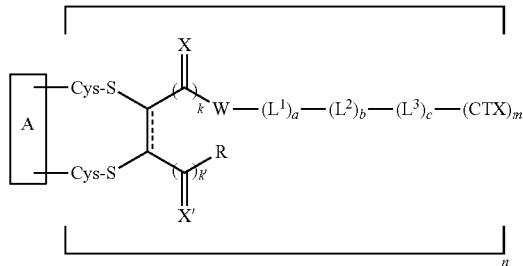

(III)

| Entry | ====== | A | X, X' | W | $L^1$ | $L^2$ | $L^3$ | Bond to CTX |
|---|---|---|---|---|---|---|---|---|
| 12 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_5$CO— | —NH$CH_2CH_2$— | —NHC(O)— | amide, N-alkylamide, carbamate, N-alkyl-carbamate, amine, N-alkylamine, ether, thioether, urea, N-alkylurea, or N,N-dialkylurea |
| 13 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2)_2$— | —N$CH_3$C(O)— | amide, N-alkylamide, carbamate, N-alkyl-carbamate, amine, N-alkylamine, ether, thioether, urea, N-alkylurea, or N,N-dialkylurea |
| 14 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2CH_2O)_{12}$— | —N$CH_3$C(O)— | amide, N-alkylamide, carbamate, N-alkyl-carbamate, amine, N-alkylamine, ether, thioether, urea, N-alkylurea, or N,N-dialkylurea |
| 15 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | — | —$(CH_2CH_2O)_6$— | —N$CH_3$C(O)— | amide, N-alkylamide, carbamate, N-alkyl-carbamate, amine, N-alkylamine, ether, thioether, urea, N-alkylurea, or N,N-dialkylurea |
| 16 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_2$CO— | —NH$CH_2CH_2$— | —N$CH_3$C(O)— | amide, N-alkylamide, carbamate, N-alkyl-carbamate, amine, N-alkylamine, ether, thioether, urea, N-alkylurea, or N,N-dialkylurea |
| 17 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_4$CO— | —NH$CH_2CH_2$— | —N$CH_3$C(O)— | amide, N-alkylamide, carbamate, N-alkyl-carbamate, amine, N-alkylamine, ether, thioether, urea, N-alkylurea, or N,N-dialkylurea |
| 18 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_5$CO— | —NH$CH_2CH_2$— | —N$CH_3$C(O)— | amide, N-alkylamide, carbamate, N-alkyl-carbamate, amine, N-alkylamine, ether, thioether, urea, N-alkylurea, or N,N-dialkylurea |
| 19 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —CH($R^2$)—, or —$CH_2$CH($R^2$)— | — | —$(CH_2)_2$— | —OC(O)— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

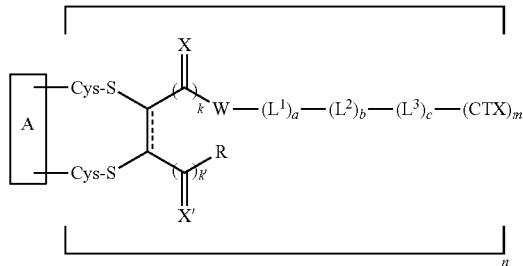

(III)

| Entry | ===== | A | X, X' | W | L¹ | L² | L³ | Bond to CTX |
|---|---|---|---|---|---|---|---|---|
| 20 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | — | —(CH$_2$CH$_2$O)$_{12}$— | —CH$_2$CH$_2$C(O)— | amide, N-alkylamide, carbamate, N-alkyl-carbamate, amine, N-alkylamine, ether, thioether, urea, N-alkylurea, or N,N-dialkylurea |
| 21 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | — | —(CH$_2$CH$_2$O)$_6$— | —CH$_2$CH$_2$C(O)— | amide, N-alkylamide, carbamate, N-alkyl-carbamate, amine, N-alkylamine, ether, thioether, urea, N-alkylurea, or N,N-dialkylurea |
| 22 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | —(CH$_2$)$_2$CO— | —NHCH$_2$CH$_2$— | —OC(O)— | amide, N-alkylamide, carbamate, N-alkyl-carbamate, amine, N-alkylamine, ether, thioether, urea, N-alkylurea, or N,N-dialkylurea |
| 23 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | —(CH$_2$)$_4$CO— | —NHCH$_2$CH$_2$— | —OC(O)— | amide, N-alkylamide, carbamate, N-alkyl-carbamate, amine, N-alkylamine, ether, thioether, urea, N-alkylurea, or N,N-dialkylurea |
| 24 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | —(CH$_2$)$_5$CO— | —NHCH$_2$CH$_2$— | —OC(O)— | amide, N-alkylamide, carbamate, N-alkyl-carbamate, amine, N-alkylamine, ether, thioether, urea, N-alkylurea, or N,N-dialkylurea |
| 25 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | — | —(CH$_2$)$_2$— | —NHC(O)— | amide, N-alkylamide, carbamate, N-alkyl-carbamate, amine, N-alkylamine, ether, thioether, urea, N-alkylurea, or N,N-dialkylurea |
| 26 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | — | —(CH$_2$CH$_2$O)$_{12}$— | —NHC(O)— | amide, N-alkylamide, carbamate, N-alkyl-carbamate, amine, N-alkylamine, ether, thioether, urea, N-alkylurea, or N,N-dialkylurea |
| 27 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —CH$_2$—, —CH$_2$CH$_2$—, —CH(R$^2$)—, or —CH$_2$CH(R$^2$)— | — | —(CH$_2$CH$_2$O)$_6$— | —NHC(O)— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

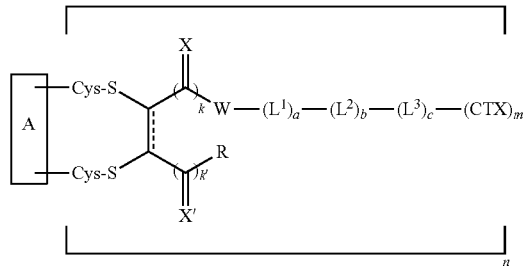

(III)

| Entry | ===== | A | X, X' | W | $L^1$ | $L^2$ | $L^3$ | Bond to CTX |
|---|---|---|---|---|---|---|---|---|
| 28 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_2CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 29 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_4CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 30 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_5CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 31 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2)_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 32 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_{12}$— | —$NCH_3C(O)$— | amide, N-alkylamide, carbamate, N-alkyl-carbamate, amine, N-alkylamine, ether, thioether, urea, N-alkylurea, or N,N-dialkylurea |
| 33 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | amide, N-alkylamide, carbamate, N-alkyl-carbamate, amine, N-alkylamine, ether, thioether, urea, N-alkylurea, or N,N-dialkylurea |
| 34 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 35 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

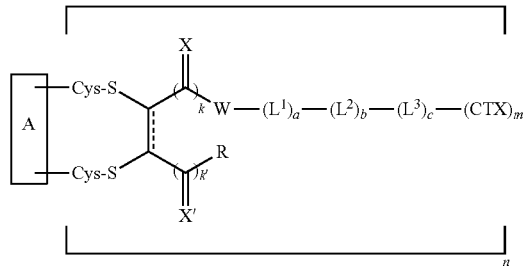

(III)

| Entry | ===== | A | X, X' | W | L¹ | L² | L³ | Bond to CTX |
|---|---|---|---|---|---|---|---|---|
| 36 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | amide, N-alkylamide, carbamate, N-alkylcarbamate, amine, N-alkylamine, ether, thioether, urea, N-alkylurea, or N,N-dialkylurea |
| 37 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | — | —$(CH_2)_2$— | —OC(O)— | amide, N-alkylamide, carbamate, N-alkylcarbamate, amine, N-alkylamine, ether, thioether, urea, N-alkylurea, or N,N-dialkylurea |
| 38 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | — | —$(CH_2CH_2O)_{12}$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 39 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | — | —$(CH_2CH_2O)_6$— | —$CH_2CH_2C(O)$— | amide, N-alkylamide, carbamate, N-alkylcarbamate, amine, N-alkylamine, ether, thioether, urea, N-alkylurea, or N,N-dialkylurea |
| 40 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | —$(CH_2)_2CO$— | —$NHCH_2CH_2$— | —OC(O)— | amide, N-alkylamide, carbamate, N-alkylcarbamate, amine, N-alkylamine, ether, thioether, urea, N-alkylurea, or N,N-dialkylurea |
| 41 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | —$(CH_2)_4CO$— | —$NHCH_2CH_2$— | —OC(O)— | amide, N-alkylamide, carbamate, N-alkylcarbamate, amine, N-alkylamine, ether, thioether, urea, N-alkylurea, or N,N-dialkylurea |
| 42 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | —$(CH_2)_5CO$— | —$NHCH_2CH_2$— | —OC(O)— | amide, N-alkylamide, carbamate, N-alkylcarbamate, amine, N-alkylamine, ether, thioether, urea, N-alkylurea, or N,N-dialkylurea |
| 43 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | — | —$(CH_2)_2$— | —NHC(O)— | amide, N-alkylamide, carbamate, N-alkylcarbamate, amine, N-alkylamine, ether, thioether, urea, N-alkylurea, or N,N-dialkylurea |

TABLE 3-continued

Antibody-Drug Conjugates

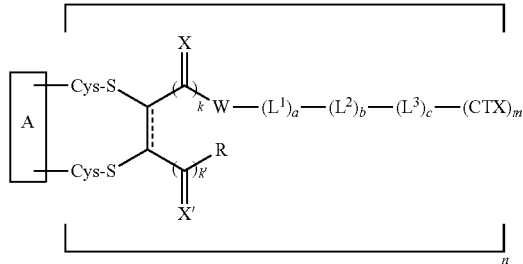

(III)

| Entry | ----- | A | X, X' | W | L¹ | L² | L³ | Bond to CTX |
|---|---|---|---|---|---|---|---|---|
| 44 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | — | —(CH$_2$CH$_2$O)$_{12}$— | —NHC(O)— | amide, N-alkylamide, carbamate, N-alkyl-carbamate, amine, N-alkylamine, ether, thioether, urea, N-alkylurea, or N,N-dialkylurea |
| 45 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | — | —(CH$_2$CH$_2$O)$_6$— | —NHC(O)— | amide, N-alkylamide, carbamate, N-alkyl-carbamate, amine, N-alkylamine, ether, thioether, urea, N-alkylurea, or N,N-dialkylurea |
| 46 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | —(CH$_2$)$_2$CO— | —NHCH$_2$CH$_2$— | —NHC(O)— | amide, N-alkylamide, carbamate, N-alkyl-carbamate, amine, N-alkylamine, ether, thioether, urea, N-alkylurea, or N,N-dialkylurea |
| 47 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | —(CH$_2$)$_4$CO— | —NHCH$_2$CH$_2$— | —NHC(O)— | amide, N-alkylamide, carbamate, N-alkyl-carbamate, amine, N-alkylamine, ether, thioether, urea, N-alkylurea, or N,N-dialkylurea |
| 48 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | —(CH$_2$)$_5$CO— | —NHCH$_2$CH$_2$— | —NHC(O)— | amide, N-alkylamide, carbamate, N-alkyl-carbamate, amine, N-alkylamine, ether, thioether, urea, N-alkylurea, or N,N-dialkylurea |
| 49 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | — | —(CH$_2$)$_2$— | —NCH$_3$C(O)— | amide, N-alkylamide, carbamate, N-alkyl-carbamate, amine, N-alkylamine, ether, thioether, urea, N-alkylurea, or N,N-dialkylurea |
| 50 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | — | —(CH$_2$CH$_2$O)$_{12}$— | —NCH$_3$C(O)— | amide, N-alkylamide, carbamate, N-alkyl-carbamate, amine, N-alkylamine, ether, thioether, urea, N-alkylurea, or N,N-dialkylurea |
| 51 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N(R¹)— | — | —(CH$_2$CH$_2$O)$_6$— | —NCH$_3$C(O)— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

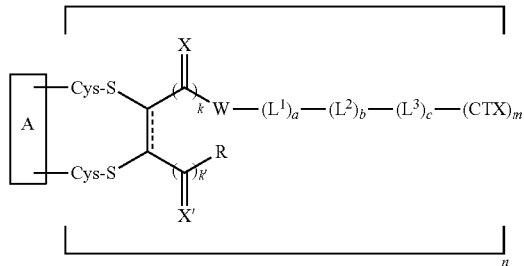
(III)

| Entry | ====== | A | X, X' | W | $L^1$ | $L^2$ | $L^3$ | Bond to CTX |
|---|---|---|---|---|---|---|---|---|
| 52 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_2CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 53 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_4CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 54 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_5CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 55 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2)_2$— | —$OC(O)$— | amide, N-alkylamide, carbamate, N-alkyl-carbamate, amine, N-alkylamine, ether, thioether, urea, N-alkylurea, or N,N-dialkylurea |
| 56 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_{12}$— | —$CH_2CH_2C(O)$— | amide, N-alkylamide, carbamate, N-alkyl-carbamate, amine, N-alkylamine, ether, thioether, urea, N-alkylurea, or N,N-dialkylurea |
| 57 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_6$— | —$CH_2CH_2C(O)$— | amide, N-alkylamide, carbamate, N-alkyl-carbamate, amine, N-alkylamine, ether, thioether, urea, N-alkylurea, or N,N-dialkylurea |
| 58 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_2CO$— | —$NHCH_2CH_2$— | —$OC(O)$— | amide, N-alkylamide, carbamate, N-alkyl-carbamate, amine, N-alkylamine, ether, thioether, urea, N-alkylurea, or N,N-dialkylurea |
| 59 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_4CO$— | —$NHCH_2CH_2$— | —$OC(O)$— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

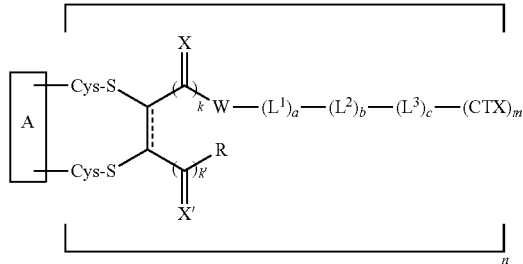

(III)

| En-try | ----- | A | X, X' | W | $L^1$ | $L^2$ | $L^3$ | Bond to CTX |
|---|---|---|---|---|---|---|---|---|
| 60 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_5CO$— | —$NHCH_2CH_2$— | —$OC(O)$— | amide, N-alkylamide, carbamate, N-alkyl-carbamate, amine, N-alkylamine, ether, thioether, urea, N-alkylurea, or N,N-dialkylurea |
| 61 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2)_2$— | —$NHC(O)$— | amide, N-alkylamide, carbamate, N-alkyl-carbamate, amine, N-alkylamine, ether, thioether, urea, N-alkylurea, or N,N-dialkylurea |
| 62 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_{12}$— | —$NHC(O)$— | amide, N-alkylamide, carbamate, N-alkyl-carbamate, amine, N-alkylamine, ether, thioether, urea, N-alkylurea, or N,N-dialkylurea |
| 63 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_6$— | —$NHC(O)$— | amide, N-alkylamide, carbamate, N-alkyl-carbamate, amine, N-alkylamine, ether, thioether, urea, N-alkylurea, or N,N-dialkylurea |
| 64 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_2CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 65 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_4CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 66 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_5CO$— | —$NHCH_2CH_2$— | —$NHC(O)$— | amide, N-alkylamide, carbamate, N-alkyl-carbamate, amine, N-alkylamine, ether, thioether, urea, N-alkylurea, or N,N-dialkylurea |
| 67 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2)_2$- | —$NCH_3C(O)$— | amide, N-alkylamide, carbamate, N-alkyl-carbamate, amine, N-alkylamine, ether, thioether, urea, N-alkylurea, or N,N-dialkylurea |

TABLE 3-continued

Antibody-Drug Conjugates

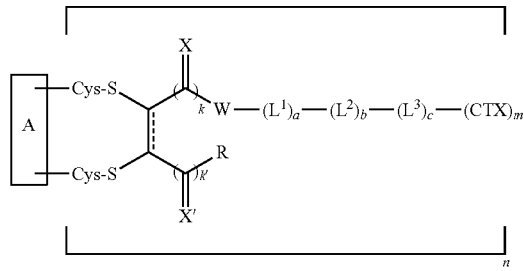

(III)

| Entry | ------ | A | X, X' | W | $L^1$ | $L^2$ | $L^3$ | Bond to CTX |
|---|---|---|---|---|---|---|---|---|
| 68 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_{12}$— | —$NCH_3C(O)$— | amide, N-alkylamide, carbamate, N-alkyl-carbamate, amine, N-alkylamine, ether, thioether, urea, N-alkylurea, or N,N-dialkylurea |
| 69 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | — | —$(CH_2CH_2O)_6$— | —$NCH_3C(O)$— | amide, N-alkylamide, carbamate, N-alkyl-carbamate, amine, N-alkylamine, ether, thioether, urea, N-alkylurea, or N,N-dialkylurea |
| 70 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_2CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 71 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_4CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |
| 72 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_5CO$— | —$NHCH_2CH_2$— | —$NCH_3C(O)$— | amide, N-alkylamide, carbamate, N-alkyl-carbamate, amine, N-alkylamine, ether, thioether, urea, N-alkylurea, or N,N-dialkylurea |

For all Entries 1-72 Provided in Table 3 Above, CTX, R, k, k', a, b, c, and n May be Defined as Follows:

CTX: Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, or Vincristine R: W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, W-$(L^1)_a$-$(L^2)_b$-$(L^3)_c$-Z, W-$(L^1)_a$-$(L^2)_b$-$(L^3)_c$-CTX, a detectable probe, a ligand, or an antibody fragment k, k': each independently 0 or 1 a, b and c: each independently 0, 1, 2 or 3, provided that at least one of a, b or c is 1 m: an integer of 1 to 4 n: an integer of 1 to 4

Abbreviations for "A" are as Follows:

alemtuzumab (ATZ), anitumumab (ATM), bevacizumab (BCZ), brentuximab (BTX), cetuximab (CTX), gemtuzumab (GTZ), glembatumumab (GBT), inotuzumab (ITZ), ipilimumab (ILM), lovortumumab (LVT), milatuzumab (MTZ), ofatumumab (OTM), rituximab (RTX), tositumomab (TTM), and trastuzumab (TTZ)

TABLE 4

Linkers

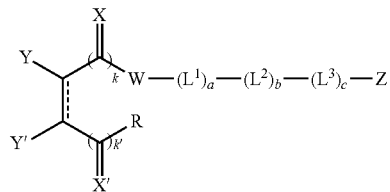

(I)

| Entry | ====== | Y, Y' | X, X' | W | (L¹)a | L² | L³ | Z |
|---|---|---|---|---|---|---|---|---|
| 1 | single | halo | O or S | —NH— or —N(R¹)— | —(CH$_2$)$_n$— | — | — | —CO$_2$H, —NH$_2$, —OH, —NH—R$^{3a}$, or —CO$_2$R$^{3b}$ |
| 2 | single | halo | O or S | —NH— or —N(R¹)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 3 | single | halo | O or S | —NH— or —N(R¹)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 4 | single | halo | O or S | —NH— or —N(R¹)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 5 | single | halo | O or S | —NH— or —N(R¹)— | —(CH$_2$)$_n$CO— | -Val-Ala- or -Val-Cit- | PAB | —CO$_2$H or —CO$_2$R$^{3b}$ |
| 6 | single | halo | O or S | —NH— or —N(R¹)— | —(CH$_2$)$_n$(OCH$_2$CH$_2$)$_n$—CO— | -Val-Ala- or -Val-Cit- | PAB | —CO$_2$H or —CO$_2$R$^{3b}$ |
| 7 | single | halo | O or S | —NH— or —N(R¹)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 8 | single | halo | O or S | —NH— or —N(R¹)— | —(CH$_2$CH$_2$O)$_n$(CH$_2$)$_n$—CO— | -Val-Ala- or -Val-Cit- | PAB | —CO$_2$H or —CO$_2$R$^{3b}$ |
| 9 | single | halo | O or S —CH$_2$—, —CH$_2$CH$_2$—, —CH(R²)—, or —CH$_2$CH(R²)— | —(CH$_2$)$_n$— | — | — | —CO$_2$H, —NH$_2$, —OH, —NH—R$^{3a}$, or —CO$_2$R$^{3b}$ |
| 10 | single | halo | O or S —CH$_2$—, —CH$_2$CH$_2$—, —CH(R²)—, or —CH$_2$CH(R²)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 11 | single | halo | O or S —CH$_2$—, —CH$_2$CH$_2$—, —CH(R²)—, or —CH$_2$CH(R²)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 12 | single | halo | O or S —CH$_2$—, —CH$_2$CH$_2$—, —CH(R²)—, or —CH$_2$CH(R²)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 13 | single | halo | O or S —CH$_2$—, —CH$_2$CH$_2$—, —CH(R²)—, or —CH$_2$CH(R²)— | —(OCH$_2$CH$_2$)$_n$— | —(CH$_2$)$_n$— | — | —CO$_2$H, —NH$_2$, —OH, —NH—R$^{3a}$, or —CO$_2$R$^{3b}$ |
| 14 | single | halo | O or S —CH$_2$—, —CH$_2$CH$_2$—, —CH(R²)—, or —CH$_2$CH(R²)— | —(CH$_2$)CO— | -Val-Ala- or -Val-Cit- | PAB | —CO$_2$H or —CO$_2$R$^{3b}$ |
| 15 | single | halo | O or S —CH$_2$—, —CH$_2$CH$_2$—, —CH(R²)—, or —CH$_2$CH(R²)— | —(CH$_2$)$_n$(OCH$_2$CH$_2$)$_n$—CO— | -Val-Ala- or -Val-Cit- | PAB | —CO$_2$H or —CO$_2$R$^{3b}$ |
| 16 | single | halo | O or S —CH$_2$—, —CH$_2$CH$_2$—, —CH(R²)—, or —CH$_2$CH(R²)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 17 | single | halo | O or S —CH$_2$—, —CH$_2$CH$_2$—, —CH(R²)—, or —CH$_2$CH(R²)— | —(CH$_2$CH$_2$O)$_n$(CH$_2$)$_n$—CO— | -Val-Ala- or -Val-Cit- | PAB | —CO$_2$H or —CO$_2$R$^{3b}$ |
| 18 | single | halo | O or S —CH$_2$—, —CH$_2$CH$_2$—, —CH(R²)—, or —CH$_2$CH(R²)— | —(OCH$_2$CH$_2$)$_n$(CH$_2$)$_n$—CO— | -Val-Ala- or -Val-Cit- | PAB | —CO$_2$H or —CO$_2$R$^{3b}$ |
| 19 | single | substituted thiol | O or S | —NH— or —N(R¹)— | —(CH$_2$)$_n$— | — | — | —CO$_2$H, —NH$_2$, —OH, —NH—R$^{3a}$, or —CO$_2$R$^{3b}$ |
| 20 | single | substituted thiol | O or S | —NH— or —N(R¹)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 21 | single | substituted thiol | O or S | —NH— or —N(R¹)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 22 | single | substituted thiol | O or S | —NH— or —N(R¹)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 23 | single | substituted thiol | O or S | —NH— or —N(R¹)— | —(CH$_2$)$_n$CO— | -Val-Ala- or -Val-Cit- | PAB | —CO$_2$H or —CO$_2$R$^{3b}$ |
| 24 | single | substituted thiol | O or S | —NH— or —N(R¹)— | —(CH$_2$)$_n$(OCH$_2$CH$_2$)$_n$—CO— | -Val-Ala- or -Val-Cit- | PAB | —CO$_2$H or —CO$_2$R$^{3b}$ |
| 25 | single | substituted thiol | O or S | —NH— or —N(R¹)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 26 | single | substituted thiol | O or S | —NH— or —N(R¹)— | —(CH$_2$CH$_2$O)$_n$(CH$_2$)$_n$—CO— | -Val-Ala- or -Val-Cit- | PAB | —CO$_2$H or —CO$_2$R$^{3b}$ |
| 27 | single | substituted thiol | O or S —CH$_2$—, —CH$_2$CH$_2$—, —CH(R²)—, or —CH$_2$CH(R²)— | —(CH$_2$)$_n$— | — | — | —CO$_2$H, —NH$_2$, —OH, —NH—R$^{3a}$, or —CO$_2$R$^{3b}$ |
| 28 | single | substituted thiol | O or S —CH$_2$—, —CH$_2$CH$_2$—, —CH(R²)—, or —CH$_2$CH(R²)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 29 | single | substituted thiol | O or S —CH$_2$—, —CH$_2$CH$_2$—, —CH(R²)—, or —CH$_2$CH(R²)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |

TABLE 4-continued

Linkers

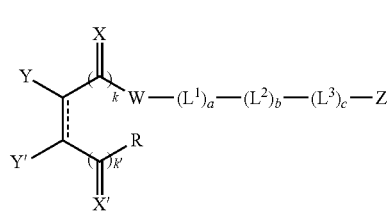

(I)

| Entry | ------ | Y, Y' | X, X' | W | $(L^1)_a$ | $L^2$ | $L^3$ | Z |
|---|---|---|---|---|---|---|---|---|
| 30 | single | substituted thiol | O or S | —$CH_2$—, —$CH_2CH_2$—, —$CH(R^2)$—, or —$CH_2CH(R^2)$— | —$(CH_2CH_2O)_n$— | —$(CH_2)_n$— | — | —$CO_2H$, —$NH_2$, —OH, —NH—$R^{3a}$, or —$CO_2R^{3b}$ |
| 31 | single | substituted thiol | O or S | —$CH_2$—, —$CH_2CH_2$—, —$CH(R^2)$—, or —$CH_2CH(R^2)$— | —$(OCH_2CH_2)_n$— | —$(CH_2)_n$— | — | —$CO_2H$, —$NH_2$, —OH, —NH—$R^{3a}$, or —$CO_2R^{3b}$ |
| 32 | single | substituted thiol | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | —$CO_2H$ or —$CO_2R^{3b}$ |
| 33 | single | substituted thiol | O or S | —$CH_2$—, —$CH_2CH_2$—, —$CH(R^2)$—, or —$CH_2CH(R^2)$— | —$(CH_2)_n$—$(OCH_2CH_2)_n$—CO— | -Val-Ala- or -Val-Cit- | PAB | —$CO_2H$ or —$CO_2R^{3b}$ |
| 34 | single | substituted thiol | O or S | —$CH_2$—, —$CH_2CH_2$—, —$CH(R^2)$—, or —$CH_2CH(R^2)$— | —$(CH_2)_n$—$(CH_2CH_2O)_n$—CO— | -Val-Ala- or -Val-Cit- | PAB | —$CO_2H$ or —$CO_2R^{3b}$ |
| 35 | single | substituted thiol | O or S | —$CH_2$—, —$CH_2CH_2$—, —$CH(R^2)$—, or —$CH_2CH(R^2)$— | —$(CH_2CH_2O)_n$—$(CH_2)_n$—CO— | -Val-Ala- or -Val-Cit- | PAB | —$CO_2H$ or —$CO_2R^{3b}$ |
| 36 | single | substituted thiol | O or S | —$CH_2$—, —$CH_2CH_2$—, —$CH(R^2)$—, or —$CH_2CH(R^2)$— | —$(OCH_2CH_2)_n$—$(CH_2)_n$—CO— | -Val-Ala- or -Val-Cit- | PAB | —$CO_2H$ or —$CO_2R^{3b}$ |
| 37 | single | substituted sulfonate | O or S | —NH— or —N($R^1$)— | —$(CH_2)_n$— | — | — | —$CO_2H$, —$NH_2$, —OH, —NH—$R^{3a}$, or —$CO_2R^{3b}$ |
| 38 | single | substituted sulfonate | O or S | —NH— or —N($R^1$)— | —$(CH_2)_n$— | —$(CH_2CH_2O)_n$— | — | —$CO_2H$, —$NH_2$, —OH, —NH—$R^{3a}$, or —$CO_2R^{3b}$ |
| 39 | single | substituted sulfonate | O or S | —NH— or —N($R^1$)— | —$(CH_2)_n$— | —$(OCH_2CH_2)_n$— | — | —$CO_2H$, —$NH_2$, —OH, —NH—$R^{3a}$, or —$CO_2R^{3b}$ |
| 40 | single | substituted sulfonate | O or S | —NH— or —N($R^1$)— | —$(CH_2CH_2O)_n$— | —$(CH_2)_n$— | — | —$CO_2H$, —$NH_2$, —OH, —NH—$R^{3a}$, or —$CO_2R^{3b}$ |
| 41 | single | substituted sulfonate | O or S | —NH— or —N($R^1$)— | —$(CH_2)_nCO$— | -Val-Ala- or -Val-Cit- | PAB | —$CO_2H$ or —$CO_2R^{3b}$ |
| 42 | single | substituted sulfonate | O or S | —NH— or —N($R^1$)— | —$(CH_2)_n$—$(OCH_2CH_2)_n$—CO— | -Val-Ala- or -Val-Cit- | PAB | —$CO_2H$ or —$CO_2R^{3b}$ |
| 43 | single | substituted sulfonate | O or S | —NH— or —N($R^1$)— | —$(CH_2)_n$—$(CH_2CH_2O)_n$—CO— | -Val-Ala- or -Val-Cit- | PAB | —$CO_2H$ or —$CO_2R^{3b}$ |
| 44 | single | substituted sulfonate | O or S | —NH— or —N($R^1$)— | —$(CH_2CH_2O)_n$—$(CH_2)_n$—CO— | -Val-Ala- or -Val-Cit- | PAB | —$CO_2H$ or —$CO_2R^{3b}$ |
| 45 | single | substituted sulfonate | O or S | —$CH_2$—, —$CH_2CH_2$—, —$CH(R^2)$—, or —$CH_2CH(R^2)$— | —$(CH_2)_n$— | — | — | —$CO_2H$, —$NH_2$, —OH, —NH—$R^{3a}$, or —$CO_2R^{3b}$ |
| 46 | single | substituted sulfonate | O or S | —$CH_2$—, —$CH_2CH_2$—, —$CH(R^2)$—, or —$CH_2CH(R^2)$— | —$(CH_2)_n$— | —$(CH_2CH_2O)_n$— | — | —$CO_2H$, —$NH_2$, —OH, —NH—$R^{3a}$, or —$CO_2R^{3b}$ |
| 47 | single | substituted sulfonate | O or S | —$CH_2$—, —$CH_2CH_2$—, —$CH(R^2)$—, or —$CH_2CH(R^2)$— | —$(CH_2)_n$— | —$(OCH_2CH_2)_n$— | — | —$CO_2H$, —$NH_2$, —OH, —NH—$R^{3a}$, or —$CO_2R^{3b}$ |
| 48 | single | substituted sulfonate | O or S | —$CH_2$—, —$CH_2CH_2$—, —$CH(R^2)$—, or —$CH_2CH(R^2)$— | —$(CH_2CH_2O)_n$— | —$(CH_2)_n$— | — | —$CO_2H$, —$NH_2$, —OH, —NH—$R^{3a}$, or —$CO_2R^{3b}$ |
| 49 | single | substituted sulfonate | O or S | —$CH_2$—, —$CH_2CH_2$—, —$CH(R^2)$—, or —$CH_2CH(R^2)$— | —$(OCH_2CH_2)_n$— | —$(CH_2)_n$— | — | —$CO_2H$, —$NH_2$, —OH, —NH—$R^{3a}$, or —$CO_2R^{3b}$ |
| 50 | single | substituted sulfonate | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | —$CO_2H$ or —$CO_2R^{3b}$ |
| 51 | single | substituted sulfonate | O or S | —$CH_2$—, —$CH_2CH_2$—, —$CH(R^2)$—, or —$CH_2CH(R^2)$— | —$(CH_2)_n$—$(OCH_2CH_2)_n$—CO— | -Val-Ala- or -Val-Cit- | PAB | —$CO_2H$ or —$CO_2R^{3b}$ |
| 52 | single | substituted sulfonate | O or S | —$CH_2$—, —$CH_2CH_2$—, —$CH(R^2)$—, or —$CH_2CH(R^2)$— | —$(CH_2)_n$—$(CH_2CH_2O)_n$—CO— | -Val-Ala- or -Val-Cit- | PAB | —$CO_2H$ or —$CO_2R^{3b}$ |
| 53 | single | substituted sulfonate | O or S | —$CH_2$—, —$CH_2CH_2$—, —$CH(R^2)$—, or —$CH_2CH(R^2)$— | —$(CH_2CH_2O)_n$—$(CH_2)_n$—CO— | -Val-Ala- or -Val-Cit- | PAB | —$CO_2H$ or —$CO_2R^{3b}$ |
| 54 | single | substituted sulfonate | O or S | —$CH_2$—, —$CH_2CH_2$—, —$CH(R^2)$—, or —$CH_2CH(R^2)$— | —$(OCH_2CH_2)_n$—$(CH_2)_n$—CO— | -Val-Ala- or -Val-Cit- | PAB | —$CO_2H$ or —$CO_2R^{3b}$ |
| 55 | double | halo | O or S | —NH— or —N($R^1$)— | —$(CH_2)_n$— | — | — | —$CO_2H$, —$NH_2$, —OH, —NH—$R^{3a}$, or —$CO_2R^{3b}$ |
| 56 | double | halo | O or S | —NH— or —N($R^1$)— | —$(CH_2)_n$— | —$(CH_2CH_2O)_n$— | — | —$CO_2H$, —$NH_2$, —OH, —NH—$R^{3a}$, or —$CO_2R^{3b}$ |
| 57 | double | halo | O or S | —NH— or —N($R^1$)— | —$(CH_2)_n$— | —$(OCH_2CH_2)_n$— | — | —$CO_2H$, —$NH_2$, —OH, —NH—$R^{3a}$, or —$CO_2R^{3b}$ |
| 58 | double | halo | O or S | —NH— or —N($R^1$)— | —$(CH_2CH_2O)_n$— | —$(CH_2)_n$— | — | —$CO_2H$, —$NH_2$, —OH, —NH—$R^{3a}$, or —$CO_2R^{3b}$ |

TABLE 4-continued

Linkers

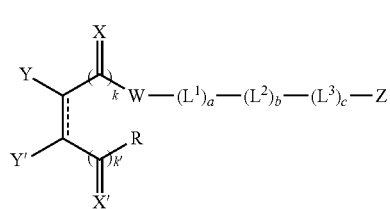

(I)

| Entry | ------ | Y, Y' | X, X' | W | (L¹)a | L² | L³ | Z |
|---|---|---|---|---|---|---|---|---|
| 59 | double | halo | O or S | —NH— or —N(R¹)— | —(CH$_2$)$_n$CO— | -Val-Ala- or -Val-Cit- | PAB | —CO$_2$H or —CO$_2$R$^{3b}$ |
| 60 | double | halo | O or S | —NH— or —N(R¹)— | —(CH$_2$)$_n$(OCH$_2$CH$_2$)$_n$—CO— | -Val-Ala- or -Val-Cit- | PAB | —CO$_2$H or —CO$_2$R$^{3b}$ |
| 61 | double | halo | O or S | —NH— or —N(R¹)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 62 | double | halo | O or S | —NH— or —N(R¹)— | —(CH$_2$CH$_2$O)$_n$(CH$_2$)$_n$—CO— | -Val-Ala- or -Val-Cit- | PAB | —CO$_2$H or —CO$_2$R$^{3b}$ |
| 63 | double | halo | O or S | —CH$_2$—, —CH$_2$CH$_2$—, —CH(R²)—, or —CH$_2$CH(R²)— | —(CH$_2$)$_n$— | — | — | —CO$_2$H, —NH$_2$, —OH, —NH—R$^{3a}$, or —CO$_2$R$^{3b}$ |
| 64 | double | halo | O or S | —CH$_2$—, —CH$_2$CH$_2$—, —CH(R²)—, or —CH$_2$CH(R²)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 65 | double | halo | O or S | —CH$_2$—, —CH$_2$CH$_2$—, —CH(R²)—, or —CH$_2$CH(R²)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 66 | double | halo | O or S | —CH$_2$—, —CH$_2$CH$_2$—, —CH(R²)—, or —CH$_2$CH(R²)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 67 | double | halo | O or S | —CH$_2$—, —CH$_2$CH$_2$—, —CH(R²)—, or —CH$_2$CH(R²)— | —(OCH$_2$CH$_2$)$_n$— | —(CH$_2$)$_n$— | — | —CO$_2$H, —NH$_2$, —OH, —NH—R$^{3a}$, or —CO$_2$R$^{3b}$ |
| 68 | double | halo | O or S | —CH$_2$—, —CH$_2$CH$_2$—, —CH(R²)—, or —CH$_2$CH(R²)— | —(CH$_2$)$_n$CO— | -Val-Ala- or -Val-Cit- | PAB | —CO$_2$H or —CO$_2$R$^{3b}$ |
| 69 | double | halo | O or S | —CH$_2$—, —CH$_2$CH$_2$—, —CH(R²)—, or —CH$_2$CH(R²)— | —(CH$_2$)$_n$(OCH$_2$CH$_2$)$_n$—CO— | -Val-Ala- or -Val-Cit- | PAB | —CO$_2$H or —CO$_2$R$^{3b}$ |
| 70 | double | halo | O or S | —CH$_2$—, —CH$_2$CH$_2$—, —CH(R²)—, or —CH$_2$CH(R²)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 71 | double | halo | O or S | —CH$_2$—, —CH$_2$CH$_2$—, —CH(R²)—, or —CH$_2$CH(R²)— | —(CH$_2$CH$_2$O)$_n$(CH$_2$)$_n$—CO— | -Val-Ala- or -Val-Cit- | PAB | —CO$_2$H or —CO$_2$R$^{3b}$ |
| 72 | double | halo | O or S | —CH$_2$—, —CH$_2$CH$_2$—, —CH(R²)—, or —CH$_2$CH(R²)— | —(OCH$_2$CH$_2$)$_n$(CH$_2$)$_n$—CO— | -Val-Ala- or -Val-Cit- | PAB | —CO$_2$H or —CO$_2$R$^{3b}$ |
| 73 | double | substituted thiol | O or S | —NH— or —N(R¹)— | —(CH$_2$)$_n$— | — | — | —CO$_2$H, —NH$_2$, —OH, —NH—R$^{3a}$, or —CO$_2$R$^{3b}$ |
| 74 | double | substituted thiol | O or S | —NH— or —N(R¹)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 75 | double | substituted thiol | O or S | —NH— or —N(R¹)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 76 | double | substituted thiol | O or S | —NH— or —N(R¹)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 77 | double | substituted thiol | O or S | —NH— or —N(R¹)— | —(CH$_2$)$_n$CO— | -Val-Ala- or -Val-Cit- | PAB | —CO$_2$H or —CO$_2$R$^{3b}$ |
| 78 | double thiol | substituted | O or S | —NH— or —N(R¹)— (OCH$_2$CH$_2$)$_n$— | —(CH$_2$)$_n$— -Val-Cit- CO— | -Val-Ala- or | PAB | —CO$_2$H or —CO$_2$R$^{3b}$ |
| 79 | double | substituted thiol | O or S | —NH— or —N(R¹)— | —(CH$_2$)$_n$(CH$_2$CH$_2$O)$_n$—CO— | -Val-Ala- or -Val-Cit- | PAB | —CO$_2$H or —CO$_2$R$^{3b}$ |
| 80 | double | substituted thiol | O or S | —NH— or —N(R¹)— | —(CH$_2$CH$_2$O)$_n$—(CH$_2$)$_n$—CO— | -Val-Ala- or -Val-Cit- | PAB | —CO$_2$H or —CO$_2$R$^{3b}$ |
| 81 | double | substituted thiol | O or S | —CH$_2$—, —CH$_2$CH$_2$—, —CH(R²)—, or —CH$_2$CH(R²)— | —(CH$_2$)$_n$— | — | — | —CO$_2$H, —NH$_2$, —OH, —NH—R$^{3a}$, or —CO$_2$R$^{3b}$ |
| 82 | double | substituted thiol | O or S | —CH$_2$—, —CH$_2$CH$_2$—, —CH(R²)—, or —CH$_2$CH(R²)— | —(CH$_2$)$_n$— | —(CH$_2$CH$_2$O)$_n$— | — | —CO$_2$H, —NH$_2$, —OH, —NH—R$^{3a}$, or —CO$_2$R$^{3b}$ |
| 83 | double | substituted thiol | O or S | —CH$_2$—, —CH$_2$CH$_2$—, —CH(R²)—, or —CH$_2$CH(R²)— | —(CH$_2$)$_n$— | —(OCH$_2$CH$_2$)$_n$— | — | —CO$_2$H, —NH$_2$, —OH, —NH—R$^{3a}$, or —CO$_2$R$^{3b}$ |
| 84 | double | substituted thiol | O or S | —CH$_2$—, —CH$_2$CH$_2$—, —CH(R²)—, or —CH$_2$CH(R²)— | —(CH$_2$CH$_2$O)$_n$— | —(CH$_2$)$_n$— | — | —CO$_2$H, —NH$_2$, —OH, —NH—R$^{3a}$, or —CO$_2$R$^{3b}$ |
| 85 | double | substituted thiol | O or S | —CH$_2$—, —CH$_2$CH$_2$—, —CH(R²)—, or —CH$_2$CH(R²)— | —(OCH$_2$CH$_2$)$_n$— | —(CH$_2$)$_n$— | — | —CO$_2$H, —NH$_2$, —OH, —NH—R$^{3a}$, or —CO$_2$R$^{3b}$ |
| 86 | double | substituted thiol | O or S | —CH$_2$—, —CH$_2$CH$_2$—, —CH(R²)—, or —CH$_2$CH(R²)— | —(CH$_2$)$_n$CO— | -Val-Ala- or -Val-Cit- | PAB | —CO$_2$H or —CO$_2$R$^{3b}$ |
| 87 | double | substituted thiol | O or S | —CH$_2$—, —CH$_2$CH$_2$—, —CH(R²)—, or —CH$_2$CH(R²)— | —(CH$_2$)$_n$(OCH$_2$CH$_2$)$_n$—CO— | -Val-Ala- or -Val-Cit- | PAB | —CO$_2$H or —CO$_2$R$^{3b}$ |

TABLE 4-continued

Linkers

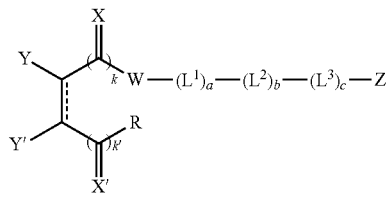

(I)

| Entry | ===== | Y, Y' | X, X' | W | $(L^1)a$ | $L^2$ | $L^3$ | Z |
|---|---|---|---|---|---|---|---|---|
| 88 | double | substituted thiol | O or S | —$CH_2$—, —$CH_2CH_2$—, —$CH(R^2)$—, or —$CH_2CH(R^2)$— | —$(CH_2)_n$—($CH_2CH_2O)_n$—CO— | -Val-Ala- or -Val-Cit- | PAB | —$CO_2H$ or —$CO_2R^{3b}$ |
| 89 | double | substituted thiol | O or S | —$CH_2$—, —$CH_2CH_2$—, —$CH(R^2)$—, or —$CH_2CH(R^2)$— | —($CH_2CH_2O)_n$—($CH_2)_n$—CO— | -Val-Ala- or -Val-Cit- | PAB | —$CO_2H$ or —$CO_2R^{3b}$ |
| 90 | double | substituted thiol | O or S | —$CH_2$—, —$CH_2CH_2$—, —$CH(R^2)$—, or —$CH_2CH(R^2)$— | —($OCH_2CH_2)_n$—($CH_2)_n$—CO— | -Val-Ala- or -Val-Cit- | PAB | —$CO_2H$ or —$CO_2R^{3b}$ |
| 91 | double | substituted sulfonate | O or S | —NH— or —$N(R^1)$— | —$(CH_2)_n$— | — | — | —$CO_2H$, —$NH_2$, —OH, —NH—$R^{3a}$, or —$CO_2R^{3b}$ |
| 92 | double | substituted sulfonate | O or S | —NH— or —$N(R^1)$— | —$(CH_2)_n$— | —($CH_2CH_2O)_n$— | — | —$CO_2H$, —$NH_2$, —OH, —NH—$R^{3a}$, or —$CO_2R^{3b}$ |
| 93 | double | substituted sulfonate | O or S | —NH— or —$N(R^1)$— | —$(CH_2)_n$— | —($OCH_2CH_2)_n$— | — | —$CO_2H$, —$NH_2$, —OH, —NH—$R^{3a}$, or —$CO_2R^{3b}$ |
| 94 | double | substituted sulfonate | O or S | —NH— or —$N(R^1)$— | —($CH_2CH_2O)_n$— | —$(CH_2)_n$— | — | —$CO_2H$, —$NH_2$, —OH, —NH—$R^{3a}$, or —$CO_2R^{3b}$ |
| 95 | double | substituted sulfonate | O or S | —NH— or —$N(R^1)$— | —$(CH_2)_nCO$— | -Val-Ala- or -Val-Cit- | PAB | —$CO_2H$ or —$CO_2R^{3b}$ |
| 96 | double | substituted sulfonate | O or S | —NH— or —$N(R^1)$— | —$(CH_2)_n$($OCH_2CH_2)_n$—CO— | -Val-Ala- or -Val-Cit- | PAB | —$CO_2H$ or —$CO_2R^{3b}$ |
| 97 | double | substituted sulfonate | O or S | —NH— or —$N(R^1)$— | —$(CH_2)_n$($CH_2CH_2O)_n$—CO— | -Val-Ala- or -Val-Cit- | PAB | —$CO_2H$ or —$CO_2R^{3b}$ |
| 98 | double | substituted sulfonate | O or S | —NH— or —$N(R^1)$— | —($CH_2CH_2O)_n$—($CH_2)_n$—CO— | -Val-Ala- or -Val-Cit- | PAB | —$CO_2H$ or —$CO_2R^{3b}$ |
| 99 | double | substituted sulfonate | O or S | —$CH_2$—, —$CH_2CH_2$—, —$CH(R^2)$—, or —$CH_2CH(R^2)$— | —$(CH_2)_n$— | — | — | —$CO_2H$, —$NH_2$, —OH, —NH—$R^{3a}$, or —$CO_2R^{3b}$ |
| 100 | double | substituted sulfonate | O or S | —$CH_2$—, —$CH_2CH_2$—, —$CH(R^2)$—, or —$CH_2CH(R^2)$— | —$(CH_2)_n$— | —($CH_2CH_2O)_n$— | — | —$CO_2H$, —$NH_2$, —OH, —NH—$R^{3a}$, or —$CO_2R^{3b}$ |
| 101 | double | substituted sulfonate | O or S | —$CH_2$—, —$CH_2CH_2$—, —$CH(R^2)$—, or —$CH_2CH(R^2)$— | —$(CH_2)_n$— | —($OCH_2CH_2)_n$— | — | —$CO_2H$, —$NH_2$, —OH, —NH—$R^{3a}$, or —$CO_2R^{3b}$ |
| 102 | double | substituted sulfonate | O or S | —$CH_2$—, —$CH_2CH_2$—, —$CH(R^2)$—, or —$CH_2CH(R^2)$— | —($CH_2CH_2O)_n$— | —$(CH_2)_n$— | — | —$CO_2H$, —$NH_2$, —OH, —NH—$R^{3a}$, or —$CO_2R^{3b}$ |
| 103 | double | substituted sulfonate | O or S | —$CH_2$—, —$CH_2CH_2$—, —$CH(R^2)$—, or —$CH_2CH(R^2)$— | —($OCH_2CH_2)_n$— | —$(CH_2)_n$— | — | —$CO_2H$, —$NH_2$, —OH, —NH—$R^{3a}$, or —$CO_2R^{3b}$ |
| 104 | double | substituted sulfonate | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | —$CO_2H$ or —$CO_2R^{3b}$ |
| 105 | double | substituted sulfonate | O or S | —$CH_2$—, —$CH_2CH_2$—, —$CH(R^2)$—, or —$CH_2CH(R^2)$— | —$(CH_2)_n$($OCH_2CH_2)_n$—CO— | -Val-Ala- or -Val-Cit- | PAB | —$CO_2H$ or —$CO_2R^{3b}$ |
| 106 | double | substituted sulfonate | O or S | —$CH_2$—, —$CH_2CH_2$—, —$CH(R^2)$—, or —$CH_2CH(R^2)$— | —$(CH_2)_n$($CH_2CH_2O)_n$—CO— | -Val-Ala- or -Val-Cit- | PAB | —$CO_2H$ or —$CO_2R^{3b}$ |
| 107 | double | substituted sulfonate | O or S | —$CH_2$—, —$CH_2CH_2$—, —$CH(R^2)$—, or —$CH_2CH(R^2)$— | —($CH_2CH_2O)_n$—($CH_2)_n$—CO— | -Val-Ala- or -Val-Cit- | PAB | —$CO_2H$ or —$CO_2R^{3b}$ |
| 108 | double | substituted sulfonate | O or S | —$CH_2$—, —$CH_2CH_2$—, —$CH(R^2)$—, or —$CH_2CH(R^2)$— | —($OCH_2CH_2)_n$—($CH_2)_n$—CO— | -Val-Ala- or -Val-Cit- | PAB | —$CO_2H$ or —$CO_2R^{3b}$ |

For all Entries 1-108 Provided in Table 1 Above, R, k, k', a, b and c May be Defined as Follows:

R: W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, W-$(L^1)_a$-$(L^2)_b$-$(L^3)_c$-Z, a detectable probe, a ligand, or an antibody fragment k, k': each independently 0 or 1 a, b and c: each independently 0, 1, 2 or 3, provided that at least one of a, b or c is 1

TABLE 5

Linker-Cytotoxin Conjugates (II)

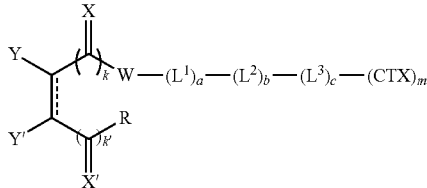

| Entry | ====== | Y, Y' | X, X' | W | $(L^1)a$ | $L^2$ | $L^3$ | Bond to CTX |
|---|---|---|---|---|---|---|---|---|
| 1 | single | halo | O or S | —NH— or —N(R$^1$)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 2 | single | halo | O or S | —NH— or —N(R$^1$)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 3 | single | halo | O or S | —NH— or —N(R$^1$)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 4 | single | halo | O or S | —NH— or —N(R$^1$)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 5 | single | halo | O or S | —NH— or —N(R$^1$)— | —(CH$_2$)$_n$CO— | -Val-Ala- or -Val-Cit- | PAB | amide |
| 6 | single | halo | O or S | —NH— or —N(R$^1$)— | —(CH$_2$)$_n$—(OCH$_2$CH$_2$)$_n$—CO— | -Val-Ala- or -Val-Cit- | PAB | amide |
| 7 | single | halo | O or S | —NH— or —N(R$^1$)— | —(CH$_2$)$_n$—(CH$_2$CH$_2$O)$_n$—CO— | -Val-Ala- or -Val-Cit- | PAB | amide |
| 8 | single | halo | O or S | —NH— or —N(R$^1$)— | —(CH$_2$CH$_2$O)$_n$—(CH$_2$)$_n$—CO— | -Val-Ala- or -Val-Cit- | PAB | amide |
| 9 | single | halo | O or S | —CH$_2$—, —CH$_2$CH$_2$—, —CH(R$^2$)—, or —CH$_2$CH(R$^2$)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 10 | single | halo | O or S | —CH$_2$—, —CH$_2$CH$_2$—, —CH(R$^2$)—, or —CH$_2$CH(R$^2$)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |

TABLE 5-continued

Linker-Cytotoxin Conjugates

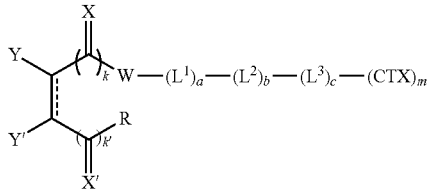

(II)

| Entry | ====== | Y, Y' | X, X' | W | (L$^1$)a | L$^2$ | L$^3$ | Bond to CTX |
|---|---|---|---|---|---|---|---|---|
| 11 | single | halo | O or S | —CH$_2$—, —CH$_2$CH$_2$—, —CH(R$^2$)—, or —CH$_2$CH(R$^2$)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 12 | single | halo | O or S | —CH$_2$—, —CH$_2$CH$_2$—, —CH(R$^2$)—, or —CH$_2$CH(R$^2$)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 13 | single | halo | O or S | —CH$_2$—, —CH$_2$CH$_2$—, —CH(R$^2$)—, or —CH$_2$CH(R$^2$)— | —(OCH$_2$CH$_2$)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 14 | single | halo | O or S | —CH$_2$—, —CH$_2$CH$_2$—, —CH(R$^2$)—, or —CH$_2$CH(R$^2$)— | —(CH$_2$)$_n$CO— | -Val-Ala- or -Val-Cit- | PAB | amide |
| 15 | single | halo | O or S | —CH$_2$—, —CH$_2$CH$_2$—, —CH(R$^2$)—, or —CH$_2$CH(R$^2$)— | —(CH$_2$)$_n$—(OCH$_2$CH$_2$)$_n$—CO— | -Val-Ala- or -Val-Cit- | PAB | amide |
| 16 | single | halo | O or S | —CH$_2$—, —CH$_2$CH$_2$—, —CH(R$^2$)—, or —CH$_2$CH(R$^2$)— | —(CH$_2$)$_n$—(OCH$_2$CH$_2$O)$_n$—CO— | -Val-Ala- or -Val-Cit- | PAB | amide |
| 17 | single | halo | O or S | —CH$_2$—, —CH$_2$CH$_2$—, —CH(R$^2$)—, or —CH$_2$CH(R$^2$)— | —(CH$_2$CH$_2$O)$_n$—(CH$_2$)$_n$—CO— | -Val-Ala- or -Val-Cit- | PAB | amide |
| 18 | single | halo | O or S | —CH$_2$—, —CH$_2$CH$_2$—, —CH(R$^2$)—, or —CH$_2$CH(R$^2$)— | —(OCH$_2$CH$_2$)$_n$—(CH$_2$)$_n$—CO— | -Val-Ala- or -Val-Cit- | PAB | amide |
| 19 | single | substituted thiol | O or S | —NH— or —N(R$^1$)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 20 | single | substituted thiol | O or S | —NH— or —N(R$^1$)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 21 | single | substituted thiol | O or S | —NH— or —N(R$^1$)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |

TABLE 5-continued

Linker-Cytotoxin Conjugates (II)
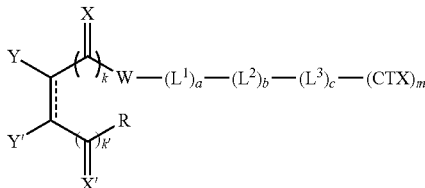

| Entry | ====== | Y, Y' | X, X' | W | $(L^1)a$ | $L^2$ | $L^3$ | Bond to CTX |
|---|---|---|---|---|---|---|---|---|
| 22 | single | substituted thiol | O or S | —NH— or —N($R^1$)— | —($CH_2CH_2O)_n$— | —($CH_2)_n$— | — | amide, N-alkylamide, carbamate, N-alkylcarbamate, amine, N-alkylamine, ether, thioether, urea, N-alkylurea, or N,N-dialkylurea |
| 23 | single | substituted thiol | O or S | —NH— or —N($R^1$)— | —($CH_2)_n$CO— | -Val-Ala- or -Val-Cit- | PAB | amide |
| 24 | single | substituted thiol | O or S | —NH— or —N($R^1$)— | —($CH_2)_n$—($OCH_2CH_2)_n$—CO— | -Val-Ala- or -Val-Cit- | PAB | amide |
| 25 | single | substituted thiol | O or S | —NH— or —N($R^1$)— | —($CH_2)_n$—($CH_2CH_2O)_n$—CO— | -Val-Ala- or -Val-Cit- | PAB | amide |
| 26 | single | substituted thiol | O or S | —NH— or —N($R^1$)— | —($CH_2CH_2O)_n$—($CH_2)_n$—CO— | -Val-Ala- or -Val-Cit- | PAB | amide |
| 27 | single | substituted thiol | O or S | —$CH_2$—, —$CH_2CH_2$—, —CH($R^2$)—, or —$CH_2$CH($R^2$)— | —($CH_2)_n$— | — | — | amide, N-alkylamide, carbamate, N-alkylcarbamate, amine, N-alkylamine, ether, thioether, urea, N-alkylurea, or N,N-dialkylurea |
| 28 | single | substituted thiol | O or S | —$CH_2$—, —$CH_2CH_2$—, —CH($R^2$)—, or —$CH_2$CH($R^2$)— | —($CH_2)_n$— | —($CH_2CH_2O)_n$— | — | amide, N-alkylamide, carbamate, N-alkylcarbamate, amine, N-alkylamine, ether, thioether, urea, N-alkylurea, or N,N-dialkylurea |
| 29 | single | substituted thiol | O or S | —$CH_2$—, —$CH_2CH_2$—, —CH($R^2$)—, or —$CH_2$CH($R^2$)— | —($CH_2)_n$— | —($OCH_2CH_2)_n$— | — | amide, N-alkylamide, carbamate, N-alkylcarbamate, amine, N-alkylamine, ether, thioether, urea, N-alkylurea, or N,N-dialkylurea |
| 30 | single | substituted thiol | O or S | —$CH_2$—, —$CH_2CH_2$—, —CH($R^2$)—, or —$CH_2$CH($R^2$)— | —($CH_2CH_2O)_n$— | —($CH_2)_n$— | — | amide, N-alkylamide, carbamate, N-alkylcarbamate, amine, N-alkylamine, ether, thioether, urea, N-alkylurea, or N,N-dialkylurea |
| 31 | single | substituted thiol | O or S | —$CH_2$—, —$CH_2CH_2$—, —CH($R^2$)—, or —$CH_2$CH($R^2$)— | —($OCH_2CH_2)_n$— | —($CH_2)_n$— | — | amide, N-alkylamide, carbamate, N-alkylcarbamate, amine, N-alkylamine, ether, thioether, urea, N-alkylurea, or N,N-dialkylurea |
| 32 | single | substituted thiol | O or S | —$CH_2$—, —$CH_2CH_2$—, —CH($R^2$)—, or —$CH_2$CH($R^2$)— | —($CH_2)_n$CO— | -Val-Ala- or -Val-Cit- | PAB | amide |
| 33 | single | substituted thiol | O or S | —$CH_2$—, —$CH_2CH_2$—, —CH($R^2$)—, or —$CH_2$CH($R^2$)— | —($CH_2)_n$—($OCH_2CH_2)_n$—CO— | -Val-Ala- or -Val-Cit- | PAB | amide |
| 34 | single | substituted thiol | O or S | —$CH_2$—, —$CH_2CH_2$—, —CH($R^2$)—, or —$CH_2$CH($R^2$)— | —($CH_2)_n$—($CH_2CH_2O)_n$—CO— | -Val-Ala- or -Val-Cit- | PAB | amide |

TABLE 5-continued

Linker-Cytotoxin Conjugates

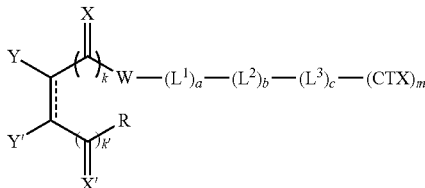

(II)

| Entry | ====== | Y, Y' | X, X' | W | (L¹)a | L² | L³ | Bond to CTX |
|---|---|---|---|---|---|---|---|---|
| 35 | single | substituted thiol | O or S | —CH₂—, —CH₂CH₂—, —CH(R²)—, or —CH₂CH(R²)— | —(CH₂CH₂O)$_n$—(CH₂)$_n$—CO— | -Val-Ala- or -Val-Cit- | PAB | amide |
| 36 | single | substituted thiol | O or S | —CH₂—, —CH₂CH₂—, —CH(R²)—, or —CH₂CH(R²)— | —(CH₂)$_n$CO— | -Val-Ala- or -Val-Cit- | PAB | amide |
| 37 | single | substituted sulfonate | O or S | —NH— or —N(R¹)— | —(CH₂)$_n$— | — | — | amide, N-alkylamide, carbamate, N-alkylcarbamate, amine, N-alkylamine, ether, thioether, urea, N-alkylurea, or N,N-dialkylurea |
| 38 | single | substituted sulfonate | O or S | —NH— or —N(R¹)— | —(CH₂)$_n$— | —(CH₂CH₂O)$_n$— | — | amide, N-alkylamide, carbamate, N-alkylcarbamate, amine, N-alkylamine, ether, thioether, urea, N-alkylurea, or N,N-dialkylurea |
| 39 | single | substituted sulfonate | O or S | —NH— or —N(R¹)— | —(CH₂)$_n$— | —(OCH₂CH₂)$_n$— | — | amide, N-alkylamide, carbamate, N-alkylcarbamate, amine, N-alkylamine, ether, thioether, urea, N-alkylurea, or N,N-dialkylurea |
| 40 | single | substituted sulfonate | O or S | —NH— or —N(R¹)— | —(CH₂CH₂O)$_n$— | —(CH₂)$_n$— | — | amide, N-alkylamide, carbamate, N-alkylcarbamate, amine, N-alkylamine, ether, thioether, urea, N-alkylurea, or N,N-dialkylurea |
| 41 | single | substituted sulfonate | O or S | —NH— or —N(R¹)— | —(CH₂)$_n$CO— | -Val-Ala- or -Val-Cit- | PAB | amide |
| 42 | single | substituted sulfonate | O or S | —NH— or —N(R¹)— | —(CH₂)$_n$—(OCH₂CH₂)$_n$—CO— | -Val-Ala- or -Val-Cit- | PAB | amide |
| 43 | single | substituted sulfonate | O or S | —NH— or —N(R¹)— | —(CH₂)$_n$—(CH₂CH₂O)$_n$—CO— | -Val-Ala- or -Val-Cit- | PAB | amide |
| 44 | single | substituted sulfonate | O or S | —NH— or —N(R¹)— | —(CH₂CH₂O)$_n$—(CH₂)$_n$—CO— | -Val-Ala- or -Val-Cit- | PAB | amide |
| 45 | single | substituted sulfonate | O or S | —CH₂—, —CH₂CH₂—, —CH(R²)—, or —CH₂CH(R²)— | —(CH₂)$_n$— | — | — | amide, N-alkylamide, carbamate, N-alkylcarbamate, amine, N-alkylamine, ether, thioether, urea, N-alkylurea, or N,N-dialkylurea |
| 46 | single | substituted sulfonate | O or S | —CH₂—, —CH₂CH₂—, —CH(R²)—, or —CH₂CH(R²)— | —(CH₂)$_n$— | —(CH₂CH₂O)$_n$— | — | amide, N-alkylamide, carbamate, N-alkylcarbamate, amine, N-alkylamine, ether, thioether, urea, N-alkylurea, or N,N-dialkylurea |
| 47 | single | substituted sulfonate | O or S | —CH₂—, —CH₂CH₂—, —CH(R²)—, or —CH₂CH(R²)— | —(CH₂)$_n$— | —(OCH₂CH₂)$_n$— | — | amide, N-alkylamide, carbamate, N-alkylcarbamate, amine, N-alkylamine, ether, thioether, urea, N-alkylurea, or N,N-dialkylurea |

TABLE 5-continued

Linker-Cytotoxin Conjugates

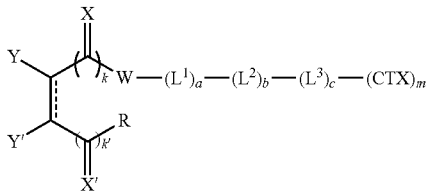

(II)

| Entry | ===== | Y, Y' | X, X' | W | (L¹)a | L² | L³ | Bond to CTX |
|---|---|---|---|---|---|---|---|---|
| 48 | single | substituted sulfonate | O or S | —$CH_2$—, —$CH_2CH_2$—, —$CH(R^2)$—, or —$CH_2CH(R^2)$— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 49 | single | substituted sulfonate | O or S | —$CH_2$—, —$CH_2CH_2$—, —$CH(R^2)$—, or —$CH_2CH(R^2)$— | —$(OCH_2CH_2)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 50 | single | substituted sulfonate | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | amide |
| 51 | single | substituted sulfonate | O or S | —$CH_2$—, —$CH_2CH_2$—, —$CH(R^2)$—, or —$CH_2CH(R^2)$— | —$(CH_2)_n$—$(OCH_2CH_2)_n$—CO— | -Val-Ala- or -Val-Cit- | PAB | amide |
| 52 | single | substituted sulfonate | O or S | —$CH_2$—, —$CH_2CH_2$—, —$CH(R^2)$—, or —$CH_2CH(R^2)$— | —$(CH_2)_n$—$(CH_2CH_2O)_n$—CO— | -Val-Ala- or -Val-Cit- | PAB | amide |
| 53 | single | substituted sulfonate | O or S | —$CH_2$—, —$CH_2CH_2$—, —$CH(R^2)$—, or —$CH_2CH(R^2)$— | —$(CH_2CH_2O)_n$—$(CH_2)_n$—CO— | -Val-Ala- or -Val-Cit- | PAB | amide |
| 54 | single | substituted sulfonate | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | amide |
| 55 | double | halo | O or S | —NH— or —$N(R^1)$— | —$(CH_2)_n$— | — | — | amide, N-alkylamide, carbamate, N-alkylcarbamate, amine, N-alkylamine, ether, thioether, urea, N-alkylurea, or N,N-dialkylurea |
| 56 | double | halo | O or S | —NH— or —$N(R^1)$— | —$(CH_2)_n$— | —$(CH_2CH_2O)_n$— | — | amide, N-alkylamide, carbamate, N-alkylcarbamate, amine, N-alkylamine, ether, thioether, urea, N-alkylurea, or N,N-dialkylurea |
| 57 | double | halo | O or S | —NH— or —$N(R^1)$— | —$(CH_2)_n$— | —$(OCH_2CH_2)_n$— | — | amide, N-alkylamide, carbamate, N-alkylcarbamate, amine, N-alkylamine, ether, thioether, urea, N-alkylurea, or N,N-dialkylurea |
| 58 | double | halo | O or S | —NH— or —$N(R^1)$— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 59 | double | halo | O or S | —NH— or —$N(R^1)$— | —$(CH_2)_nCO$— | -Val-Ala- or -Val-Cit- | PAB | amide |

TABLE 5-continued

Linker-Cytotoxin Conjugates

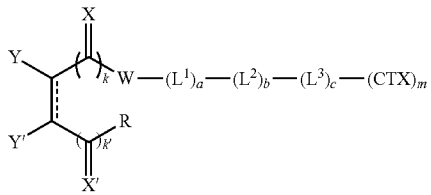

(II)

| Entry | ═══ | Y, Y' | X, X' | W | $(L^1)_a$ | $L^2$ | $L^3$ | Bond to CTX |
|---|---|---|---|---|---|---|---|---|
| 60 | double | halo | O or S | —NH— or —N(R$^1$)— | —(CH$_2$)$_n$—(OCH$_2$CH$_2$)$_n$—CO— | -Val-Ala- or -Val-Cit- | PAB | amide |
| 61 | double | halo | O or S | —NH— or —N(R$^1$)— | —(CH$_2$)$_n$—(CH$_2$CH$_2$O)$_n$—CO— | -Val-Ala- or -Val-Cit- | PAB | amide |
| 62 | double | halo | O or S | —NH— or —N(R$^1$)— | —(CH$_2$CH$_2$O)$_n$—(CH$_2$)$_n$—CO— | -Val-Ala- or -Val-Cit- | PAB | amide |
| 63 | double | halo | O or S | —CH$_2$—, —CH$_2$CH$_2$—, —CH(R$^2$)—, or —CH$_2$CH(R$^2$)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 64 | double | halo | O or S | —CH$_2$—, —CH$_2$CH$_2$—, —CH(R$^2$)—, or —CH$_2$CH(R$^2$)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 65 | double | halo | O or S | —CH$_2$—, —CH$_2$CH$_2$—, —CH(R$^2$)—, or —CH$_2$CH(R$^2$)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 66 | double | halo | O or S | —CH$_2$—, —CH$_2$CH$_2$—, —CH(R$^2$)—, or —CH$_2$CH(R$^2$)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 67 | double | halo | O or S | —CH$_2$—, —CH$_2$CH$_2$—, —CH(R$^2$)—, or —CH$_2$CH(R$^2$)— | —(OCH$_2$CH$_2$)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 68 | double | halo | O or S | —CH$_2$—, —CH$_2$CH$_2$—, —CH(R$^2$)—, or —CH$_2$CH(R$^2$)— | —(CH$_2$)$_n$CO— | -Val-Ala- or -Val-Cit- | PAB | amide |
| 69 | double | halo | O or S | —CH$_2$—, —CH$_2$CH$_2$—, —CH(R$^2$)—, or —CH$_2$CH(R$^2$)— | —(CH$_2$)$_n$—(OCH$_2$CH$_2$)$_n$—CO— | -Val-Ala- or -Val-Cit- | PAB | amide |
| 70 | double | halo | O or S | —CH$_2$—, —CH$_2$CH$_2$—, —CH(R$^2$)—, or —CH$_2$CH(R$^2$)— | —(CH$_2$)$_n$—(CH$_2$CH$_2$O)$_n$—CO— | -Val-Ala- or -Val-Cit- | PAB | amide |
| 71 | double | halo | O or S | —CH$_2$—, —CH$_2$CH$_2$—, —CH(R$^2$)—, or —CH$_2$CH(R$^2$)— | —(CH$_2$CH$_2$O)$_n$—(CH$_2$)$_n$—CO— | -Val-Ala- or -Val-Cit- | PAB | amide |
| 72 | double | halo | O or S | —CH$_2$—, —CH$_2$CH$_2$—, —CH(R$^2$)—, or —CH$_2$CH(R$^2$)— | —(OCH$_2$CH$_2$)$_n$—(CH$_2$)$_n$—CO— | -Val-Ala- or -Val-Cit- | PAB | amide |

TABLE 5-continued

Linker-Cytotoxin Conjugates $$Y \underset{Y'}{\overset{X}{\underset{(\phantom{x})_{k'}}{\overset{(\phantom{x})_k}{\bigg(}}}} W-(L^1)_a-(L^2)_b-(L^3)_c-(CTX)_m \qquad (II)$$

| Entry | ====== | Y, Y' | X, X' | W | (L¹)a | L² | L³ | Bond to CTX |
|---|---|---|---|---|---|---|---|---|
| 73 | double | substituted thiol | O or S | —NH— or —N(R¹)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 74 | double | substituted thiol | O or S | —NH— or —N(R¹)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 75 | double | substituted thiol | O or S | —NH— or —N(R¹)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 76 | double | substituted thiol | O or S | —NH— or —N(R¹)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 77 | double | substituted thiol | O or S | —NH— or —N(R¹)— | —(CH$_2$)$_n$CO— | -Val-Ala- or -Val-Cit- | PAB | amide |
| 78 | double | substituted thiol | O or S | —NH— or —N(R¹)— | —(CH$_2$)$_n$—(OCH$_2$CH$_2$)$_n$—CO— | -Val-Ala- or -Val-Cit- | PAB | amide |
| 79 | double | substituted thiol | O or S | —NH— or —N(R¹)— | —(CH$_2$)$_n$—(CH$_2$CH$_2$O)$_n$—CO— | -Val-Ala- or -Val-Cit- | PAB | amide |
| 80 | double | substituted thiol | O or S | —NH— or —N(R¹)— | —(CH$_2$CH$_2$O)$_n$—(CH$_2$)$_n$—CO— | -Val-Ala- or -Val-Cit- | PAB | amide |
| 81 | double | substituted thiol | O or S | —CH$_2$—, —CH$_2$CH$_2$—, —CH(R²)—, or —CH$_2$CH(R²)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 82 | double | substituted thiol | O or S | —CH$_2$—, —CH$_2$CH$_2$—, —CH(R²)—, or —CH$_2$CH(R²)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 83 | double | substituted thiol | O or S | —CH$_2$—, —CH$_2$CH$_2$—, —CH(R²)—, or —CH$_2$CH(R²)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 84 | double | substituted thiol | O or S | —CH$_2$—, —CH$_2$CH$_2$—, —CH(R²)—, or —CH$_2$CH(R²)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |

TABLE 5-continued

Linker-Cytotoxin Conjugates

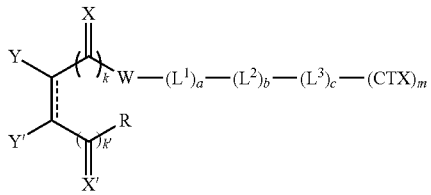

(II)

| Entry | ===== | Y, Y' | X, X' | W | $(L^1)_a$ | $L^2$ | $L^3$ | Bond to CTX |
|---|---|---|---|---|---|---|---|---|
| 85 | double | substituted thiol | O or S | $-CH_2-$, $-CH_2CH_2-$, $-CH(R^2)-$, or $-CH_2CH(R^2)-$ | $-(OCH_2CH_2)_n-$ | $-(CH_2)_n-$ | — | amide, N-alkylamide, carbamate, N-alkylcarbamate, amine, N-alkylamine, ether, thioether, urea, N-alkylurea, or N,N-dialkylurea |
| 86 | double | substituted thiol | O or S | $-CH_2-$, $-CH_2CH_2-$, $-CH(R^2)-$, or $-CH_2CH(R^2)-$ | $-(CH_2)_nCO-$ | -Val-Ala- or -Val-Cit- | PAB | amide |
| 87 | double | substituted thiol | O or S | $-CH_2-$, $-CH_2CH_2-$, $-CH(R^2)-$, or $-CH_2CH(R^2)-$ | $-(CH_2)_n-(OCH_2CH_2)_n-CO-$ | -Val-Ala- or -Val-Cit- | PAB | amide |
| 88 | double | substituted thiol | O or S | $-CH_2-$, $-CH_2CH_2-$, $-CH(R^2)-$, or $-CH_2CH(R^2)-$ | $-(CH_2)_n-(CH_2CH_2O)_n-CO-$ | -Val-Ala- or -Val-Cit- | PAB | amide |
| 89 | double | substituted thiol | O or S | $-CH_2-$, $-CH_2CH_2-$, $-CH(R^2)-$, or $-CH_2CH(R^2)-$ | $-(CH_2CH_2O)_n-(CH_2)_n-CO-$ | -Val-Ala- or -Val-Cit- | PAB | amide |
| 90 | double | substituted thiol | O or S | $-CH_2-$, $-CH_2CH_2-$, $-CH(R^2)-$, or $-CH_2CH(R^2)-$ | $-(CH_2)_nCO-$ | -Val-Ala- or -Val-Cit- | PAB | amide |
| 91 | double | substituted sulfonate | O or S | $-NH-$ or $-N(R^1)-$ | $-(CH_2)_n-$ | — | — | amide, N-alkylamide, carbamate, N-alkylcarbamate, amine, N-alkylamine, ether, thioether, urea, N-alkylurea, or N,N-dialkylurea |
| 92 | double | substituted sulfonate | O or S | $-NH-$ or $-N(R^1)-$ | $-(CH_2)_n-$ | $-(CH_2CH_2O)_n-$ | — | amide, N-alkylamide, carbamate, N-alkylcarbamate, amine, N-alkylamine, ether, thioether, urea, N-alkylurea, or N,N-dialkylurea |
| 93 | double | substituted sulfonate | O or S | $-NH-$ or $-N(R^1)-$ | $-(CH_2)_n-$ | $-(OCH_2CH_2)_n-$ | — | amide, N-alkylamide, carbamate, N-alkylcarbamate, amine, N-alkylamine, ether, thioether, urea, N-alkylurea, or N,N-dialkylurea |
| 94 | double | substituted sulfonate | O or S | $-NH-$ or $-N(R^1)-$ | $-(CH_2CH_2O)_n-$ | $-(CH_2)_n-$ | — | amide, N-alkylamide, carbamate, N-alkylcarbamate, amine, N-alkylamine, ether, thioether, urea, N-alkylurea, or N,N-dialkylurea |
| 95 | double | substituted sulfonate | O or S | $-NH-$ or $-N(R^1)-$ | $-(CH_2)_nCO-$ | -Val-Ala- or -Val-Cit- | PAB | amide |
| 96 | double | substituted sulfonate | O or S | $-NH-$ or $-N(R^1)-$ | $-(CH_2)_n-(OCH_2CH_2)_n-CO-$ | -Val-Ala- or -Val-Cit- | PAB | amide |
| 97 | double | substituted sulfonate | O or S | $-NH-$ or $-N(R^1)-$ | $-(CH_2)_n-(CH_2CH_2O)_n-CO-$ | -Val-Ala- or -Val-Cit- | PAB | amide |
| 98 | double | substituted sulfonate | O or S | $-NH-$ or $-N(R^1)-$ | $-(CH_2CH_2O)_n-(CH_2)_n-CO-$ | -Val-Ala- or -Val-Cit- | PAB | amide |

TABLE 5-continued

Linker-Cytotoxin Conjugates

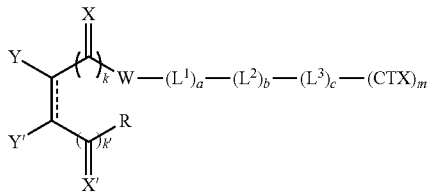
(II)

| Entry | ------ | Y, Y' | X, X' | W | (L¹)a | L² | L³ | Bond to CTX |
|---|---|---|---|---|---|---|---|---|
| 99 | double | substituted sulfonate | O or S | —CH$_2$—, —CH$_2$CH$_2$—, —CH(R$^2$)—, or —CH$_2$CH(R$^2$)— | —(CH$_2$)$_n$— | — | — | amide, N-alkylamide, carbamate, N-alkylcarbamate, amine, N-alkylamine, ether, thioether, urea, N-alkylurea, or N,N-dialkylurea |
| 100 | double | substituted sulfonate | O or S | —CH$_2$—, —CH$_2$CH$_2$—, —CH(R$^2$)—, or —CH$_2$CH(R$^2$)— | —(CH$_2$)$_n$— | —(CH$_2$CH$_2$O)$_n$— | — | amide, N-alkylamide, carbamate, N-alkylcarbamate, amine, N-alkylamine, ether, thioether, urea, N-alkylurea, or N,N-dialkylurea |
| 101 | double | substituted sulfonate | O or S | —CH$_2$—, —CH$_2$CH$_2$—, —CH(R$^2$)—, or —CH$_2$CH(R$^2$)— | —(CH$_2$)$_n$— | —(OCH$_2$CH$_2$)$_n$— | — | amide, N-alkylamide, carbamate, N-alkylcarbamate, amine, N-alkylamine, ether, thioether, urea, N-alkylurea, or N,N-dialkylurea |
| 102 | double | substituted sulfonate | O or S | —CH$_2$—, —CH$_2$CH$_2$—, —CH(R$^2$)—, or —CH$_2$CH(R$^2$)— | —(CH$_2$CH$_2$O)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 103 | double | substituted sulfonate | O or S | —CH$_2$—, —CH$_2$CH$_2$—, —CH(R$^2$)—, or —CH$_2$CH(R$^2$)— | —(OCH$_2$CH$_2$)$_n$— | —(CH$_2$)$_n$— | — | amide, N-alkylamide, carbamate, N-alkylcarbamate, amine, N-alkylamine, ether, thioether, urea, N-alkylurea, or N,N-dialkylurea |
| 104 | double | substituted sulfonate | O or S | —CH$_2$—, —CH$_2$CH$_2$—, —CH(R$^2$)—, or —CH$_2$CH(R$^2$)— | —(CH$_2$)$_n$CO— | -Val-Ala- or -Val-Cit- | PAB | amide |
| 105 | double | substituted sulfonate | O or S | —CH$_2$—, —CH$_2$CH$_2$—, —CH(R$^2$)—, or —CH$_2$CH(R$^2$)— | —(CH$_2$)$_n$—(OCH$_2$CH$_2$)$_n$—CO— | -Val-Ala- or -Val-Cit- | PAB | amide |
| 106 | double | substituted sulfonate | O or S | —CH$_2$—, —CH$_2$CH$_2$—, —CH(R$^2$)—, or —CH$_2$CH(R$^2$)— | —(CH$_2$)$_n$—(CH$_2$CH$_2$O)$_n$—CO— | -Val-Ala- or -Val-Cit- | PAB | amide |
| 107 | double | substituted sulfonate | O or S | —CH$_2$—, —CH$_2$CH$_2$—, —CH(R$^2$)—, or —CH$_2$CH(R$^2$)— | —(CH$_2$CH$_2$O)$_n$—(CH$_2$)$_n$—CO— | -Val-Ala- or -Val-Cit- | PAB | amide |
| 108 | double | substituted sulfonate | O or S | —CH$_2$—, —CH$_2$CH$_2$—, —CH(R$^2$)—, or —CH$_2$CH(R$^2$)— | —(CH$_2$)$_n$CO— | -Val-Ala- or -Val-Cit- | PAB | amide |

For all Entries 1-108 Provided in Table 2 Above, CTX, R, k, k', a, b, and c May be Defined as Follows:

CTX: Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, or Vincristine R: W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, W-$(L^1)_a$-$(L^2)_b$-$(L^3)_c$-Z, W-$(L^1)_a$-$(L^2)_b$-$(L^3)_c$-CTX, a detectable probe, a ligand, or an antibody fragment k, k': each independently 0 or 1 a, b and c: each independently 0, 1, 2 or 3, provided that at least one of a, b or c is 1 m: an integer of 1 to 4

TABLE 6

Antibody-Drug Conjugates (III)

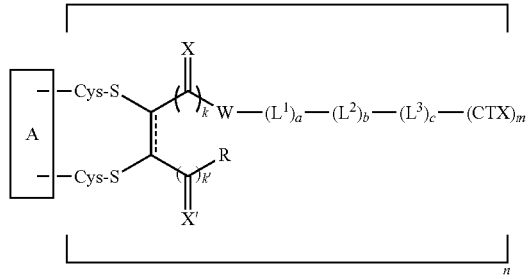

| Entry | ===== | A | X, X' | W | $(L^1)a$ | $L^2$ | $L^3$ | Bond to CTX |
|---|---|---|---|---|---|---|---|---|
| 1 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$— | — | — | amide, N-alkylamide, carbamate, N-alkylcarbamate, amine, N-alkylamine, ether, thioether, urea, N-alkylurea, or N,N-dialkylurea |
| 2 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$— | —$(CH_2CH_2O)_n$— | — | amide, N-alkylamide, carbamate, N-alkylcarbamate, amine, N-alkylamine, ether, thioether, urea, N-alkylurea, or N,N-dialkylurea |
| 3 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$— | —$(OCH_2CH_2)_n$— | — | amide, N-alkylamide, carbamate, N-alkylcarbamate, amine, N-alkylamine, ether, thioether, urea, N-alkylurea, or N,N-dialkylurea |
| 4 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 5 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$CO— | -Val-Ala- or -Val-Cit- | PAB | amide |

TABLE 6-continued

Antibody-Drug Conjugates

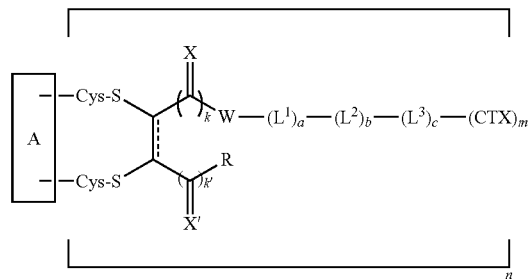

(III)

| Entry | ------ | A | X, X' | W | $(L^1)a$ | $L^2$ | $L^3$ | Bond to CTX |
|---|---|---|---|---|---|---|---|---|
| 6 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$—$(OCH_2CH_2)_n$—CO— | -Val-Ala- or -Val-Cit- | PAB | amide |
| 7 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$—$(CH_2CH_2O)_n$—CO— | -Val-Ala- or -Val-Cit- | PAB | amide |
| 8 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2CH_2O)_n$—$(CH_2)_n$—CO— | -Val-Ala- or -Val-Cit- | PAB | amide |
| 9 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —CH($R^2$)—, or —$CH_2$CH($R^2$)— | —$(CH_2)_n$— | — | — | amide, N-alkylamide, carbamate, N-alkylcarbamate, amine, N-alkylamine, ether, thioether, urea, N-alkylurea, or N,N-dialkylurea |
| 10 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —CH($R^2$)—, or —$CH_2$CH($R^2$)— | —$(CH_2)_n$— | —$(CH_2CH_2O)_n$— | — | amide, N-alkylamide, carbamate, N-alkylcarbamate, amine, N-alkylamine, ether, thioether, urea, N-alkylurea, or N,N-dialkylurea |
| 11 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —CH($R^2$)—, or —$CH_2$CH($R^2$)— | —$(CH_2)_n$— | —$(OCH_2CH_2)_n$— | — | amide, N-alkylamide, carbamate, N-alkylcarbamate, amine, N-alkylamine, ether, thioether, urea, N-alkylurea, or N,N-dialkylurea |
| 12 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —CH($R^2$)—, or —$CH_2$CH($R^2$)— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |

TABLE 6-continued

Antibody-Drug Conjugates

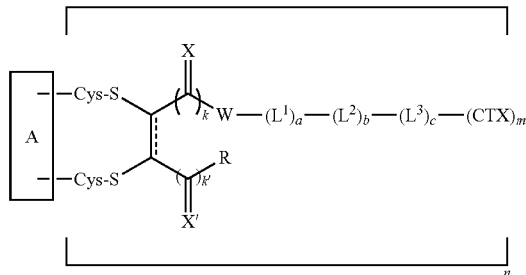

(III)

| Entry | ------ | A | X, X' | W | (L¹)a | L² | L³ | Bond to CTX |
|---|---|---|---|---|---|---|---|---|
| 13 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(OCH_2CH_2)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 14 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | amide |
| 15 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_n$—$(OCH_2CH_2)_n$—$CO$— | -Val-Ala- or -Val-Cit- | PAB | amide |
| 16 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_n$—$(CH_2CH_2O)_n$—$CO$— | -Val-Ala- or -Val-Cit- | PAB | amide |
| 17 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2CH_2O)_n$—$(CH_2)_n$—$CO$— | -Val-Ala- or -Val-Cit- | PAB | amide |
| 18 | single | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | amide |
| 19 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —$N(R^1)$— | —$(CH_2)_n$— | — | — | amide, N-alkylamide, carbamate, N-alkylcarbamate, amine, N-alkylamine, ether, thioether, urea, N-alkylurea, or N,N-dialkylurea |

TABLE 6-continued

Antibody-Drug Conjugates

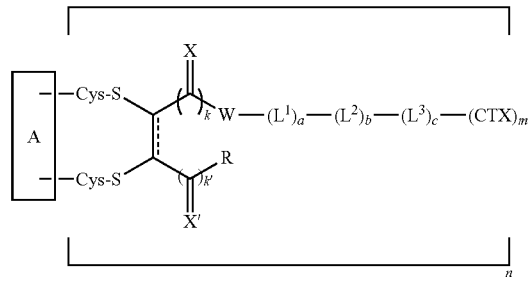

(III)

| Entry | ------ | A | X, X' | W | $(L^1)a$ | $L^2$ | $L^3$ | Bond to CTX |
|---|---|---|---|---|---|---|---|---|
| 20 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$— | —$(CH_2CH_2O)_n$— | — | amide, N-alkylamide, carbamate, N-alkylcarbamate, amine, N-alkylamine, ether, thioether, urea, N-alkylurea, or N,N-dialkylurea |
| 21 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$— | —$(OCH_2CH_2)_n$— | — | amide, N-alkylamide, carbamate, N-alkylcarbamate, amine, N-alkylamine, ether, thioether, urea, N-alkylurea, or N,N-dialkylurea |
| 22 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 23 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$CO— | -Val-Ala- or -Val-Cit- | PAB | amide |
| 24 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$—$(OCH_2CH_2)_n$—CO— | -Val-Ala- or -Val-Cit- | PAB | amide |
| 25 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2)_n$—$(CH_2CH_2O)_n$—CO— | -Val-Ala- or -Val-Cit- | PAB | amide |
| 26 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —NH— or —N($R^1$)— | —$(CH_2CH_2O)_n$—$(CH_2)_n$—CO— | -Val-Ala- or -Val-Cit- | PAB | amide |

TABLE 6-continued

Antibody-Drug Conjugates

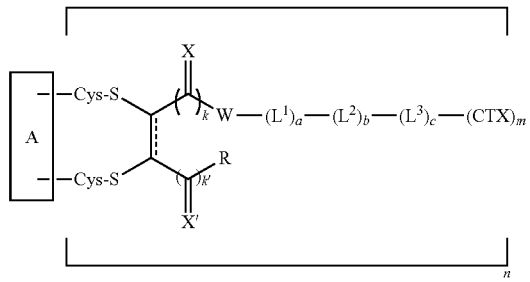

(III)

| Entry | ------ | A | X, X' | W | $(L^1)_a$ | $L^2$ | $L^3$ | Bond to CTX |
|---|---|---|---|---|---|---|---|---|
| 27 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_n$— | — | — | amide, N-alkylamide, carbamate, N-alkylcarbamate, amine, N-alkylamine, ether, thioether, urea, N-alkylurea, or N,N-dialkylurea |
| 28 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_n$— | —$(CH_2CH_2O)_n$— | — | amide, N-alkylamide, carbamate, N-alkylcarbamate, amine, N-alkylamine, ether, thioether, urea, N-alkylurea, or N,N-dialkylurea |
| 29 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_n$— | —$(OCH_2CH_2)_n$— | — | amide, N-alkylamide, carbamate, N-alkylcarbamate, amine, N-alkylamine, ether, thioether, urea, N-alkylurea, or N,N-dialkylurea |
| 30 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2CH_2O)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 31 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(OCH_2CH_2)_n$— | —$(CH_2)_n$— | — | amide, N-alkylamide, carbamate, N-alkylcarbamate, amine, N-alkylamine, ether, thioether, urea, N-alkylurea, or N,N-dialkylurea |
| 32 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | —$CH_2$—, —$CH_2CH_2$—, —$CH(R^2)$—, or —$CH_2CH(R^2)$— | —$(CH_2)_nCO$— | -Val-Ala- or -Val-Cit- | PAB | amide |

TABLE 6-continued

Antibody-Drug Conjugates

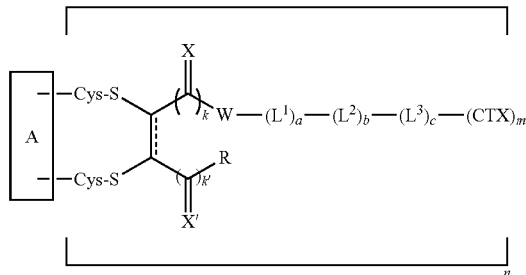

(III)

| Entry | ===== | A | X, X' | W | (L¹)a | L² | L³ | Bond to CTX |
|---|---|---|---|---|---|---|---|---|
| 33 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | $-CH_2-$, $-CH_2CH_2-$, $-CH(R^2)-$, or $-CH_2CH(R^2)-$ | $-(CH_2)_n-(OCH_2CH_2)_n-CO-$ | -Val-Ala- or -Val-Cit- | PAB | amide |
| 34 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | $-CH_2-$, $-CH_2CH_2-$, $-CH(R^2)-$, or $-CH_2CH(R^2)-$ | $-(CH_2)_n-(CH_2CH_2O)_n-CO-$ | -Val-Ala- or -Val-Cit- | PAB | amide |
| 35 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | $-CH_2-$, $-CH_2CH_2-$, $-CH(R^2)-$, or $-CH_2CH(R^2)-$ | $-(CH_2CH_2O)_n-(CH_2)_n-CO-$ | -Val-Ala- or -Val-Cit- | PAB | amide |
| 36 | double | antibody or antibody fragment (e.g., ATZ, ATM, BCZ, BTX, CTX, GTZ, GBT, ITZ, ILM, LVT, MTZ, OTM, RTX, TTM, or TTZ) | O or S | $-CH_2-$, $-CH_2CH_2-$, $-CH(R^2)-$, or $-CH_2CH(R^2)-$ | $-(CH_2)_nCO-$ | -Val-Ala- or -Val-Cit- | PAB | amide |

For all Entries 1-36 Provided in Table 3 Above, CTX, R, k, k', a, b, c, and n May be Defined as Follows:
CTX: Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, or Vincristine
R: W, $(L^1)_a$, $(L^2)_b$, $(L^3)_c$, Z, W-$(L^1)_a$-$(L^2)_b$-$(L^3)_c$, $(L^1)_a$-$(L^2)_b$-$(L^3)_c$-Z, W-$(L^1)_a$-$(L^2)_b$-$(L^3)_c$-Z, W-$(L^1)_a$-$(L^2)_b$-$(L^3)_c$-CYX, a detectable probe, a ligand, or an antibody fragment
k, k': each independently 0 or 1
a, b and c: each independently 0, 1, 2 or 3, provided that at least one of a, b or c is 1
m: an integer of 1 to 4
n: an integer of 1 to 4
Abbreviations for "A" are as Follows:
alemtuzumab (ATZ), anitumumab (ATM), bevacizumab (BCZ), brentuximab (BTX), cetuximab (CTX), gemtuzumab (GTZ), glembatumumab (GBT), inotuzumab (ITZ), ipilimumab (ILM), lovortumumab (LVT), milatuzumab (MTZ), ofatumumab (OTM), rituximab (RTX), tositumomab (TTM), and trastuzumab (TTZ)

Assays

The ADCs disclosed herein may be assayed for binding affinity to and specificity for the desired antigen by any of the methods conventionally used for the assay of antibodies; and they may be assayed for efficacy as anticancer agents by any of the methods conventionally used for the assay of cytostatic/cytotoxic agents, such as assays for potency against cell cultures, xenograft assays, and the like. A person of ordinary skill in the art will have no difficulty, considering that skill and the literature available, in determining suitable assay techniques; from the results of those assays, in determining suitable doses to test in humans as anticancer agents, and, from the results of those tests, in determining suitable doses to use to treat cancers in humans.

Formulation and Administration

The ADCs disclosed herein will typically be formulated as solutions for intravenous administration, or as lyophilized concentrates for reconstitution to prepare intravenous solutions (to be reconstituted, e.g., with normal saline, 5% dextrose, or similar isotonic solutions). They will typically be administered by intravenous injection or infusion. A person of ordinary skill in the art of pharmaceutical formulation, especially the formulation of anticancer antibodies, will have no difficulty, considering that skill and the literature available, in developing suitable formulations.

EXAMPLES

Synthesis of Linkers

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

Example 1

Synthesis of R-substituted 6-(2,3-dibromo-4-(amino)-4-oxobutanamido)hexanoic acid (5)

Scheme 1

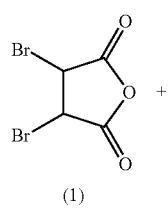

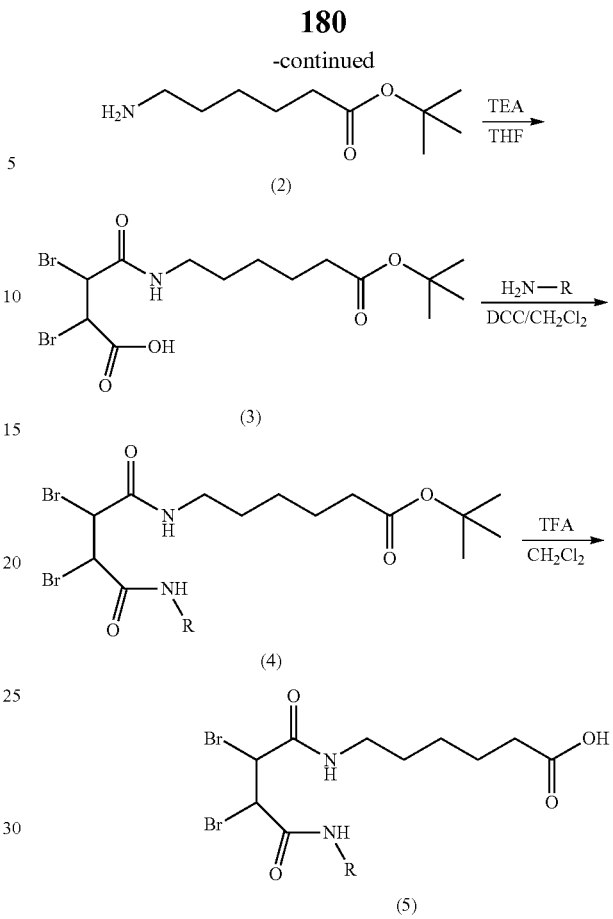

3,4-dibromodihydrofuran-2,5-dione (1) is reacted with tert-butyl 6-aminohexanoate (2) in anhydrous THF in the presence of TEA to yield 2,3-dibromo-4-((6-(tert-butoxy)-6-oxohexyl)amino)-4-oxobutanoic acid (3).

The purified product (3) is then added to a clean, flame-dried 50 mL round bottom flask, and the free carboxylic acid is coupled to reactant, $H_2N$—R, in 3 mL of $CH_2Cl_2$ in the presence of DCC to yield R-substituted tert-butyl 6-(2,3-dibromo-4-(amino)-4-oxobutanamido)hexanoate (4).

To fully deprotect (4) to the free acid, R-substituted 6-(2,3-dibromo-4-(amino)-4-oxobutanamido)hexanoic acid (5), the lyophilized material is treated with 5% TFA in $CH_2Cl_2$, concentrated to dryness and lyophilized in acetonitrile:water (50:50) overnight.

tert-butyl 6-aminohexanoate (2) may be substituted in Example 1 with tert-butyl 1-amino-3,6,9,12-tetraoxapentadecan-15-oate to produce R-substituted 20-amino-18,19-dibromo-17,20-dioxo-4,7,10,13-tetraoxa-16-azaicosan-1-oic acid (6):

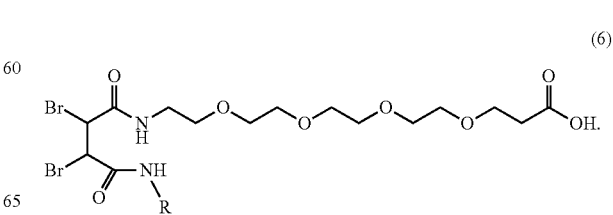

Example 2

Synthesis of 6-(2,3-dibromopropanamido)hexanoic acid (10)

Scheme 2

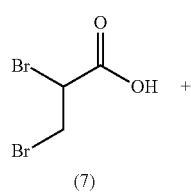

(7)

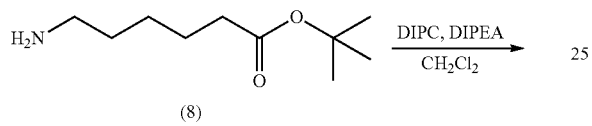

(8)

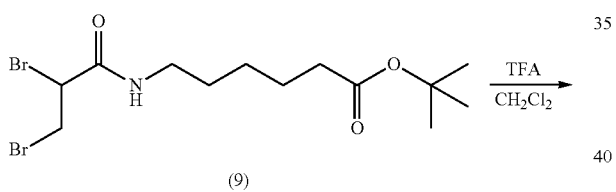

(9)

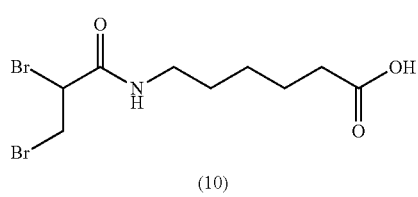

(10)

2,3-dibromopropanoic acid (7) is added to a clean, flame-dried 50 mL round bottom flask, and the free carboxylic acid is coupled to the free amine of tert-butyl 6-aminohexanoate (8) in 3 mL of $CH_2Cl_2$ in the presence of DIPC/DIPEA to yield tert-butyl 6-(2,3-dibromopropanamido)hexanoate (9).

To fully deprotect (9) to the free acid, 6-(2,3-dibromopropanamido)hexanoic acid (10), the lyophilized material is treated with 5% TFA in $CH_2Cl_2$, concentrated to dryness and lyophilized in acetonitrile:water (50:50) overnight.

tert-butyl 6-aminohexanoate (8) may be substituted in Example 2 with tert-butyl 1-amino-3,6,9,12-tetraoxapentadecan-15-oate to produce 1,2-dibromo-3-oxo-7,10,13,16-tetraoxa-4-azanonadecan-19-oic acid (11):

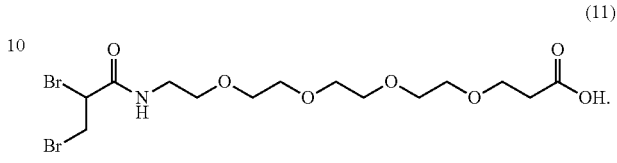

(11)

Example 3

Synthesis of 7,8-dibromooctanoic acid (13)

Scheme 3

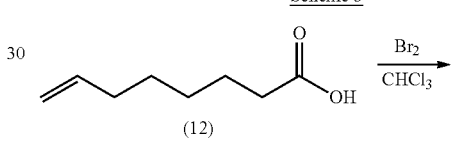

(12)

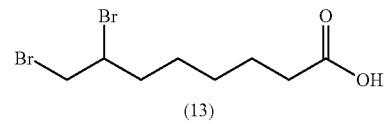

(13)

Oct-7-enoic acid (12) is treated with 0.5 equivalents of bromine in chloroform followed by refluxing overnight to give 7,8-dibromooctanoic acid (13) after flash purification on silica gel.

Example 4

Synthesis of $L^1$, $L^2$ and $L^3$

General procedures for the synthesis of $L^1$, $L^2$ and $L^3$ may be performed using standard synthetic procedures as described in Larock, above, or *Modern Synthetic Reactions*, Second Edition, H. O. House, The Benjamin/Cummings Publishing Company, Menlo Park, Calif. 1972; the chemistry of amino acids and peptide synthesis described in *The Chemistry of the Amino Acids*, J. P. Greenstein, M. Winitz, Robert E. Krieger Publishing Company, Malabar, Florid 1986, Volumes 1, 2 and 3.

Example 5
Synthesis of 4-((S)-2-((S)-2-(6-(2-bromoacrylamido)hexanamido)-3-methylbutanamido)propanamido)benzyl (4-nitrophenyl) carbonate (23)
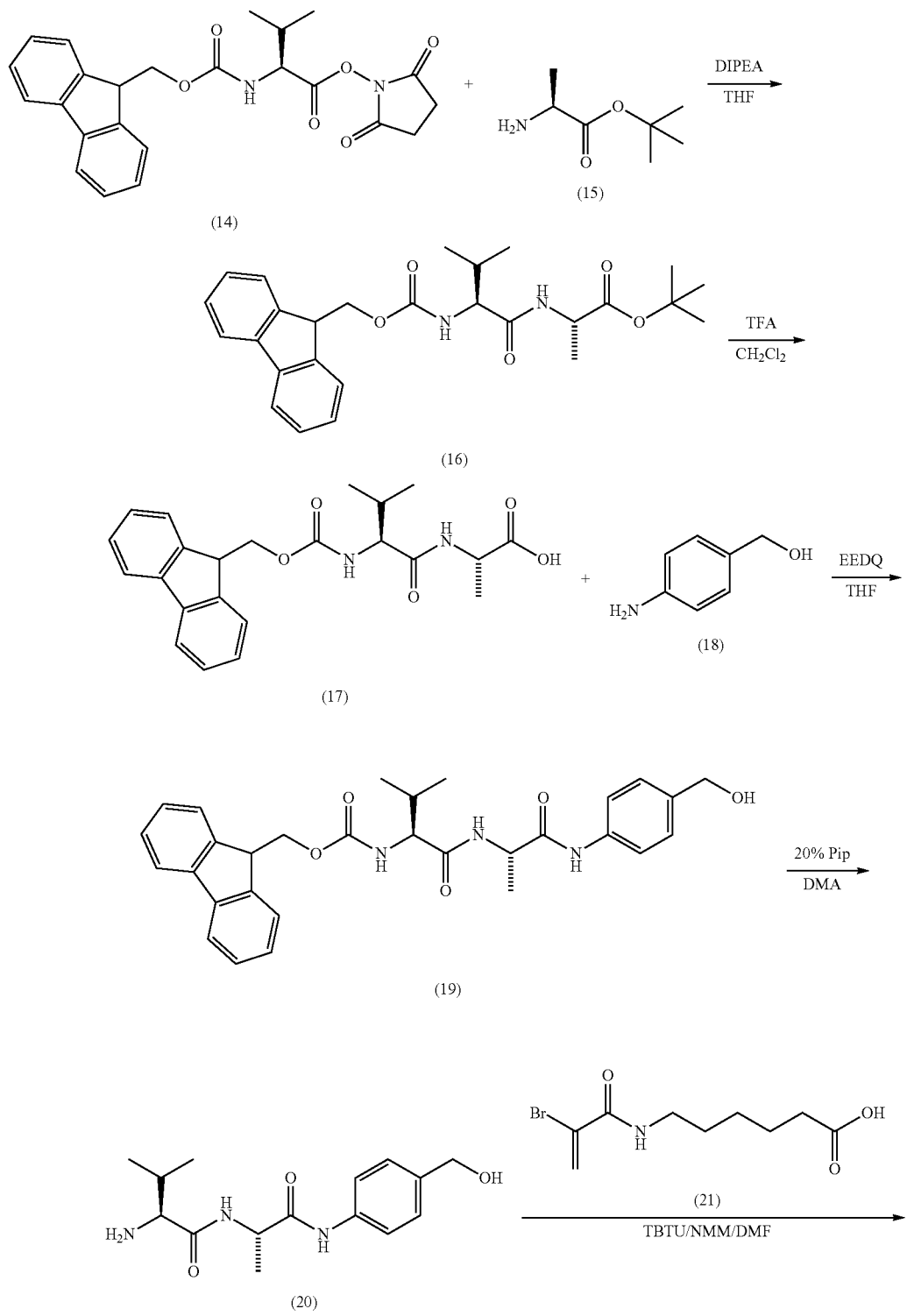
Scheme 4

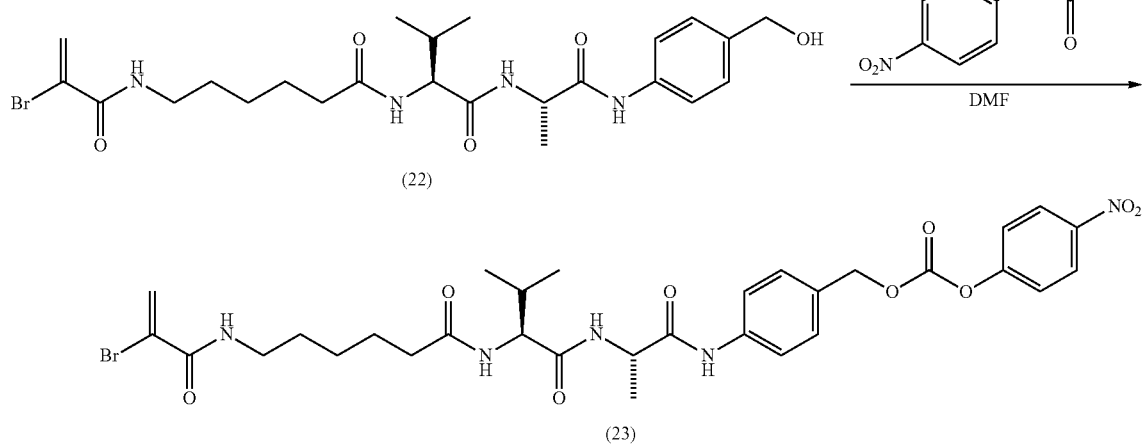

(S)-2,5-dioxopyrrolidin-1-yl 2-((((9H-fluoren-9-yl)methoxy)carbonyl)amino)-3-methylbutanoate (14) was reacted with (S)-tert-butyl 2-aminopropanoate (15) in the presence of 2 equivalents of DIPEA in THF to yield (S)-tert-butyl 2-((S)-2-((((9H-fluoren-9-yl)methoxy)carbonyl)amino)-3-methylbutanamido)propanoate (16). To fully deprotect (16) to the free acid, (S)-2-((S)-2-((((9H-fluoren-9-yl)methoxy)carbonyl)amino)-3-methylbutanamido)propanoic acid (17), the lyophilized material was treated with 5% TFA in $CH_2Cl_2$. The free carboxylic acid of the purified product (17) was then coupled to (4-aminophenyl)methanol (18), in the presence of 2 equivalents of EEDQ in THF to yield (9H-fluoren-9-yl)methyl ((S)-1-(((S)-1-((4-(hydroxymethyl)phenyl)amino)-1-oxopropan-2-yl)amino)-3-methyl-1-oxobutan-2-yl)carbamate (19). The product (19) was treated with 20% piperidine in DMA to yield (S)-2-amino-N—((S)-1-((4-(hydroxymethyl)phenyl)amino)-1-oxopropan-2-yl)-3-methylbutanamide (20). Coupling of the product (20) with 6-(2-bromoacrylamido)hexanoic acid (21) was performed by activation with 1 equivalent of TBTU in the presence of 2 equivalents of NMM in DMF for 72 hours at room temperature to produce 6-(2-bromoacrylamido)-N—((S)-1-(((S)-1-((4-(hydroxymethyl)phenyl)amino)-1-oxopropan-2-yl)amino)-3-methyl-1-oxobutan-2-yl)hexanamide (22). The product (22) was then reacted with 4-nitrophenyl carbonochloridate to produce 4-((S)-2-((S)-2-(6-(2-bromoacrylamido)hexanamido)-3-methylbutanamido)propanamido)benzyl (4-nitrophenyl) carbonate (23).

Synthesis of Linker-Cytotoxin Conjugate

Example 6

Synthesis of T4

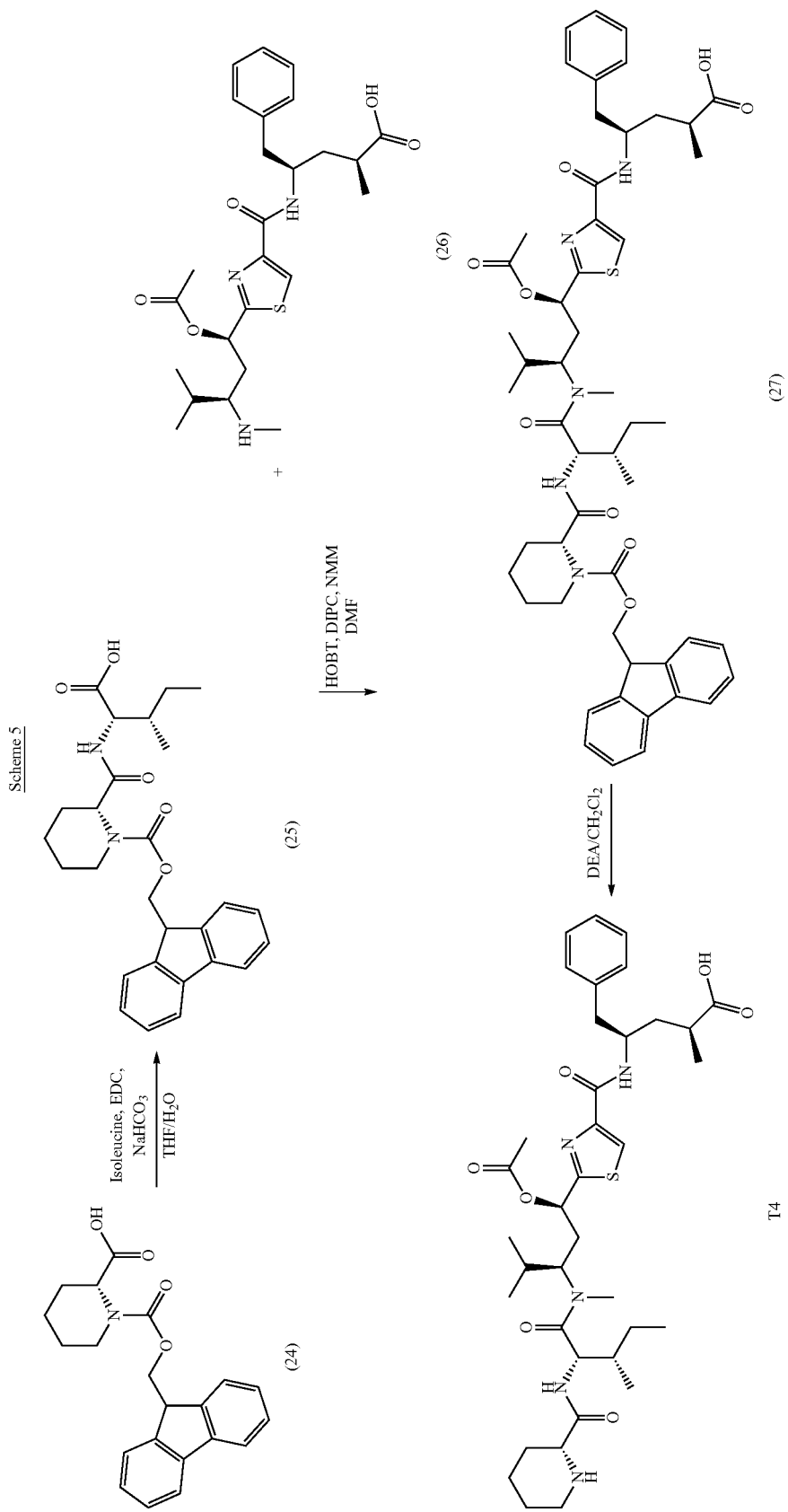

Fmoc-T4 was prepared by coupling Fmoc-D-2-piperidinecarboxylic acid (24) to isoleucine in the presence of EDC and sodium bicarbonate, then coupling the resulting Fmoc-D-Pip-Ile-OH (25) to the N-methylvaline intermediate (26) (purchased from Concortis) by mixing with 1 equivalent of HOBT and DIPC in DMF followed by addition of 2.5 equivalents of NMM. The reaction mixture was stirred overnight and purified by flash chromatography on silica gel using a gradient of hexane and ethyl acetate. Evaporation of solvent gave Fmoc-T4 (27) as a yellow oil. The Fmoc-T4 was then deprotected by treatment with 20% DEA in methylene chloride for 30 minutes to give T4, which was purified by preparative HPLC on a C18 reverse phase column eluted with acetonitrile/water.

Example 7

Synthesis of R-substituted (2S,4R)-4-(2-((1R,3R)-1-acetoxy-3-((2S,3S)-2-((2R)-1-(6-(2,3-dibromo-4-(amino)-4-oxobutanamido)hexanoyl)piperidine-2-carboxamido)-N,3-dimethylpentanamido)-4-methylpentyl)thiazole-4-carboxamido)-2-methyl-5-phenylpentanoic acid (28)

Coupling of T4 to the linker described in Example 1 (R-substituted 6-(2,3-dibromo-4-(amino)-4-oxobutanamido)hexanoic acid (5)) was performed by activating the linker with 1 equivalent of HATU in the presence of 2 equivalents of DIPEA in DMF, then coupling with the T4 for 72 hours at room temperature. Another coupling reagent, for example, TBTU may be substituted for HATU to activate the linker. Purification by preparative C18 HPLC (acetonitrile-water gradient) gave a linker-T4 conjugate suitable for conjugation to antibodies.

Similar syntheses using other linkers give the corresponding linker-T4 conjugates. Similar syntheses using T3, MMAF, or other cytotoxins with a basic amine give the corresponding linker-cytotoxin conjugates. Similar syntheses using amine-terminated linkers and cytotoxins with a carboxyl group, activating the cytotoxin in the same manner as the linker was activated in the above Example, give other linker-cytotoxin conjugates.

Scheme 6

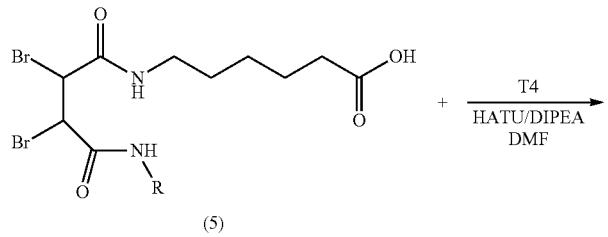

(5)

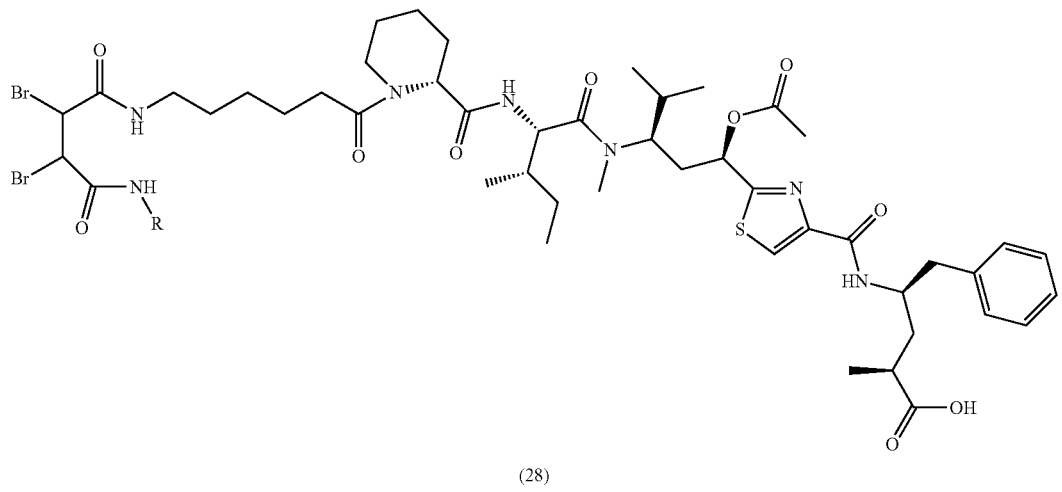

(28)

Example 8

Synthesis of (2S)-2-((2R,3R)-3-((2S)-1-((12S,15S,18S,19R)-1,2-dibromo-18-((R)-sec-butyl)-12,15-diisopropyl-19-methoxy-11,17-dimethyl-3,10,13,16-tetraoxo-4,11,14,17-tetraazahenicosan-21-oyl)pyrrolidin-2-yl)-3-methoxy-2-methylpropanamido)-3-phenylpropanoic acid (29)

Scheme 7

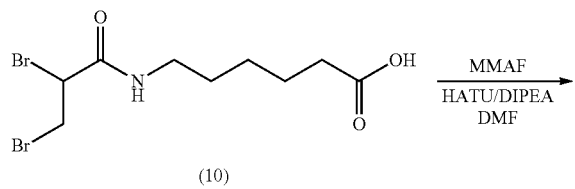

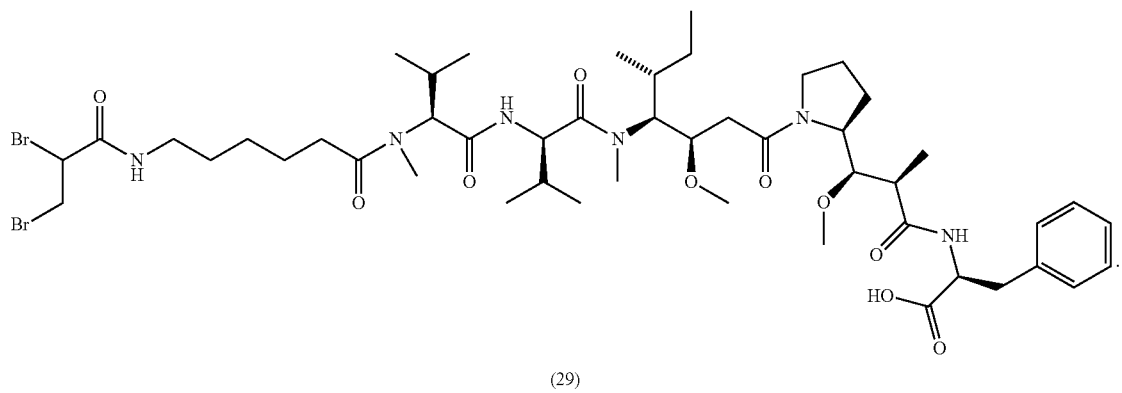

(29)

Coupling of MMAF to the linker described in Example 2 (6-(2,3-dibromopropanamido)hexanoic acid (10)) was performed by activating the linker with 1 equivalent of HATU in the presence of 2 equivalents of DIPEA in DMF, then coupling with the MMAF for 72 hours at room temperature. Another coupling reagent, for example, TBTU may be substituted for HATU to activate the linker. Purification by preparative C18 HPLC (acetonitrile-water gradient) gave the linker-MMAF conjugate suitable for conjugation to antibodies.

MMAF generally refers to (S)-2-((2R,3R)-3-((S)-1-((3R,4S,5S)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanamido)-3-phenylpropanoic acid. Pictured above in Scheme 7 is ((2R,3R)-3-((S)-1-((3R,4S,5R)-4-((S)—N,3-dimethyl-2-((S)-3-methyl-2-(methylamino)butanamido)butanamido)-3-methoxy-5-methylheptanoyl)pyrrolidin-2-yl)-3-methoxy-2-methylpropanoyl)-L-phenylalanine.

Similar syntheses using other linkers give the corresponding linker-MMAF conjugates. Similar syntheses using T3, T4, or other cytotoxins with a basic amine give the corresponding linker-cytotoxin conjugates. Similar syntheses using amine-terminated linkers and cytotoxins with a carboxyl group, activating the cytotoxin in the same manner as the linker was activated in the above Example, give other linker-cytotoxin conjugates.

Example 9

Synthesis of (2S)-2-((2R,3R)-3-((2S)-1-((3R,4S,5R)-4-((2S)-2-((2S)-2-(7,8-dibromo-N-methyloctanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid (30)

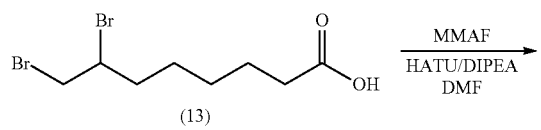

Scheme 8

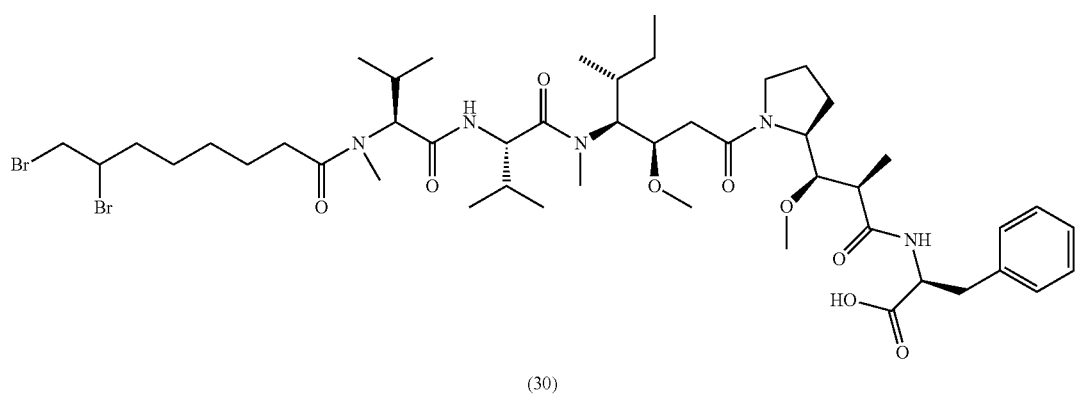

(30)

Coupling of MMAF to the linker described in Example 3 (7,8-dibromooctanoic acid (13)) was performed by activating the linker with 1 equivalent of HATU in the presence of 2 equivalents of DIPEA in DMF, then coupling with the MMAF for 72 hours at room temperature. Another coupling reagent, for example, TBTU may be substituted for HATU to activate the linker. Purification by preparative C18 HPLC (acetonitrile-water gradient) gave the linker-MMAF conjugate, (2S)-2-((2R,3R)-3-((2S)-1-((3R,4S,5R)-4-((2S)-2-((2S)-2-(7,8-dibromo-N-methyloctanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid (30) suitable for conjugation to antibodies.

Similar syntheses using other linkers give the corresponding linker-MMAF conjugates. Similar syntheses using T3, T4, or other cytotoxins with a basic amine give the corresponding linker-cytotoxin conjugates. Similar syntheses using amine-terminated linkers and cytotoxins with a carboxyl group, activating the cytotoxin in the same manner as the linker was activated in the above Example, give other linker-cytotoxin conjugates.

Example 10

Synthesis of (S)-2-((2R,3R)-3-((S)-1-((12S,15S,18S,19R)-2-bromo-18-((S)-sec-butyl)-12,15-diisopropyl-19-methoxy-11,17-dimethyl-3,10,13,16-tetraoxo-4,11,14,17-tetraazahenicos-1-en-21-oyl)pyrrolidin-2-yl)-3-methoxy-2-methylpropanamido)-3-phenylpropanoic acid (36)

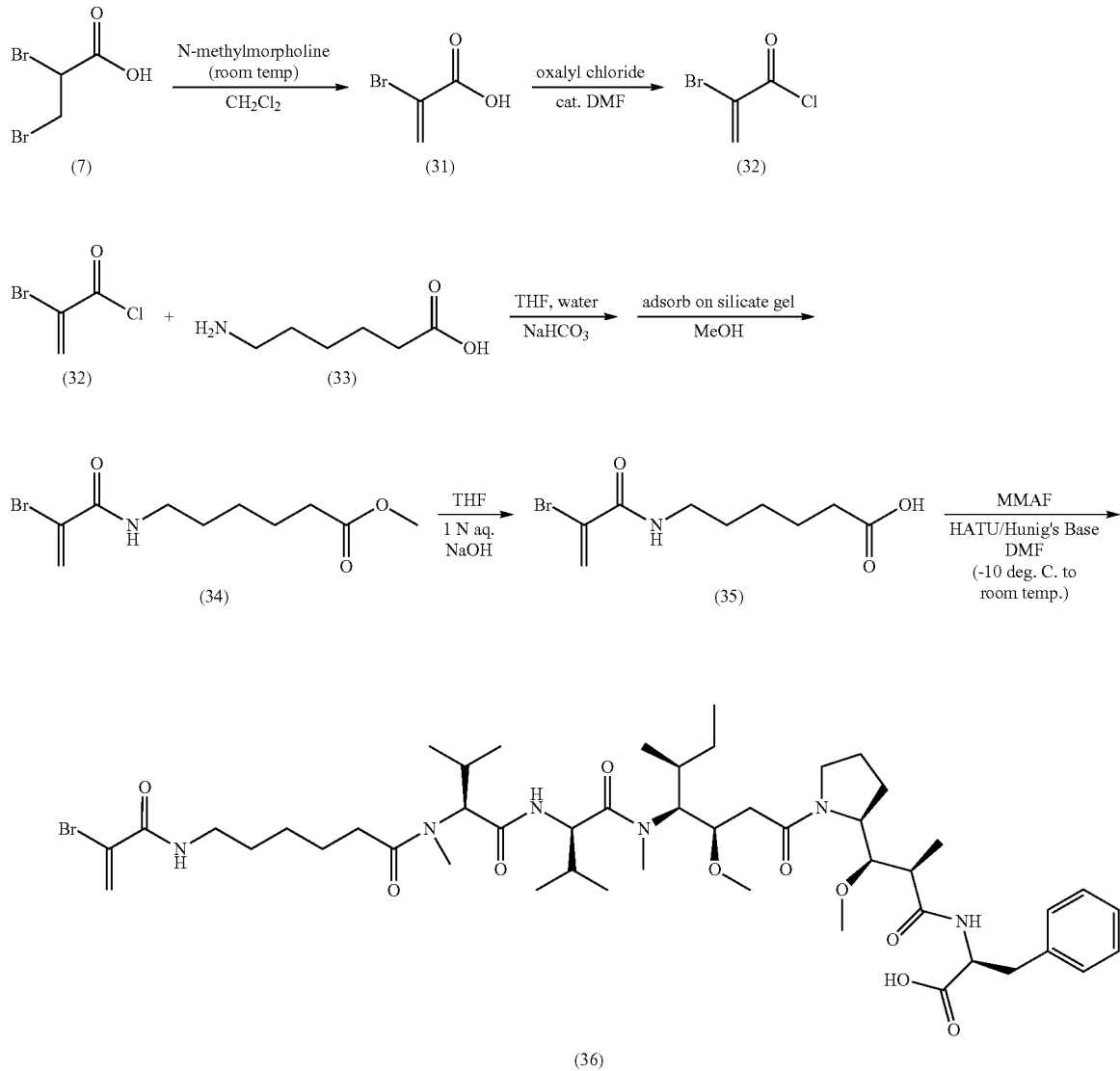

2,3-dibromopropanoic acid (7) was treated with N-methylmorpholine in CH$_2$Cl$_2$ at room temperature to produce 2-bromoacrylic acid (31), which following treatment with oxalyl chloride in catalytic DMF produced 2-bromoacryloyl chloride (32). The product (32) was reacted with 6-aminohexanoic acid (33) in THF and sodium bicarbonate, followed by absorption on silicate gel in the presence of MeOH, to produce methyl 6-(2-bromoacrylamido)hexanoate (34). Deprotection of (34) with 1N aqueous NaOH in THF produced the free acid, 6-(2-bromoacrylamido)hexanoic acid (35).

Coupling of MMAF to (35) was performed by activation with 2 equivalents of HATU/Hunig's Base in DMF, then coupling with the MMAF for 72 hours at −10° C. to room temperature. Purification by preparative C18 HPLC (acetonitrile-water gradient) gave the linker-MMAF conjugate, (S)-2-((2R,3R)-3-((S)-1-((12S,15S,18S,19R)-2-bromo-18-((S)-sec-butyl)-12,15-diisopropyl-19-methoxy-11,17-dimethyl-3,10,13,16-tetraoxo-4,11,14,17-tetraazahenicos-1-en-21-oyl)pyrrolidin-2-yl)-3-methoxy-2-methylpropanamido)-3-phenylpropanoic acid (36) suitable for conjugation to antibodies.

Example 11

Synthesis of (S)-2-((2R,3R)-3-((S)-1-((5S,8S,11S,12R)-1-(4-((R)-2-((R)-2-(6-(2-bromoacrylamido)hexanamido)-3-methylbutanamido)propanamido)phenyl)-11-((S)-sec-butyl)-5,8-diisopropyl-12-methoxy-4,10-dimethyl-3,6,9-trioxo-2-oxa-4,7,10-triazatetradecan-14-oyl)pyrrolidin-2-yl)-3-methoxy-2-methylpropanamido)-3-phenylpropanoic acid (37)

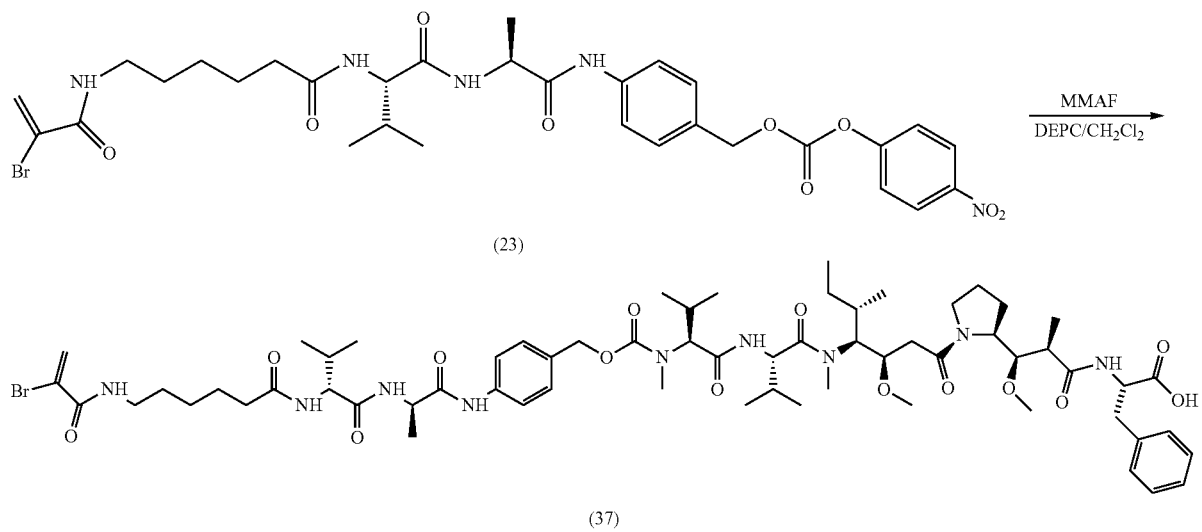

Coupling of MMAF to the linker described in Example 5 (4-((S)-2-((S)-2-(6-(2-bromoacrylamido)hexanamido)-3-methylbutanamido)propanamido)benzyl (4-nitrophenyl) carbonate (23)) was performed by activating the linker with 1 equivalent of DEPC in CH$_2$Cl$_2$, then coupling with the MMAF for 72 hours at room temperature. Purification by preparative C18 HPLC (acetonitrile-water gradient) gave the linker-MMAF conjugate, (S)-2-((2R,3R)-3-((S)-1-((5S,8S,11S,12R)-1-(4-((R)-2-((R)-2-(6-(2-bromoacrylamido)hexanamido)-3-methylbutanamido)propanamido)phenyl)-11-((S)-sec-butyl)-5,8-diisopropyl-12-methoxy-4,10-dimethyl-3,6,9-trioxo-2-oxa-4,7,10-triazatetradecan-14-oyl)pyrrolidin-2-yl)-3-methoxy-2-methyl propanamido)-3-phenylpropanoic acid (37) suitable for conjugation to antibodies.

Example 12

Screening and Optimization of Bifunctional Linkers for ADCs

Antibody-drug conjugates were prepared comprising a linker and cytotoxin as described in Examples 7-11. In some experiments, Herceptin was used in the preparation of ADCs. Exemplary conjugates were analyzed by SDS-PAGE, HIC and LC-MS, as shown in FIGS. 4 and 5.

Figure 4:
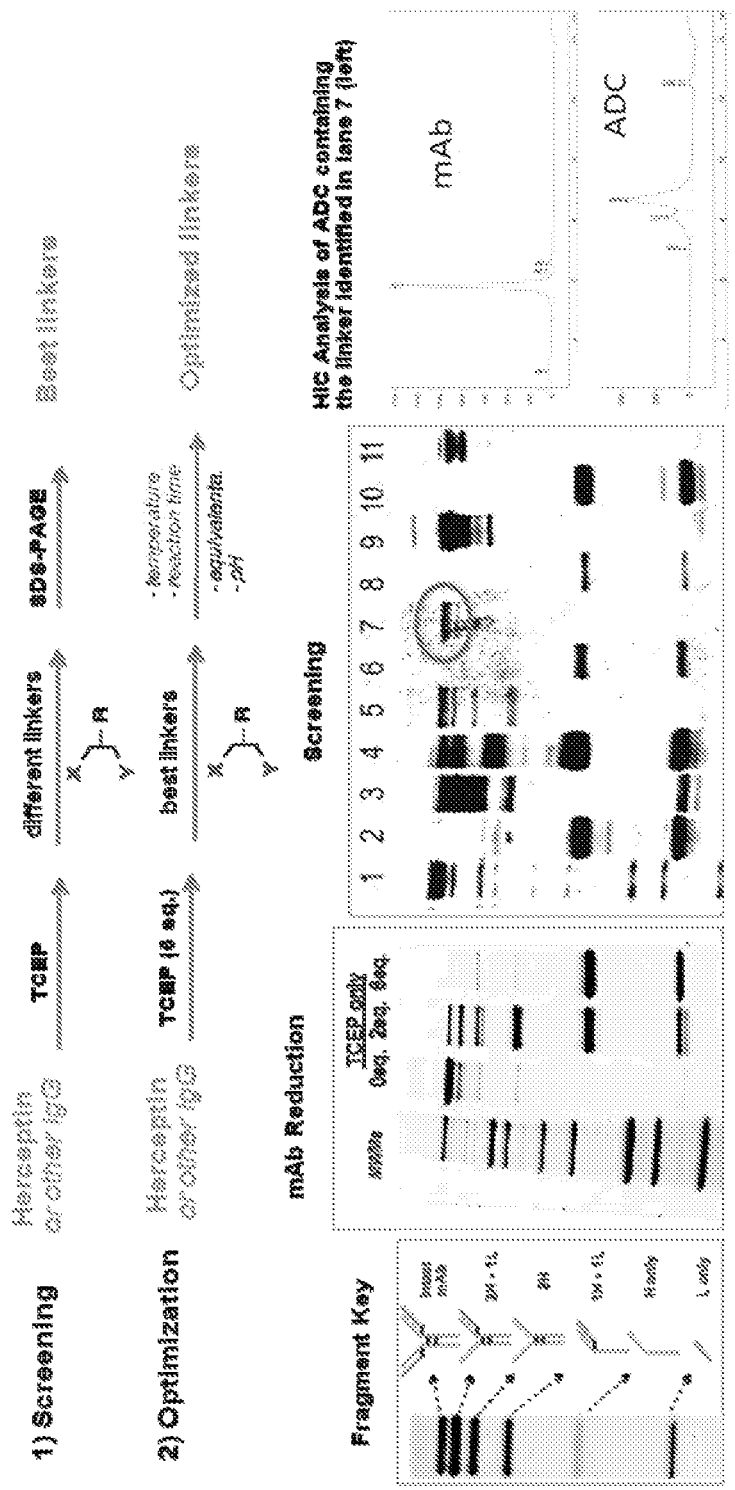
FIG. 4: Rapid Screening and Optimization of Bifunctional Linkers
Figure 5:
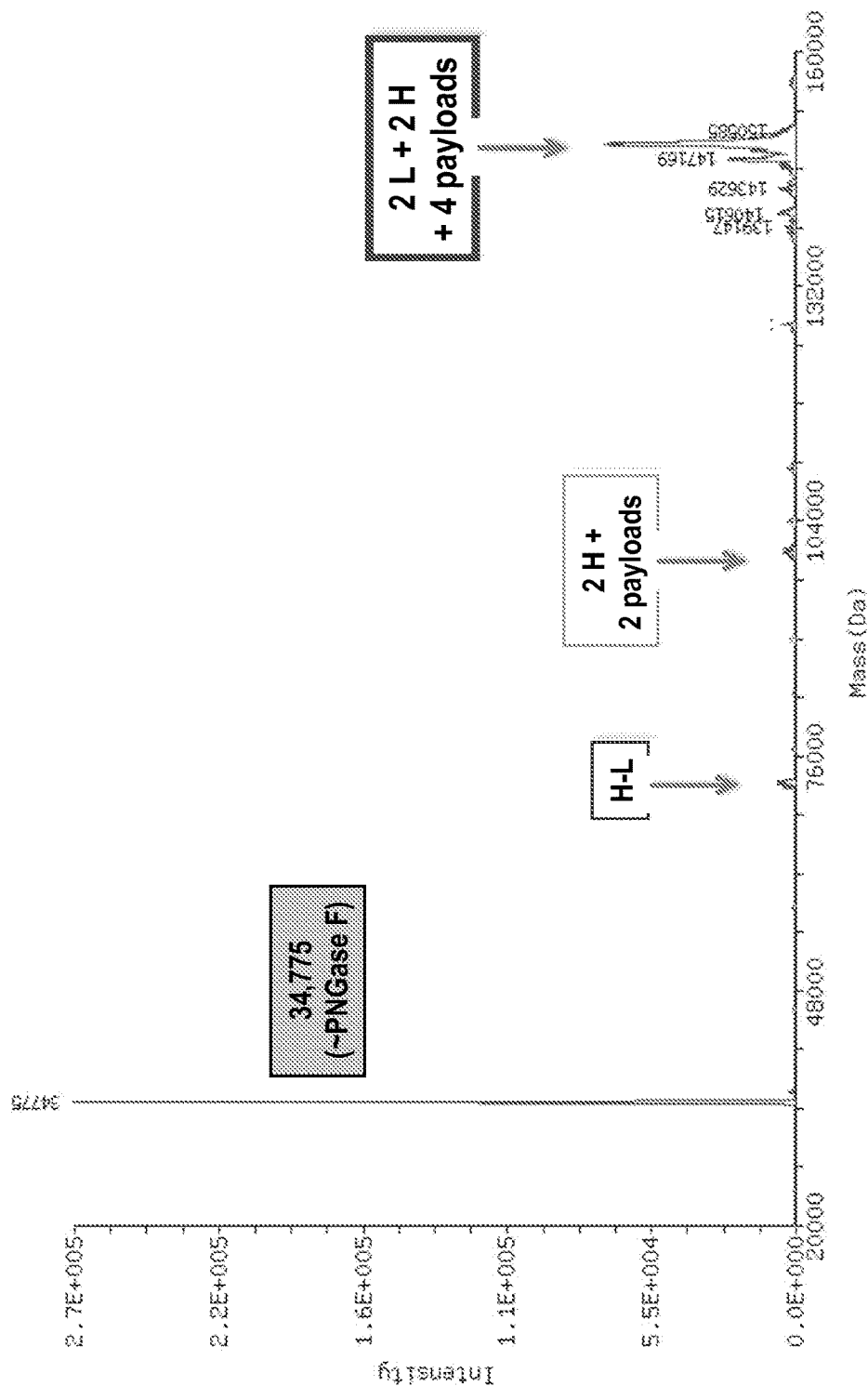
FIG. 5: Mass Spectrometric Analysis of a Homogeneous ADC

Bifunctional linkers may be rapidly screened and/or optimized by SDS-PAGE, as illustrated in FIG. 4, for optimal properties (e.g., resulting in 1 drug/payload per 1 disulfide bond).

In some experiments, for SDS-PAGE under non-reducing conditions, sample preparation were as follows: In a 1 ml eppendorf vial was pipetted Novex Tris-Glycine SDS sample buffer (2×) (300 μL) (Life Technologies catalog #LC2676) and deionized water (150 ul). 30 μL of the sample buffer was pipetted into a 1 ml eppendorf vial and 10 μL of the sample was added.

In some experiments, for SDS-PAGE under reducing conditions, sample preparation were as follows: In a 1 ml eppendorf vial was pipetted Novex Tris-Glycine SDS sample buffer (2×) (300 μL) (Life Technologies catalog #LC2676), deionized water (120 μl), and 1 M dithiothreitol (Sigma catalog #D0632). 30 μL of the sample buffer was pipetted into a 1 ml eppendorf vial and 10 μL of the sample was added. The vials were placed in a sand bath at 100° C. for 2 minutes and cooled to ambient temperature.

In some experiments, for SDS-PAGE, running buffer preparation were as follows: Novex Tris-Glycine SDS running buffer (10×) (100 ml) (Life Technologies catalog #LC2675-4) was added to deionized water (900 ml).

In some experiments, denaturing electrophoresis gel was as follows: Life Technologies Novex 4-20% Tris-Glycine midi gel (Life Technologies catalog #WT4201BX10) was placed into a gel box. The running buffer was poured into the gel box until full. To the outermost lanes on the left and right side was added Novex Mark 12™ unstained standard (Life Technologies catalog #LC5677). To each of the interior lanes was added either a non-reducing or reducing sample. The lid was placed onto the gel box and the electric current was started (125 V). Bubbling was observed. The starting amps were ca. 90 mA then falling to ca. 50 mA at the end of the run over ca. a 90 min period.

In some experiments, staining of the gels was as follows: The gels were carefully removed from their enclosures and placed directly into a plastic container for staining. A staining solution consisting of SYPRO Orange protein stain (20 μl) (Life Technologies catalog #S6651) in a 7.5% aqueous glacial acetic acid solution (100 ml) was gently poured over the gel(s) and gently rocked for 30 min. The staining solution was decanted and the gels were gently washed with deionized water and decanted (3×). 7.5% aqueous glacial acetic acid solution (100 ml) was gently poured over the gel(s) and gently rocked for an additional 30 min. The destaining solution was decanted and the gels were gently washed with deionized water and decanted (3×). The gels were imaged using a GE Healthcare Typhoon Trio+ scanner.

Exemplary SDS-PAGE screening of a bifunctional linker as described in Example 12 is shown in FIG. 4. Additional analysis by HIC and LC-MS is shown in FIGS. 4 and 5. Lane 7 in FIG. 4 corresponds to Herceptin conjugated to a bromocrylamide (BRA) linker, as described herein.

Synthesis of ADC

Example 13

Antibody Disulfide Reduction and Linker-Cytotoxin Conjugation to Antibody

This example provides an exemplary protocol for reduction of the disulfides of the antibodies disclosed herein, and conjugation of the reduced antibodies to the linker-cytotoxin conjugates disclosed herein.

Protocol:

Step 1: Antibody Disulfide Reduction

A) Dilute antibody to 15 mg/mL (0.1 mM IgG) in PBS, pH 7.4.

B) Prepare a fresh 20 mM (5.7 mg/mL) stock solution of TCEP in $H_2O$.

C) Add 25 µL of TCEP stock solution from B to 1 mL of antibody from A (0.5 mM final concentration TCEP).

D) Incubate at 37° C. for 2 hours (check for free thiols using DTNB test).

E) Aliquat the reduced antibody into 4 tubes (250 µL each).

Step 1: Linker-Cytotoxin Conjugation to Antibody

A) Prepare 10 mM stock solution of linker-cytotoxin conjugate in DMSO (DMA, DMF or $CH_3CN$ are also acceptable).

B) Add 5 equivalents of 12.5 µL stock solution from A to each tube of reduced antibody (0.5 mM final concentration linker-cytotoxin conjugate stock solution).

C) Incubate overnight at 4° C. for 4 hours at room temperature; check for free thiols using DTNB test.

D) Run analytical HIC to determine DAR and homogeneity.

Example 14

Reduction and Purification of Herceptin for Conjugation to Linker-Cytotoxin Conjugate This example provides an exemplary protocol for reduction and purification of herceptin for conjugation to the linker-cytotoxin conjugates disclosed herein.

Purpose:

Determine the effect of purifying reduced antibody on conjugation efficiency.

Protocol:

Purge all buffers and DMSO stock solutions with Argon for 1 h prior to use.

1) Aliquat 1 mL of Herceptin or IGN 523 from 10 mg/mL stock into a 2 mL eppendorf tube.

2) Dilute with 1 mL 100 mM Borate (pH 8.4) to afford a 10 mg/mL stock solution (67 µM).

3) Prepare a 50 mM stock solution of TCEP in water.

4) Add 20 mL of TCEP to 2 mL of Herceptin and incubate at 37° C. for 3 hours.

5) Aliquat into 4×0.5 mL eppendorf tubes and place 3 tubes in storage at −20° C.

6) Purify one 0.5 mL aliquat (approx. 5 mg) via SEC on Biorad using degassed PBS.

7) Collect monomeric antibody peak in a sealed tube (approx. 4 mL total volume) at 4° C.

8) Aliquat into 4 equal 1 mL eppendorf tubes (1 mg/mL).

9) Add 6 equivalents of the cytotoxin-linker conjugate from 2 mM stock solutions in DMSO to each tube.

10) Incubate at 4° C. for 48 hours.

11) Analyze by HIC, SDS-PAGE and LC/MS, and compare against control.

Example 15

Synthesis of ADC

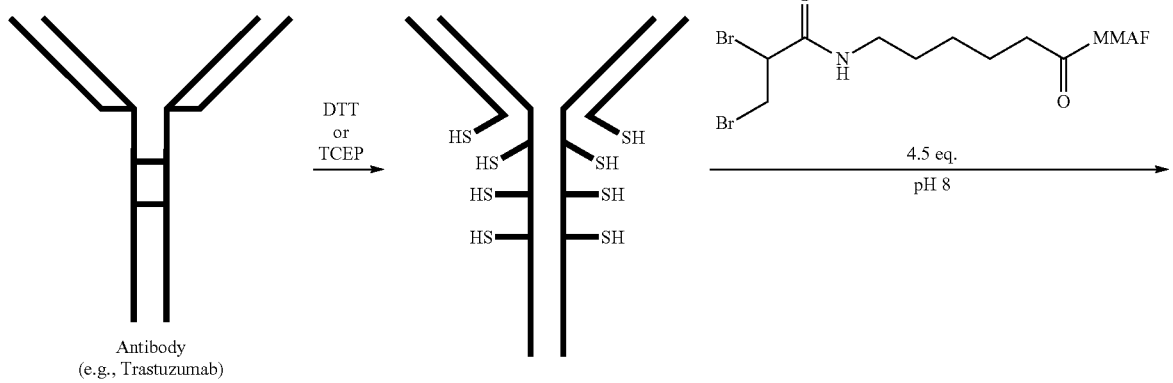

Scheme 11

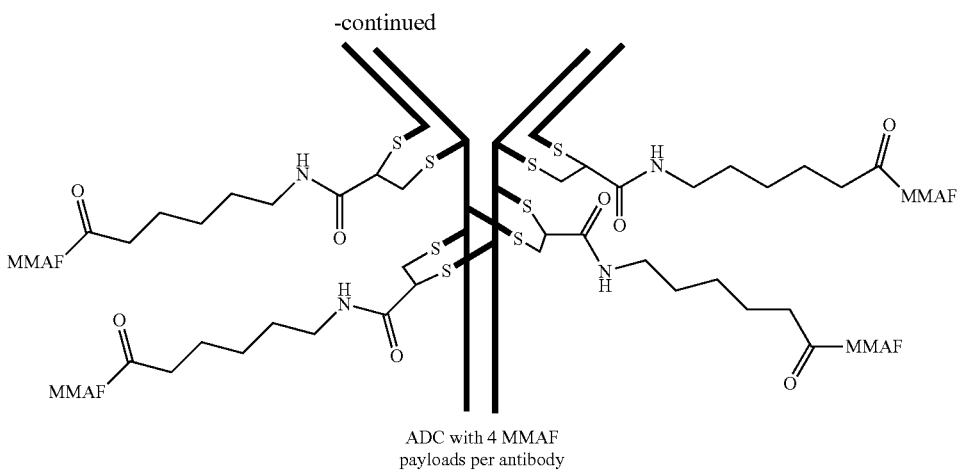

ADC with 4 MMAF
payloads per antibody

Trastuzumab, 1 mL of a 20 mg/mL solution in pH 7.4 PBS (Gibco Mg and Ca free) with 1 mM DTPA, is loaded into a sterile 1.7 mL Eppendorf tube, then 2.75 equivalents of TCEP hydrochloride (Sigma ampule 0.5M concentration), is added and the mixture incubated at 37° C. for 1 hour to give an average of 4 free thiol pairs per trastuzumab (this can be verified by Ellman's colorimetric assay—see Ellman, "Tissue sulfhydryl groups", *Arch. Biochem. Biophys*, 1959, 82, 70-77 or later papers referring to this assay). The reduced antibody solution is cooled in an ice-bath at about 0° C. for 15 minutes; then a solution of about 4.5 equivalents of (2S)-2-((2R,3R)-3-((2S)-1-((12S,15S,18S,19R)-1,2-dibromo-18-((R)-sec-butyl)-12,15-diisopropyl-19-methoxy-11,17-dimethyl-3,10,13,16-tetraoxo-4,11,14,17-tetraazahenicosan-21-oyl)pyrrolidin-2-yl)-3-methoxy-2-methylpropanamido)-3-phenylpropanoic acid (19) of Example 7 in dimethylsulfoxide is added and the mixture incubated at 37° C. for 2 hours (or at 4° C. for 20 hours). The resulting ADC is purified by size-exclusion chromatography (GE ÄKTA pure chromatographic system) or PD10 desalting column.

Similar syntheses using other linker-cytotoxin conjugates, and/or other antibodies, give the corresponding ADCs.

In certain embodiments, the ADCs prepared from the method of the present application provides the products with significant homogeneity as shown by HIC traces, when compared with the ADCs prepared by conventional methods that provide inhomogeneous ADCs with multiple products and positional isomers.

Assays

The ADCs disclosed herein are tested for potency and selectivity in vitro by determining their cytotoxicity in cancer cell lines of interest, such as those cancer cell lines expressing the antigen corresponding to the antibody portion of the ADC and similar cancer cell lines lacking the antigen. The ADCs disclosed herein are tested for potency and safety in vivo in such animal models as the mouse subcutaneous cancer xenograft and mouse orthotopic cancer xenograft models well known to those of skill in the art of cancer research.

Example 16

Cytotoxicity of ADCs Compared to Antibody

The cytotoxicity of the ADCs disclosed herein, where the antibody is conjugated to a cytotoxin through one of the linkers disclosed herein, is compared to the cytotoxicity of antibody alone in HER2-positive and HER2-negative tumor cells. In certain embodiments, the ADCs are considerably more potent than their parental antibodies.

Example 17

Binding Affinity of ADCs for Antigen-Expressing Cells

Binding of the antibodies and ADCs to antigen-expressing cells are measured using a cell ELISA. Sarcoma cells transduced to express the target (F279 cells for HER2, F244 cells for CD98) are plated the day at 5000 cells per well in a 384-well plate. The following day, antibodies are serially diluted in a separate plate, and then transferred to the cell plate, which has previously had media removed by aspiration. After a 2 hour incubation at room temperature, the plate is washed with wash buffer (DPBS at pH7.4 with 0.1% bovine serum albumin) and then 25 µL horseradish peroxidase-labeled secondary antibody diluted in media is added and incubated for 30 minutes at room temperature. The plate is then washed and 15 µL of a chemiluminescent substrate (Pierce catalog #37069) is added; and the plate is read in a plate-based luminescence reader. Antibodies and ADCs demonstrating comparable affinity for F244 cells indicate that conjugation of the drug payloads does not affect antigen binding.

Example 18

Potency of ADCs Against Antigen-Expressing Cells

The potency of ADCs disclosed herein for inhibition of tumor cell growth is tested in cell proliferation assays. The Ramos (B-cell lymphoma) and BT474 (HER2+ human breast carcinoma) cell lines are seeded into 96 well half-area plates the day before drug treatment at 3000 and 5000 cells per well respectively. ADCs and controls are serially diluted in a master plate, and then transferred to the cell plates, which are incubated at 37° C. and 5% $CO_2$ for 3 days. The cells are quantitated by measuring the level of ATP in the wells using the ATPLite 1 Step kit (Perkin Elmer catalog #50-904-9883) as described by the manufacturer.

Example 19

Efficacy of ADCs in Murine Xenograft Models

The Ramos cell xenograft model.

The Ramos cell line is obtained from ATCC and cultured according to the supplier's protocols. 4-6 Week-old immunodeficient female mice (Taconic C.B-17 scid) are subcutaneously injected on the right flank with 1×10⁷ viable cells in a mixture of PBS (without magnesium or calcium) and BD Matrigel (BD Biosciences) at a 1:1 ratio. The injected total volume per mouse is 200 μL with 50% being Matrigel. Once the tumor reaches a size of 65-200 mm³, mice are randomized. ADCs are formulated in PBS and administered once intravenously at a dose of 1 mg/Kg into the lateral tail vein, and body weights and tumors are measured twice weekly. Tumor volume are calculated as described in van der Horst et al., "Discovery of Fully Human Anti-MET Monoclonal Antibodies with Antitumor Activity against Colon Cancer Tumor Models In Vivo", *Neoplasia*, 2009, 11, 355-364. The experiments are performed on groups of 8 animals per experimental point. The negative control group receives HB121 (an IgG2a-negative antibody) and free MMAF or T4, as appropriate, at a concentration equimolar to the concentration that would be released by the ADC, while the positive control group receives 18-2 A.

The BT474 cell xenograft model.

The BT474 cell line is obtained from ATCC and cultured according to the supplier's protocols. 4-6 Week-old immunodeficient female mice (Taconic C.B-17 scid) are implanted with a β-estradiol pellet 3 days before being subcutaneously injected on the right flank with 1×10⁷ viable cells in a mixture of PBS (without magnesium or calcium) and BD Matrigel (BD Biosciences) at a 1:1 ratio. The injected total volume per mouse is 200 μL with 50% being Matrigel. Once the tumor reaches a size of 100-150 mm³, mice are randomized. ADCs are formulated in PBS and administered once intravenously at a dose of 1 mg/Kg into the lateral tail vein, and body weights and tumors are measured twice weekly. Tumor volume is calculated as described in van der Horst et al., cited above. The experiments are performed on groups of 8 animals per experimental point. The negative control group receives HB121 and free MMAF or T4, as appropriate, at a concentration equimolar to the concentration that would be released by the ADCs, while the positive control group receives trastuzumab at 1 mg/Kg.

Similar tests are conducted with other cancers (those expressing different antigens) and ADCs where the antibody corresponds to the antigen expressed by the cancer.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

What is claimed is:

1. An antibody-drug conjugate of the following formula (III):

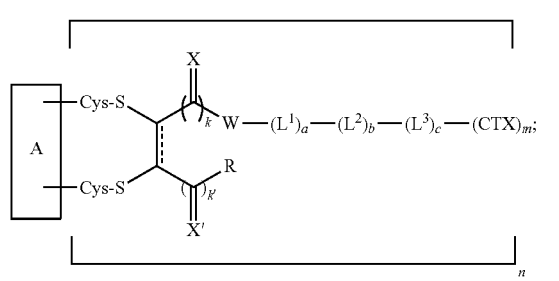

or a pharmaceutically acceptable salt thereof,
wherein:
A is an antibody selected from the group consisting of alemtuzumab, anitumumab, bevacizumab, brentuximab, cetuximab, gemtuzumab, glembatumumab, inotuzumab, ipilimumab, lovortumumab, milatuzumab, ofatumumab, rituximab, tositumomab, and trastuzumab;
the two depicted cysteine residues are from an opened cysteine-cysteine disulfide bond in A;
each X and X' is O;
W is —NH—;
CTX is a releasable cytotoxin that is toxic to a cancer cell when released in the cancer cell and is selected from the group consisting of Actinomycin-D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Bortezomib, and Vincristine; wherein CTX is bonded to $(L^1)_a$-$(L^2)_b$-$(L^3)_c$ via an amide, an N—($C_{1-6}$alkyl)amide, a carbamate, an N—($C_{1-6}$alkyl)carbamate, an amine, an N—($C_{1-6}$alkyl)amine, an ether, a thioether, an urea, an N—($C_{1-6}$alkyl)urea, or an N,N-di($C_{1-6}$alkyl)urea bond;
R is absent;
$L^1$ is selected from the group consisting of —O—, —C(O)—, —$(CH_2)_q$—, —$(CH_2CH_2O)_p$,
$L^2$ is selected from the group consisting of —O—, —$(CH_2)_q$—, —$(CH_2CH_2O)_p$, and —$NH(CH_2)_2$;
$L^3$ is selected from the group consisting of —OC(O)—, —NHC(O)—, and —$NCH_3C(O)$—;
a, b and c are each independently 0, 1, or 2, provided that at least one of a, b or c is 1;
k is 1 and k' is 0;
each p is independently an integer of 1 to 14;
each q is independently an integer or 1 to 12;
m is an integer of 1 to 4;
n is an integer of 1 to 4; and
the ═ bond represents a single bond.

2. The antibody-drug conjugate or pharmaceutically acceptable salt of claim 1, wherein A is trastuzumab.

3. The antibody-drug conjugate or pharmaceutically acceptable salt of claim 1, wherein the CTX is an auristatin, a calicheamicin, a maytansinoid, or a tubulysin.

4. The antibody-drug conjugate or pharmaceutically acceptable salt of claim 1, wherein the CTX is monomethylauristatin E, monomethylauristatin F, calicheamicin γ, a pyrrolobenzodiazepine, mertansine, tubulysin T2, tubulysin T3, or tubulysin T4.

5. The antibody-drug conjugate or pharmaceutically acceptable salt of claim 1, wherein CTX is bonded to $(L^1)_a$-$(L^2)_b$-$(L^3)_c$ via a bond selected from the group consisting of:

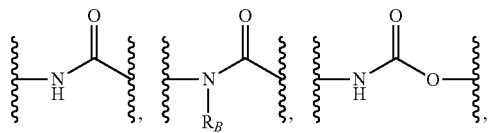

-continued

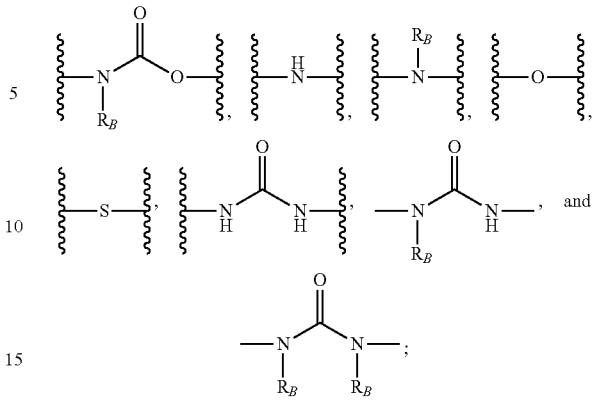

wherein each $R_B$ is independently branched or unbranched $C_{1-6}$ alkyl.

* * * * *

UNITED STATES PATENT AND TRADEMARK OFFICE
CERTIFICATE OF CORRECTION

| | |
|---|---|
| PATENT NO. | : 11,229,711 B2 |
| APPLICATION NO. | : 14/895893 |
| DATED | : January 25, 2022 |
| INVENTOR(S) | : Jackson et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 333 days.

Signed and Sealed this
Eleventh Day of February, 2025

Coke Morgan Stewart
*Acting Director of the United States Patent and Trademark Office*